(12) United States Patent
Kawamura et al.

(10) Patent No.: US 9,741,943 B2
(45) Date of Patent: Aug. 22, 2017

(54) CONDENSED FLUORANTHENE COMPOUND, MATERIAL FOR ORGANIC ELECTROLUMINESCENT ELEMENT USING THIS COMPOUND, ORGANIC ELECTROLUMINESCENT ELEMENT USING THIS MATERIAL, AND ELECTRONIC DEVICE

(71) Applicant: IDEMITSU KOSAN CO., LTD., Tokyo (JP)

(72) Inventors: Masahiro Kawamura, Chiba (JP); Kazuki Nishimura, Sodegaura (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 0 days.

(21) Appl. No.: 15/205,686

(22) Filed: Jul. 8, 2016

(65) Prior Publication Data
US 2016/0322587 A1    Nov. 3, 2016

Related U.S. Application Data

(63) Continuation of application No. 14/697,189, filed on Apr. 27, 2015, now Pat. No. 9,419,226, which is a (Continued)

(30) Foreign Application Priority Data
Mar. 27, 2013  (JP) .................. 2013-067597

(51) Int. Cl.
*H01L 51/50* (2006.01)
*H01L 51/00* (2006.01)
(Continued)

(52) U.S. Cl.
CPC ........ *H01L 51/0072* (2013.01); *C07C 209/56* (2013.01); *C07D 209/86* (2013.01);
(Continued)

(58) Field of Classification Search
None
See application file for complete search history.

(56) References Cited

U.S. PATENT DOCUMENTS

| 4,507,126 A | 3/1985 | Balliello |
| 2004/0247933 A1 | 12/2004 | Thoms |

(Continued)

FOREIGN PATENT DOCUMENTS

| DE | 196 13 251 A1 | 11/1984 |
| JP | 59-207968 | 11/1984 |

(Continued)

OTHER PUBLICATIONS

Feng-Ling Liu, "Heterofullerene Molecules $C_{58}X$ (X=S,Se,Te): A DFT Study", Chemical Physics Letters, 471 (2009), pp. 116-121.

(Continued)

*Primary Examiner* — Gregory Clark
(74) *Attorney, Agent, or Firm* — Oblon, McClelland, Maier & Neustadt, L.L.P.

(57) ABSTRACT

A fused fluoranthene compound which includes an indeno [3,2-b]fluoranthene skeleton having a hetero atom is a novel compound, which is useful as a material for organic electroluminescence devices for use in an organic electroluminescence device and an electronic equipment.

24 Claims, 1 Drawing Sheet

Related U.S. Application Data continuation of application No. PCT/JP2014/059009, filed on Mar. 27, 2014.

(51) Int. Cl.

| | | |
|---|---|---|
| C07D 403/10 | (2006.01) | |
| C07D 403/14 | (2006.01) | |
| C07D 405/04 | (2006.01) | |
| C07D 409/04 | (2006.01) | |
| C07D 307/77 | (2006.01) | |
| C09K 11/06 | (2006.01) | |
| C07D 333/50 | (2006.01) | |
| C07D 401/04 | (2006.01) | |
| C07D 403/04 | (2006.01) | |
| C07D 405/10 | (2006.01) | |
| C07D 409/10 | (2006.01) | |
| C07D 471/04 | (2006.01) | |
| C07D 487/04 | (2006.01) | |
| C07D 491/048 | (2006.01) | |
| C07D 495/04 | (2006.01) | |
| C07C 209/56 | (2006.01) | |
| C07D 209/86 | (2006.01) | |
| C07D 209/88 | (2006.01) | |
| C07D 209/94 | (2006.01) | |
| C07D 405/14 | (2006.01) | |
| C07D 409/14 | (2006.01) | |
| C09K 11/02 | (2006.01) | |

(52) U.S. Cl.
CPC ......... *C07D 209/88* (2013.01); *C07D 209/94* (2013.01); *C07D 307/77* (2013.01); *C07D 333/50* (2013.01); *C07D 401/04* (2013.01); *C07D 403/04* (2013.01); *C07D 403/10* (2013.01); *C07D 403/14* (2013.01); *C07D 405/04* (2013.01); *C07D 405/10* (2013.01); *C07D 405/14* (2013.01); *C07D 409/04* (2013.01); *C07D 409/10* (2013.01); *C07D 409/14* (2013.01); *C07D 471/04* (2013.01); *C07D 487/04* (2013.01); *C07D 491/048* (2013.01); *C07D 495/04* (2013.01); *C09K 11/025* (2013.01); *C09K 11/06* (2013.01); *H01L 51/0052* (2013.01); *H01L 51/0054* (2013.01); *H01L 51/0061* (2013.01); *H01L 51/0067* (2013.01); *H01L 51/0071* (2013.01); *H01L 51/0073* (2013.01); *H01L 51/0085* (2013.01); *C09K 2211/1007* (2013.01); *C09K 2211/1011* (2013.01); *C09K 2211/1014* (2013.01); *C09K 2211/1029* (2013.01); *C09K 2211/1044* (2013.01); *C09K 2211/1059* (2013.01); *C09K 2211/1088* (2013.01); *C09K 2211/1092* (2013.01); *C09K 2211/185* (2013.01); *H01L 51/0074* (2013.01); *H01L 51/5012* (2013.01); *H01L 51/5016* (2013.01); *H01L 51/5024* (2013.01); *H01L 51/5056* (2013.01); *H01L 51/5072* (2013.01); *H01L 51/5088* (2013.01); *H01L 51/5092* (2013.01); *H01L 51/5096* (2013.01); *H01L 2251/5376* (2013.01)

(56) References Cited

U.S. PATENT DOCUMENTS

| | | |
|---|---|---|
| 2010/0273816 A1 | 10/2010 | Bernotas et al. |
| 2014/0353640 A1 | 12/2014 | Haketa et al. |
| 2015/0034938 A1 | 2/2015 | Kang et al. |

FOREIGN PATENT DOCUMENTS

| | | |
|---|---|---|
| JP | 2003-45662 | 2/2003 |
| JP | 2014-183315 | 9/2014 |
| JP | 2010-166070 | 11/2014 |
| KR | 10-2012-0020816 A | 3/2012 |
| KR | 10-2012-0081539 | 7/2012 |
| KR | 10-2014-0094408 | 7/2014 |
| WO | 2011/037429 | 3/2011 |
| WO | 2011/081429 | 7/2011 |
| WO | 2012/089294 A1 | 7/2012 |
| WO | 2013/012296 A1 | 1/2013 |
| WO | 2013/187894 A1 | 12/2013 |
| WO | 2014/014310 A1 | 1/2014 |
| WO | 2014/054596 A1 | 4/2014 |
| WO | 2014/157708 A1 | 10/2014 |
| WO | 2014/178434 A1 | 11/2014 |

OTHER PUBLICATIONS

Zhurnal Organicheskoi Khimii, 1977, 13(11), pp. 2411-2416, compound VIII.
Jayasree Pattanayak, et al., "Substitution Patterns in Mono-BN-Fullerenes: $C_n$(n=20, 24, 28, 32, 36, and 40)", J. Phys. Chem. A 2004, 108, pp. 7681-7685.
Donglai Wang, et al, "Theoretical study on $C_{100}$ fullerenes and $C_{96}X_4$(X=N, P, B, Si)", Physica B, 2011, 406, pp. 1233-1237.
STN File Registry[Online], 1997, RN:185840-20-4.
STN File Registry[Online], 1985, RN:97337-97-8.
STN File Registry[Online], 1984. RN:85536-98-7.
STN File Registry[Online], 1984, RN:61902-46-3.
International Search Report issued Jun. 3. 2014 in PCT/JP2014/059009 filed Mar. 27, 2014.
Office Action issued Jan. 5, 2016, in Chinese Patent Application No. 201480003000.5 filed Mar. 27, 2014.

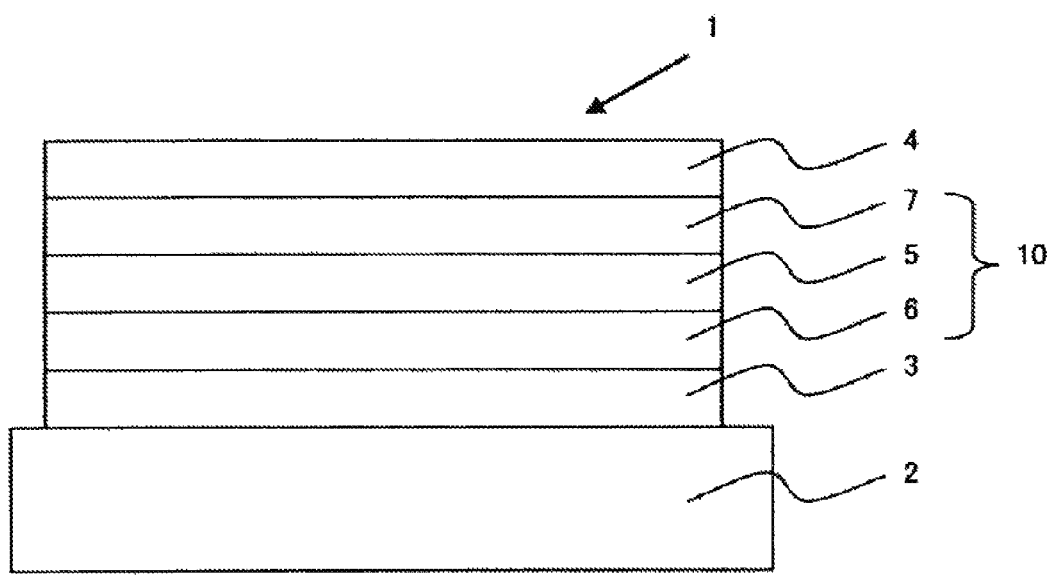

CONDENSED FLUORANTHENE COMPOUND, MATERIAL FOR ORGANIC ELECTROLUMINESCENT ELEMENT USING THIS COMPOUND, ORGANIC ELECTROLUMINESCENT ELEMENT USING THIS MATERIAL, AND ELECTRONIC DEVICE

TECHNICAL FIELD

The present invention relates to fused fluoranthene compounds, materials for organic electroluminescence devices comprising the compound, organic electroluminescence devices comprising the compound, and electronic equipment.

BACKGROUND ART

An organic electroluminescence (EL) device is generally composed of an anode, a cathode, and one or more organic thin film layers sandwiched between the anode and the cathode. When a voltage is applied between the electrodes, electrons are injected from the cathode and holes are injected from the anode into a light emitting region. The injected electrons recombine with the injected holes in the light emitting region to form excited states. When the excited states return to the ground state, the energy is released as light.

Many researches have been made on the applications of organic EL device to display, etc. because of its possibility of a wide selection of emission colors by using various emitting materials in a light emitting layer. Particularly, the research on the materials which emit three primary red, green, blue colors has been made most actively, and the intensive research has been made to improve their properties.

As a material for organic EL devices, Patent Documents 1 to 3 disclose compounds in which an indole structure is fused to a specific position of a fluoranthene ring.

However, there is a demand for new materials which can further improve the performance of organic EL devices.

PRIOR ART

Patent Documents

Patent Document 1: WO 2011/081429
Patent Document 2: KR 10-2012-0020816A
Patent Document 3: WO 2011/037429

SUMMARY OF THE INVENTION

Problems to be Solved by the Invention

The present invention has been made to solve the above problems and an object of the invention is to provide a new material useful for organic EL devices.

Means for Solving the Problem

Patent Documents 1 to 3 disclose only specific compounds which include an indro[f]fluoranthene skeleton or an indro[2,3-b]fluoranthene skeleton.

As a result of extensive research, the inventors have found that a fused fluoranthene compound which is different from the above compounds in the fused position and orientation is useful as a material for organic EL devices.

In an aspect of the present invention, the following (1) to (4) are provided:
(1) a fused fluoranthene compound represented by formula (a):

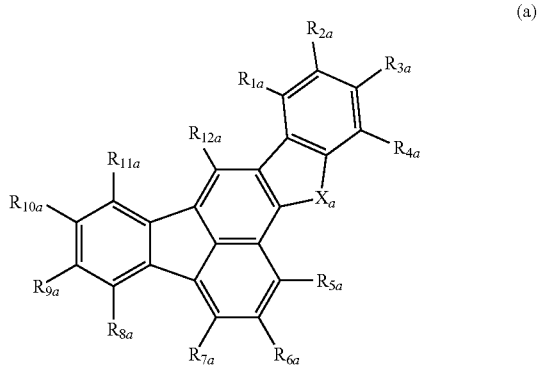

wherein:
$X_a$ represents $Si(R_{13a})(R_{14a})$, $N(R_{15a})$, a sulfur atom, or an oxygen atom; and
each of $R_{1a}$ to $R_{15a}$ independently represents a hydrogen atom or a substituent, and adjacent groups of $R_{1a}$ to $R_{15a}$ may be bonded to each other to form a saturated or unsaturated ring structure;
(2) a material for organic electroluminescence devices comprising the fused fluoranthene compound of item 1;
(3) an organic electroluminescence device which comprises a cathode, an anode and an organic thin film layer comprising one or more layers between the cathode and the anode, wherein the organic thin film layer comprises a light emitting layer and at least one layer of the organic thin film layer comprises the fused fluoranthene compound of item 1 or 2; and
(4) an electronic equipment comprising the organic electroluminescence device of item 3.

Effects of the Invention

The present invention provides a novel material useful for organic EL devices and an organic EL device comprising the material.

BRIEF DESCRIPTION OF THE DRAWINGS

FIG. 1 is a schematic illustration showing an example of the structure of an organic electroluminescence device (hereinafter also referred to as "organic EL device") according to an embodiment of the invention.

MODE FOR CARRYING OUT THE INVENTION

The term of "XX to YY carbon atoms" referred to by "a substituted or unsubstituted group ZZ having XX to YY carbon atoms" used herein is the number of carbon atoms of the unsubstituted group ZZ and does not include any carbon atom in the substituent of the substituted group ZZ. "YY" is larger than "XX" and each of "XX" and "YY" represents an integer of 1 or more.

The term of "XX to YY atoms" referred to by "a substituted or unsubstituted group ZZ having XX to YY atoms" used herein is the number of atoms of the unsubstituted group ZZ and does not include any atom in the substituent of the substituted group ZZ. "YY" is larger than "XX" and each of "XX" and "YY" represents an integer of 1 or more.

The term of "unsubstituted group ZZ" referred to by "a substituted or unsubstituted group ZZ" used herein means the group ZZ wherein no hydrogen atom is substituted with a substituent.

The definition of "hydrogen atom" used herein includes isotopes different in the neutron numbers, i.e., light hydrogen (protium), heavy hydrogen (deuterium), and tritium.

The number of "ring carbon atoms" referred to herein means the number of the carbon atoms included in the atoms which are members forming the ring itself of a compound in which a series of atoms is bonded to form the ring (for example, a monocyclic compound, a fused ring compound, a cross-linked compound, a carbocyclic compound, and a heterocyclic compound). If the ring has a substituent, the carbon atom in the substituent is not included in the ring carbon atom. The same applies to the number of "ring carbon atom" described below, unless otherwise noted. For example, a benzene ring has 6 ring carbon atoms, a naphthalene ring has 10 ring carbon atoms, a pyridinyl group has 5 ring carbon atoms, and a furanyl group has 4 ring carbon atoms. If a benzene ring or a naphthalene ring has, for example, an alkyl substituent, the carbon atom in the alkyl substituent is not counted as the ring carbon atom of the benzene or naphthalene ring. In case of a fluorene ring to which a fluorene substituent is bonded (inclusive of a spirofluorene ring), the carbon atom in the fluorene substituent is not counted as the ring carbon atom of the fluorene ring.

The number of "ring atom" referred to herein means the number of the atoms which are members forming the ring itself (for example, a monocyclic ring, a fused ring, and a ring assembly) of a compound in which a series of atoms is bonded to form the ring (for example, a monocyclic compound, a fused ring compound, a cross-linked compound, a carbocyclic compound, and a heterocyclic compound). The atom not forming the ring (for example, hydrogen atom(s) for saturating the valence of the atom which forms the ring) and the atom in a substituent, if the ring is substituted, are not counted as the ring atom. The same applies to the number of "ring atoms" described below, unless otherwise noted. For example, a pyridine ring has 6 ring atoms, a quinazoline ring has 10 ring atoms, and a furan ring has 5 ring atoms. The hydrogen atom on the ring carbon atom of a pyridine ring or a quinazoline ring and the atom in a substituent are not counted as the ring atom. In case of a fluorene ring to which a fluorene substituent is bonded (inclusive of a spirofluorene ring), the atom in the fluorene substituent is not counted as the ring atom of the fluorene ring.

The optional substituent referred to by "substituted or unsubstituted" used herein is preferably selected from the group consisting of an alkyl group having 1 to 50, preferably 1 to 18, more preferably 1 to 8 carbon atoms; a cycloalkyl group having 3 to 50, preferably 3 to 10, more preferably 3 to 8, still more preferably 5 or 6 ring carbon atoms; an aryl group having 6 to 50, preferably 6 to 25, more preferably 6 to 18 ring carbon atoms; an aralkyl group having 7 to 51, preferably 7 to 30, more preferably 7 to 20 carbon atoms which includes an aryl group having 6 to 50, preferably 6 to 25, more preferably 6 to 18 ring carbon atoms; an amino group; a mono- or di-substituted amino group, wherein the substituent is selected from an alkyl group having 1 to 50, preferably 1 to 18, more preferably 1 to 8 carbon atoms and an aryl group having 6 to 50, preferably 6 to 25, more preferably 6 to 18 ring carbon atoms; an alkoxy group having an alkyl group having 1 to 50, preferably 1 to 18, more preferably 1 to 8 carbon atoms; an aryloxy group having an aryl group having 6 to 50, preferably 6 to 25, more preferably 6 to 18 ring carbon atoms; a mono-, di- or tri-substituted silyl group, wherein the substituent is selected from an alkyl group having 1 to 50, preferably 1 to 18, more preferably 1 to 8 carbon atoms and an aryl group having 6 to 50, preferably 6 to 25, more preferably 6 to 18 ring carbon atoms; a heteroaryl group having 5 to 50, preferably 5 to 24, more preferably 5 to 13 ring atoms; a haloalkyl group having 1 to 50, preferably 1 to 18, more preferably 1 to 8 carbon atoms; a halogen atom selected from a fluorine atom, a chlorine atom, a bromine atom and an iodine atom; a cyano group; a nitro group; a substituted sulfonyl group, wherein the substituent is selected from an alkyl group having 1 to 50, preferably 1 to 18, more preferably 1 to 8 carbon atoms and an aryl group having 6 to 50, preferably 6 to 25, more preferably 6 to 18 ring carbon atoms; a di-substituted phosphoryl group, wherein the substituent is selected from an alkyl group having 1 to 50, preferably 1 to 18, more preferably 1 to 8 carbon atoms and an aryl group having 6 to 50, preferably 6 to 25, more preferably 6 to 18 ring carbon atoms; an alkylsulfonyloxy group; an arylsulfonyloxy group; an alkylcarbonyloxy group; an arylcarbonyloxy group; a boron-containing group; a zinc-containing group; a tin-containing group; a silicon-containing group; a magnesium-containing group; a lithium-containing group; a hydroxyl group; an alkyl-substituted or aryl-substituted carbonyl group; a carboxyl group; a vinyl group; a (meth) acryloyl group; an epoxy group; and an oxetanyl group.

The optional substituent may be further substituted with an optional substituent mentioned above. The optional substituents may be bonded to each other to form a ring.

Fused Fluoranthene Compound

The fused fluoranthene compound of the invention is represented by formula (a):

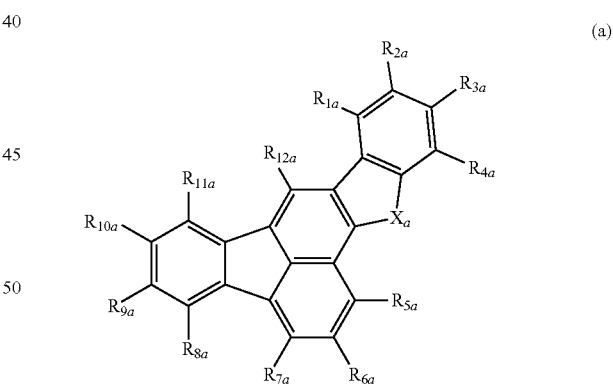

(a)

wherein:

$X_a$ represents $Si(R_{13a})(R_{14a})$, $N(R_{15a})$, a sulfur atom, or an oxygen atom; and each of $R_{1a}$ to $R_{15a}$ independently represents a hydrogen atom or a substituent, and adjacent groups of $R_{1a}$ to $R_{15a}$ may be bonded to each other to form a saturated or unsaturated ring structure.

A polymer comprising a repeating unit represented by formula (b) and a polymer comprising a repeating unit represented by formula (d) are also preferred as the fused fluoranthene compound.

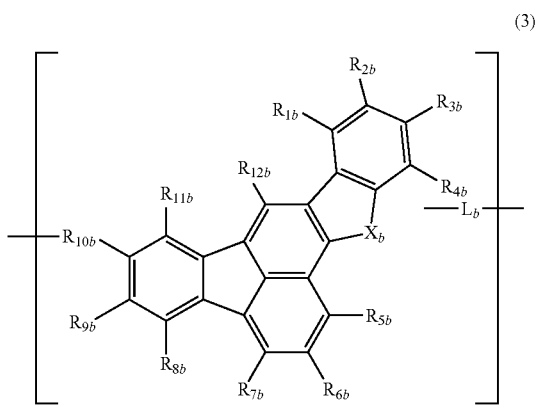

(3)

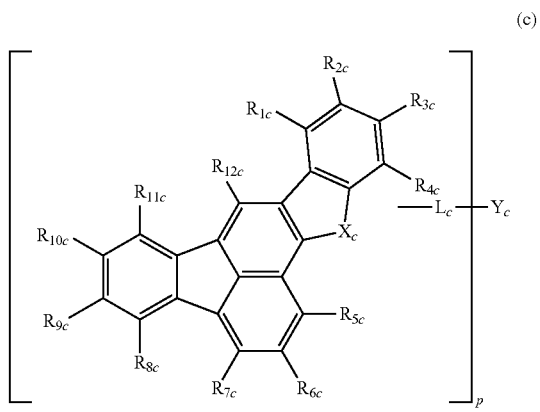

(c)

wherein:

$X_b$ represents $Si(R_{13b})(R_{14b})$, $N(R_{15b})$, a sulfur atom, or an oxygen atom; each of $R_{1b}$ to $R_{15b}$ independently represents, a hydrogen atom, a substituent, or a bond to $L_b$, and adjacent groups of $R_{1b}$ to $R_{15b}$ may be bonded to each other to form a saturated or unsaturated ring structure; and $L_b$ represents a single bond or a divalent linking group.

Examples of the divalent linking group represented by $L_b$ include a substituted or unsubstituted aromatic heterocyclic group (arylene group) having 6 to 60 ring carbon atoms, a substituted or unsubstituted heterocyclic group (heteroarylene group) having 3 to 60 ring atoms, and a substituted or unsubstituted alkylene group having 1 to 50 carbon atoms.

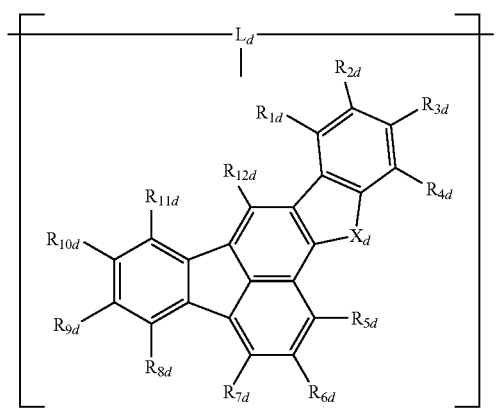

(d)

wherein:

$X_d$ represents $Si(R_{13d})(R_{14d})$, $N(R_{15d})$, a sulfur atom, or an oxygen atom;

each of $R_{1d}$ to $R_{15d}$ independently represents a hydrogen atom, a substituent, or a bond to $L_d$, and adjacent groups of $R_{1d}$ to $R_{15d}$ may be bonded to each other to form a saturated or unsaturated ring structure; and $L_d$ represents a trivalent organic group.

The fused fluoranthene compound is more preferably represented by formula (c):

wherein:

$X_c$ represents $Si(R_{13c})(R_{14c})$, $N(R_{15c})$, a sulfur atom, or an oxygen atom;

each of $R_{1c}$ to $R_{15c}$ independently represents a hydrogen atom, a substituent, or a bond to $L_c$, and adjacent groups of $R_{1c}$ to $R_{15c}$ may be bonded to each other to form a saturated or unsaturated ring structure;

$Y_c$ represents a substituted or unsubstituted p-valent aromatic hydrocarbon group having 6 to 60 ring carbon atoms or a substituted or unsubstituted p-valent heterocyclic group having 3 to 60 ring atoms;

$L_c$ represents a single bond, a substituted or unsubstituted divalent aromatic hydrocarbon group (arylene group) having 6 to 60 ring carbon atoms, a substituted or unsubstituted divalent heterocyclic group (heteroarylene group) having 3 to 60 ring atoms, or a substituted or unsubstituted alkylene group having 1 to 50 carbon atoms; and p represents an integer of 1 to 6, preferably 1 to 3, and more preferably 1 or 2.

The substituent represented by $R_{1a}$ to $R_{15a}$ of formula (a), the substituent represented by $R_{1b}$ to $R_{15b}$ of formula (b), the substituent represented by $R_{1c}$ to $R_{15c}$ of formula (c), and the substituent represented by $R_{1d}$ to $R_{15d}$ of formula (d) are independently selected preferably from the group (A), more preferably from the group (B), still more preferably from the group (C), and particularly preferably from the group (D).

The group (A) consists of a substituted or unsubstituted alkyl group having 1 to 50 carbon atoms, a substitute or unsubstituted cycloalkyl group having 3 to 50 ring carbon atoms, a substituted or unsubstituted aryl group having 6 to 50 ring carbon atoms, a substituted or unsubstituted aralkyl group having 7 to 51 carbon atoms, an amino group, a mono- or disubstituted amino group having a substituent selected from a substitute or unsubstituted alkyl group having 1 to 50 carbon atoms and a substituted or unsubstituted aryl group having 6 to 50 ring carbon atoms, a substituted or unsubstituted alkoxy group having 1 to 50 carbon atoms, a substituted or unsubstituted aryloxy group having 6 to 50 ring carbon atoms, a mono-, di-, or trisubstituted silyl group having a substituent selected from a substituted or unsubstituted alkyl group having 1 to 50 carbon atoms and a substituted or unsubstituted aryl group having 6 to 50 ring carbon atoms, a substituted or unsubstituted heteroaryl group having 5 to 50 ring atoms, a substituted or unsubstituted haloalkyl group having 1 to 50 carbon atoms, a halogen atom, a cyano group, a nitro group, a sulfonyl group having a substituent selected from a substituted or unsubstituted alkyl group having 1 to 50 carbon atoms and a substituted or unsubstituted aryl group having 6 to 50 ring carbon atoms, a disubstituted phosphoryl group having a substituent selected from a substituted or unsubstituted alkyl group having 1 to 50 carbon atoms and a substituted or unsubstituted aryl group having 6 to 50 ring carbon atoms, an alkylsulfonyloxy group, an arylsulfonyloxy group, an alkylcarbonyloxy group, an arylcarbonyloxy group, a boron-containing group, a zinc-containing group, a tin-containing group, a silicon-containing group, a magnesium-containing group, a lithium-containing group, a hydroxyl group, a alkyl- or aryl substituted carbonyl group, a carboxyl group, a vinyl group, a (meth)acryloyl group, an epoxy group, and an oxetanyl group.

The group (B) consists of a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, a substituted or unsubstituted aralkyl group having 7 to 51 carbon atoms, an amino group, a mono- or disubstituted amino group having a substituent selected from a substituted or unsubstituted alkyl group having 1 to 50 carbon atoms and a substituted or unsubstituted aryl group having 6 to 50 ring carbon atoms, a substituted or unsubstituted alkoxy group having 1 to 50 carbon atoms, a substituted or unsubstituted aryloxy group having 6 to 50 ring carbon atoms, a mono-, di-, or trisubstituted silyl group having a substituent selected from a substituted or unsubstituted alkyl group having 1 to 50 carbon atoms and a substituted or unsubstituted aryl group having 6 to 50 ring carbon atoms, a substituted or unsubstituted heteroaryl group having 5 to 50 ring atoms, a substituted or unsubstituted haloalkyl group having 1 to 50 carbon atoms, a halogen atom, a cyano group, a nitro group, a sulfonyl group having a substituent selected from a substituted or unsubstituted alkyl group having 1 to 50 carbon atoms and a substituted or unsubstituted aryl group having 6 to 50 ring carbon atoms, a substituted or unsubstituted alkyl group having 1 to 50 carbon atoms, and a substituted or unsubstituted aryl group having 6 to 50 ring carbon atoms.

The group (C) consists of a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, a substituted or unsubstituted aralkyl group having 7 to 51 carbon atoms, an amino group, a mono- or disubstituted amino group having a substituent selected from a substituted or unsubstituted alkyl group having 1 to 50 carbon atoms and a substituted or unsubstituted aryl group having 6 to 50 ring carbon atoms, a substituted or unsubstituted alkoxy group having 1 to 50 carbon atoms, a substituted or unsubstituted aryloxy group having 6 to 50 ring carbon atoms, a mono-, di-, or trisubstituted silyl group having a substituent selected from a substituted or unsubstituted alkyl group having 1 to 50 carbon atoms and a substituted or unsubstituted aryl group having 6 to 50 ring carbon atoms, a substituted or unsubstituted heteroaryl group having 5 to 50 ring atoms, a substituted or unsubstituted haloalkyl group having 1 to 50 carbon atoms, a halogen atom, a cyano group, and a nitro group.

The group (D) consists of a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, a mono- or disubstituted amino group having a substituent selected from a substituted or unsubstituted alkyl group having 1 to 50 carbon atoms and a substituted or unsubstituted aryl group having 6 to 50 ring carbon atoms, a substituted or unsubstituted heteroaryl group having 5 to 50 ring atoms, a halogen atom, and a cyano group.

Examples of the alkyl group having 1 to 50, preferably 1 to 18, more preferably 1 to 8 carbon atoms include a methyl group, an ethyl group, a n-propyl group, an isopropyl group, a n-butyl group, an isobutyl group, a s-butyl group, a t-butyl group, a pentyl group (inclusive of isomeric groups), a hexyl group (inclusive of isomeric groups), a heptyl group (inclusive of isomeric groups), an octyl group (inclusive of isomeric groups), a nonyl group (inclusive of isomeric groups), a decyl group (inclusive of isomeric groups), an undecyl group (inclusive of isomeric groups), a dodecyl group (inclusive of isomeric groups), a tridecyl group, a tetradecyl group, an octadecyl group, a tetracosanyl group, and a tetracontenyl group. Preferred examples include a methyl group, an ethyl group, a n-propyl group, an isopropyl group, a n-butyl group, an isobutyl group, a s-butyl group, a t-butyl group, a pentyl group (inclusive of isomeric groups), a hexyl group (inclusive of isomeric groups), a heptyl group (inclusive of isomeric groups), an octyl group (inclusive of isomeric groups), a nonyl group (inclusive of isomeric groups), a decyl group (inclusive of isomeric groups), an undecyl group (inclusive of isomeric groups), a dodecyl group (inclusive of isomeric groups), a tridecyl group, a tetradecyl group, and an octadecyl group. More preferred examples include a methyl group, an ethyl group, a n-propyl group, an isopropyl group, a n-butyl group, an isobutyl group, a s-butyl group, a t-butyl group, a pentyl group (inclusive of isomeric groups), a hexyl group (inclusive of isomeric groups), a heptyl group (inclusive of isomeric groups), and an octyl group (inclusive of isomeric groups).

Examples of the cycloalkyl group having 3 to 50, preferably 3 to 10, more preferably 3 to 8, still more preferably 5 or 6 ring carbon atoms include a cyclopropyl group, a cyclobutyl group, a cyclopentyl group, a cyclohexyl group, a cycloheptyl group, a cyclooctyl group, and an adamantyl group, with a cyclopentyl group and a cyclohexyl group being preferred.

Examples of the aryl group having 6 to 50, preferably 6 to 25, more preferably 6 to 18 ring carbon atoms include a phenyl group, a naphthyl group, a naphthylphenyl group, a biphenylyl group, a terphenyl group, an acenaphthylenyl group, an anthryl group, a benzanthryl group, an aceanthryl group, a phenanthryl group, a benzophenanthryl group, a phenalenyl group, a fluorenyl group, a 9,9'-spirobifluorenyl group, a benzofluorenyl group, a dibenzofluorenyl group, a picenyl group, a pentaphenyl group, a pentacenyl group, a pyrenyl group, a chrysenyl group, a benzochrysenyl group, a s-indacenyl group, an as-indacenyl group, a fluoranthenyl group, a benzofluoranthenyl group, a tetracenyl group, a triphenylenyl group, a benzotriphenylenyl group, a perylenyl group, a coronyl group, and a dibenzanthryl group. Preferred are a phenyl group, a naphthyl group, a biphenylyl group, a terphenylyl group, a phenanthryl group, benzophenanthryl group, a fluorenyl group, a benzofluorenyl group, a chrysenyl group, a benzochrysenyl group, a fluoranthenyl group, and a triphenylenyl group.

Examples of the arylene group having 6 to 50, preferably 6 to 25, more preferably 6 to 18 ring carbon atoms include the groups obtained by removing one hydrogen atom from the aryl groups mentioned above. Preferred are a phenylene group, a naphthylene group, a biphenylene group, a terphenylene group, a phenanthrylene group, and a fluorenylene group.

The heteroaryl group having 5 to 50, preferably 5 to 24, more preferably 5 to 13 ring atoms include at least one, preferably 1 to 5, more preferably 1 to 3, and still more preferably 1 or 2 hetero atoms, for example, a nitrogen atom, a sulfur atom, an oxygen atom, and a phosphorus atom. Examples thereof include a pyrrolyl group, a furyl group, a thienyl group, a pyridyl group, a pyridazinyl group, a pyrimidinyl group, a pyrazinyl group, a triazinyl group, an imidazolyl group, an oxazolyl group, a thiazolyl group, a pyrazolyl group, an isooxazolyl group, an isothiazolyl group, an oxadiazolyl group, a thiadiazolyl group, a triazolyl group, a tetrazolyl group, an indolyl group, an isoindolyl group, a benzofuranyl group, an isobenzofuranyl group, a benzothiophenyl group, an isobenzothiophenyl group, an indolizinyl group, a quinolizinyl group, a quinolyl group, an isoquinolyl group, a cinnolyl group, a phthalazinyl group, a quinazolinyl group, a quinoxalinyl group, a benzimidazolyl group, a benzoxazolyl group, a benzothiazolyl group, an indazolyl group, a benzisoxazolyl group, a benzisothiazolyl group, a dibenzofuranyl group, a dibenzothiophenyl group, a carbazolyl group, a phenanthridinyl group, an acridinyl group, a phenanthrolinyl group, a phenazinyl group, a phenothiazinyl group, a phenoxazinyl group, an azatriphenylenyl group, a diazatriphenylenyl group, a xanthenyl group, an azacarbazolyl group, an azadibenzofuranyl group, an azadibenzothiophenyl group, a benzofuranobenzothiophenyl group, a benzothienobenzothiophenyl group, a dibenzofuranonaphthyl group, a dibenzothienonaphthyl group, and a dinaphthothienothiophenyl group. Preferred are a pyridyl group, a pyrimidinyl group, a pyrazinyl group, a triazinyl group, an indolyl group, a benzofuranyl group, a benzothiophenyl group, a quinolyl group, an isoquinolyl group, a quinazolinyl group, a quinoxalinyl group, a benzimidazolyl group, a dibenzofuranyl group, a dibenzothiophenyl group, a carbazolyl group, a phenanthridinyl group, a phenanthrolinyl group, and a diazatriphenylenyl group.

In addition, examples of the heteroaryl group having 5 to 50 ring atoms preferably include mono-valent groups derived from the following compounds by removing one hydrogen atom:

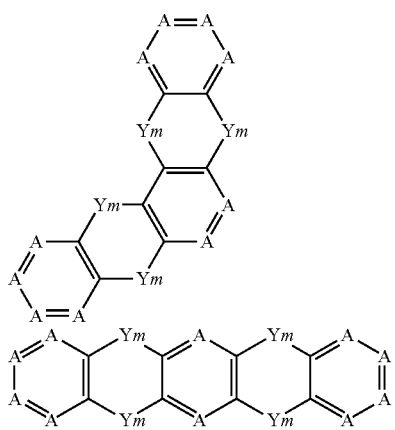
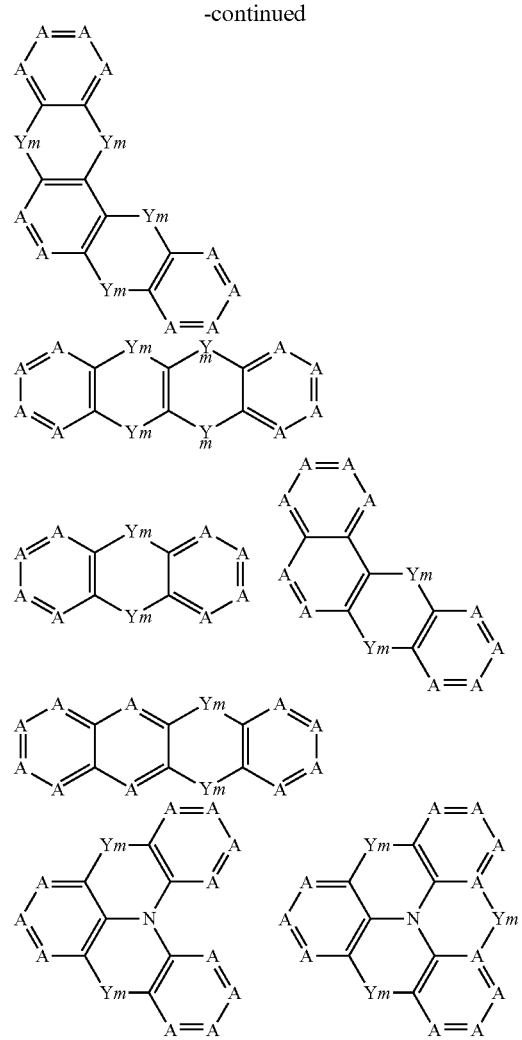

wherein:
each A independently represents $CR^{100}$ or a nitrogen atom;
each $R^{100}$ independently represents a hydrogen atom or a substituent;
each Y independently represents $C(R^{101})(R^{102})$, an oxygen atom, a sulfur atom, or $N(R^{103})$;
each of $R^{101}$, $R^{102}$ and $R^{103}$ independently represents a hydrogen atom or a substituent;
m independently represents 0 or 1; and
$Y_0$ represents a single bond.

The substituent referred to above is selected from those mentioned above.

Examples of the aralkyl group having 7 to 51 total carbon atoms include those having an aryl group having 6 to 50, preferably 6 to 25, more preferably 6 to 18 ring carbon atoms which is selected from the aryl groups mentioned above.

Examples of the mono- or di-substituted amino group include those having a substituent selected from an alkyl group having 1 to 50, preferably 1 to 18, more preferably 1 to 8 carbon atoms and an aryl group having 6 to 50, preferably 6 to 25, more preferably 6 to 18 ring carbon atoms, wherein the alkyl and aryl substituents are selected from the alkyl groups and the aryl groups mentioned above.

Examples of the alkoxy group include those having an alkyl group having 1 to 50, preferably 1 to 18, more preferably 1 to 8 carbon atoms which is selected from the alkyl groups mentioned above.

Examples of the aryloxy group include those having an aryl group having 6 to 50, preferably 6 to 25, more preferably 6 to 18 ring carbon atoms which is selected from the aryl groups mentioned above.

Examples of the mono-, di- or tri-substituted silyl group include those having a substituent selected from an alkyl group having 1 to 50, preferably 1 to 18, more preferably 1 to 8 carbon atoms and an aryl group having 6 to 50, preferably 6 to 25, more preferably 6 to 18 ring carbon atoms, wherein the alkyl and aryl substituents are selected form the alkyl groups and the aryl groups mentioned above.

Examples of the haloalkyl group having 1 to 50, preferably 1 to 18, more preferably 1 to 8 carbon atoms included those obtained by replacing one or more hydrogen atoms of the alkyl groups mentioned above with a halogen atom, such as a fluorine atom, a chlorine atom, a bromine atom and an iodine atom.

Examples of the substituted sulfonyl group include those having a substituent selected from an alkyl group having 1 to 50, preferably 1 to 18, more preferably 1 to 8 carbon atoms and an aryl group having 6 to 50, preferably 6 to 25, more preferably 6 to 18 ring carbon atoms, wherein the alkyl and aryl substituents are selected from the alkyl groups and the aryl groups mentioned above.

Examples of the di-substituted phosphoryl group include those having a substituent selected from an alkyl group having 1 to 50, preferably 1 to 18, more preferably 1 to 8 carbon atoms and an aryl group having 6 to 50, preferably 6 to 25, more preferably 6 to 18 ring carbon atoms, wherein the alkyl and aryl substituents are selected from the alkyl groups and the aryl groups mentioned above.

Each of the partially saturated or saturated ring to be formed when the adjacent groups of $R_{1a}$ to $R_{15a}$ of formula (a) are bonded to each other, the partially saturated or saturated ring to be formed when the adjacent groups of $R_{1b}$ to $R_{15b}$ of formula (b) are bonded to each other, the partially saturated or saturated ring to be formed when the adjacent groups of $R_{1c}$ to $R_{15c}$ of formula (c) are bonded to each other, and the partially saturated or saturated ring to be formed when the adjacent groups of $R_{1d}$ to $R_{15d}$ of formula (b) are bonded to each other is preferably a aliphatic hydrocarbon ring having 3 to 50, preferably 3 to 6, and more preferably 5 or 6 ring carbon atoms.

Each of the unsaturated ring to be formed when the adjacent groups of $R_{1a}$ to $R_{15a}$ of formula (a) are bonded to each other, the unsaturated ring to be formed when the adjacent groups of $R_{1b}$ to $R_{15b}$ of formula (b) are bonded to each other, the unsaturated ring to be formed when the adjacent groups of $R_{1c}$ to $R_{15c}$ of formula (c) are bonded to each other, and the unsaturated ring to be formed when the adjacent groups of $R_{1d}$ to $R_{15d}$ of formula (d) are bonded to each other is preferably an aromatic hydrocarbon ring having 6 to 50, preferably 6 to 24, and more preferably 6 to 18 ring carbon atoms or an aromatic heterocyclic ring having 5 to 50, preferably 5 to 24, and more preferably 5 to 13 ring atoms.

Examples of the aliphatic hydrocarbon ring having 5 to 50 ring carbon atoms include a cyclopropane ring, a cyclobutane ring, a cyclopentane ring, a cyclohexane ring, a cycloheptane ring, a cyclooctane ring, and an adamantane ring, with a cyclopentane ring and a cyclohexane ring being preferred.

Examples of the aromatic hydrocarbon ring having 6 to 50 ring carbon atoms include a benzene ring, a naphthalene ring, an anthracene ring, a benzanthracene ring, a phenanthrene ring, a benzophenanthrene ring, a fluorene ring, a benzofluorene ring, a dibenzofluorene ring, a picene ring, a tetracene ring, a pentacene ring, a pyrene ring, a chrysene ring, a benzochrysene ring, a s-indacene ring, an as-indacene ring, a fluoranthene ring, a benzofluoranthene ring, a triphenylene ring, a benzotriphenylene ring, a perylene ring, a coronene ring, and a dibenzanthracene ring. Preferred are a benzene ring, a naphthalene ring, an anthracene ring, a benzanthracene ring, a phenanthrene ring, a benzophenanthrene ring, a fluorene ring, a benzofluorene ring, a dibenzofluorene ring, a pyrene ring, a chrysene ring, a benzochrysene ring, a fluoranthene ring, a benzofluoranthene ring, a triphenylene ring, and a benzotriphenylene ring. More preferred are a benzene ring, a naphthalene ring, a phenanthrene ring, a benzophenanthrene ring, a fluorene ring, a benzofluorene ring, a dibenzofluorene ring, a chrysene ring, a benzochrysene ring, a fluoranthene ring, and a triphenylene ring.

Examples of the aromatic heterocyclic ring having 5 to 50 ring atoms include a pyrrole ring, a pyrazole ring, an isoindole ring, a benzofuran ring, a benzothiophene ring, an isobenzofuran ring, a dibenzothiophene ring, an isoquinoline ring, a cinnoline ring, a quinoxaline ring, a quinazoline ring, a phenanthridine ring, a phenanthroline ring, a pyridine ring, a pyrazine ring, a pyrimidine ring, a pyridazine ring, a triazine ring, an imidazopyridine ring, an indole ring, an indazole ring, a benzimidazole ring, a quinoline ring, an acridine ring, a pyrrolidine ring, a dioxane ring, a piperidine ring, a morpholine ring, a piperazine ring, a carbazole ring, a furan ring, a thiophene ring, an oxazole ring, an oxadiazole ring, a benzoxazole ring, a thiazole ring, a thiadiazole ring, a benzothiazole ring, a triazole ring, an imidazole ring, a benzimidazole ring, a pyran ring, a dibenzofuran ring, a benzonaphthofuran ring, a purine ring, and an acridine ring. Preferred are a benzofuran ring, a benzothiophene ring, a benzofuran ring, a benzothiophene ring, a dibenzothiophene ring, an isoquinoline ring, a phenanthridine ring, a phenanthroline ring, a pyridine ring, a pyrazine ring, a pyrimidine ring, a triazine ring, a quinazoline ring, an imidazopyridine ring, an indole ring, a carbazole ring, a benzimidazole ring, a quinoline ring, a benzimidazole ring, a dibenzofuran ring, and a benzonaphthofuran ring. More preferred are a pyridine ring, a pyrimidine ring, a triazine ring, a quinazoline ring, a carbazole ring, a dibenzothiophene ring, and a dibenzofuran ring.

In formula (a), one or more adjacent pairs selected from $R_{8a}$ and $R_{9a}$, $R_{9a}$ and $R_{10a}$, $R_{1a}$ and $R_{2a}$, $R_{2a}$ and $R_{3a}$, and $R_{3a}$ and $R_{4a}$ are preferably bonded to each other to form a saturated ring. The pair of $R_{8a}$ and $R_{9a}$ or $R_{9a}$ and $R_{10a}$ preferably forms an aromatic hydrocarbon ring, more preferably a benzene ring. The pair of $R_{1a}$ and $R_{2a}$, $R_{2a}$ and $R_{3a}$, or $R_{3a}$ and $R_{4a}$ preferably forms an aromatic hydrocarbon ring, more preferably a benzene ring, and may form, together with the benzene ring to which each of these pairs is bonded, a dibenzofuran ring, a dibenzothiophene ring, a 9,9-dimethylfluorene ring, or a carbazole ring.

By replacing the subscript a with the subscript b, c or d, the same applies to the adjacent pairs of $R_{8b}$ and $R_{9b}$, $R_{9b}$ and $R_{10b}$, $R_{1b}$ and $R_{2b}$, $R_{2b}$ and $R_{3b}$, and $R_{3b}$ and $R_{4b}$ of formula (b) when forming a ring, the adjacent pairs of $R_{8c}$ and $R_{9c}$, $R_{9c}$ and $R_{10c}$, $R_{1c}$ and $R_{2c}$, $R_{2c}$ and $R_{3c}$, $R_{3c}$ and $R_{4c}$ of formula (c) when forming a ring, and the adjacent pairs of $R_{8d}$ and $R_{9d}$, $R_{9d}$ and $R_{10d}$, $R_{1d}$ and $R_{2d}$, $R_{2d}$ and $R_{3d}$, $R_{3d}$ and $R_{4d}$ of formula (d) when forming a ring.

A fused fluoranthene compound of the invention, wherein at least one of $R_{1a}$ to $R_{15a}$ of formula (a) or at least one of $R_{1c}$ to $R_{15c}$ of formula (c) is a substituted or unsubstituted aromatic hydrocarbon group (aryl group) having 6 to 60 ring carbon atoms or a substituted or unsubstituted heterocyclic group (heteroaryl group) having 3 to 60 ring atoms is preferred.

A fused fluoranthene compound of the invention, wherein $X_a$ of formula (a) represents $N(R_{15a})$ or $X_c$ of formula (c) represents $N(R_{15c})$ is preferred, with a fused fluoranthene compound wherein $R_{15a}$ or $R_{15c}$ represents a substituted or unsubstituted aromatic hydrocarbon group (aryl group) having 6 to 60 ring carbon atoms being more preferred and a fused fluoranthene compound wherein $R_{15a}$ or $R_{15c}$ represents a substituted or unsubstituted fused aromatic hydrocarbon group having 10 to 60 ring carbon atoms and having two or more fused rings being still more preferred.

A fused fluoranthene compound of the invention, wherein $R_{15a}$ of formula (a), $R_{15b}$ of formula (b), $R_{15c}$ of formula (c), or $R_{15d}$ of formula (d) represents a heterocyclic group (heteroaryl group) having 3 to 60 ring atoms is also preferred.

Examples of the substituted or unsubstituted divalent aromatic hydrocarbon group (arylene group) having 6 to 60 ring carbon atoms represented by $L_b$ of formula (b), and examples of the substituted or unsubstituted divalent aromatic hydrocarbon group (arylene group) having 6 to 60 ring carbon atoms represented by $L_c$ of formula (c) include those obtained by removing one hydrogen atom from the aryl groups mentioned above.

Examples of the substituted or unsubstituted divalent heterocyclic group (heteroarylene group) having 3 to 60 ring atoms represented by $L_b$ of formula (b), and examples of the substituted or unsubstituted divalent heterocyclic group (heteroarylene group) having 3 to 60 ring atoms represented by $L_c$ of formula (c) include those obtained by removing one hydrogen atom from the heteroaryl groups mentioned above.

Examples of the substituted or unsubstituted alkylene group having 1 to 50 carbon atoms represented by $L_b$ of formula (b), and examples of the substituted or unsubstituted alkylene group having 1 to 50 carbon atoms represented by $L_c$ of formula (c) include those obtained by removing one hydrogen atom from the alkyl groups mentioned above.

Examples of the trivalent organic group represented by $L_d$ of formula (d) include those obtained by removing one hydrogen atom from the divalent groups mentioned above with respect to $L_b$ and $L_c$.

The fused fluoranthene compound of the invention preferably includes a ring-containing group as the group. A fused fluoranthene compound, wherein the group represented by $R_{1a}$ to $R_{15a}$ of formula (a), the group represented by $R_{1b}$ to $R_{15b}$ of formula (b), the group represented by $R_{1c}$ to $R_{15c}$ of formula (c), or the group represented by $R_{1d}$ to $R_{15d}$ of formula (d) is the ring-containing group is more preferred. A fused fluoranthene compound, wherein $X_a$ of formula (a) represents $N(R_{15a})$ and $R_{15a}$ represents the ring-containing group, $X_b$ of formula (b) represents $N(R_{15b})$ and $R_{15b}$ represents the ring-containing group, $X_c$ of formula (c) represents $N(R_{15c})$ and $R_{15c}$ represents the ring-containing group, or $X_d$ of formula (d) represents the $N(R_{15d})$ and $R_{15d}$ represents the ring-containing group is still more preferred.

A material for organic EL devices which comprises a fused fluoranthene compound including the ring-containing group exhibits an effect of, for example, improving the uniformity and denseness of an organic thin film which comprises the material.

Examples of the ring-containing group include groups which includes a group selected from a substituted or unsubstituted cycloalkyl group having 5 to 50, preferably 3 to 6, and more preferably 5 or 6 ring carbon atoms, a substituted or unsubstituted aryl group having 6 to 50, preferably 6 to 24, and more preferably 6 to 18 ring carbon atoms, an aralkyl group having 7 to 51 carbon atoms in total, which includes a substituted or unsubstituted aryl group having 6 to 50, preferably 6 to 24, and more preferably 6 to 18 ring carbon atoms, a mono- or diarylamino group having a substituted or unsubstituted aryl group having 6 to 50, preferably 6 to 24, and more preferably 6 to 18 ring carbon atoms, an aryloxy group having a substituted or unsubstituted aryl group having 6 to 50, preferably 6 to 24, and more preferably 6 to 18 ring carbon atoms, a mono-, di-, or triarylsilyl group having a substituted or unsubstituted aryl group having 6 to 50, preferably 6 to 24, and more preferably 6 to 18 ring carbon atoms, a substituted or unsubstituted heteroaryl group having 5 to 50, preferably 5 to 24, and more preferably 5 to 13 ring atoms, a sulfonyl group substituted with a substituted or unsubstituted aryl group having 6 to 50, preferably 6 to 24, and more preferably 6 to 18 ring carbon atoms, and a phosphonyl group substituted with a substituted or unsubstituted aryl group having 6 to 50, preferably 6 to 24, and more preferably 6 to 18 ring carbon atoms. Preferred are those including a substituted or unsubstituted aryl group having 6 to 50 ring carbon atoms, a substituted or unsubstituted heteroaryl group having 5 to 50 ring atoms, or a mono- or diarylamino group having a substituted or unsubstituted aryl group having 6 to 50 ring carbon atoms. The details of the above groups are the same as mentioned above.

The ring-containing group may be a group having the ring-containing group thereon. Examples of such a group are those as mentioned above.

The ring-containing group is preferably represented by formula (1), more preferably represented by formula (1a), and particularly preferably represented by formula (1b).

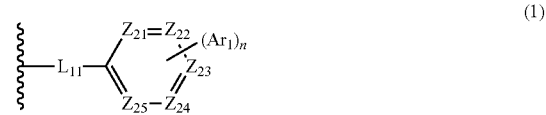

(1)

In formula (1):
each of $Z_{21}$ to $Z_{25}$ independently represents $C(R_1)$ or a nitrogen atom;
each $R_1$ independently represents a hydrogen atom, a substituent, or a bond to $Ar_1$;
each $Ar_1$ independently represents a hydrogen atom or a substituent, preferably a substituted or unsubstituted aryl group having 6 to 50 ring carbon atoms or a substituted or unsubstituted heteroaryl group having 5 to 50 ring atoms;
$L_{11}$ represents a single bond, a substituted or unsubstituted divalent aromatic hydrocarbon group (arylene group) having 6 to 60 ring carbon atoms or a substituted or unsubstituted divalent heterocyclic group (heteroarylene group) having 3 to 60 ring atoms; and
m represents an integer of 0 to 5.

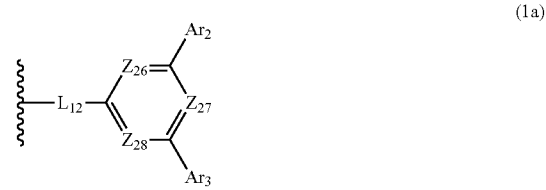

(1a)

In formula (1a):

each of $Z_{26}$ to $Z_{28}$ independently represents $C(R_1)$ or a nitrogen atom;

each $R_1$ independently represents a hydrogen atom or a substituent;

each of $Ar_2$ and $Ar_3$ independently represents a hydrogen atom or a substituent, preferably a substituted or unsubstituted aryl group having 6 to 50 ring carbon atoms or a substituted or unsubstituted heteroaryl group having 5 to 50 ring atoms; and $L_{12}$ represents a single bond, a substituted or unsubstituted divalent aromatic hydrocarbon group (arylene group) having 6 to 60 ring carbon atoms or a substituted or unsubstituted divalent heterocyclic group (heteroarylene group) having 3 to 60 ring atoms.

At least one of $Z_{26}$ to $Z_{28}$ is preferably a nitrogen atom.

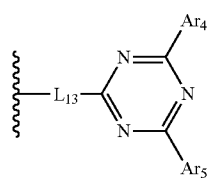

(1b)

In formula (1b):

each of $Ar_4$ and $Ar_5$ independently represents a hydrogen atom or a substituent, preferably a substituted or unsubstituted aryl group having 6 to 50 ring carbon atoms or a substituted or unsubstituted heteroaryl group having 5 to 50 ring atoms, and more preferably a substituted or unsubstituted aryl group having 6 to 18 ring carbon atoms or a substituted or unsubstituted heteroaryl group having 5 to 13 ring atoms; and $L_{13}$ represents a single bond, a substituted or unsubstituted divalent aromatic hydrocarbon group (arylene group) having 6 to 60 ring carbon atoms or a substituted or unsubstituted divalent heterocyclic group (heteroarylene group) having 3 to 60 ring atoms.

The group represented by each of $Ar_1$ of formula (1), $Ar_2$ and $Ar_3$ of formula (1a), and $Ar_4$ and $Ar_5$ of formula (1b) is selected preferably from the group (A), more preferably from the group (B), and still more preferably from the group (C) each mentioned above.

Examples of $L_{11}$ of formula (1), $L_{12}$ of formula (2), and $L_{13}$ of formula (3) include those mentioned above with respect to $L_b$ of formula (b) and $L_c$ of formula (c).

The group represented by formula (2) is also preferred as the ring-containing group:

$-L_{14}-Ar_{15}$ (2)

wherein:

$Ar_{15}$ represents a substituted or unsubstituted aryl group having 6 to 50 ring carbon atoms or a substituted or unsubstituted heteroaryl group having 5 to 50 ring atoms; and $L_{14}$ represents a single bond, a substituted or unsubstituted divalent aromatic hydrocarbon group (arylene group) having 6 to 60 ring carbon atoms or a substituted or unsubstituted divalent heterocyclic group (heteroarylene group) having 3 to 60 ring atoms.

Examples of the aryl group having 6 to 50 ring carbon atoms for $Ar_{15}$ of formula (2) include those mentioned above with respect to the aryl group having 6 to 50 ring carbon atoms for formulae (a) to (d). Examples of the heteroaryl group having 5 to 50 ring atoms for $Ar_{15}$ of formula (2) include those mentioned above with respect to the heteroaryl group having 5 to 50 ring atoms of formulae (a) to (d).

Examples of $L_{14}$ of formula (1) include those mentioned above with respect to $L_b$ of formula (b) and $L_c$ of formula (c).

$Ar_{15}$ of formula (2) is particularly preferably a phenyl group, a naphthyl group, a biphenylyl group, a terphenylyl group, a phenanthryl group, a benzophenanthryl group, a fluorenyl group, a benzofluorenyl group, a chrysenyl group, a benzochrysenyl group, a fluoranthenyl group, a triphenylenyl group, a pyridyl group, a pyrimidinyl group, a pyrazinyl group, a triazinyl group, an indolyl group, a benzofuranyl group, a benzothiophenyl group, a quinolyl group, an isoquinolyl group, a quinazolinyl group, a quinoxalinyl group, a benzimidazolyl group, a dibenzofuranyl group, a dibenzothiophenyl group, a carbazolyl group, a phenanthridinyl group, a phenanthrolinyl group, or a diazatriphenylenyl group.

$L_{14}$ of formula (2) is particularly preferably a single bond, a phenylene group, a naphthylene group, a biphenylene group, a terphenylene group, a phenanthrylene group, or a fluorenylene group.

Material for Organic Electroluminescence Devices

The material for organic electroluminescence devices of the invention comprises the fused fluoranthene compound mentioned above. The content of the fused fluoranthene compound in the material for organic electroluminescence devices is, but not particularly limited, 1% by mass or more, preferably 10% by mass or more, more preferably 50% by mass or more, still more preferably 80% by mass or more, and particularly preferably 90% by mass or more.

The material for organic EL devices of the invention is useful as a material for producing an organic EL device and may be used, for example, in a light emitting layer of a fluorescent emitting unit as a host material or a dopant material and in a light emitting layer of a phosphorescent emitting unit as a host material. In addition, in either a fluorescent emitting unit or a phosphorescent emitting unit, the material for organic EL devices of the invention is also useful as a material for an anode-side organic thin film layer which is formed between an anode and a light emitting layer and a material for a cathode-side organic thin film layer which is formed between a cathode and a light emitting layer, i.e., also useful as a material for a hole transporting layer, a hole injecting layer, an electron transporting layer, an electron injecting layer, a hole blocking layer, and an electron blocking layer.

The "emission unit" referred to herein is the smallest unit for emitting light by the recombination of injected holes and injected electrons, which comprises one or more organic layers wherein at least one layer is a light emitting layer.

Examples of the fused fluoranthene compound represented by formulae (a) to (d) are shown below, although not limited thereto.

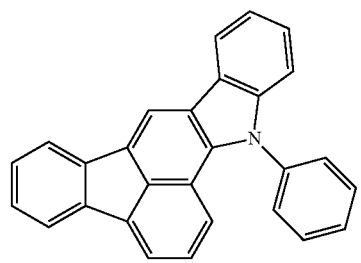

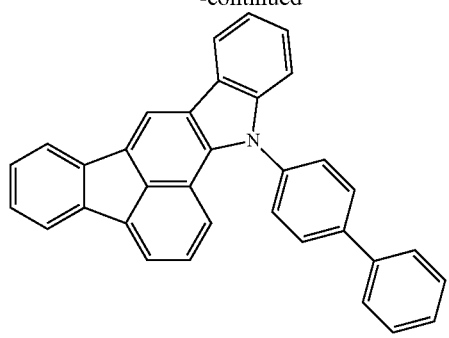
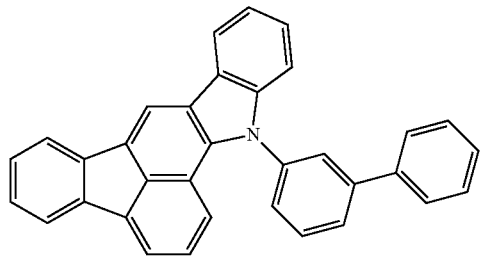
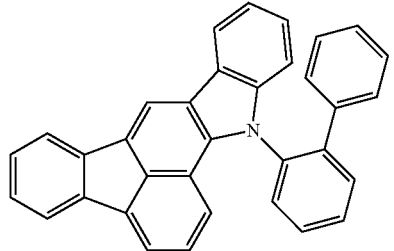
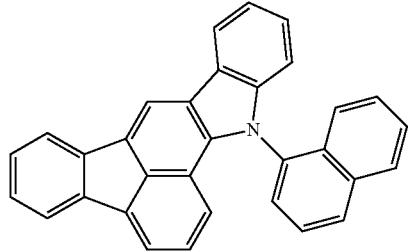
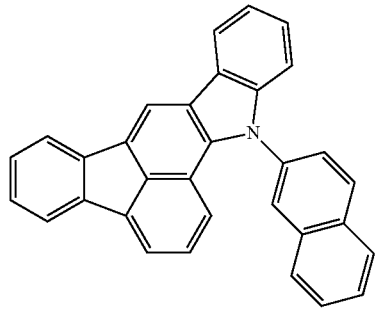
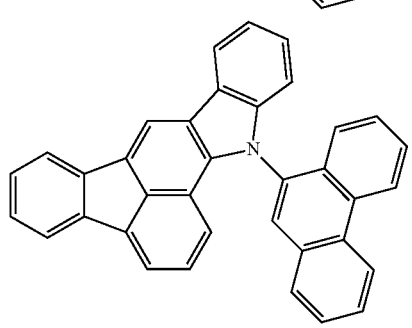
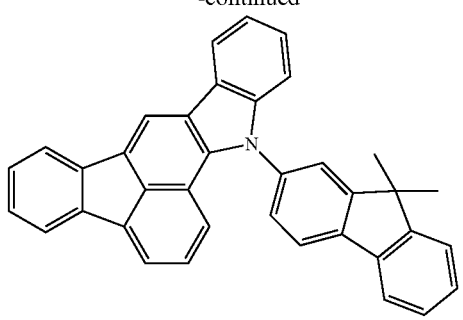
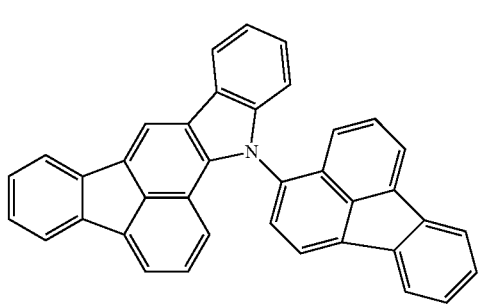
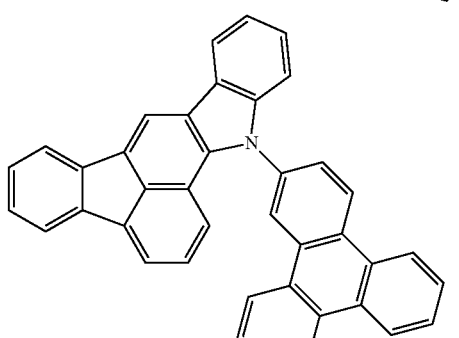
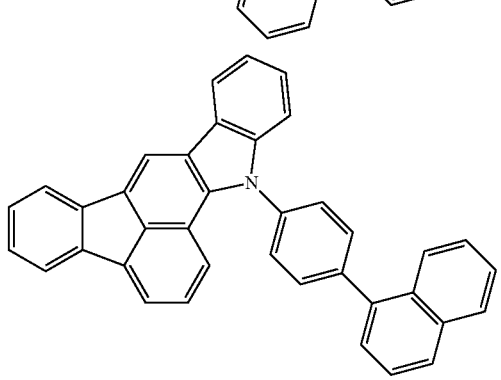
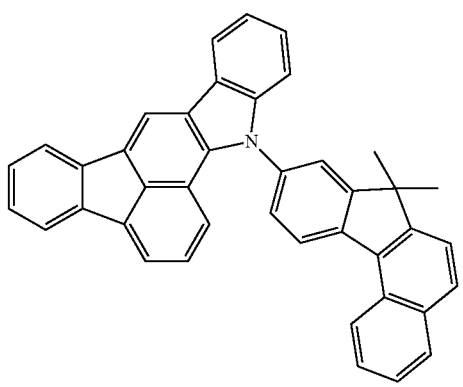

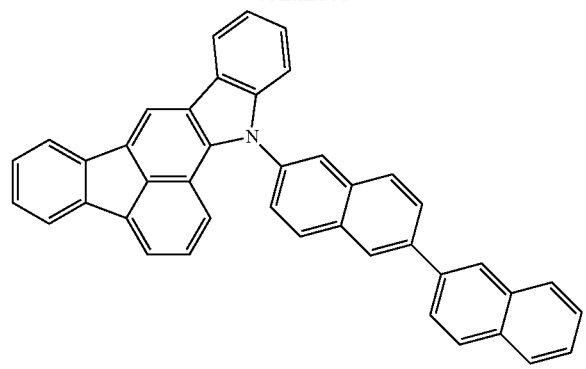
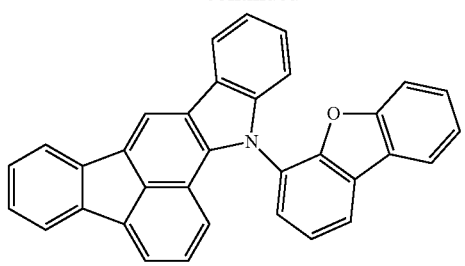
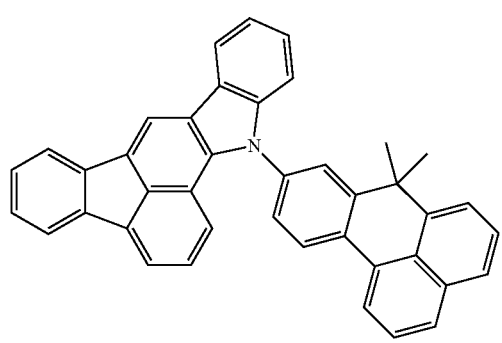
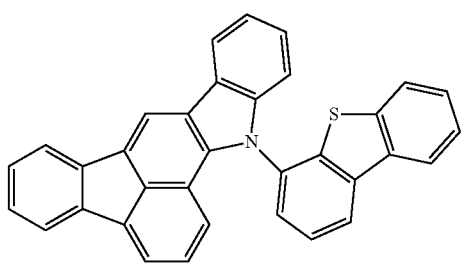
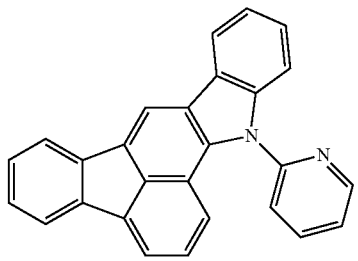
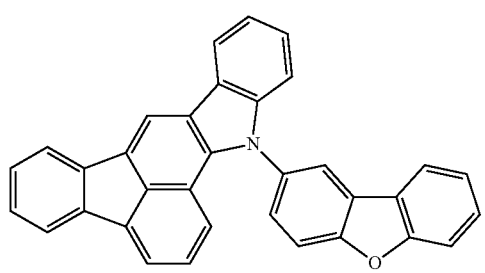
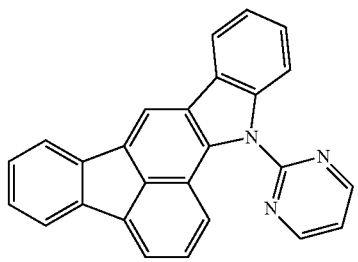
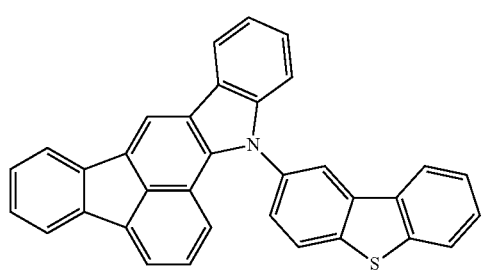
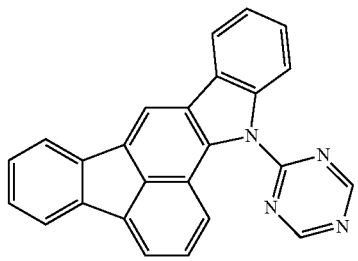
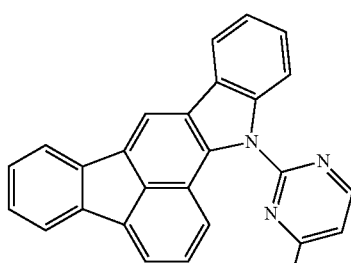

-continued
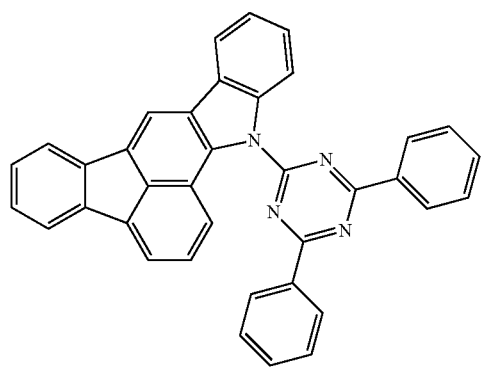
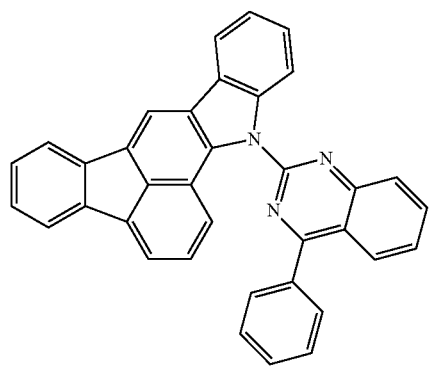
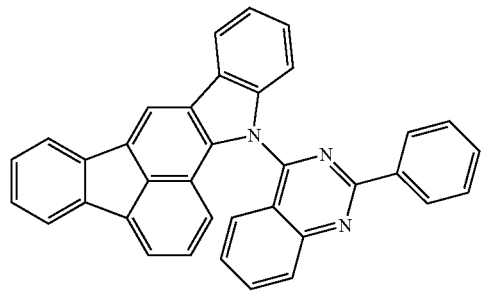
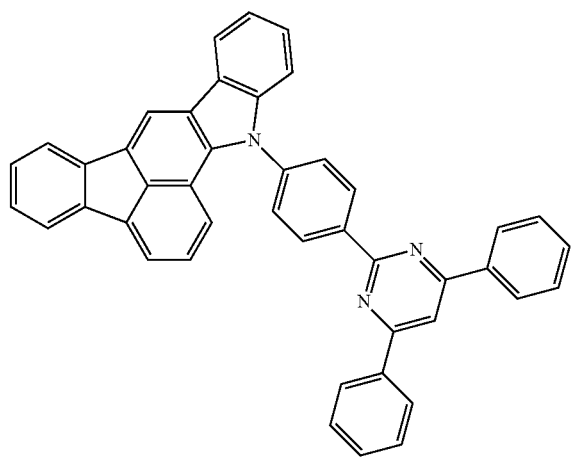
-continued
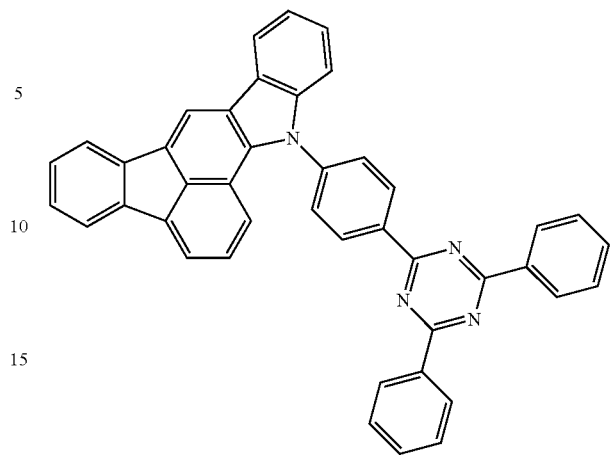
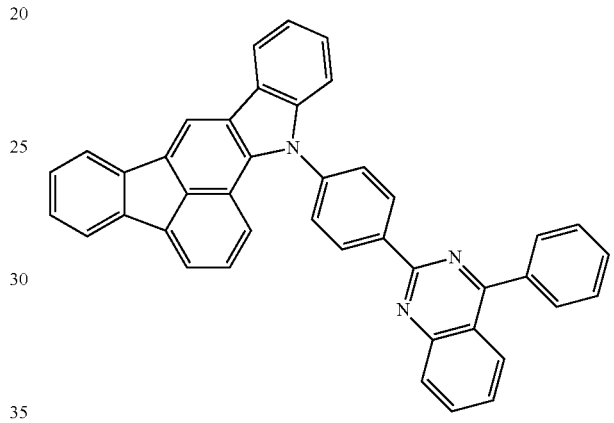
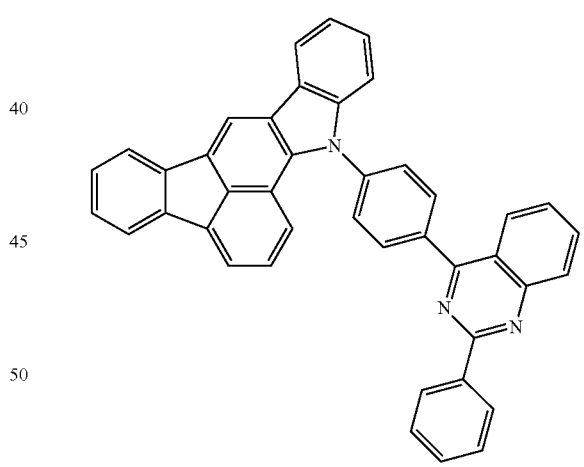
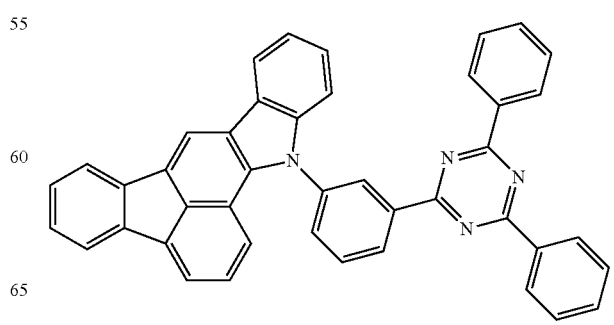

23
-continued
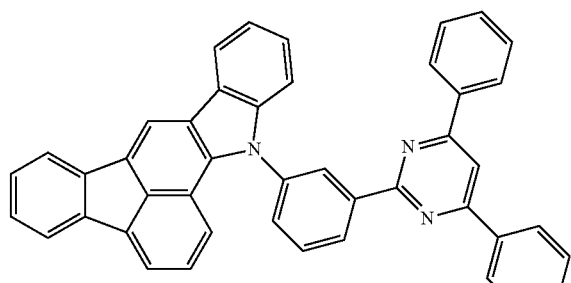
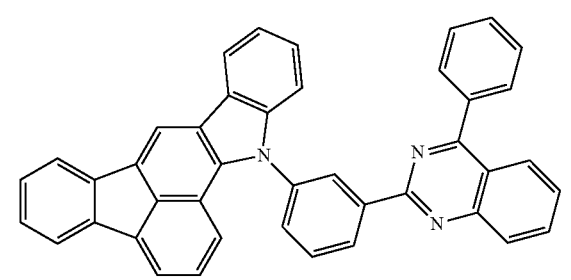
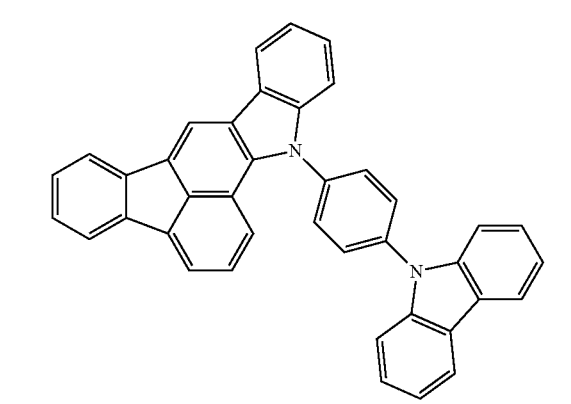
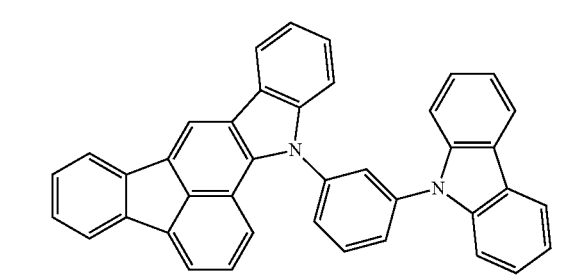
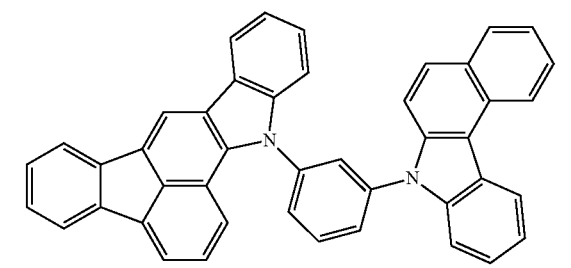
24
-continued
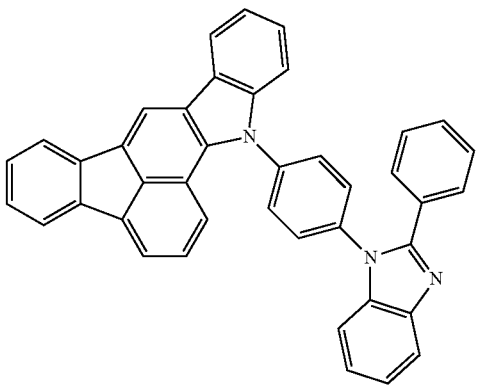
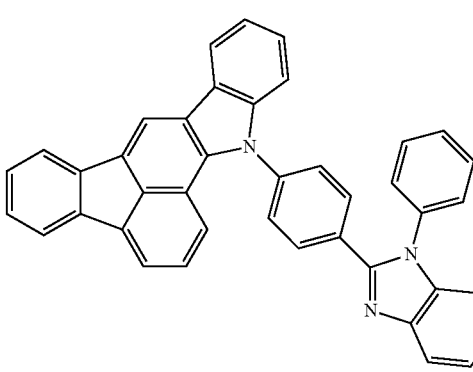
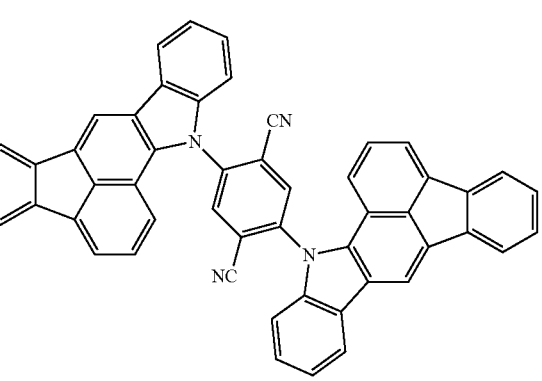
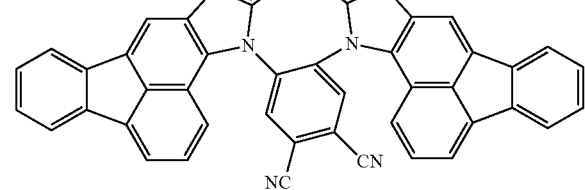

25
-continued
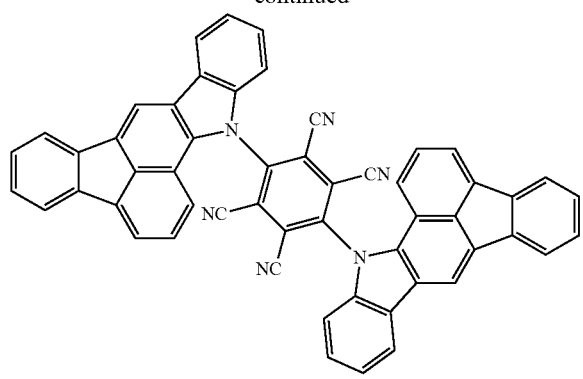
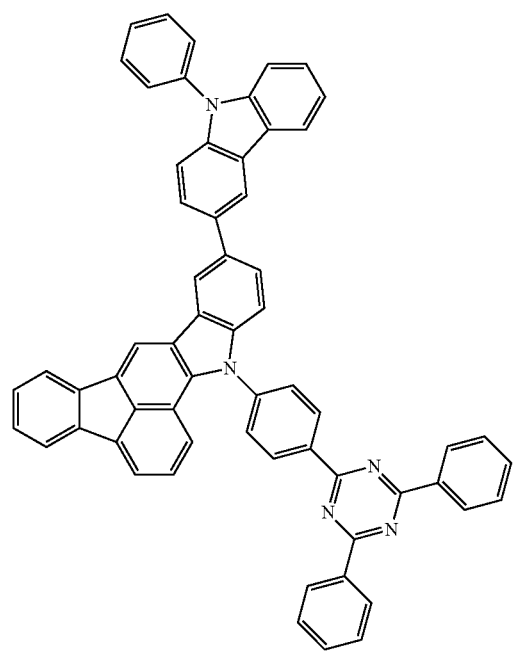
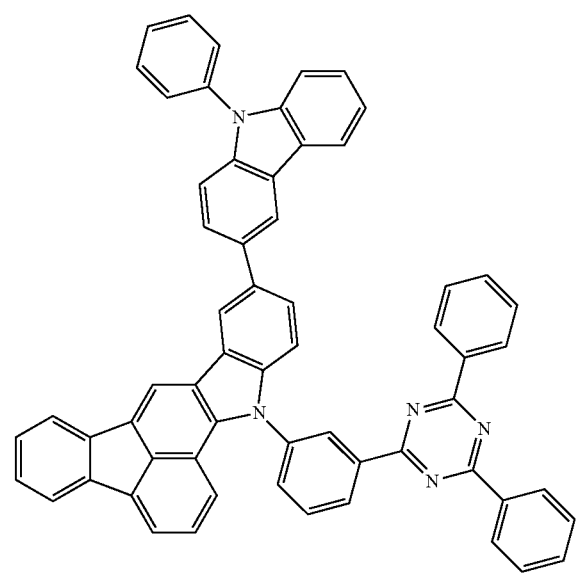
26
-continued
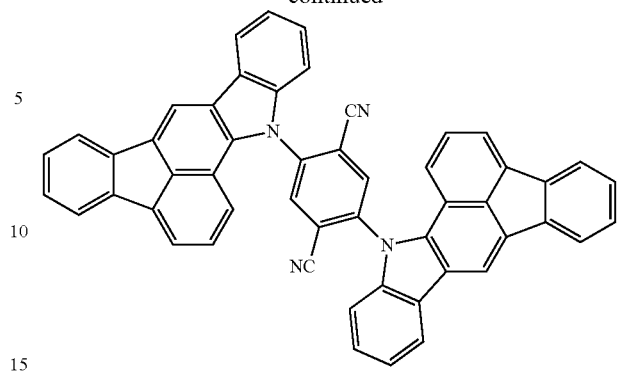
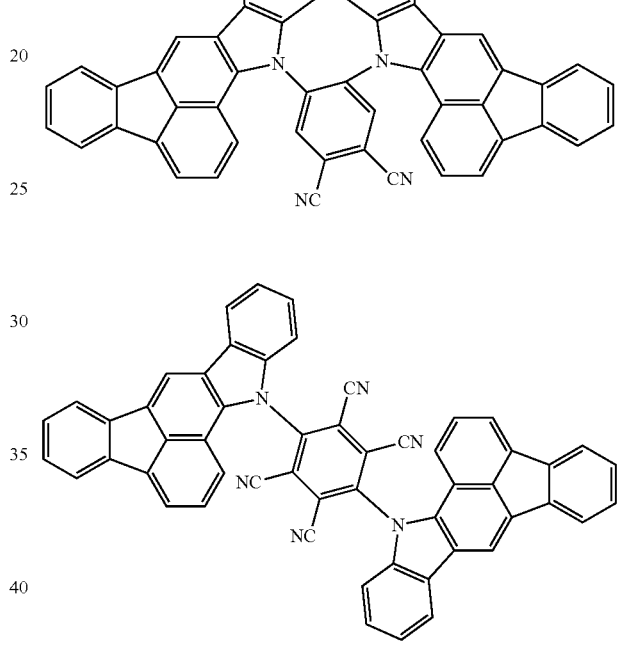
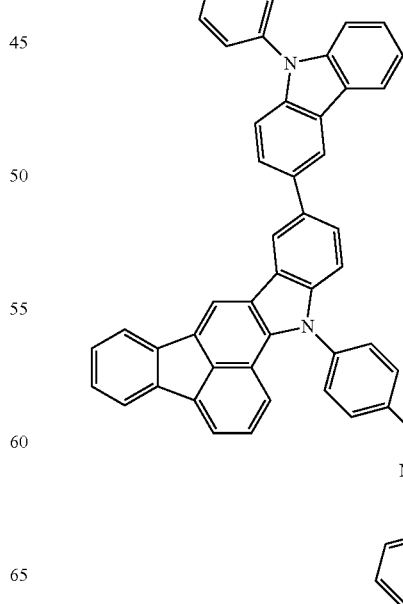

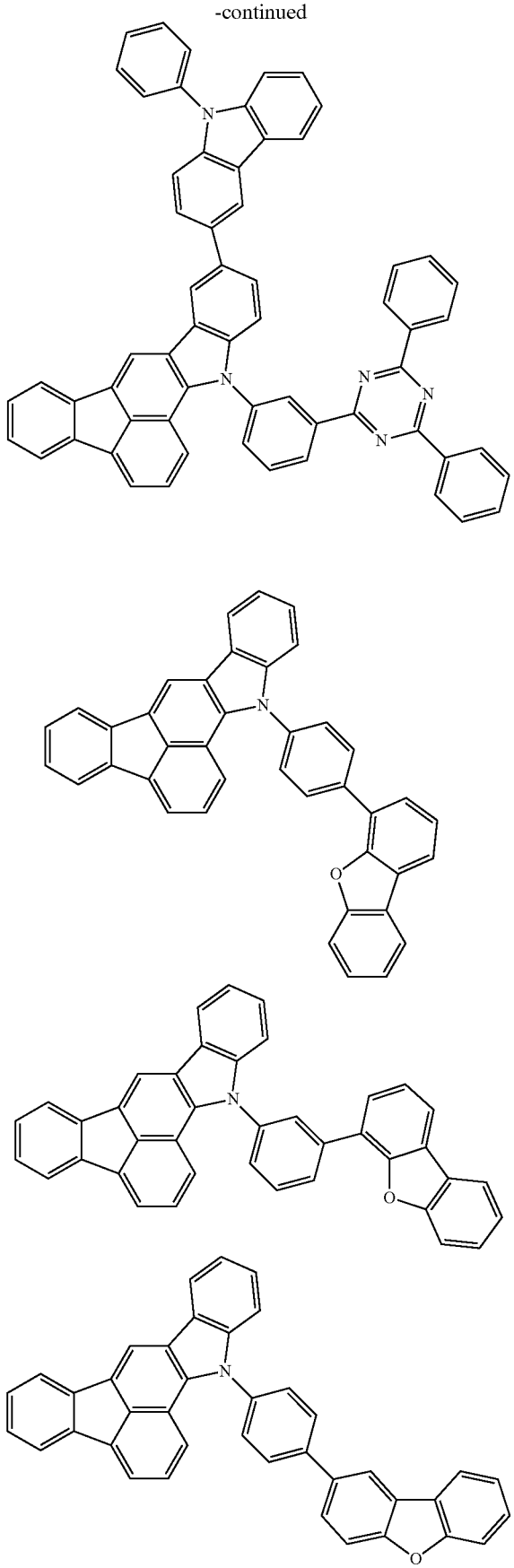
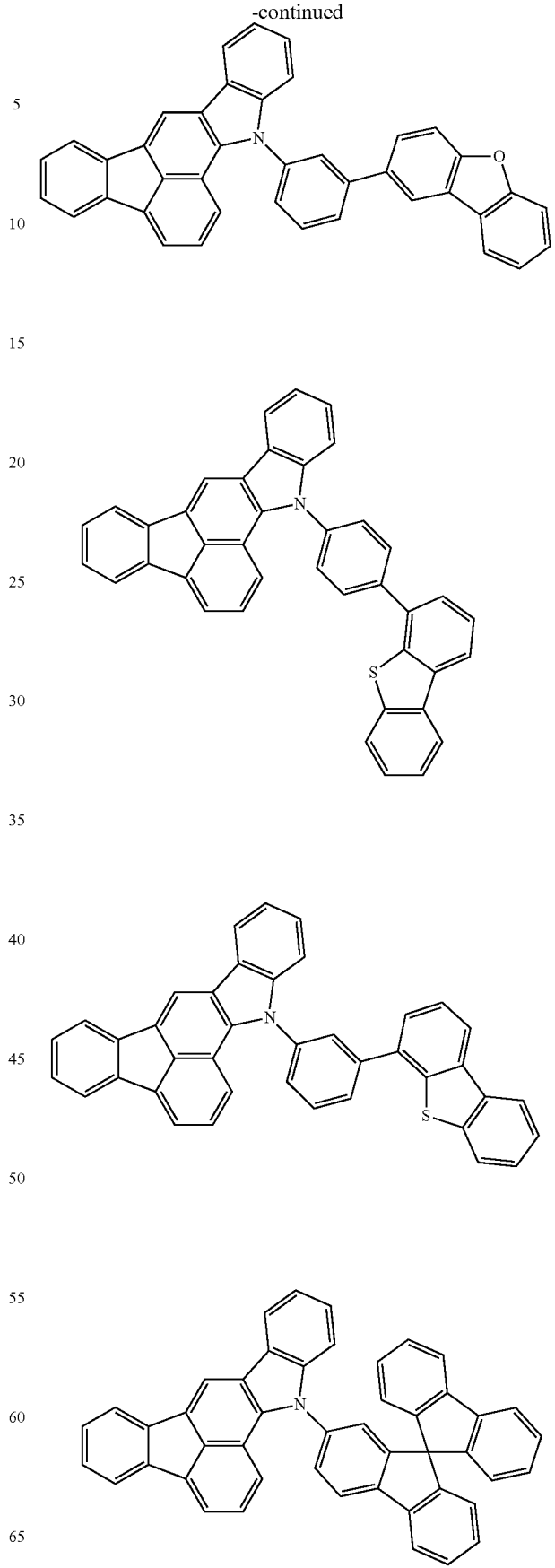

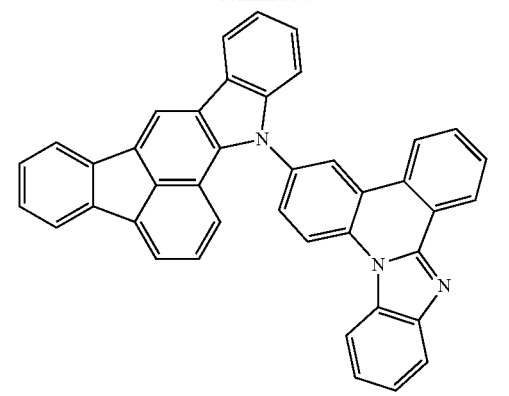
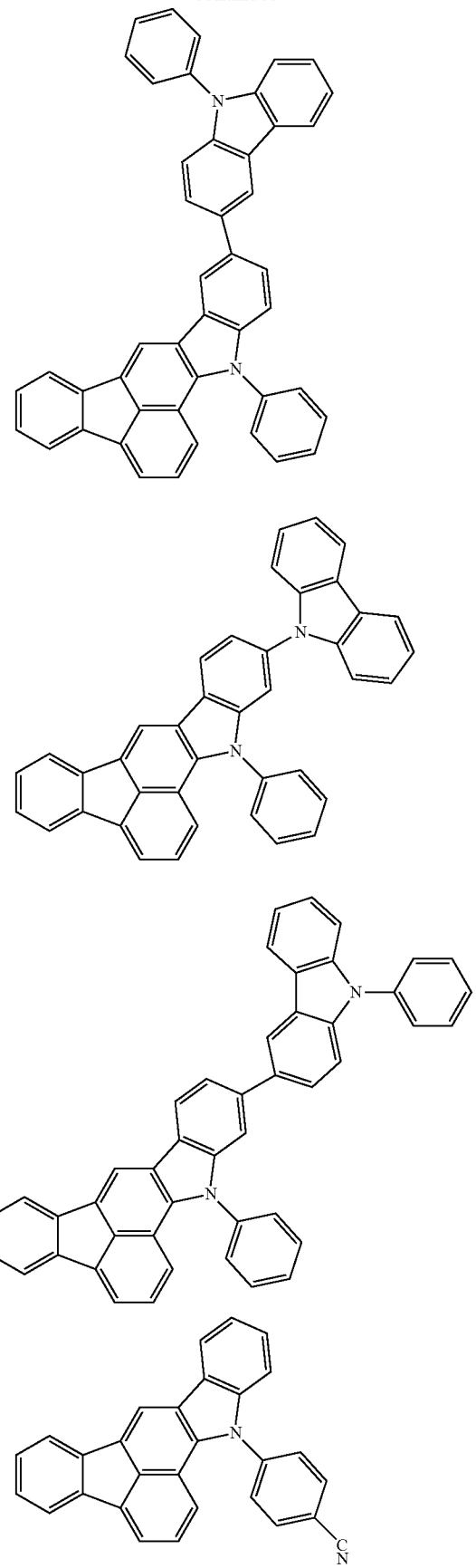

31
-continued
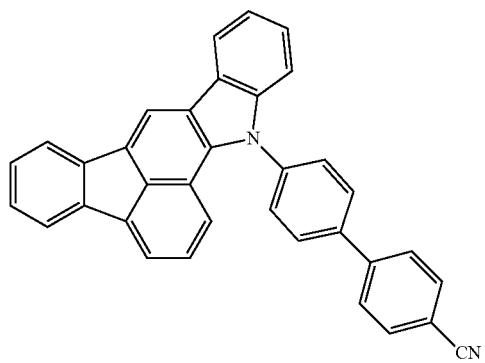
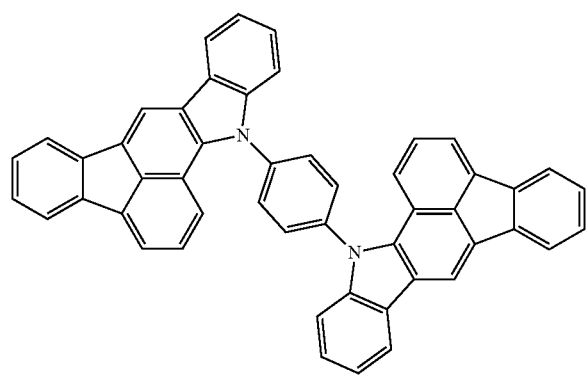
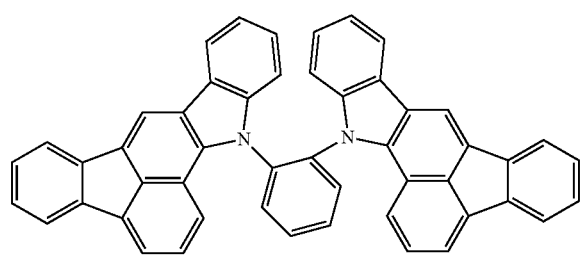
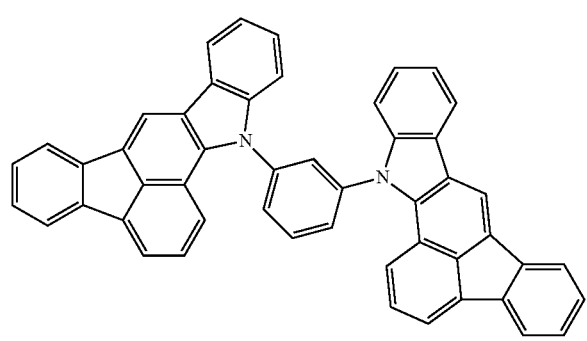
32
-continued
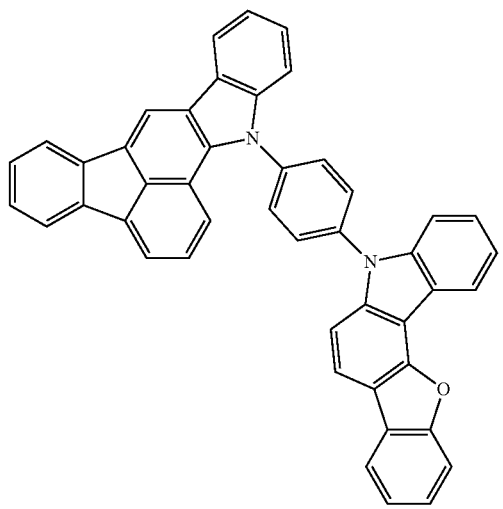
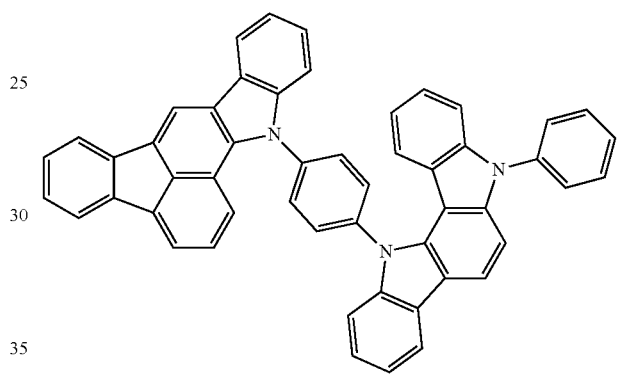
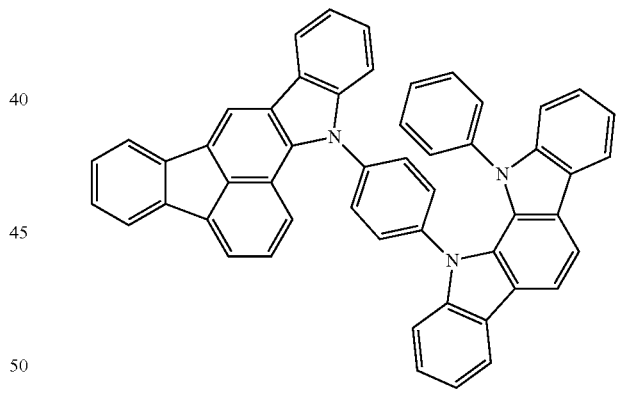
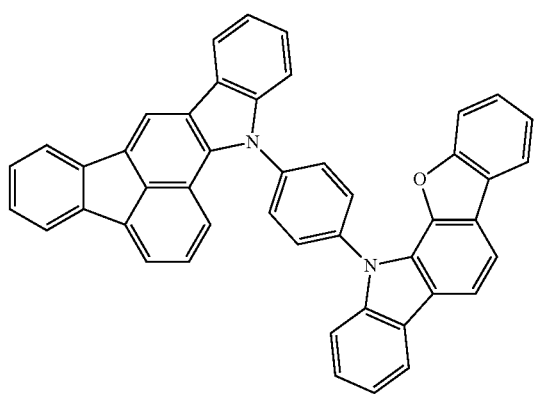

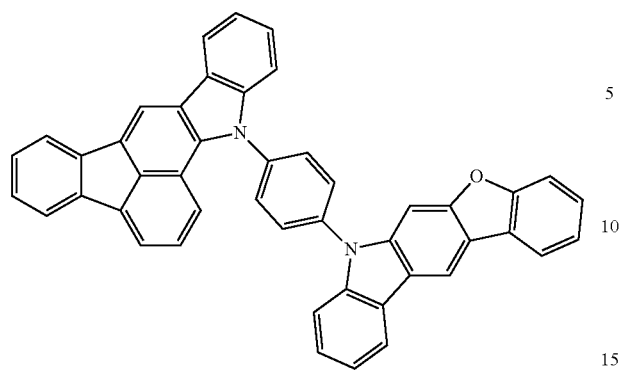
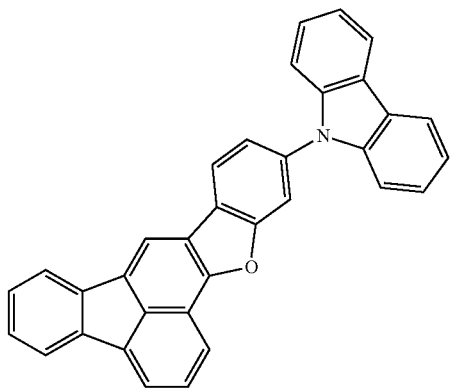

-continued
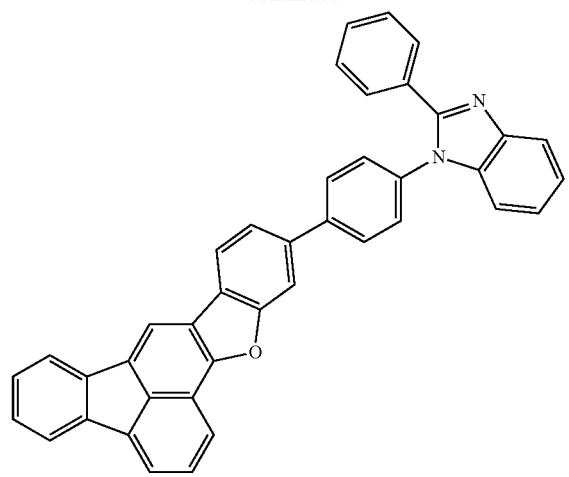
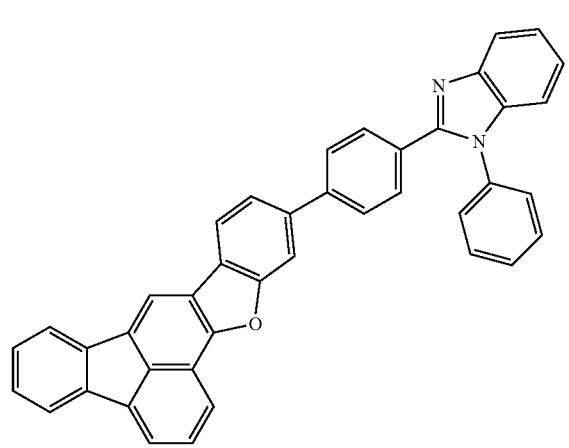
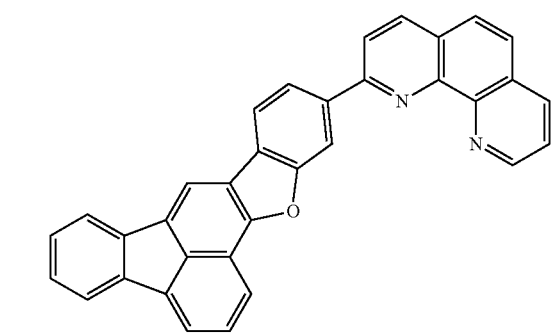
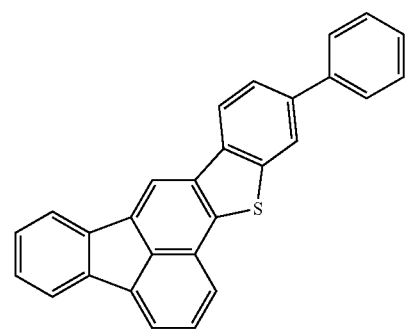
-continued
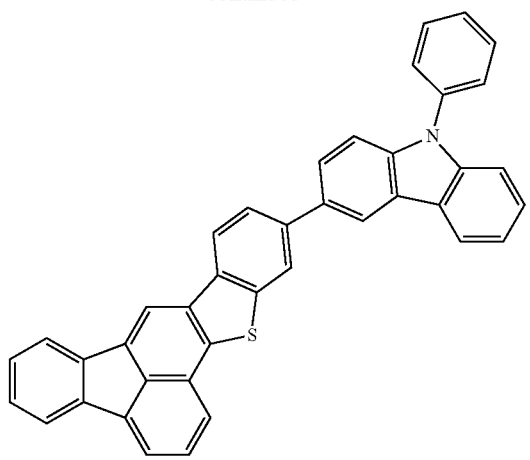
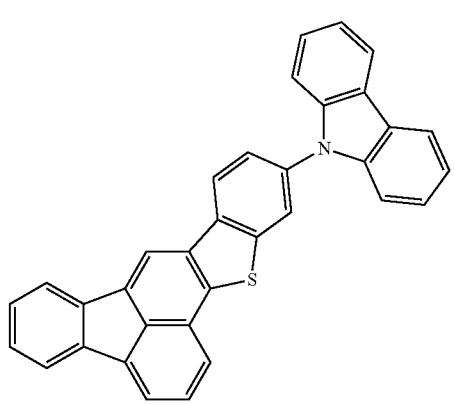
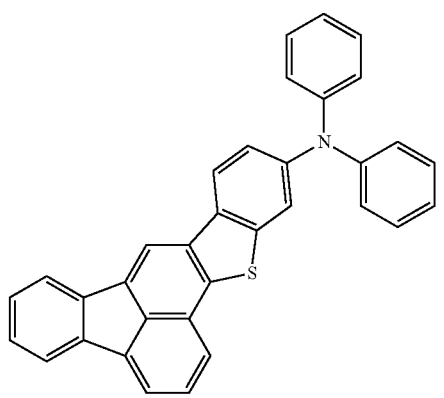
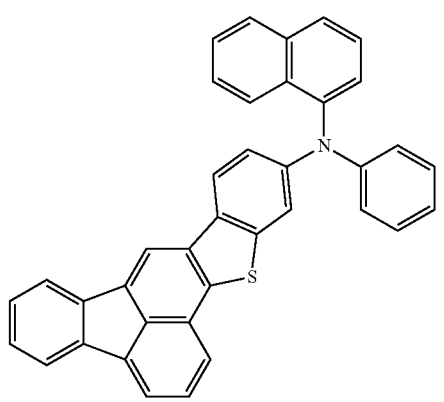

-continued
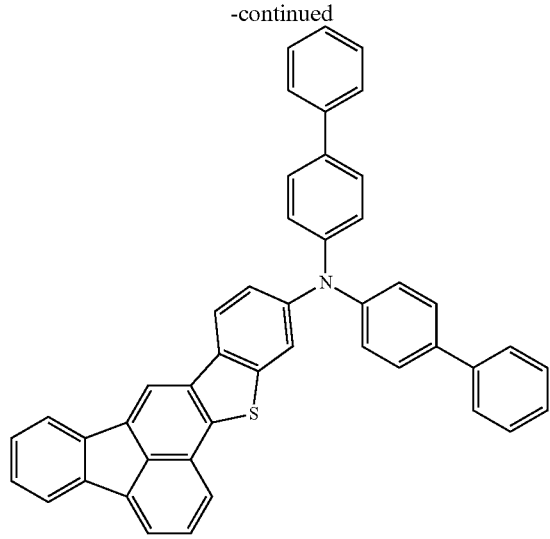
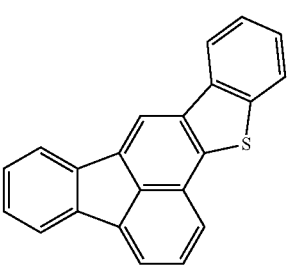
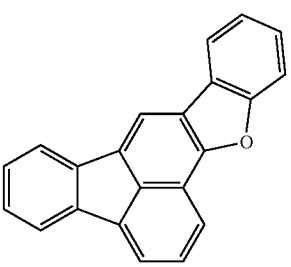
-continued
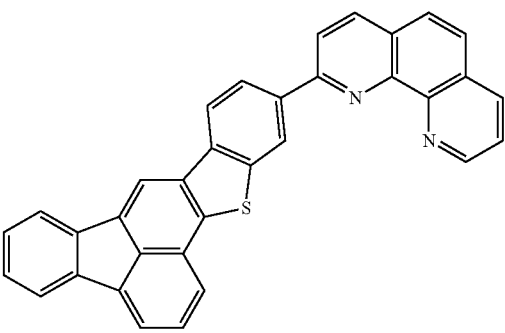
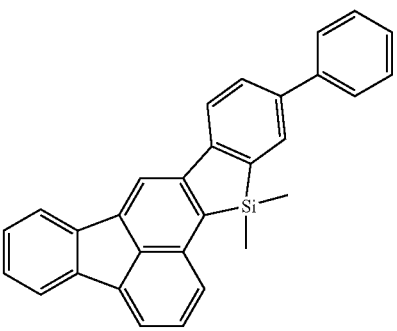
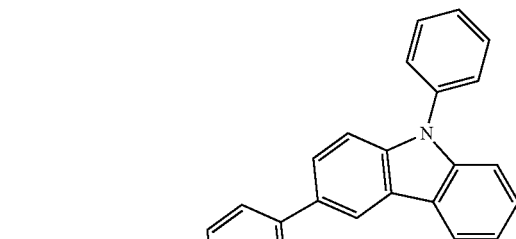
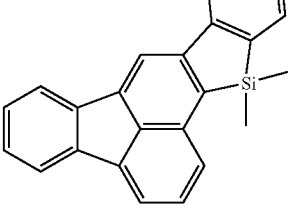

39
-continued
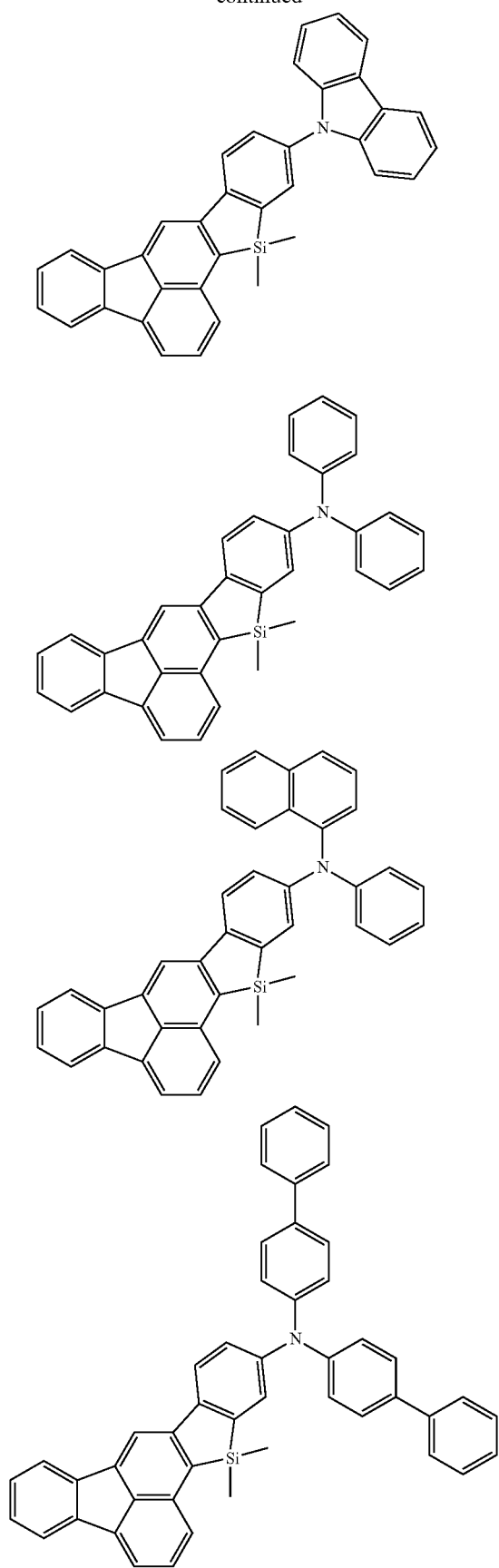
40
-continued
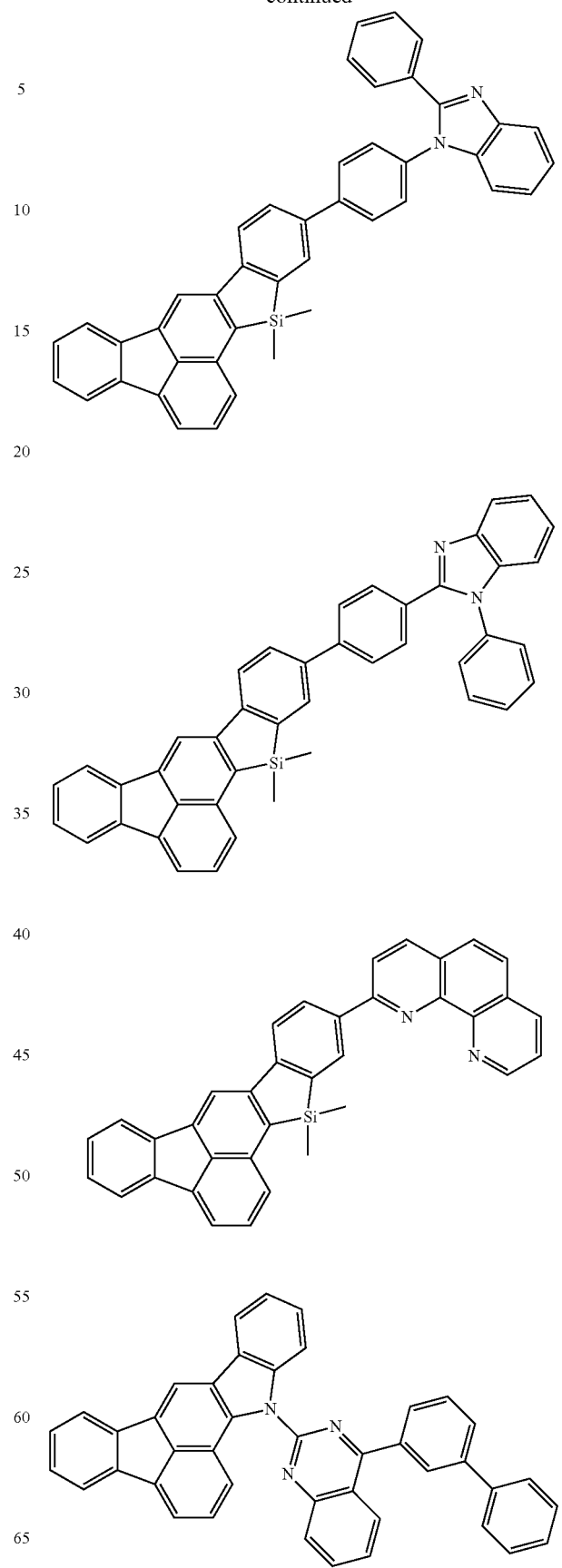

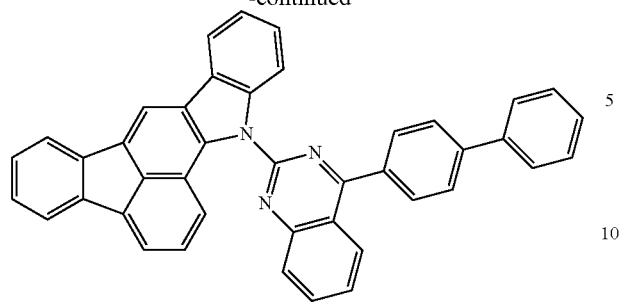
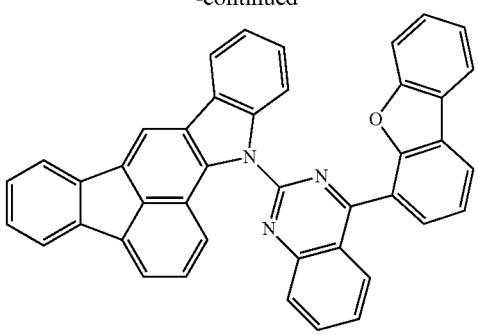
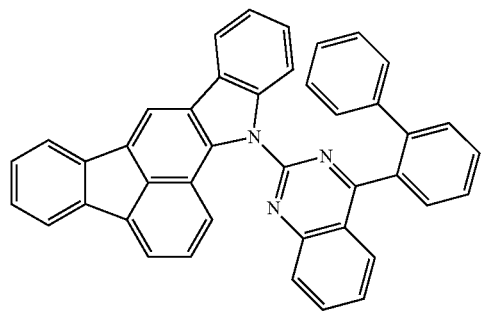
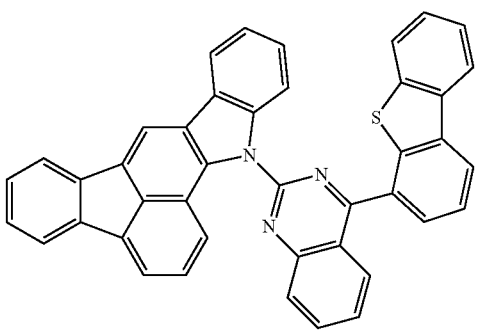
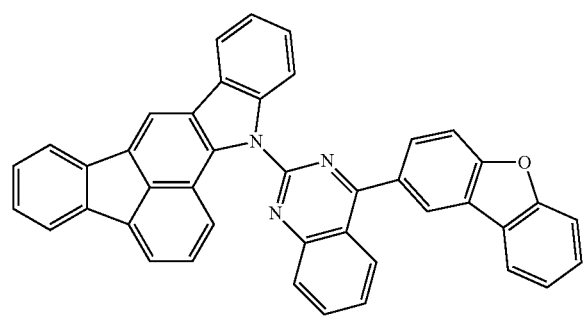
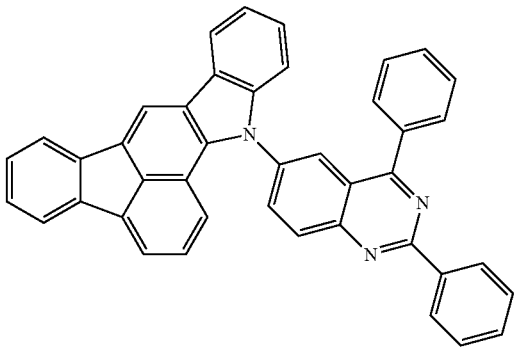
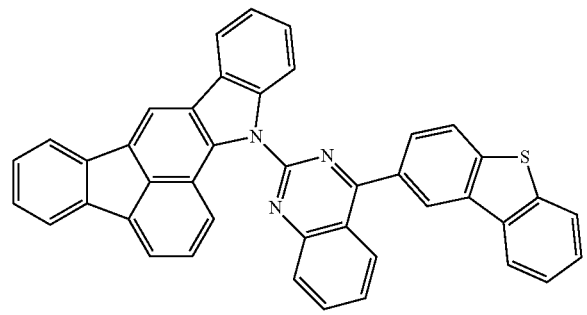
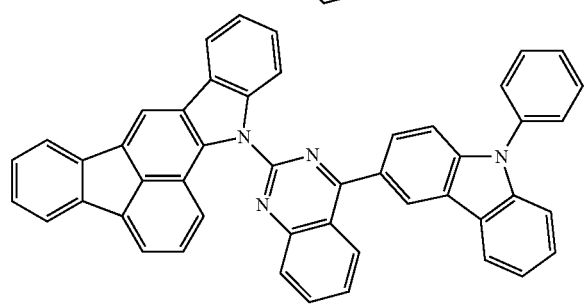
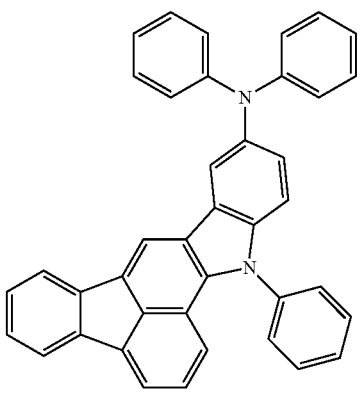

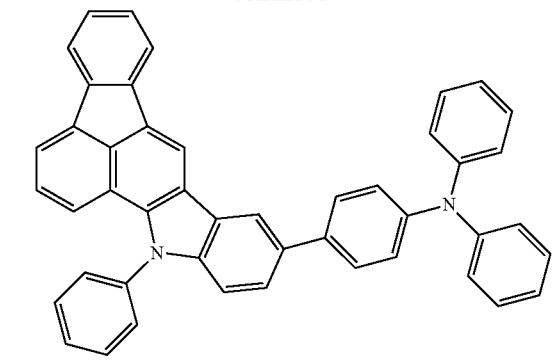
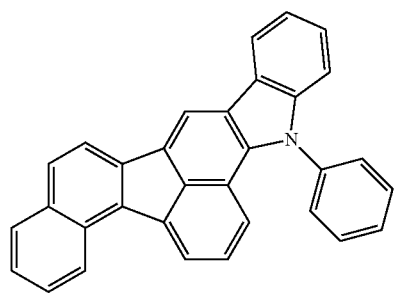
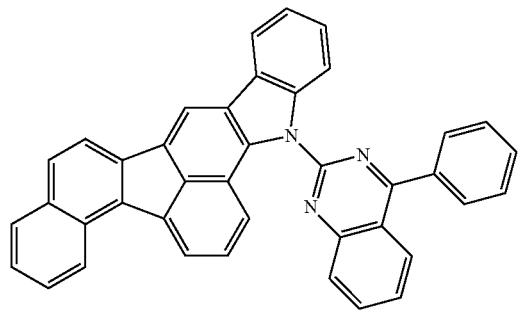
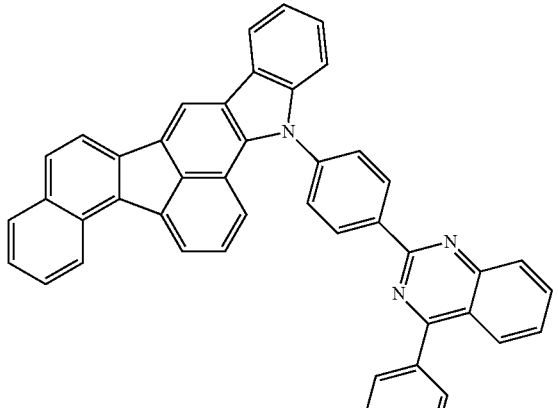
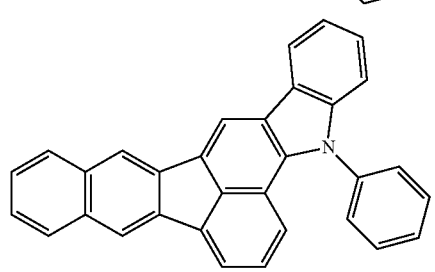
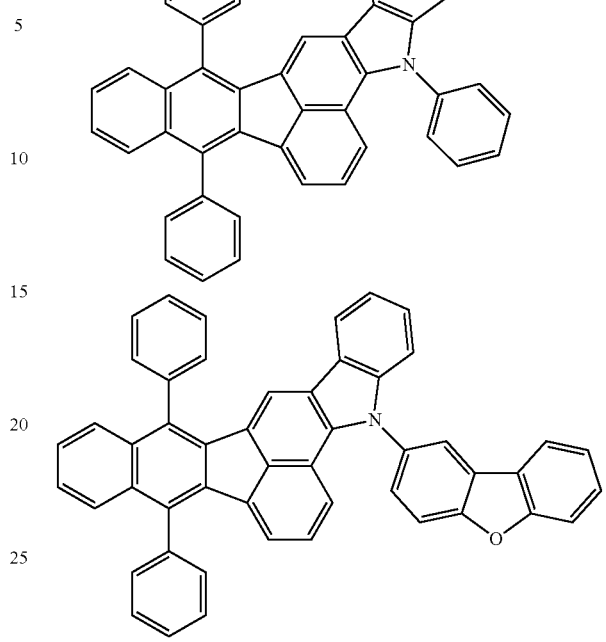
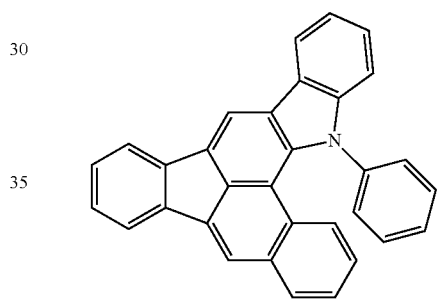
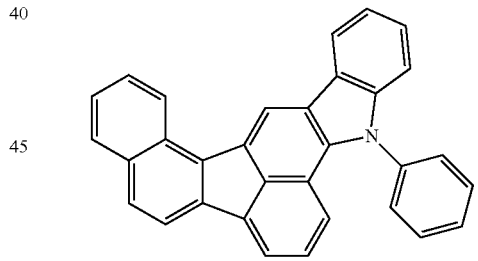
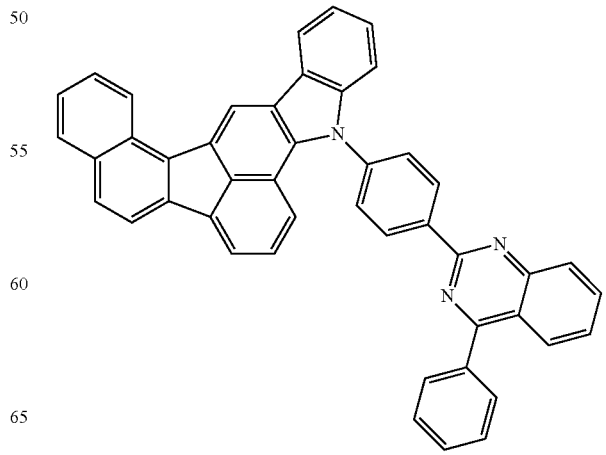

-continued
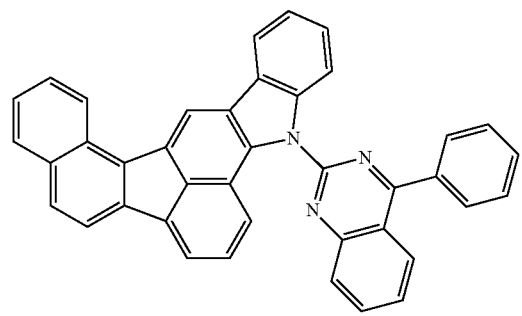
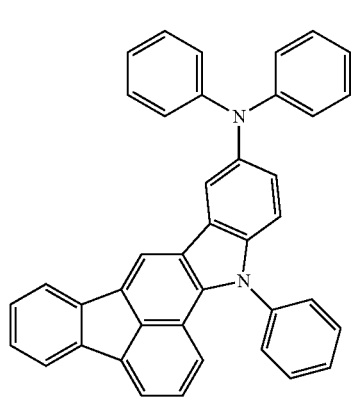
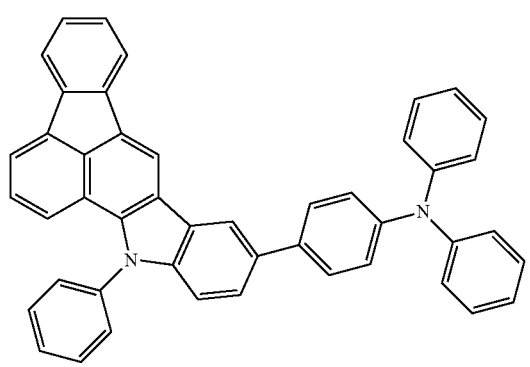
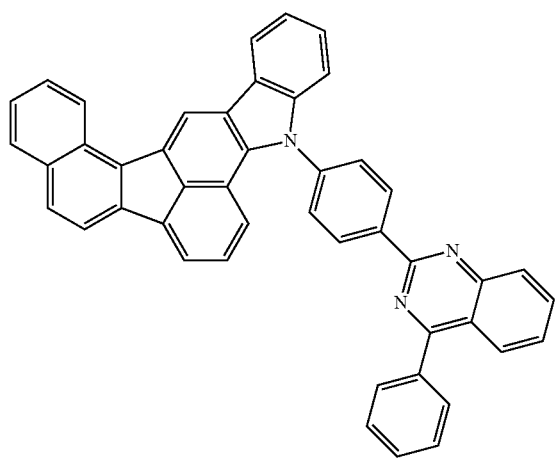
-continued
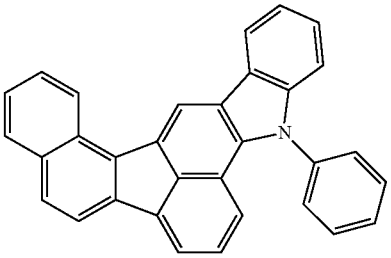
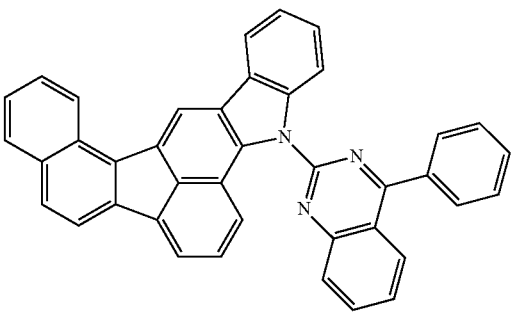
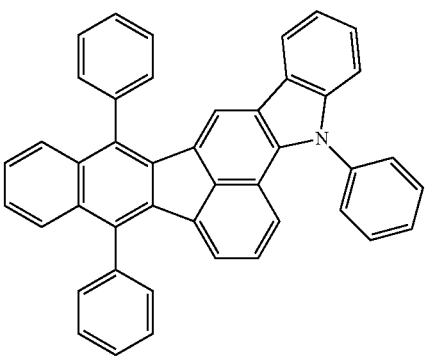
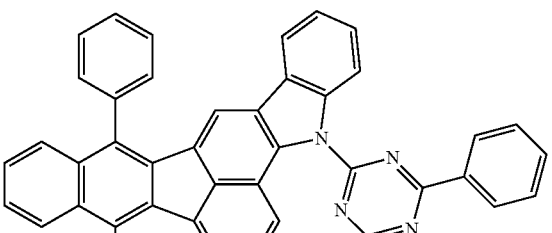
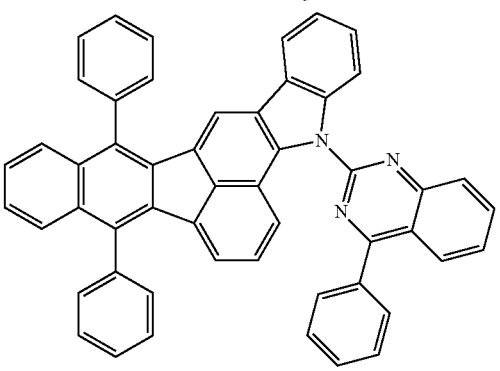

47
-continued
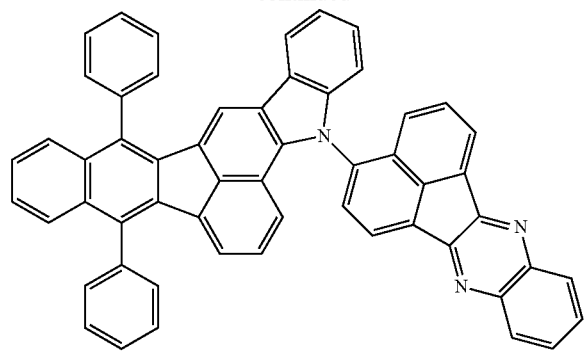
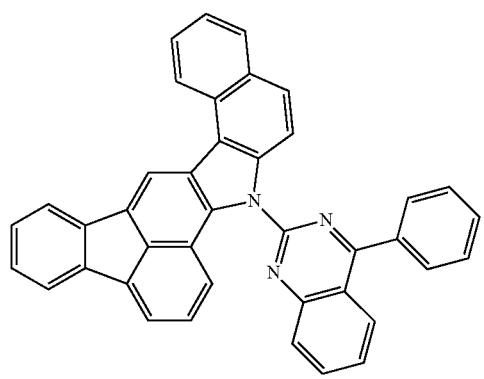
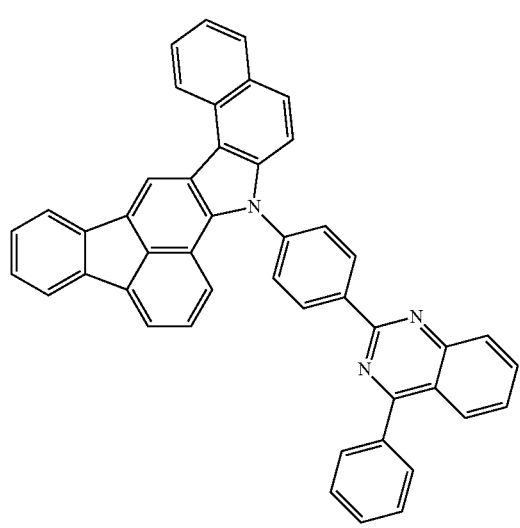
48
-continued
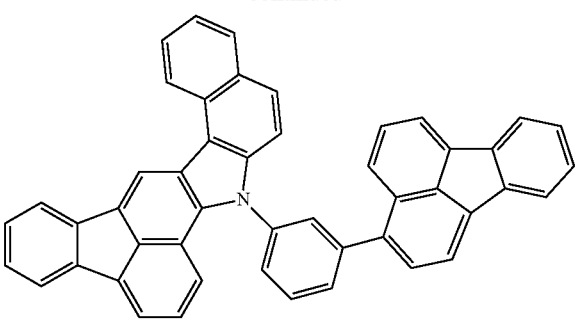
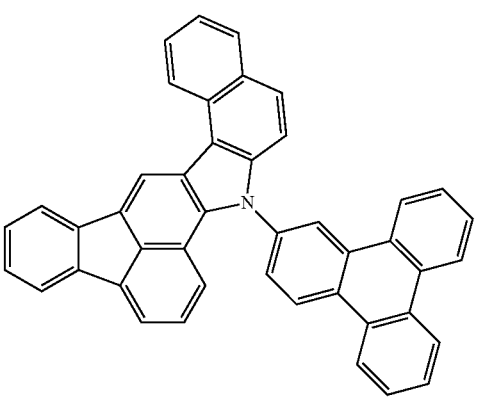
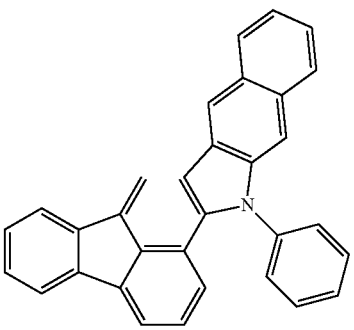
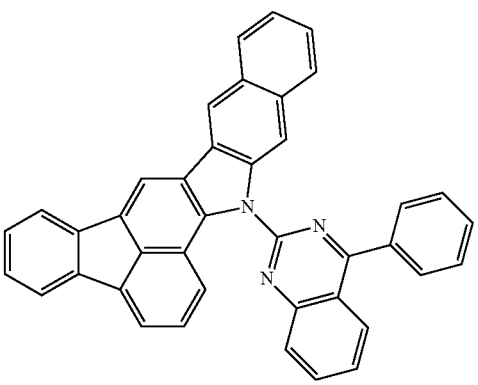

49
-continued
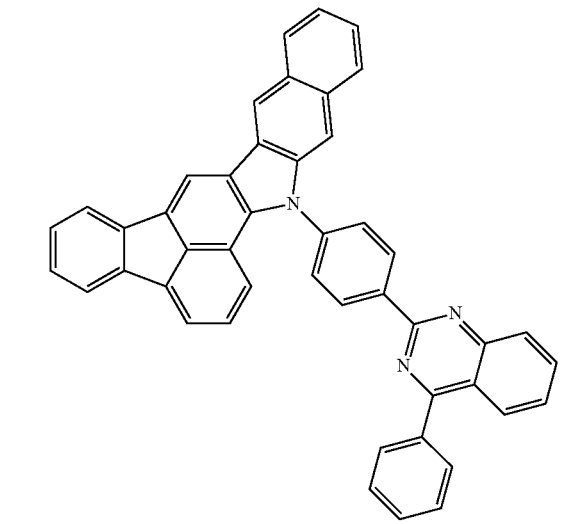
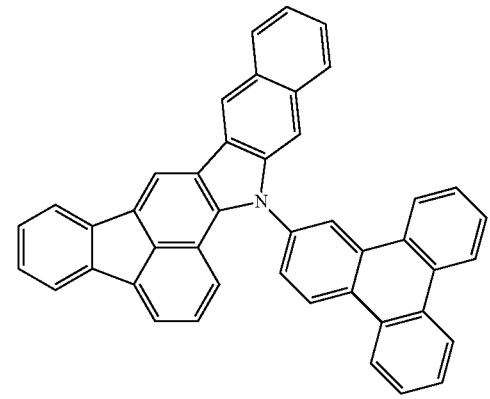
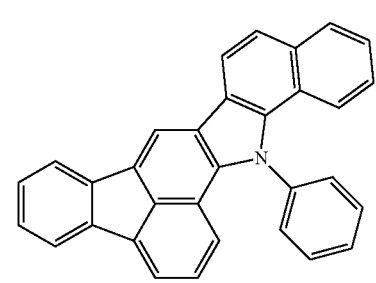
50
-continued
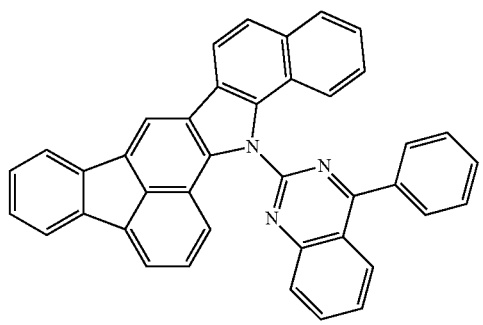
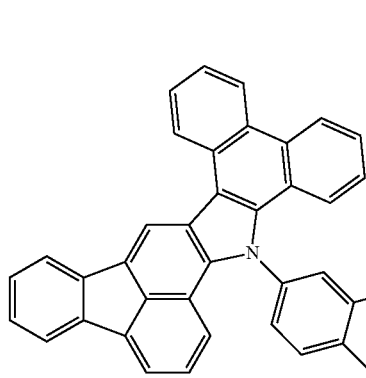
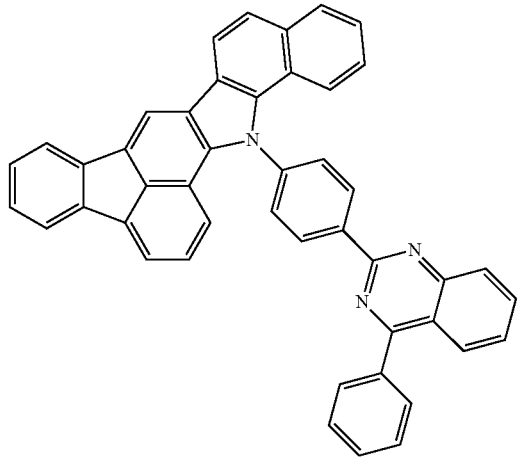
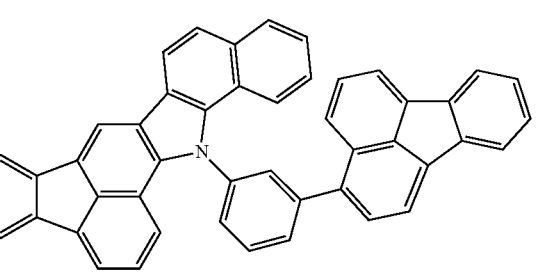

51
-continued
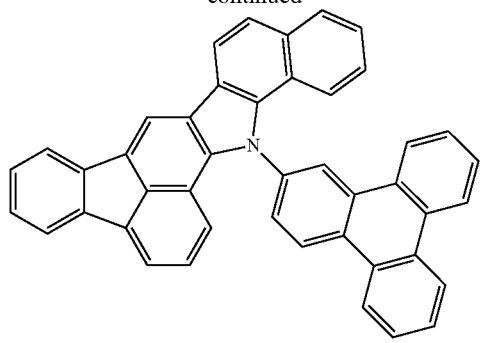
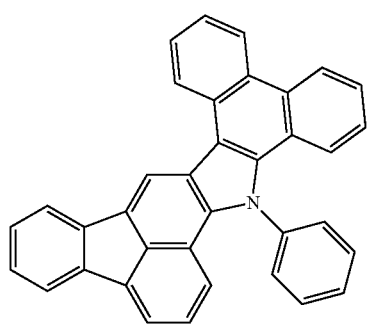
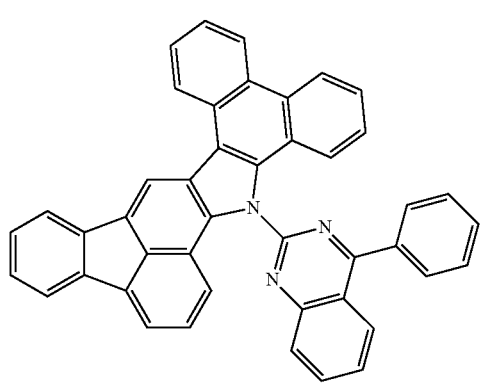
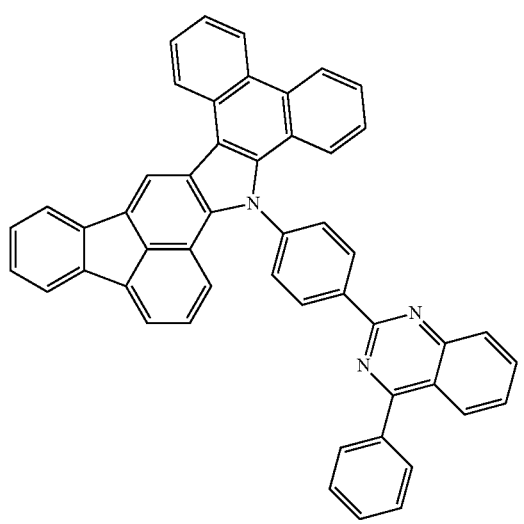
52
-continued
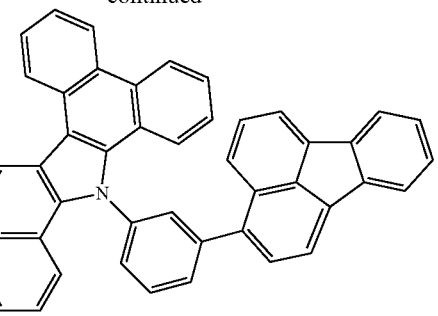
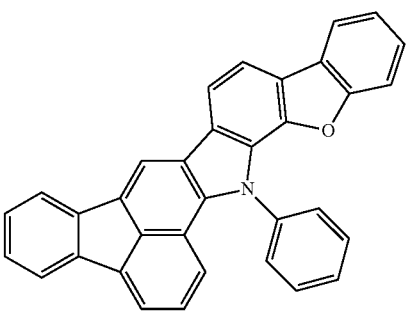
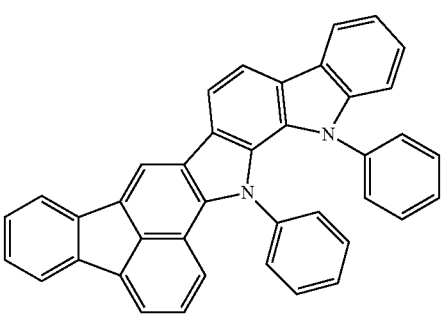
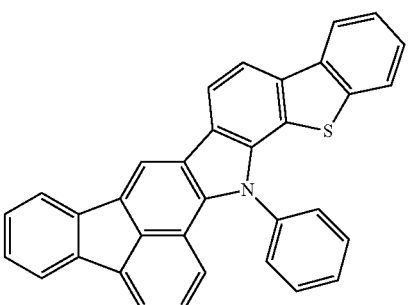
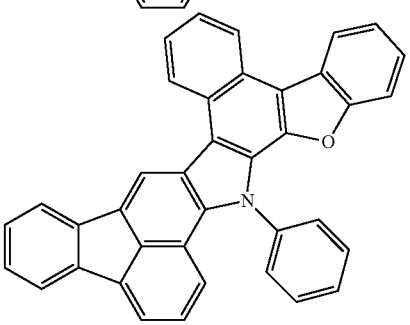

-continued
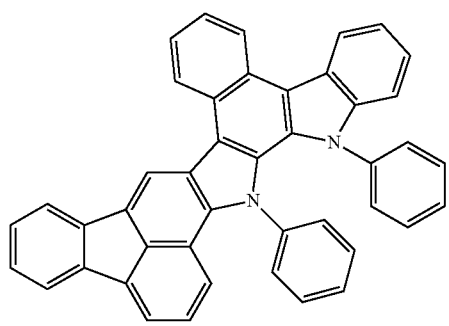
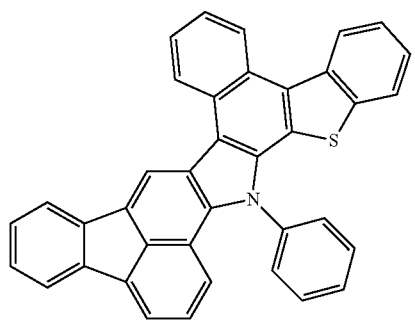
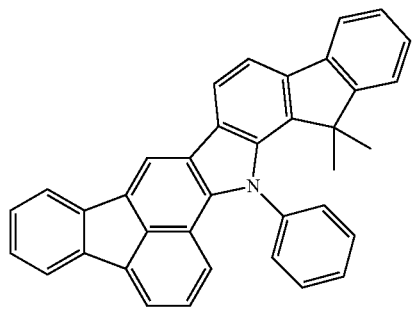
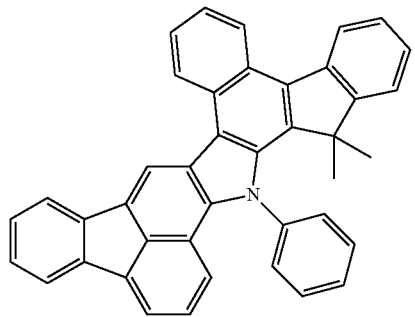
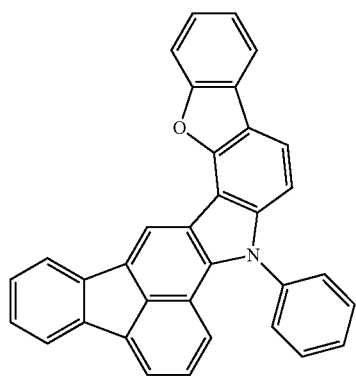
-continued
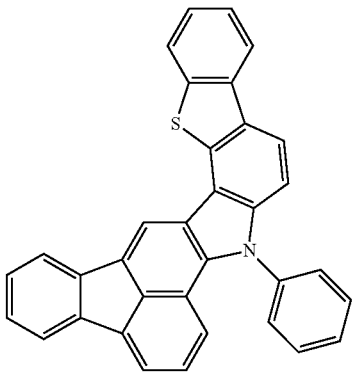
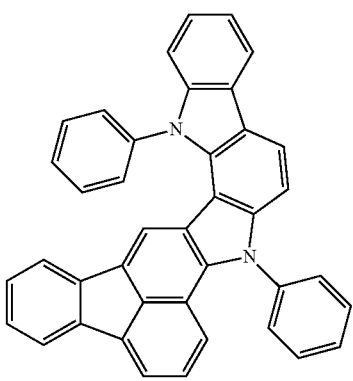
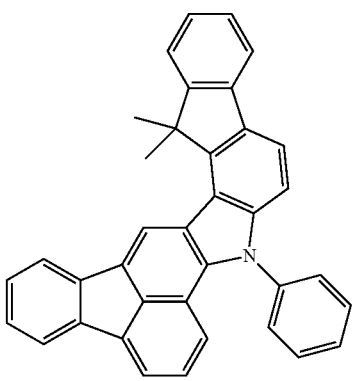
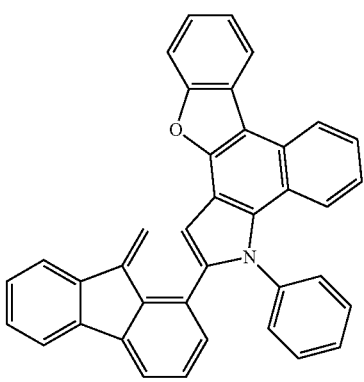

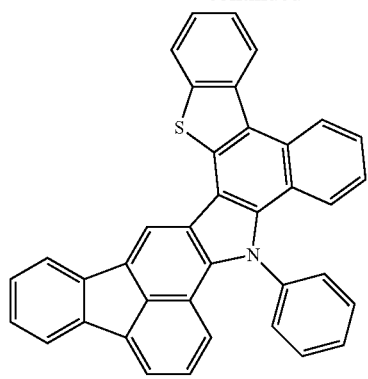
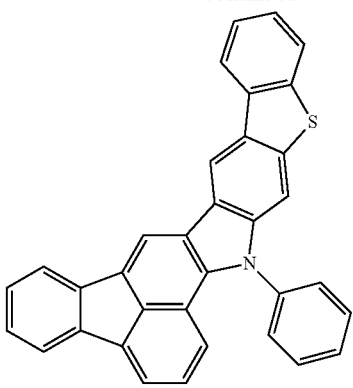
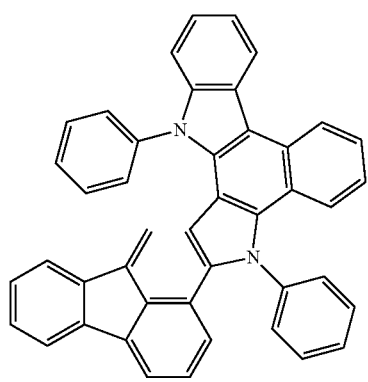
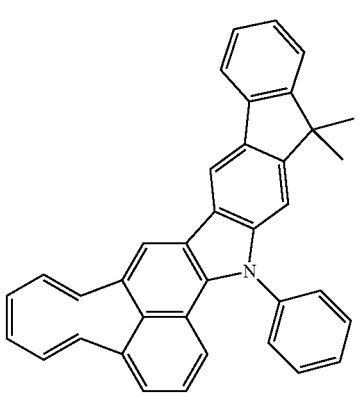
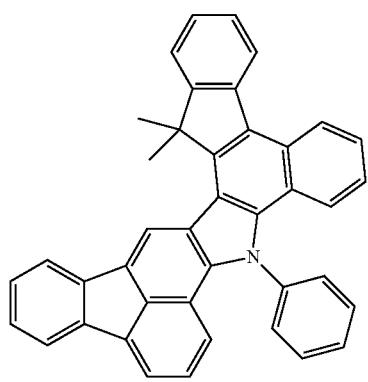
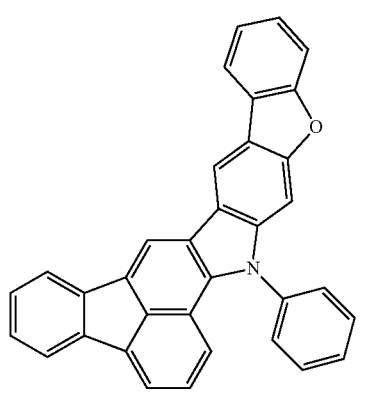
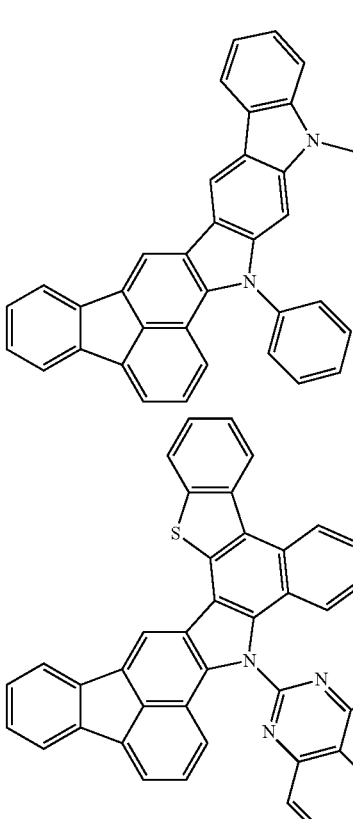

57
-continued
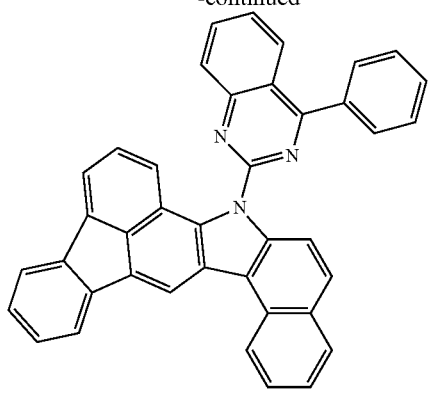
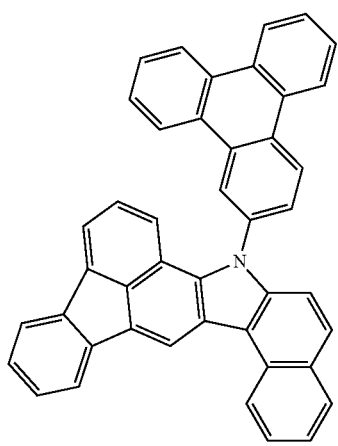
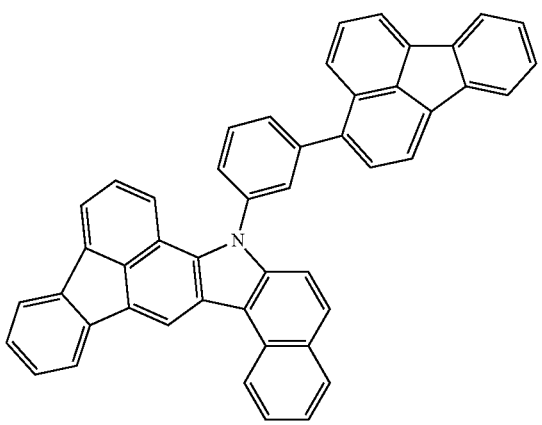
58
-continued
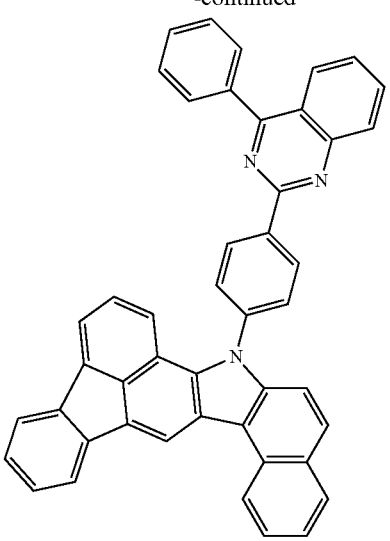
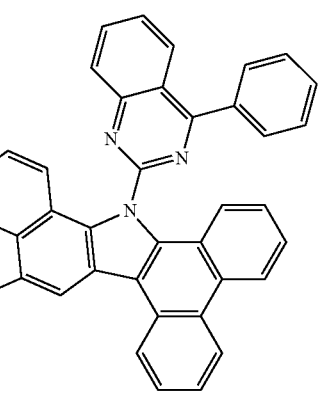
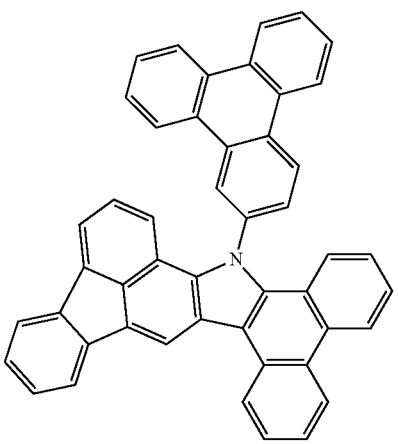

-continued
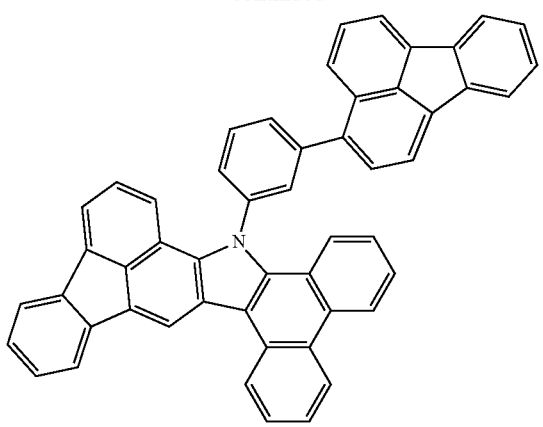
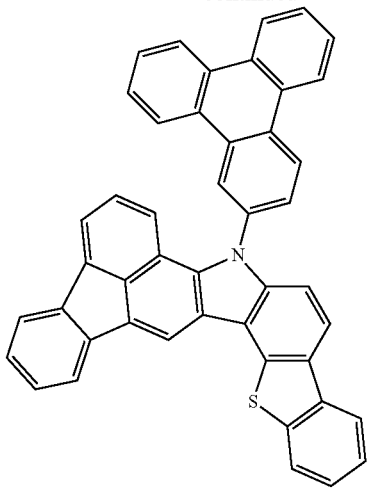
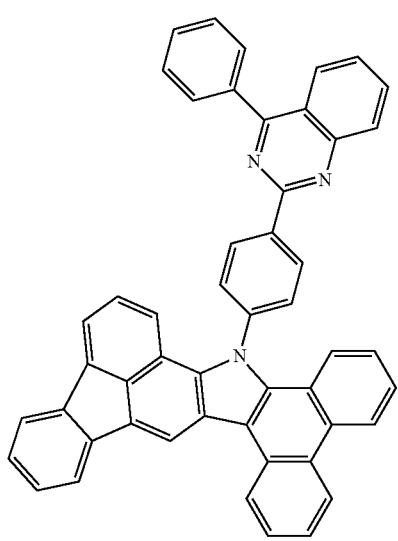
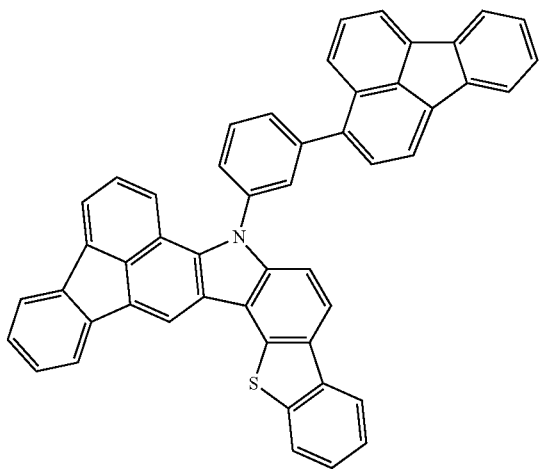
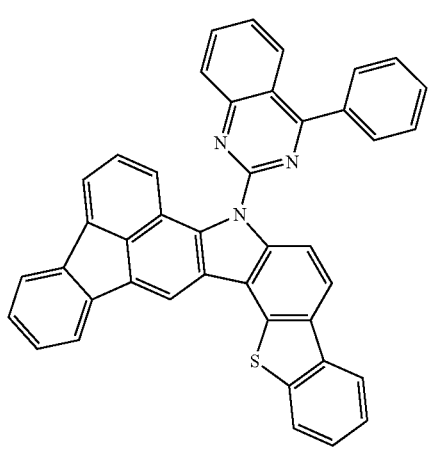
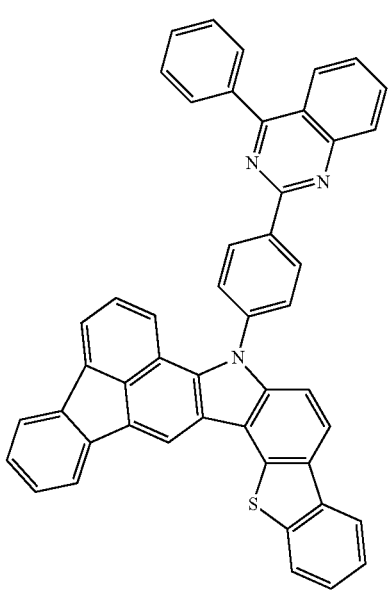

-continued
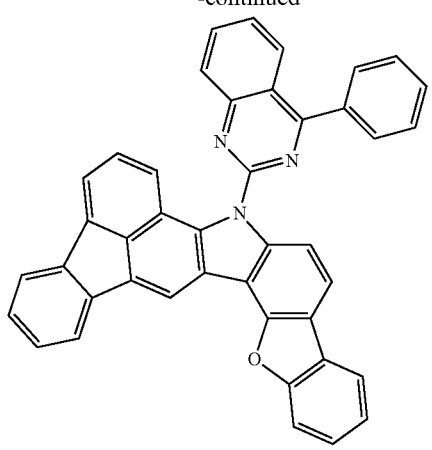
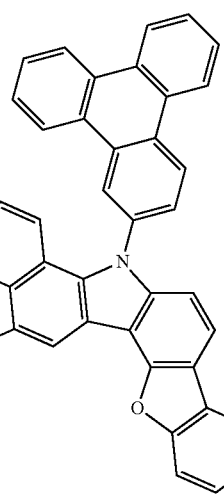
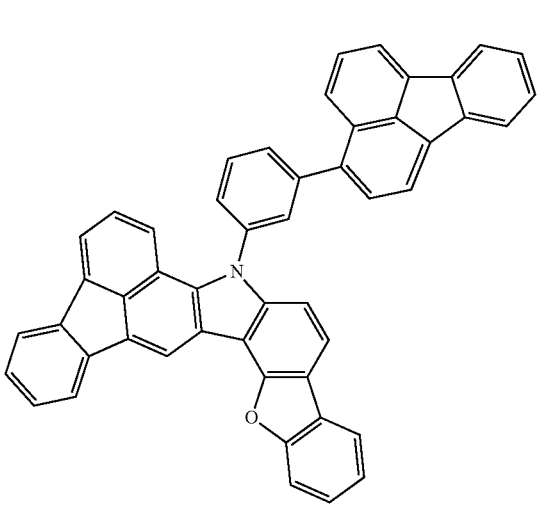
-continued
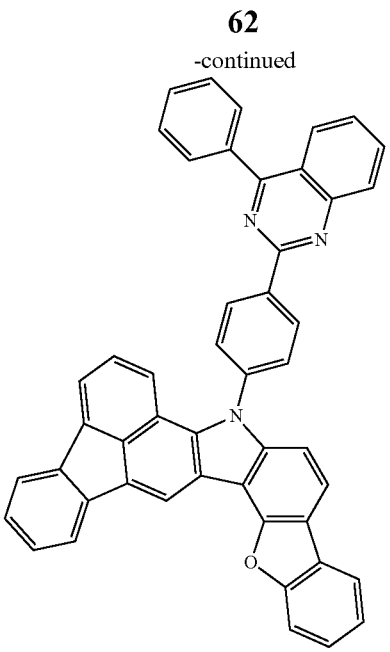
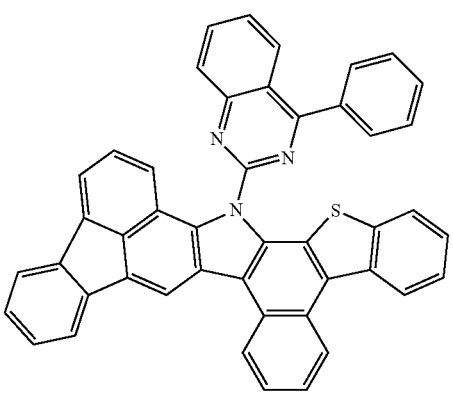
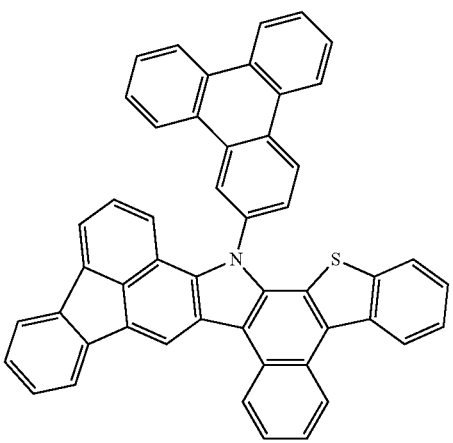

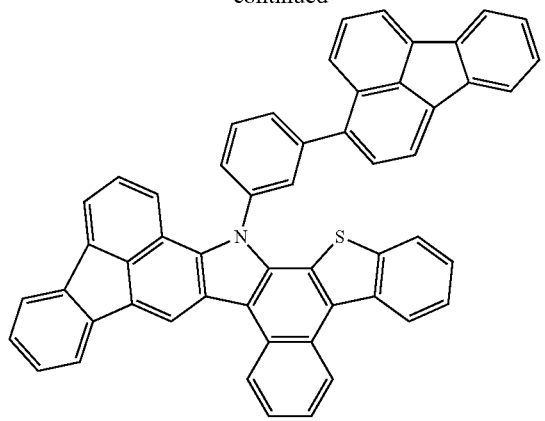
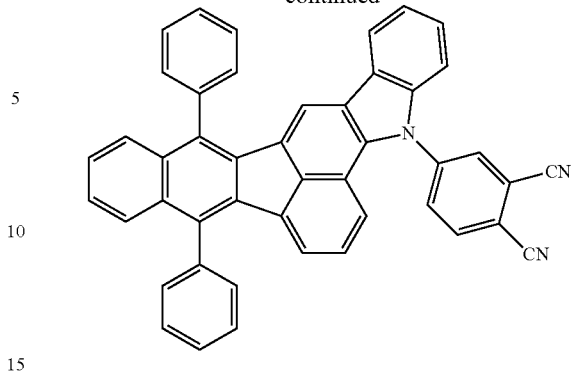
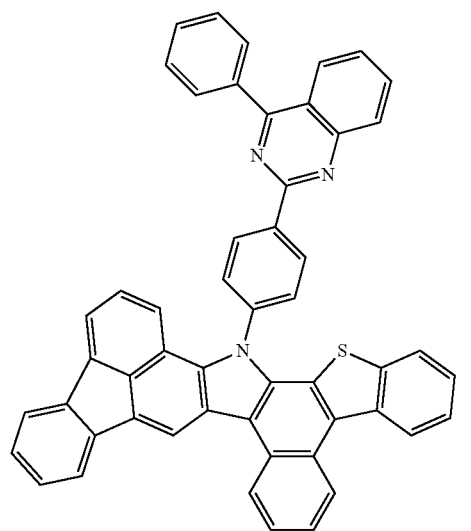
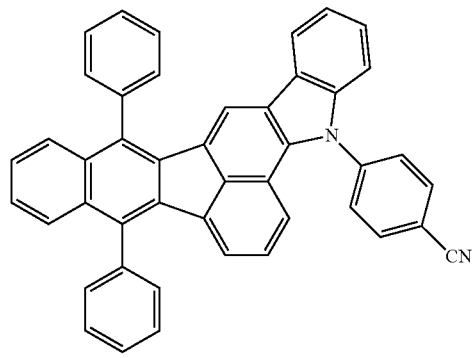
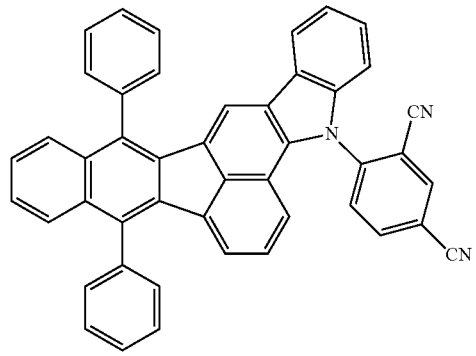

Organic EL Device

The organic EL device of the invention will be described below.

The organic EL device comprises an organic thin film layer between a cathode and an anode. The organic thin film layer comprise a light emitting layer and at least one layer of the organic thin film layer comprises the material for organic EL device mentioned above.

Examples of the organic thin film layer comprising the material for organic EL device include an anode-side organic thin film layer formed between an anode and a light emitting layer (hole transporting layer, hole injecting layer, etc.), a light emitting layer, a cathode-side organic thin film layer formed between a cathode and a light emitting layer (electron transporting layer, electron injecting layer, etc.), a space layer, and a blocking layer, although not limited thereto. The material for organic EL device may be used in any of the above layers, for example, used in a light emitting layer of a fluorescent emitting unit as a host material or a dopant material, in a light emitting layer of a phosphorescent emitting unit as a host material, and in a hole transporting layer or an electron transporting layer of an emitting unit.

The organic EL device of the invention may be any of a single color emitting device of fluorescent or phosphorescent type, a white-emitting device of fluorescent-phosphorescent hybrid type, an emitting device of a simple type having a single emission unit, and an emitting device of a tandem type having two or more emission units, with the phosphorescent device being preferred. The "emission unit" referred to herein is the smallest unit for emitting light by the recombination of injected holes and injected electrons, which comprises one or more organic layers wherein at least one layer is a light emitting layer.

Representative device structures of the simple-type organic EL device are shown below.

(1) Anode/Emission Unit/Cathode

The emission unit may be a laminate comprising two or more layers selected from a phosphorescent light emitting layer and a fluorescent light emitting layer. A space layer may be disposed between the light emitting layers to prevent the diffusion of excitons generated in the phosphorescent light emitting layer into the fluorescent light emitting layer. Representative layered structures of the emission unit are shown below.

(a) hole transporting layer/light emitting layer (/electron transporting layer);
(b) hole transporting layer/first phosphorescent light emitting layer/second phosphorescent light emitting layer (/electron transporting layer);

(c) hole transporting layer/phosphorescent light emitting layer/space layer/fluorescent light emitting layer (/electron transporting layer);
(d) hole transporting layer/first phosphorescent light emitting layer/second phosphorescent light emitting layer/space layer/fluorescent light emitting layer (/electron transporting layer);
(e) hole transporting layer/first phosphorescent light emitting layer/space layer/second phosphorescent light emitting layer/space layer/fluorescent light emitting layer (/electron transporting layer);
(f) hole transporting layer/phosphorescent light emitting layer/space layer/first fluorescent light emitting layer/second fluorescent light emitting layer (/electron transporting layer);
(g) hole transporting layer/electron blocking layer/light emitting layer (/electron transporting layer);
(h) hole transporting layer/light emitting layer/hole blocking layer (/electron transporting layer); and
(i) hole transporting layer/fluorescent light emitting layer/triplet blocking layer (/electron transporting layer).

The emission color of the phosphorescent light emitting layer and that of the fluorescent light emitting layer may be different. For example, the layered structure of the laminated light emitting layer (d) may be hole transporting layer/first phosphorescent light emitting layer (red emission)/second phosphorescent light emitting layer (green emission)/space layer/fluorescent light emitting layer (blue emission)/electron transporting layer.

An electron blocking layer may be disposed between the light emitting layer and the hole transporting layer or between the light emitting layer and the space layer, if necessary. Also, a hole blocking layer may be disposed between the light emitting layer and the electron transporting layer, if necessary. With such a electron blocking layer or a hole blocking layer, electrons and holes are confined in the light emitting layer to increase the degree of charge recombination in the light emitting layer, thereby improving the lifetime.

Representative device structure of the tandem-type organic EL device is shown below.

(2) Anode/First Emission Unit/Intermediate Layer/Second Emission Unit/Cathode

The layered structure of the first emission unit and the second emission unit may be selected from those described above with respect to the emission unit.

Generally, the intermediate layer is also called an intermediate electrode, an intermediate conductive layer, a charge generation layer, an electron withdrawing layer, a connecting layer, or an intermediate insulating layer. The intermediate layer may be formed by known materials so as to supply electrons to the first emission unit and holes to the second emission unit.

A schematic structure of an example of the organic EL device of the invention is shown in FIG. 1 wherein the organic EL device 1 comprises a substrate 2, an anode 3, a cathode 4, and an emission unit 10 disposed between the anode 3 and the cathode 4. The emission unit 10 comprises a light emitting layer 5 which comprises at least one phosphorescent emitting layer containing a phosphorescent host material and a phosphorescent dopant material (phosphorescent material). A hole injecting/transporting layer 6 may be disposed between the light emitting layer 5 and the anode 3, and an electron injecting/transporting layer 7 may be disposed between the light emitting layer 5 and the cathode 4. An electron blocking layer may be disposed on the anode 3 side of the light emitting layer 5, and a hole blocking layer may be disposed on the cathode 4 side of the light emitting layer 5. With these blocking layers, electrons and holes are confined in the light emitting layer 5 to increase the degree of exciton generation in the light emitting layer 5.

In the present invention, a host is referred to as a fluorescent host when combinedly used with a fluorescent dopant (fluorescent material) and as a phosphorescent host when combinedly used with a phosphorescent dopant. Therefore, the fluorescent host and the phosphorescent host are not distinguished from each other merely by the difference in their molecular structures. Namely, in the present invention, the term "phosphorescent host" means a material for constituting a phosphorescent emitting layer containing a phosphorescent dopant and does not mean a material that cannot be utilized as a material for a fluorescent emitting layer. The same applies to the fluorescent host.

Substrate

The organic EL device of the invention is formed on a light-transmissive substrate. The light-transmissive substrate serves as a support for the organic EL device and preferably a flat substrate having a transmittance of 50% or more to 400 to 700 nm visible light. Examples of the substrate include a glass plate and a polymer plate. The glass plate may include a plate made of soda-lime glass, barium-strontium-containing glass, lead glass, aluminosilicate glass, borosilicate glass, barium borosilicate glass, or quartz. The polymer plate may include a plate made of polycarbonate, acryl, polyethylene terephthalate, polyether sulfide, or polysulfone.

Anode

The anode of the organic EL device injects holes to the hole transporting layer or the light emitting layer, and an anode having a work function of 4.5 eV or more is effective. Examples of the material for anode include indium tin oxide alloy (ITO), tin oxide (NESA), indium zinc oxide alloy, gold, silver, platinum, and copper. The anode is formed by making the electrode material into a thin film by a method, such as a vapor deposition method or a sputtering method. When getting the light emitted from the light emitting layer through the anode, the transmittance of anode to visible light is preferably 10% or more. The sheet resistance of anode is preferably several hundreds $\Omega$/or less. The film thickness of anode depends upon the kind of material and generally 10 nm to 1 $\mu$m, preferably 10 to 200 nm.

Cathode

The cathode injects electrons to the electron injecting layer, the electron transporting layer or the light emitting layer, and formed preferably by a material having a small work function. Examples of the material for cathode include, but not limited to, indium, aluminum, magnesium, magnesium-indium alloy, magnesium-aluminum alloy, aluminum-lithium alloy, aluminum-scandium-lithium alloy, and magnesium-silver alloy. Like the anode, the cathode is formed by making the material into a thin film by a method, such as the vapor deposition method and the sputtering method. The emitted light may be taken through the cathode, if necessary.

Light Emitting Layer

The light emitting layer is an organic layer having a light emitting function and contains a host material and a dopant material when a doping system is employed. The major function of the host material is to promote the recombination of electrons and holes and confine excitons in the light emitting layer. The dopant material causes the excitons generated by recombination to emit light efficiently.

In case of a phosphorescent device, the major function of the host material is to confine the excitons generated on the dopant in the light emitting layer.

To control the carrier balance in the light emitting layer, the light emitting layer may be made into a double host (host/co-host) layer, for example, by combinedly using an electron transporting host and a hole transporting host.

The light emitting layer may be made into a double dopant layer, in which two or more kinds of dopant materials having high quantum yield are combinedly used and each dopant material emits light with its own color. For example, to obtain a yellow emission, a light emitting layer formed by co-depositing a host, a red-emitting dopant and a green-emitting dopant is used.

In a laminate of two or more light emitting layers, electrons and holes are accumulated in the interface between the light emitting layers, and therefore, the recombination region is localized in the interface between the light emitting layers, to improve the quantum efficiency.

The easiness of hole injection to the light emitting layer and the easiness of electron injection to the light emitting layer may be different from each other. Also, the hole transporting ability and the electron transporting ability each being expressed by mobility of holes and electrons in the light emitting layer may be different from each other.

The light emitting layer is formed, for example, by a known method, such as a vapor deposition method, a spin coating method, and LB method. The light emitting layer can be formed also by making a solution of a binder, such as resin, and the material for the light emitting layer in a solvent into a thin film by a method such as spin coating.

The light emitting layer is preferably a molecular deposit film. The molecular deposit film is a thin film formed by depositing a vaporized material or a film formed by solidifying a material in the state of solution or liquid. The molecular deposit film can be distinguished from a thin film formed by LB method (molecular build-up film) by the differences in the assembly structures and higher order structures and the functional difference due to the structural differences.

The phosphorescent dopant (phosphorescent material) used in the light emitting layer is a compound which emits light by releasing the energy of excited triplet state and preferably a organometallic complex comprising at least one metal selected from Ir, Pt, Os, Au, Cu, Re, and Ru and a ligand, although not particularly limited thereto as long as emitting light by releasing the energy of excited triplet state. The ligand is preferably ortho-metallated. In view of obtaining a high phosphorescent quantum yield and further improving the external quantum efficiency of luminescent device, a metal complex comprising a metal selected from Ir, Os, and Pt is preferred, with a metal complex, particularly an ortho-metallated complex, such as an iridium complex, an osmium complex, and a platinum complex, being more preferred, an iridium complex and a platinum complex being still more preferred, and an ortho-metallated iridium complex being particularly preferred.

The content of the phosphorescent dopant in the light emitting layer is not particularly limited and selected according to the use of the device, and preferably 0.1 to 70% by mass, and more preferably 1 to 30% by mass. If being 0.1% by mass or more, the amount of light emission is sufficient. If being 70% by mass or less, the concentration quenching can be avoided.

Preferred examples of the organometallic complex for the phosphorescent dopant are shown below.

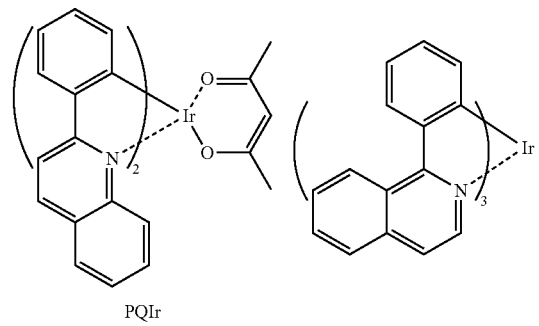

PQIr

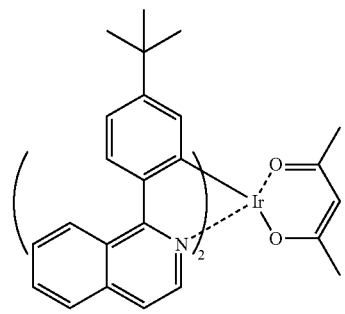

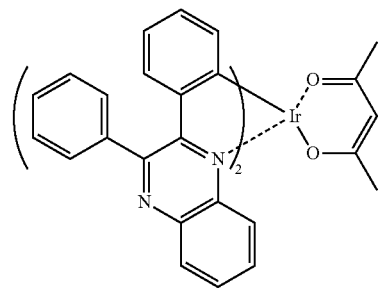

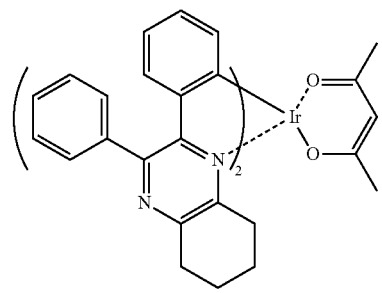

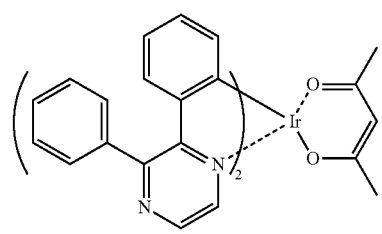

-continued
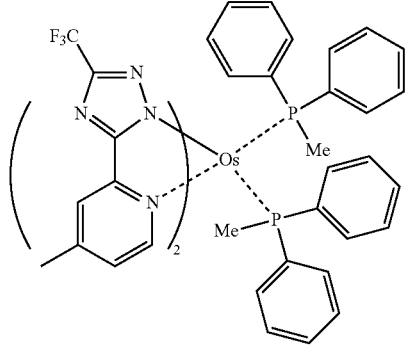
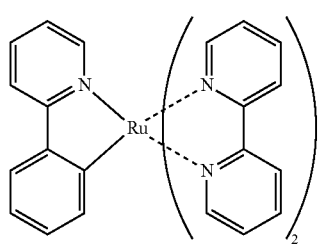
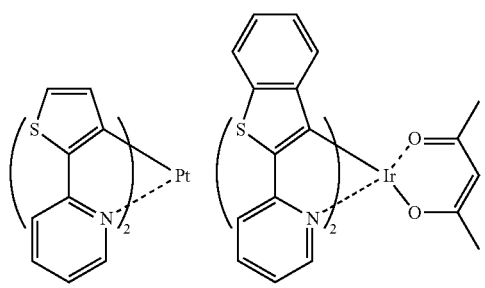
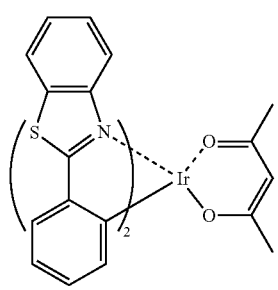
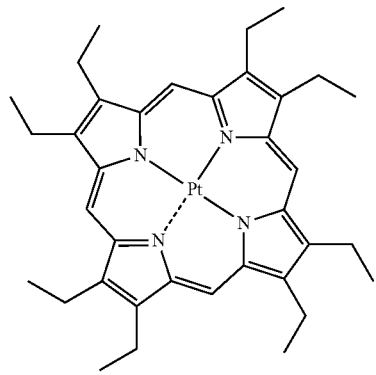
-continued
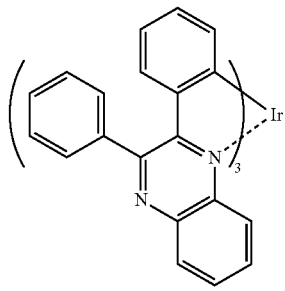
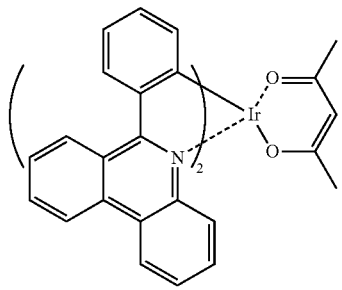
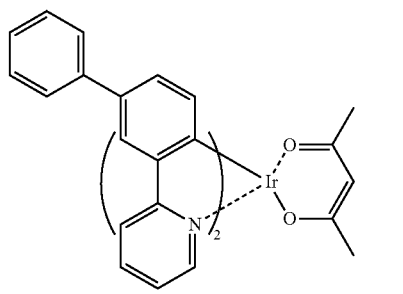
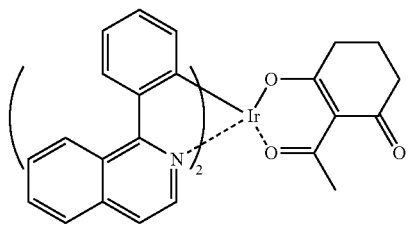
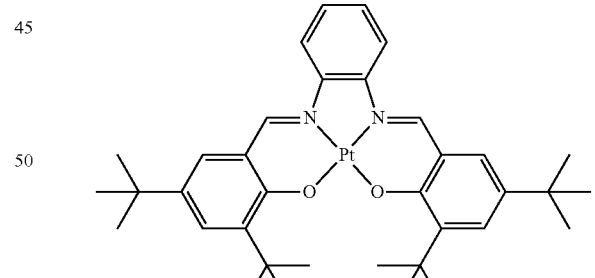
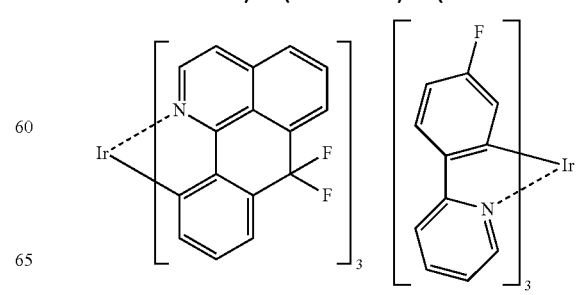

71
-continued
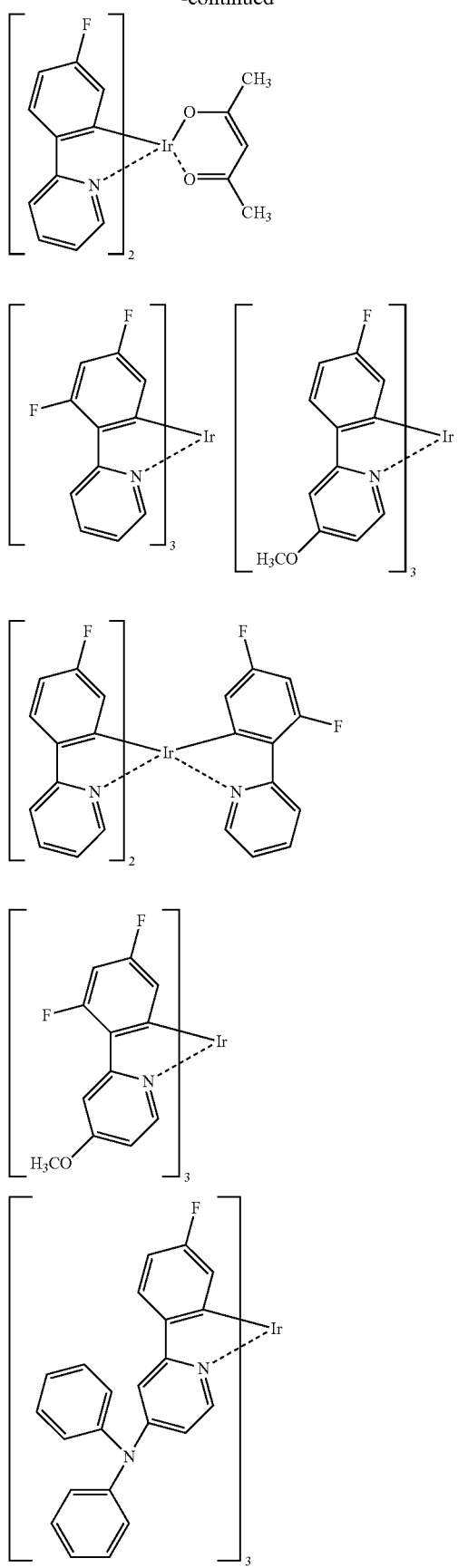
72
-continued
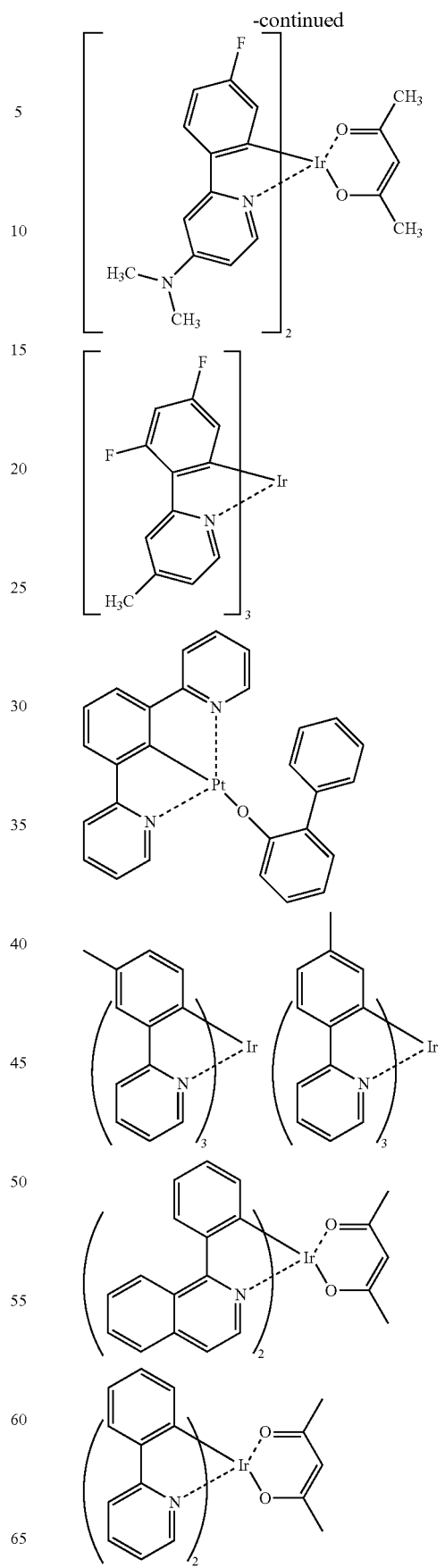

73
-continued
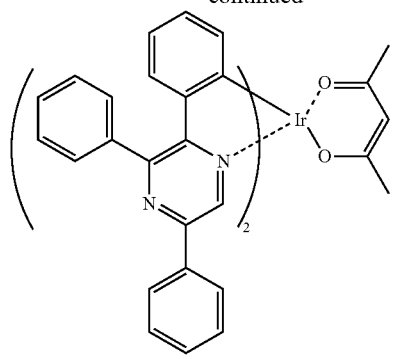
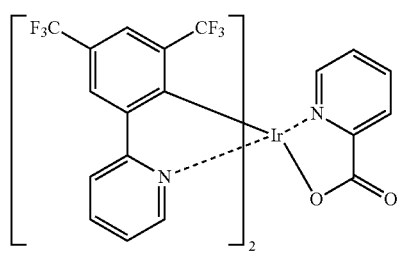
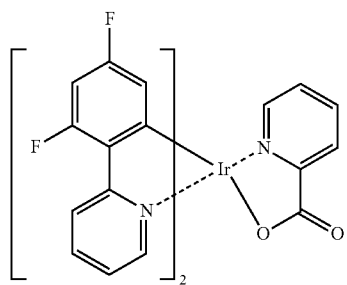
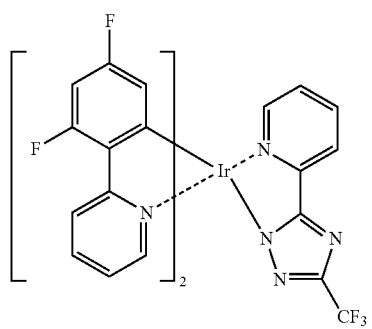
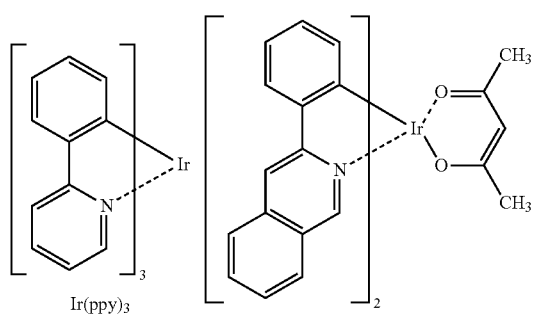
Ir(ppy)₃
74
-continued
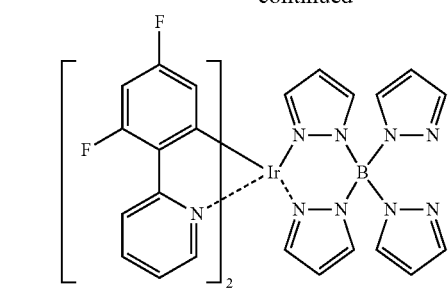
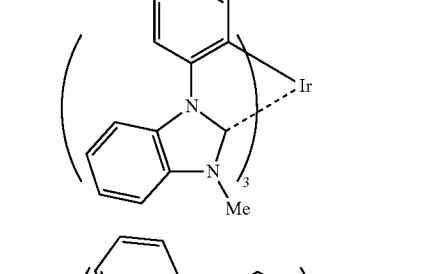
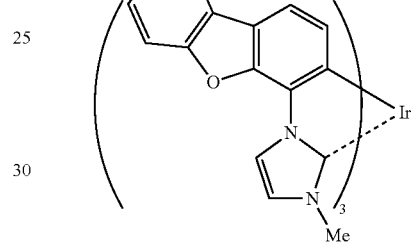
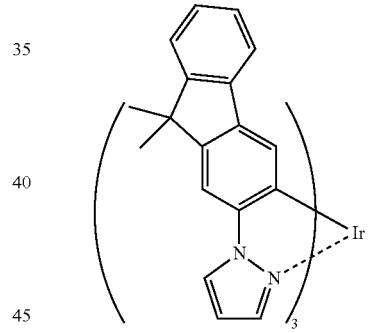
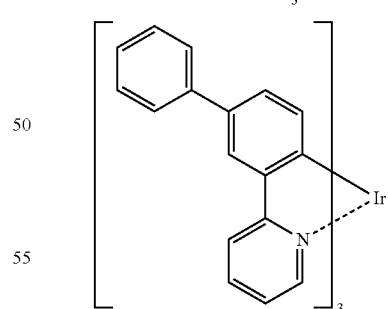
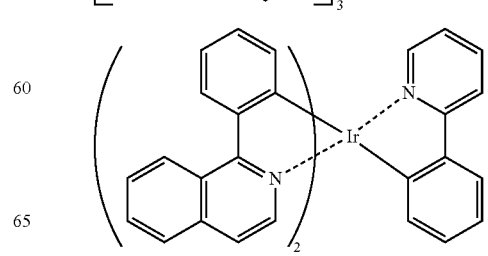

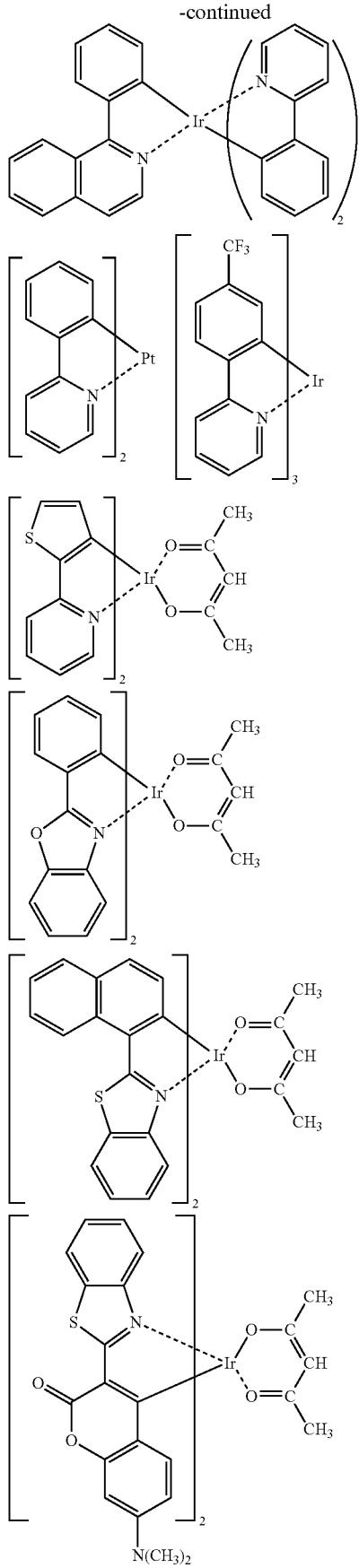
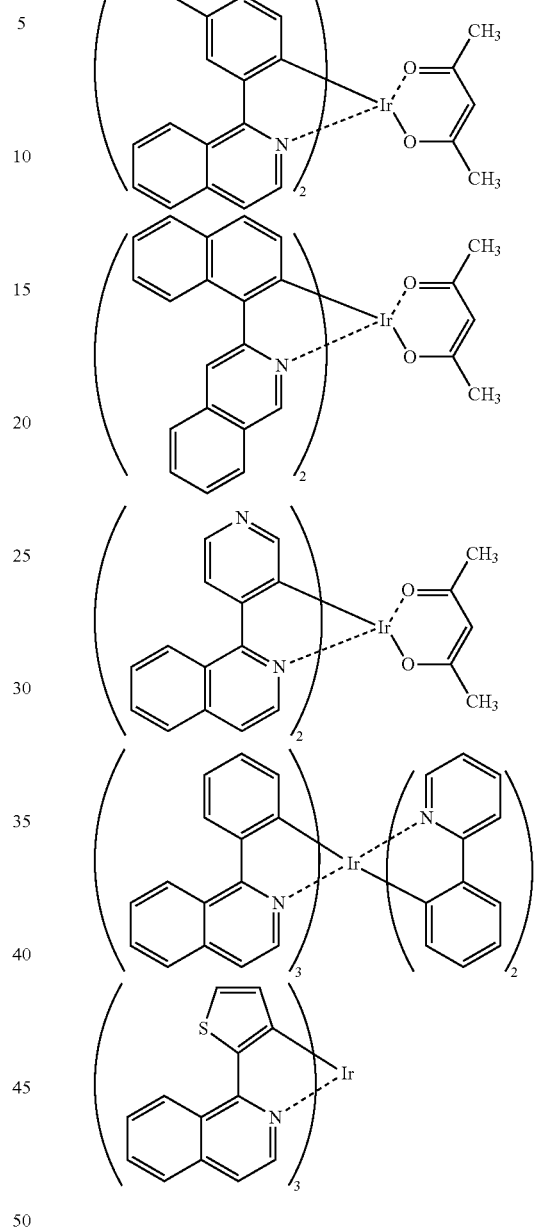

The phosphorescent host is a compound which confines the triplet energy of the phosphorescent dopant efficiently in the light emitting layer to cause the phosphorescent dopant to emit light efficiently. Although the material for organic EL device of the invention is useful as a phosphorescent host, a compound other than the material for organic EL device of the invention may be used as the phosphorescent host according to the use of the device.

The material for organic EL device of the invention and the compound other than it may be combinedly used in the same light emitting layer as the phosphorescent host material. If two or more light emitting layers are formed, the material for organic EL device of the invention can be used in one of the light emitting layers as the phosphorescent host material and a compound other than the material for organic EL device of the invention can be used in another light emitting layer as the phosphorescent host material. The material for organic EL device of the invention may be used in an organic layer other than the light emitting layer. In this case, a compound other than the material for organic EL device of the invention may be used as a phosphorescent host of the light emitting layer.

Examples of the preferred phosphorescent host other than the material for organic EL device of the invention include a carbazole derivative, a triazole derivative, a oxazole derivative, an oxadiazole derivative, an imidazole derivative, a polyarylalkane derivative, a pyrazoline derivative, a pyrazolone derivative, a phenylenediamine derivative, an arylamine derivative, an amino-substituted chalcone derivative, a styrylanthracene derivative, a fluorenone derivative, a hydrazone derivative, a stilbene derivative, a silazane derivative, an aromatic tertiary amine compound, a styrylamine compound, an aromatic methylidene compound, a porphyrin compound, an anthraquinodimethane derivative, an anthrone derivative, a diphenylquinone derivative, a thiopyran dioxide derivative, a carbodiimide derivative, a fluorenylidenemethane derivative, a distyrylpyrazine derivative, a tetracarboxylic anhydride of fused ring such as naphthalene and perylene, a phthalocyanine derivative, a metal complex of 8-quinolinol derivative, metal phthalocyanine, metal complexes having a ligand such as benzoxazole and benzothiazole, an electroconductive oligomer, such as a polysilane compound, a poly(N-vinyl-carbazole) derivative, an aniline copolymer, thiophene oligomer, and a polythiophene, and a polymer such as a polythiophene derivative, a polyphenylene derivative, a polyphenylenevinylene derivative, and a polyfluorene derivative. These phosphorescent hosts may be used alone or in combination of two or more. Examples thereof are shown below.

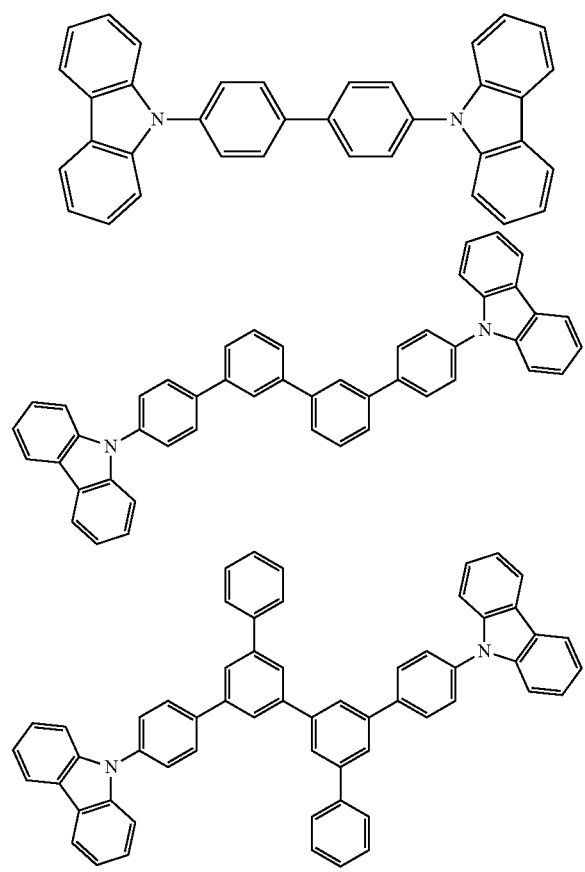

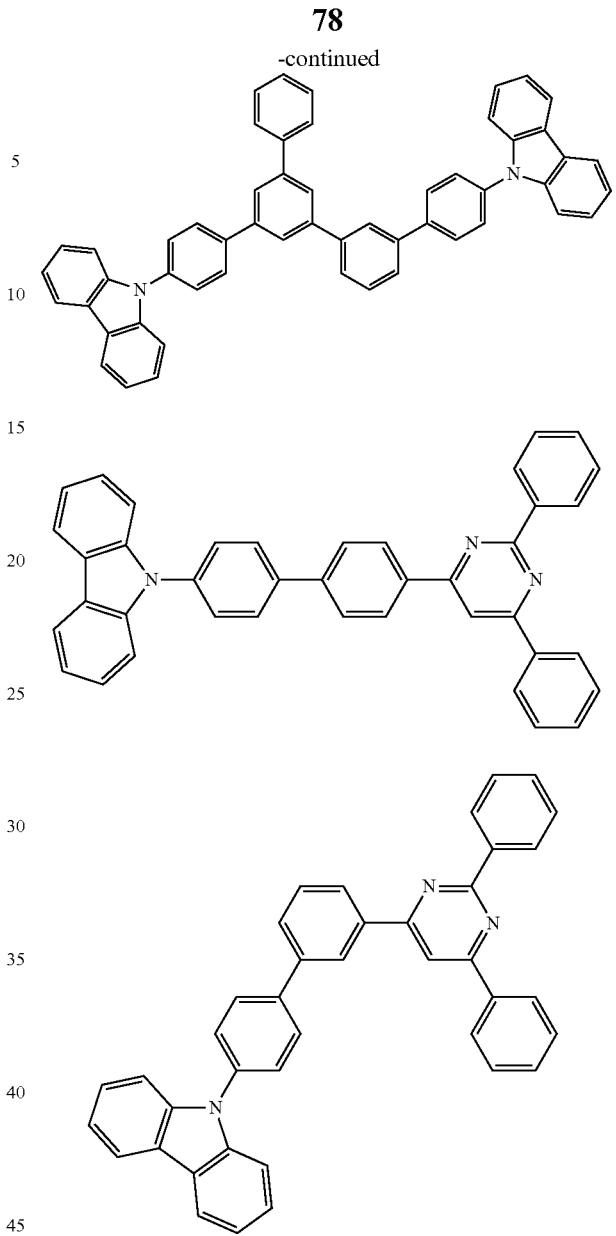

The organic EL device of the invention may comprise a light emitting layer comprising a fluorescent material, i.e., a fluorescent emitting layer. The fluorescent emitting layer may be formed from a known fluorescent material, for example, at least one material selected from an anthracene derivative, a fluoranthene derivative, a styrylamine derivative, and an arylamine derivative, with the anthracene derivative and the arylamine derivative being more preferred. In particular, the anthracene derivative is preferably used as the host material and the arylamine derivative is preferably used as the dopant. The materials described in WO 2010/134350 and WO 2010/134352 are preferably used. The material for organic EL device of the invention may be used in a fluorescent emitting layer as a fluorescent emitting material or a host material.

The anthracene derivative for use as a fluorescent material has preferably 26 to 100, more preferably 26 to 80, and still more preferably 26 to 60 ring carbon atoms. The anthracene derivative is preferably represented by formula (10):

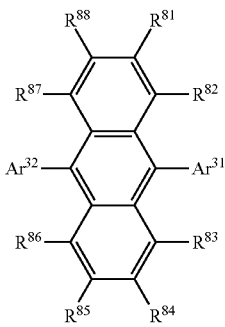

(10)

wherein:
each of $Ar^{31}$ and $Ar^{32}$ independently represents a substituted or unsubstituted aryl group having 6 to 50 ring carbon atoms or a substituted or unsubstituted heterocyclic group having 5 to 50 ring atoms; and
each of $R^{81}$ to $R^{88}$ independently represents a hydrogen atom, a substituted or unsubstituted aryl group having 6 to 50 ring carbon atoms, a substituted or unsubstituted heterocyclic group having 5 to 50 ring atoms, a substituted or unsubstituted alkyl group having 1 to 50 carbon atoms, a substituted or unsubstituted alkoxy group having 1 to 50 carbon atoms, a substituted or unsubstituted aralkyl group having 7 to 50 carbon atoms, a substituted or unsubstituted aryloxy group having 6 to 50 ring carbon atoms, a substituted or unsubstituted arylthio group having 6 to 50 ring carbon atoms, a substituted or unsubstituted alkoxycarbonyl group having 2 to 50 carbon atoms, a substituted or unsubstituted silyl group, a carboxyl group, a halogen atom, a cyano group, a nitro group, or a hydroxyl group.

The aryl group having 6 to 50 ring carbon atoms is preferably an aryl group having 6 to 40 ring carbon atoms and more preferably an aryl group having 6 to 30 ring carbon atoms.

The heterocyclic group having 5 to 50 ring atoms is preferably a heterocyclic group having 5 to 40 ring atoms and more preferably a heterocyclic group having 5 to 30 ring atoms.

The alkyl group having 1 to 50 carbon atoms is preferably an alkyl group having 1 to 30 carbon atoms, more preferably an alkyl group having 1 to 10 carbon atoms, and still more preferably an alkyl group having 1 to 5 carbon atoms.

The alkoxy group having 1 to 50 carbon atoms is preferably an alkoxy group having 1 to 30 carbon atoms, more preferably an alkoxy group having 1 to 10 carbon atoms, and still more preferably an alkoxy group having 1 to 5 carbon atoms.

The aralkyl group having 7 to 50 carbon atoms is preferably an aralkyl group having 7 to 30 carbon atoms and more preferably an aralkyl group having 7 to 20 carbon atoms.

The aryloxy group having 6 to 50 ring carbon atoms is preferably an aryloxy group having 6 to 40 ring carbon atoms and more preferably an aryloxy group having 6 to 30 ring carbon atoms.

The arylthio group having 6 to 50 ring carbon atoms is preferably an arylthio group having 6 to 40 ring carbon atoms and more preferably an arylthio group having 6 to 30 ring carbon atoms.

The alkoxycarbonyl group having 2 to 50 carbon atoms is preferably an alkoxycarbonyl group having 2 to 30 carbon atoms, more preferably an alkoxycarbonyl group having 2 to 10 carbon atoms, and still more preferably an alkoxycarbonyl group having 2 to 5 carbon atoms.

Examples of the halogen atom include a fluorine atom, a chlorine atom, and a bromine atom.

Each of $Ar^{31}$ and $Ar^{32}$ particularly preferably represents a substituted or unsubstituted aryl group having 6 to 50 ring carbon atoms.

The anthracene derivative represented by formula (10) is preferably represented by formula (10-1):

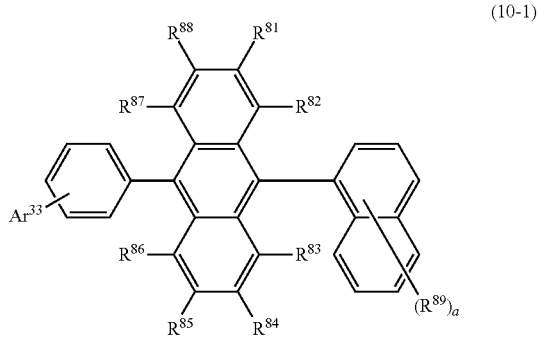

(10-1)

wherein:
$Ar^{33}$ represents a substituted or unsubstituted aryl group having 6 to 50 ring carbon atoms or a substituted or unsubstituted heterocyclic group having 5 to 50 ring atoms;
each of $R^{81}$ to $R^{88}$ is as defined above;
$R^{89}$ is defined in the same manner as in $R^{81}$ to $R^{88}$; and
a is an integer of 1 to 7.

Preferred examples of $R^{81}$ to $R^{88}$ are as described above. Preferred examples of $R^{89}$ are the same as those of $R^{81}$ to $R^{88}$. The subscript a is preferably an integer of 1 to 3 and more preferably 1 or 2.

The aryl group having 6 to 50 ring carbon atoms for $Ar^{33}$ is preferably an aryl group having 6 to 40 ring carbon atoms, more preferably an aryl group having 6 to 30 ring carbon atoms, still more preferably an aryl group having 6 to 20 ring carbon atoms, and particularly preferably an aryl group having 6 to 12 ring carbon atoms.

The arylamine derivative for use as the fluorescent material is preferably an aryldiamine derivative, more preferably an aryldiamine derivative comprising a pyrene skeleton, and still more preferably an aryldiamine derivative having a pyrene skeleton and a dibenzofuran skeleton.

The aryldiamine derivative is preferably an aryldiamine derivative represented by formula (11):

(11)

wherein:
each of $Ar^{34}$ to $Ar^{37}$ independently represents a substituted or unsubstituted aryl group having 6 to 50 ring carbon atoms or a substituted or unsubstituted heteroaryl group having 5 to 50 ring atoms; and
$L^{21}$ represents a substituted or unsubstituted arylene group having 6 to 50 ring carbon atoms or a substituted or unsubstituted heteroarylene group having 5 to 50 ring atoms.

The aryl group having 6 to 50 ring carbon atoms is preferably an aryl group having 6 to 30 ring carbon atoms, more preferably an aryl group having 6 to 20 ring carbon atoms, still more preferably an aryl group having 6 to 12 ring carbon atoms, with a phenyl group and a naphthyl group being particularly preferred.

The heteroaryl group having 5 to 50 ring atoms is preferably a heteroaryl group having 5 to 40 ring atoms, more preferably a heteroaryl group having 5 to 30 ring atoms, and still more preferably a heteroaryl group having 5 to 20 ring atoms, for example, a carbazolyl group, a dibenzofuranyl group and dibenzothiophenyl group, with a dibenzofuranyl group being preferred. Preferred examples of the substituent for the heteroaryl group include an aryl group having 6 to 30, preferably 6 to 20, and more preferably 6 to 12 ring carbon atoms, with a phenyl group and a naphthyl group being more preferred.

The arylene group having 6 to 50 ring carbon atoms is preferably an arylene group having 6 to 40 ring carbon atoms, more preferably an arylene group having 6 to 30 ring carbon atoms, and still more preferably an arylene group having 6 to 20 ring carbon atoms, with a pyrenyl group being particularly preferred.

A double host (host/co-host) system may be used for the light emitting layer. For example, to control the carrier balance in the light emitting layer, an electron transporting host and a hole transporting host may be combinedly used.

The light emitting layer may be also made into a double dopant layer. When two or more kinds of dopant materials having high quantum yield are used in the light emitting layer, each dopant emits light with its own color. For example, a yellow light emitting layer can be obtained by co-depositing a host, a red-emitting dopant and a green-emitting dopant.

The light emitting layer may further comprise a hole transporting material, a electron transporting material, and a polymer binder, if necessary.

The thickness of the light emitting layer is preferably 5 to 50 nm, more preferably 7 to 50 nm and most preferably 10 to 50 nm. If less than 5 nm, the light emitting layer may be difficult to form and the color may be difficult to control. If exceeding 50 nm, the driving voltage is likely to increase.

Electron-Donating Dopant

The organic EL device of the present invention preferably comprises an electron-donating dopant at an interfacial region between the cathode and the emitting unit. With such a construction, the organic EL device has an improved luminance and an elongated lifetime. The electron-donating dopant comprises a metal having a work function of 3.8 eV or less and examples thereof include at least one selected from alkali metal, alkali metal complex, alkali metal compound, alkaline earth metal, alkaline earth metal complex, alkaline earth metal compound, rare earth metal, rare earth metal complex, and rare earth metal compound.

Examples of the alkali metal include Na (work function: 2.36 eV), K (work function: 2.28 eV), Rb (work function: 2.16 eV), and Cs (work function: 1.95 eV), with those having a work function of 2.9 eV or less being particularly preferred. Of the above, preferred are K, Rb, and Cs, more preferred are Rb and Cs, and most preferred is Cs. Examples of the alkaline earth metal include Ca (work function: 2.9 eV), Sr (work function: 2.0 to 2.5 eV), and Ba (work function: 2.52 eV), with those having a work function of 2.9 eV or less being particularly preferred. Examples of the rare earth metal include Sc, Y, Ce, Tb, and Yb, with those having a work function of 2.9 eV or less being particularly preferred.

Examples of the alkali metal compound include alkali oxide, such as $Li_2O$, $Cs_2O$, $K_2O$, and alkali halide, such as LiF, NaF, CsF, and KF, with LiF, $Li_2O$, and NaF being preferred. Examples of the alkaline earth metal compound include BaO, SrO, CaO, and mixture thereof, such as $Ba_xSr_{1-x}O$ (0<x<1) and $Ba_xCA_{1-x}O$ (0<x<1), with BaO, SrO, and CaO being preferred. Examples of the rare earth metal compound include $YbF_3$, $ScF_3$, $ScO_3$, $Y_2O_3$, $Ce_2O_3$, $GdF_3$, and $TbF_3$, with $YbF_3$, $ScF_3$, and $ThF_3$ being preferred.

Examples of the alkali metal complex, alkaline earth metal complex, and rare earth metal are not particularly limited as long as containing at least one metal ion selected from alkali metal ions, alkaline earth metal ions, rare earth metal ions, respectively. The ligand is preferably, but not limited to, quinolinol, benzoquinolinol, acridinol, phenanthridinol, hydroxyphenyloxazole, hydroxyphenylthiazole, hydroxydiaryloxadiazole, hydroxydiarylthiadiazole, hydroxyphenylpyridine, hydroxyphenylbenzimidazole, hydroxybenzotriazole, hydroxyfulborane, bipyridyl, phenanthroline, phthalocyanine, porphyrin, cyclopentadiene, β-diketones, azomethines, and derivative thereof.

The electron-donating dopant is added to the interfacial region preferably into a form of layer or island. The electron-donating dopant is added preferably by co-depositing the electron-donating dopant with the organic compound (light emitting material, electron injecting material) for forming the interfacial region by a resistance heating deposition method, thereby dispersing the electron-donating dopant into the organic material. The disperse concentration expressed by the molar ratio of the organic material and the electron-donating dopant is 100:1 to 1:100 and preferably 5:1 to 1:5.

When the electron-donating dopant is formed into a form of layer, a light emitting material or an electron injecting material is made into a layer which serves as an organic layer in the interface, and then, the electron-donating dopant alone is deposited by a resistance heating deposition method into a layer having a thickness preferably 0.1 to 15 nm. When the electron-donating dopant is formed into a form of island, a light emitting material or an electron injecting material is made into a form of island which serves as an organic layer in the interface, and then, the electron-donating dopant alone is deposited by a resistance heating deposition method into a form of island having a thickness preferably 0.05 to 1 nm.

The molar ratio of the main component and the electron-donating dopant in the organic electroluminescence device of the invention is preferably 5:1 to 1:5 and more preferably 2:1 to 1:2.

Electron Transporting Layer

The electron transporting layer is an organic layer disposed between the light emitting layer and the cathode and transports electrons from the cathode to the light emitting layer. If two or more electron transporting layers are provided, the organic layer closer to the cathode may be called an electron injecting layer in some cases. The electron injecting layer injects electrons from the cathode to the organic layer unit efficiently. The material for organic EL device of the invention may be used in the electron transporting layer as the electron transporting material.

An aromatic heterocyclic compound having one or more heteroatoms in a molecule thereof is preferably used as an electron transporting material used in the electron transporting layer, and a nitrogen-containing ring derivative is particularly preferred. In addition, the nitrogen-containing ring derivative is preferably an aromatic ring compound having a nitrogen-containing, 6- or 5-membered ring, or a fused aromatic ring compound having a nitrogen-containing, 6- or 5-membered ring.

The nitrogen-containing ring derivative is preferably, for example, a metal chelate complex of a nitrogen-containing ring represented by formula (A):

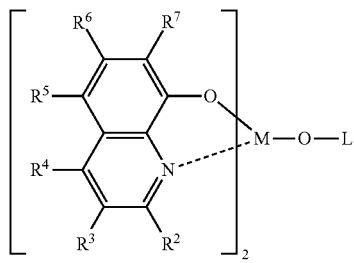

(A)

wherein each of $R^2$ to $R^7$ independently represents a hydrogen atom, a heavy hydrogen atom, a halogen atom, a hydroxyl group, an amino group, a hydrocarbon group having 1 to 40 carbon atoms, an alkoxy group having 1 to 40 carbon atoms, an aryloxy group having 6 to 50 carbon atoms, an alkoxycarbonyl group, or an aromatic heterocyclic group having 5 to 50 ring carbon atoms, each being optionally substituted.

The halogen atom may include fluorine, chlorine, bromine, and iodine.

The substituted amino group may include an alkylamino group, an arylamino group, and an aralkylamino group.

The alkylamino group and the aralkylamino group are represented by $—NQ^1Q^2$. Each of $Q^1$ and $Q^2$ independently represents an alkyl group having 1 to 20 carbon atoms or an aralkyl group having 1 to 20 carbon atoms. One of $Q^1$ and $Q^2$ may be a hydrogen atom or a heavy hydrogen atom.

The arylamino group is represented by $—NAr^1Ar^2$, wherein each of $Ar^1$ and $Ar^2$ independently represents a non-fused aromatic hydrocarbon groups or a fused aromatic hydrocarbon groups, each having 6 to 50 carbon atoms. One of $Ar^1$ and $Ar^2$ may be a hydrogen atom or a heavy hydrogen atom.

Examples of the hydrocarbon group having 1 to 40 carbon atoms include an alkyl group, an alkenyl group, a cycloalkyl group, an aryl group, and an aralkyl group.

The alkoxycarbonyl group is represented by $—COOY'$, wherein $Y'$ is an alkyl group having 1 to 20 carbon atoms.

M is aluminum (Al), gallium (Ga), or indium (In), with In being preferred.

L is a group represented by formula (A') or (A"):

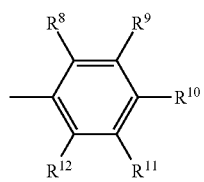

(A')

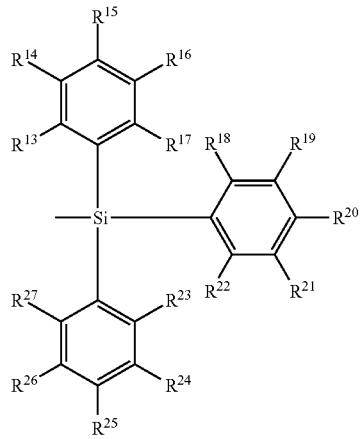

(A")

wherein each $R^8$ to $R^{12}$ independently represents a hydrogen atom, a heavy hydrogen atom or a substituted or unsubstituted hydrocarbon group having 1 to 40 carbon atoms. Two adjacent groups may form a ring structure. Each of $R^{13}$ to $R^{27}$ independently represents a hydrogen atom, a heavy hydrogen atom or a substituted or unsubstituted hydrocarbon group having 1 to 40 carbon atoms. Two adjacent groups may form a ring structure.

Examples of the hydrocarbon group having 1 to 40 carbon atoms for $R^8$ to $R^{12}$ and $R^{13}$ to $R^{27}$ in formulae (A') and (A") are the same as those described above with respect to $R^2$ to $R^7$ of formula (A). Examples of the divalent group formed by two adjacent groups of $R^3$ to $R^{12}$ and $R^{13}$ to $R^{27}$ which completes the ring structure include a tetramethylene group, a pentamethylene group, a hexamethylene group, a diphenylmethane-2,2'-diyl group, a diphenylethane-3,3'-diyl group, and a diphenylpropane-4,4'-diyl group.

The electron transporting compound for use in the electron transporting layer is preferably a metal complex including 8-hydroxyquinoline or its derivative, an oxadiazole derivative, or a nitrogen-containing heterocyclic derivative. Examples of the metal complex including 8-hydroxyquinoline or its derivative include a metal chelate oxinoid including a chelated oxine (generally, 8-quinolinol or 8-hydroxyquinoline), for example, tris(8-quinolinol)aluminum. Examples of the oxadiazole derivative are shown below:

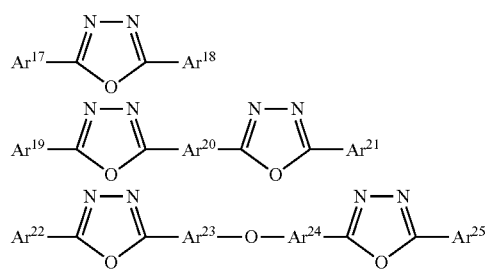

wherein each of $Ar^{17}$, $Ar^{18}$, $Ar^{19}$, $Ar^{21}$, $Ar^{22}$, and $Ar^{25}$ is a substituted or unsubstituted aromatic hydrocarbon group or a substituted or unsubstituted fused aromatic hydrocarbon group each having 6 to 50 carbon atoms, and $Ar^{17}$ and $Ar^{18}$, $Ar^{19}$ and $Ar^{21}$, and $Ar^{22}$ and $Ar^{25}$ may be the same or different. Examples of the aromatic hydrocarbon group and the fused aromatic hydrocarbon group include a phenyl group, a naphthyl group, a biphenyl group, an anthranyl group, a perylenyl group, and a pyrenyl group. The optional substituent may be an alkyl group having 1 to 10 carbon atoms, an alkoxyl group having 1 to 10 carbon atoms or a cyano group.

Each of $Ar^{20}$, $Ar^{23}$, and $Ar^{24}$ is a substituted or unsubstituted bivalent aromatic hydrocarbon group or a substituted or unsubstituted bivalent fused aromatic hydrocarbon group each having 6 to 50 carbon atoms, and $Ar^{23}$ and $Ar^{24}$ may be the same or different. Examples of the bivalent aromatic hydrocarbon group or the bivalent fused aromatic hydrocarbon group include a phenylene group, a naphthylene group, a biphenylene group, an anthranylene group, a perylenylene group, and a pyrenylene group. The optional substituent may be an alkyl group having 1 to 10 carbon atoms, an alkoxyl group having 1 to 10 carbon atoms or a cyano group.

Electron transporting compounds which have a good thin film-forming property are preferably used. Examples of the electron transporting compound are shown below.

bered ring or a 6-membered ring. If two or more nitrogen atoms are included, the nitrogen-containing aromatic polycyclic compound preferably has a skeleton of a combination of (B) and (C) or a combination of (B) and (D):

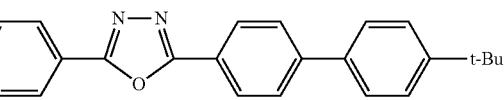

(D)

The nitrogen-containing group of the nitrogen-containing aromatic polycyclic compound is selected, for example, from the nitrogen-containing heterocyclic groups shown below:

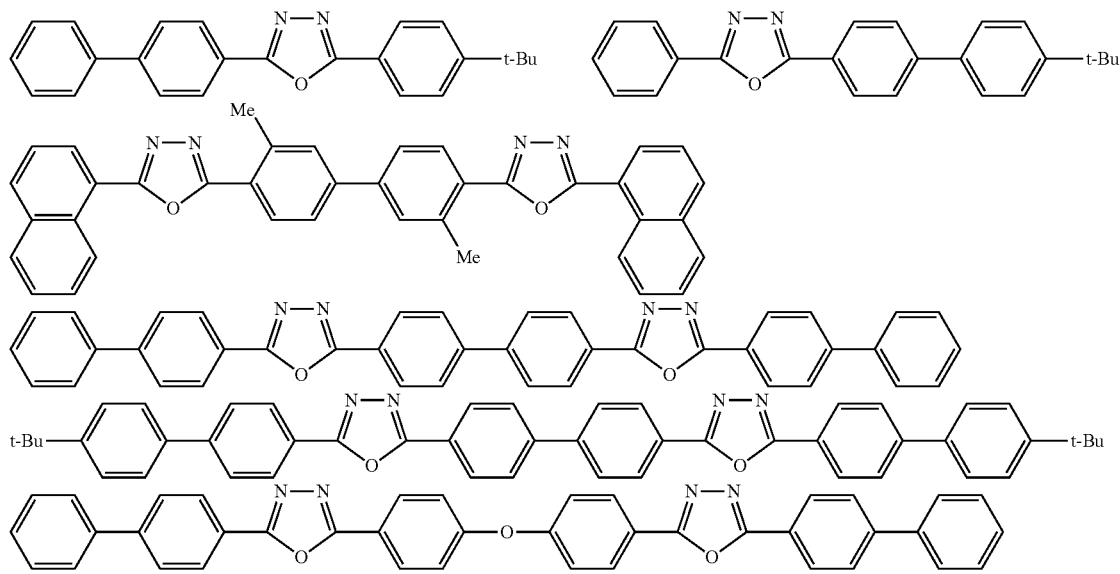

Examples of the nitrogen-containing heterocyclic derivative for use as the electron transporting compound include a nitrogen-containing heterocyclic derivative having the following formulae but exclusive of metal complex, for example, a compound having a 5- or 6-membered ring which has the skeleton represented by formula (B) or having the structure represented by formula (C):

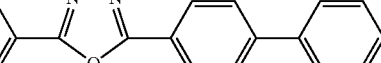

(B)

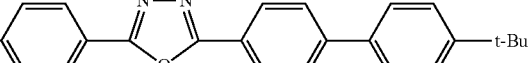

(C)

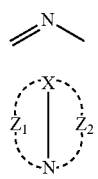

wherein X is a carbon atom or a nitrogen atom and each of $Z_1$ and $Z_2$ independently represents a group of atoms for completing the nitrogen-containing heterocyclic ring.

The nitrogen-containing heterocyclic derivative is more preferably an organic compound which has a nitrogen-containing aromatic polycyclic ring comprising a 5-mem-

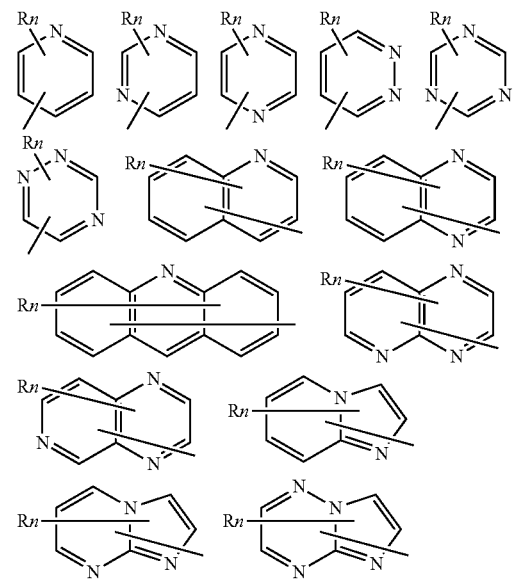

-continued

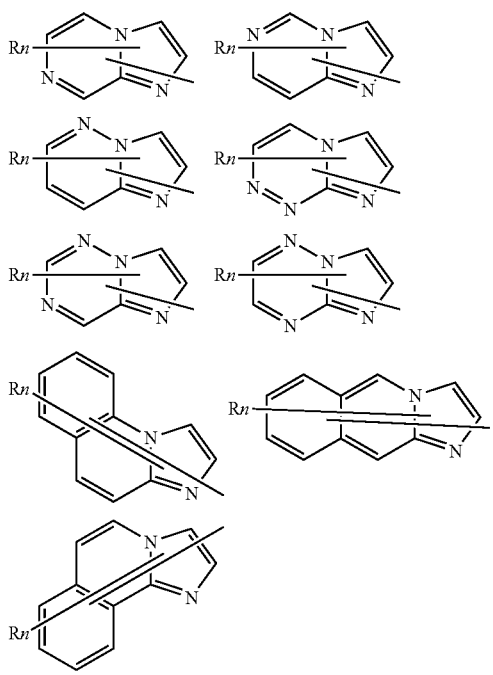

wherein R is an aromatic hydrocarbon group or a fused aromatic hydrocarbon group each having 6 to 40 carbon atoms, an aromatic heterocyclic group or a fused aromatic heterocyclic group each having 3 to 40 carbon atoms, an alkyl atoms; and n is an integer of 0 to 5. If n is an integer of 2 or more, groups R may be the same or different.

More preferred is a nitrogen-containing heterocyclic derivative represented by formula (D1):

wherein HAr is a substitute or unsubstituted nitrogen-containing heterocyclic group having 3 to 40 carbon atoms; $L^1$ is a single bond, a substituted or unsubstituted aromatic hydrocarbon group or fused aromatic hydrocarbon group each having 6 to 40 carbon atoms, or a substituted or unsubstituted aromatic heterocyclic group or fused aromatic heterocyclic group each having 3 to 40 carbon atoms; $Ar^1$ is a substitute or unsubstituted divalent aromatic hydrocarbon group having 6 to 40 carbon atoms; and $Ar^2$ is a substitute or unsubstituted aromatic hydrocarbon group or fused aromatic hydrocarbon group each having 6 to 40 carbon atoms or a substituted or unsubstituted aromatic heterocyclic group or fused aromatic heterocyclic group each having 3 to 40 carbon atoms.

HAr is selected, for example, from the following groups:

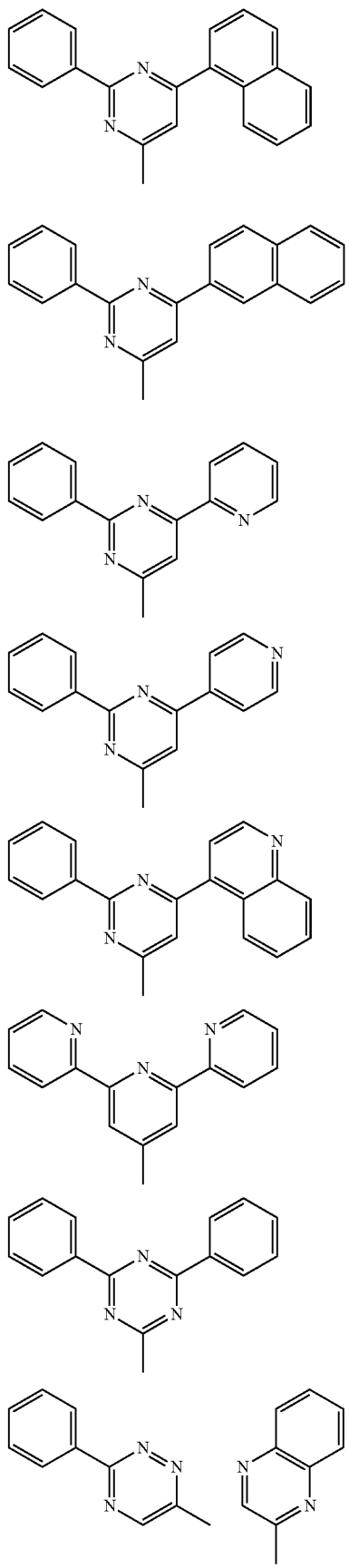

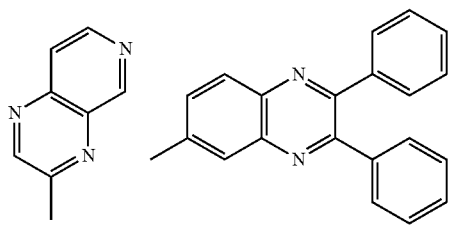
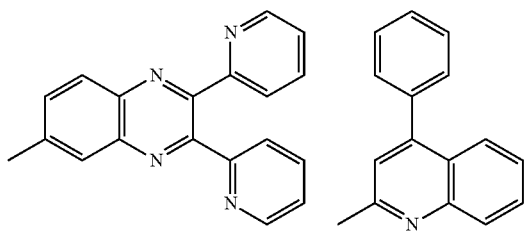
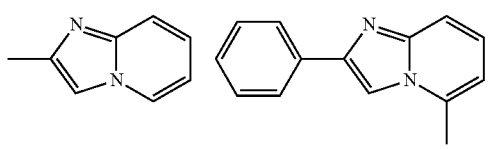
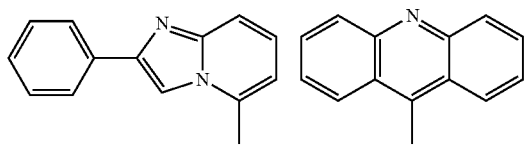
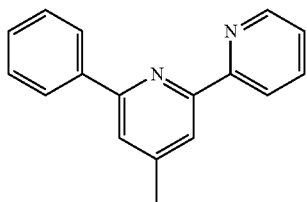

L¹ is selected, for example, from the following groups:

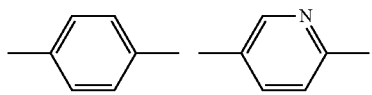

Ar¹ is selected, for example, from the following arylanthranyl group represented by formula (D2) or (D3):

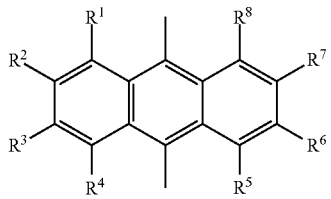

(D2)

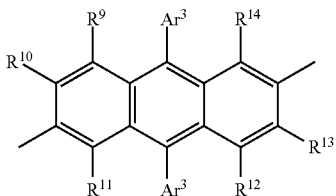

(D3)

wherein $R^1$ to $R^{14}$ are each independently a hydrogen atom, a halogen atom, an alkyl group having 1 to 20 carbon atoms, an alkoxy group having 1 to 20 carbon atoms, an aryloxy group having 6 to 40 carbon atoms, a substituted or unsubstituted aromatic hydrocarbon group or fused aromatic hydrocarbon group each having 6 to 40 carbon atoms, or a substituted or unsubstituted aromatic heterocyclic group or fused aromatic heterocyclic group each having 3 to 40 carbon atoms; and $Ar^3$ is a substituted or unsubstituted aromatic hydrocarbon group or fused aromatic hydrocarbon group each having 6 to 40 carbon atoms or a substituted or unsubstituted aromatic heterocyclic group or fused aromatic heterocyclic group each having 3 to 40 carbon atoms. Each of $R^1$ to $R^8$ may be selected from a hydrogen atom and a heavy hydrogen atom.

$Ar^2$ is selected, for example, from the following groups:

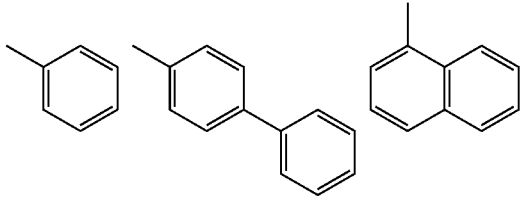
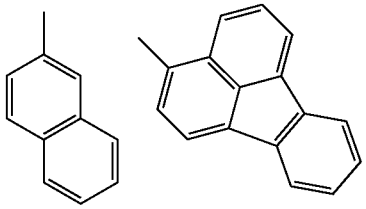
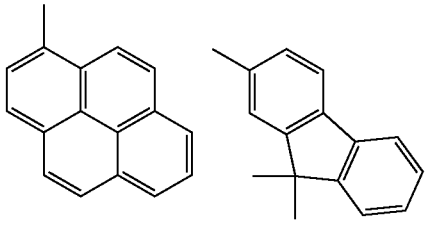

In addition, the following compound is preferably used as the nitrogen-containing aromatic polycyclic compound for use as the electron transporting compound:

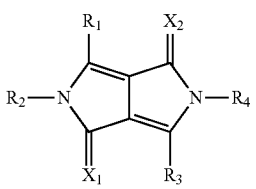

(D4)

wherein $R_1$ to $R_4$ each independently represent a hydrogen atom, a heavy hydrogen atom, a substituted or unsubstituted aliphatic group having 1 to 20 carbon atoms, a substituted or unsubstituted alicyclic group having 3 to 20 carbon atoms, a substituted or unsubstituted aromatic ring group having 6 to 50 carbon atoms, or a substituted or unsubstituted heterocyclic group having 3 to 50 carbon atoms; $X_1$ and $X_2$ each independently represent an oxygen atom, a sulfur atom, or dicyanomethylene group.

Further, the following compound is also suitable as the electron transporting compound:

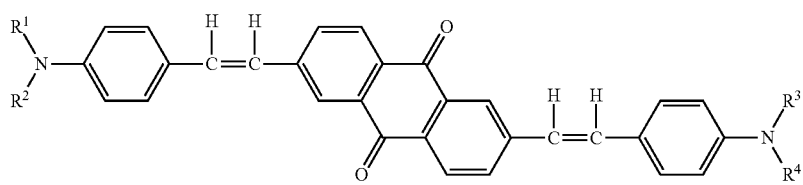
(D5)

wherein $R^1$, $R^2$, $R^3$, and $R^4$ may be the same or different and each represents an aromatic hydrocarbon group or a fused aromatic hydrocarbon group each represented by formula (D6):

(D6)

wherein $R^5$, $R^6$, $R^7$, $R^8$, and $R^9$ may be the same or different and each represents a hydrogen atom, a heavy hydrogen atom, a saturated or unsaturated alkoxyl group having 1 to 20 carbon atoms, a saturated or unsaturated alkyl group having 1 to 20 carbon atoms, an amino group, or an alkylamino group having 1 to 20 carbon atoms. At least one of $R^5$, $R^6$, $R^7$, $R^8$, and $R^9$ represents a group other than a hydrogen atom and a heavy hydrogen atom.

Further, a polymer including the nitrogen-containing heterocyclic group or the nitrogen-containing heterocyclic derivative is also usable as the electron transporting compound.

The electron transporting layer in the organic EL device of the invention preferably comprises at least one compound selected from the nitrogen-containing heterocyclic derivatives represented by formulae (E) to (G):

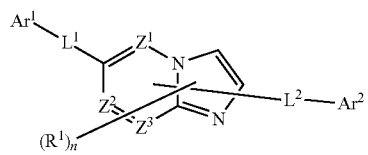
(E)

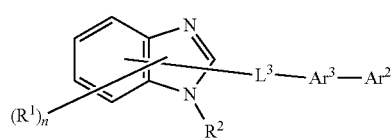
(F)

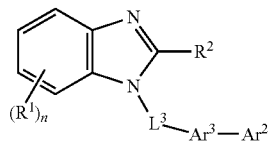
(G)

wherein $Z^1$, $Z^2$, and $Z^3$ each independently represent a nitrogen atom or a carbon atom;

$R^1$ and $R^2$ each independently represent a substituted or unsubstituted aryl group having 6 to 50 ring carbon atoms, a substituted or unsubstituted heteroaryl group having 5 to 50 ring atoms, a substituted or unsubstituted alkyl group having 1 to 20 carbon atoms, a substituted or unsubstituted haloalkyl group having 1 to 20 carbon atoms, or a substituted or unsubstituted alkoxyl group having 1 to 20 carbon atoms;

n is an integer of 0 to 5, when n is an integer of 2 or more, groups $R^1$ may be the same or different, and adjacent two groups $R^1$ may bond to each other to form a substituted or unsubstituted hydrocarbon ring;

$Ar^1$ represents a substituted or unsubstituted aryl group having 6 to 50 ring carbon atoms or a substituted or unsubstituted heteroaryl group having 5 to 50 ring atoms;

$Ar^2$ represents a hydrogen atom, a substituted or unsubstituted alkyl group having 1 to 20 carbon atoms, a substituted or unsubstituted haloalkyl group having 1 to 20 carbon atoms, a substituted or unsubstituted alkoxyl group having 1 to 20 carbon atoms, a substituted or unsubstituted aryl group having 6 to 50 ring carbon atoms, or a substituted or unsubstituted heteroaryl group having 5 to 50 ring atoms;

provided that one of $Ar^1$ and $Ar^2$ is a substituted or unsubstituted condensed aromatic hydrocarbon ring group having 10 to 50 ring carbon atoms or a substituted or unsubstituted condensed aromatic heterocyclic group having 9 to 50 ring atoms;

$Ar^3$ represents a substituted or unsubstituted arylene group having 6 to 50 ring carbon atoms or a substituted or unsubstituted heteroarylene group having 5 to 50 ring atoms; and $L^1$, $L^2$, and $L^3$ each independently represent a single bond, a substituted or unsubstituted arylene group having 6 to 50 ring carbon atoms or a substituted or unsubstituted divalent condensed aromatic heterocyclic group having 9 to 50 ring atoms.

Examples of the aryl group having 6 to 50 ring carbon atoms include a phenyl group, a naphthyl group, an anthryl group, a phenanthryl group, a naphthacenyl group, a chrysenyl group, pyrenyl group, a biphenyl group, a terphenyl group, a tolyl group, a fluoranthenyl group, and a fluorenyl group.

Examples of the heteroaryl group having 5 to 50 ring atoms include a pyrrolyl group, a furyl group, a thiophenyl group, a silolyl group, a pyridyl group, a quinolyl group, an isoquinolyl group, a benzofuryl group, an imidazolyl group, a pyrimidyl group, a carbazolyl group, a selenophenyl group, an oxadiazolyl group, a triazolyl group, a pyrazinyl group, a pyridazinyl group, a triazinyl group, a quinoxalinyl group, an acridinyl group, an imidazo[1,2-a]pyridinyl group, and an imidazo[1,2-a]pyrimidinyl.

Examples of the alkyl group having 1 to 20 carbon atoms include a methyl group, an ethyl group, a propyl group, a butyl group, a pentyl group, and a hexyl group.

Examples of the haloalkyl group having 1 to 20 carbon atoms include the groups obtained by replacing one or more hydrogen atoms of the alkyl group mentioned above with at least one halogen atom selected from fluorine, chlorine, iodine, and bromine.

Examples of the alkyl moiety of the alkoxyl group having 1 to 20 carbon atoms include the alkyl group mentioned above.

Examples of the arylene groups include the groups obtained by removing one hydrogen atom from the aryl group mentioned above.

Examples of the divalent condensed aromatic heterocyclic group having 9 to 50 ring atoms include the groups obtained by removing one hydrogen atom from the condensed aromatic heterocyclic group mentioned above as the heteroaryl group.

The thickness of the electron transporting layer is preferably, but not particularly limited to, 1 to 100 nm.

Preferred examples of the material for a electron injecting layer optionally formed adjacent to the electron transporting layer include, in addition to the nitrogen-containing ring derivative, an inorganic compound, such as an insulating material and a semiconductor. The electron injecting layer containing the insulating material or the semiconductor effectively prevents the leak of electric current to enhance the electron injecting properties.

The insulating material is preferably at least one metal compound selected from the group consisting of alkali metal chalcogenides, alkaline earth metal chalcogenides, alkali metal halides and alkaline earth metal halides. The alkali metal chalcogenide, etc. mentioned above are preferred because the electron injecting properties of the electron injecting layer are further enhanced. Examples of preferred alkali metal chalcogenide include $Li_2O$, $K_2O$, $Na_2S$, $Na_2Se$ and $Na_2O$, and examples of preferred alkaline earth metal chalcogenide include CaO, BaO, SrO, BeO, BaS and CaSe. Examples of preferred alkali metal halide include LiF, NaF, KF, LiC, KCl and NaCl. Examples of the alkaline earth metal halide include fluorides, such as $CaF_2$, $BaF_2$, $SrF_2$, $MgF_2$ and $BeF_2$, and halides other than fluorides.

Examples of the semiconductor include oxides, nitrides or oxynitrides of at least one element selected from the group consisting of Ba, Ca, Sr, Yb, Al, Ga, In, Li, Na, Cd, Mg, Si, Ta, Sb and Zn. The semiconductor may be used alone or in combination of two or more. The inorganic compound included in the electron injecting layer preferably forms a microcrystalline or amorphous insulating thin film. If the electron injecting layer is formed from such an insulating thin film, the pixel defects, such as dark spots, can be decreased because a more uniform thin film is formed. Examples of such inorganic compound include the alkali metal chalcogenide, the alkaline earth metal chalcogenide, the alkali metal halide and the alkaline earth metal halide.

When using the insulating material or the semiconductor, the thickness of its layer is preferably about 0.1 to 15 nm.

The electron injecting layer in the invention may contain the electron-donating dopant mentioned above.

Hole Transporting Layer

The hole injecting/transporting layer is an organic layer formed between the light emitting layer and the anode and has a function of transporting holes from the anode to the light emitting layer. When the hole transporting layer is formed by two or more layers, the layer closer to the anode may be defined as the hole injecting layer in some cases. The hole injecting layer has a function of efficiently injecting holes from the anode to the organic layer unit. The material for organic EL device of the invention may be used in the hole transporting layer as a hole transporting material.

Another preferred material for the hole transporting layer may include an aromatic amine compound, for example, an aromatic amine derivative represented by formula (H):

wherein:

each of $Ar^1$ to $Ar^4$ represents a substituted or unsubstituted aromatic hydrocarbon group or fused aromatic hydrocarbon group having 6 to 50 ring carbon atoms, a substituted or unsubstituted aromatic heteroaryl group or fused aromatic heteroaryl group having 5 to 50 ring atoms, or a group wherein the aromatic hydrocarbon group or fused aromatic hydrocarbon group is bonded to the aromatic heteroaryl group or fused aromatic heteroaryl group; and L represents a substituted or unsubstituted aromatic hydrocarbon group or fused aromatic hydrocarbon group having 6 to 50 ring carbon atoms or a substituted or unsubstituted aromatic heteroaryl group or fused aromatic heteroaryl group having 5 to 50 ring atoms.

Examples of the compound represented by formula (H) are shown below.

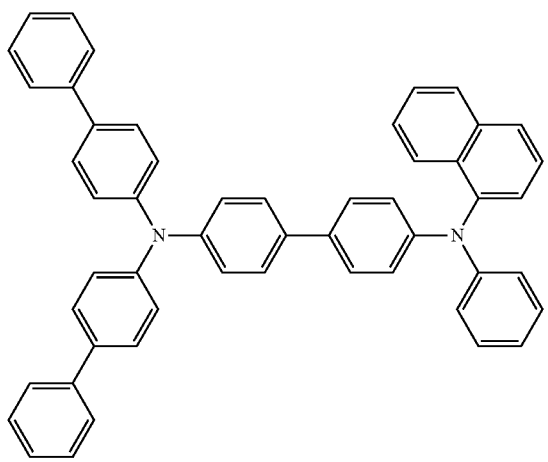

95
-continued
96
-continued
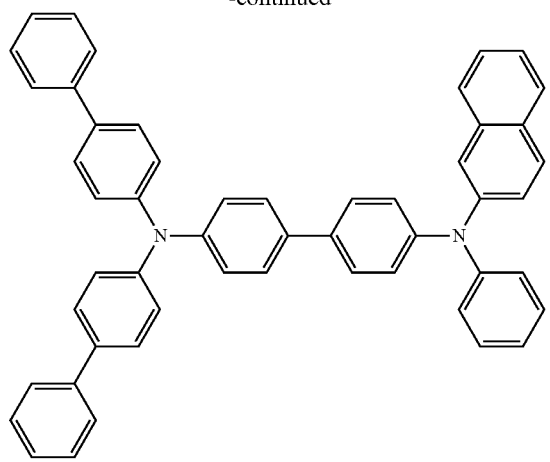
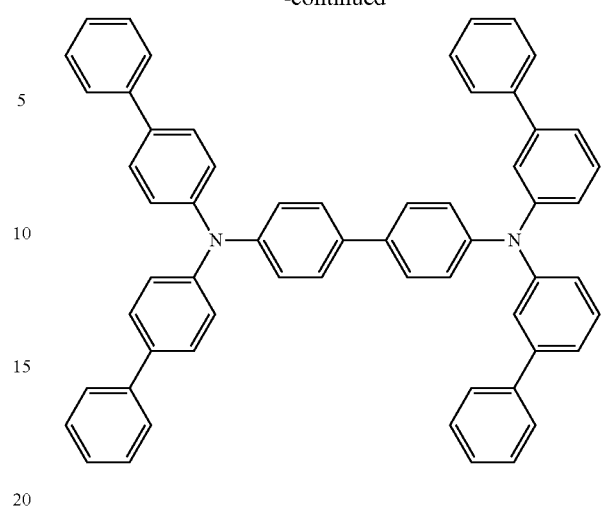
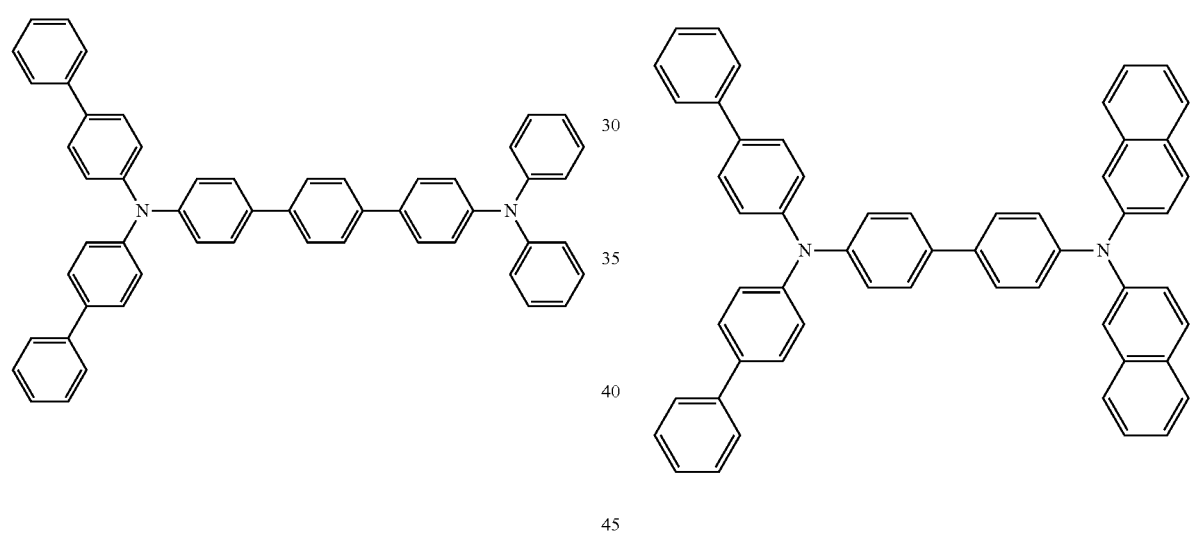
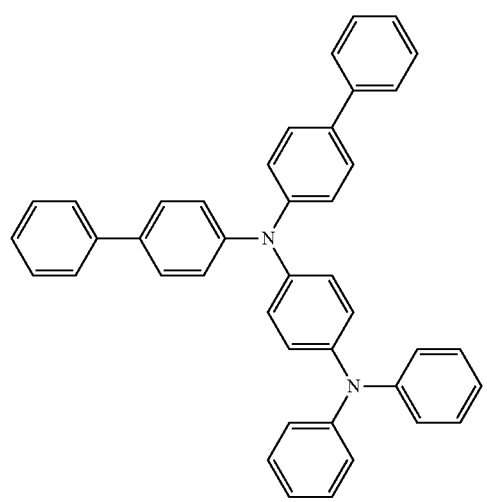

97
-continued
98
-continued
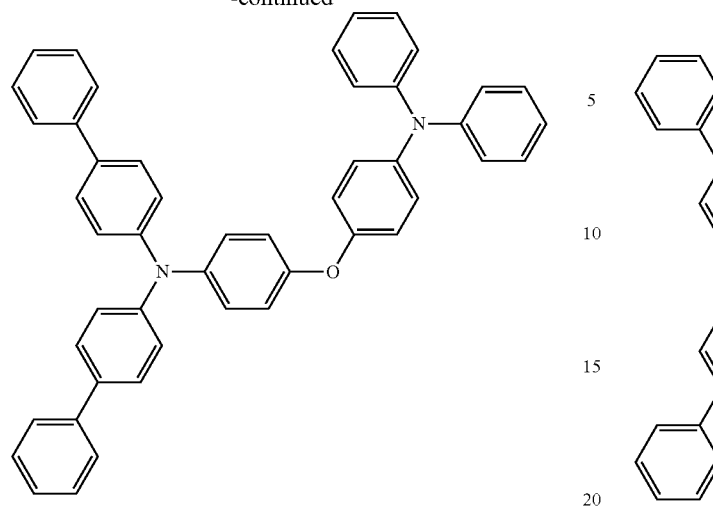
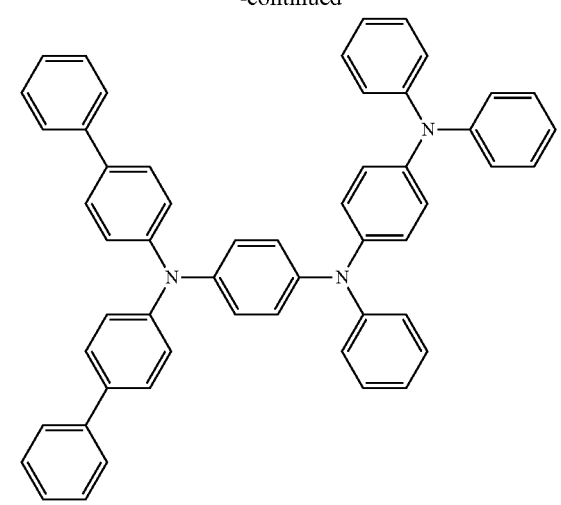
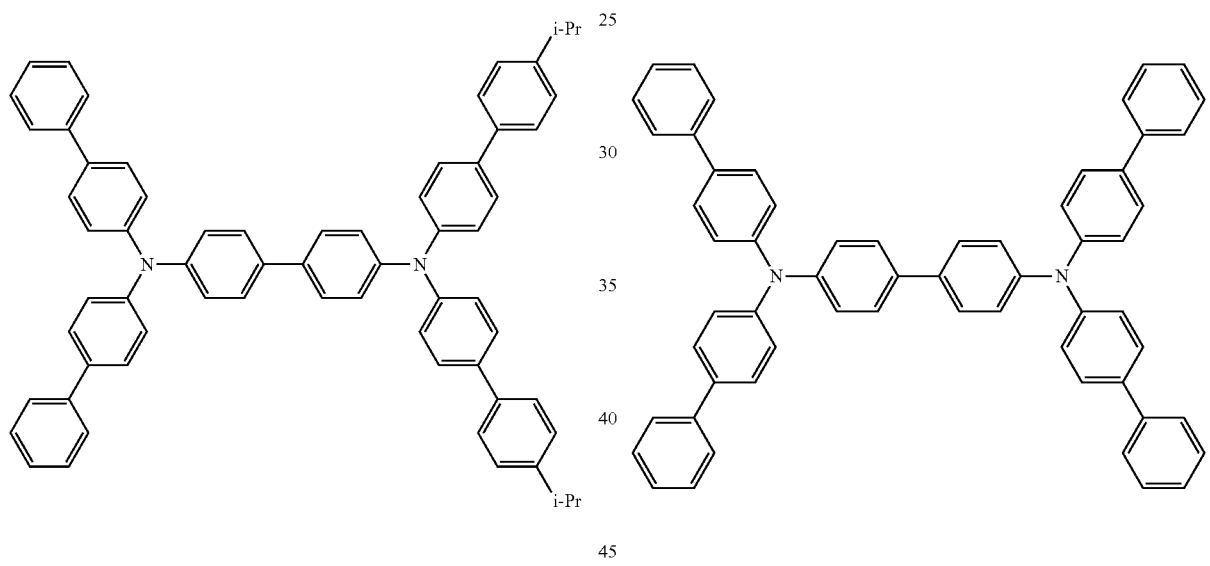
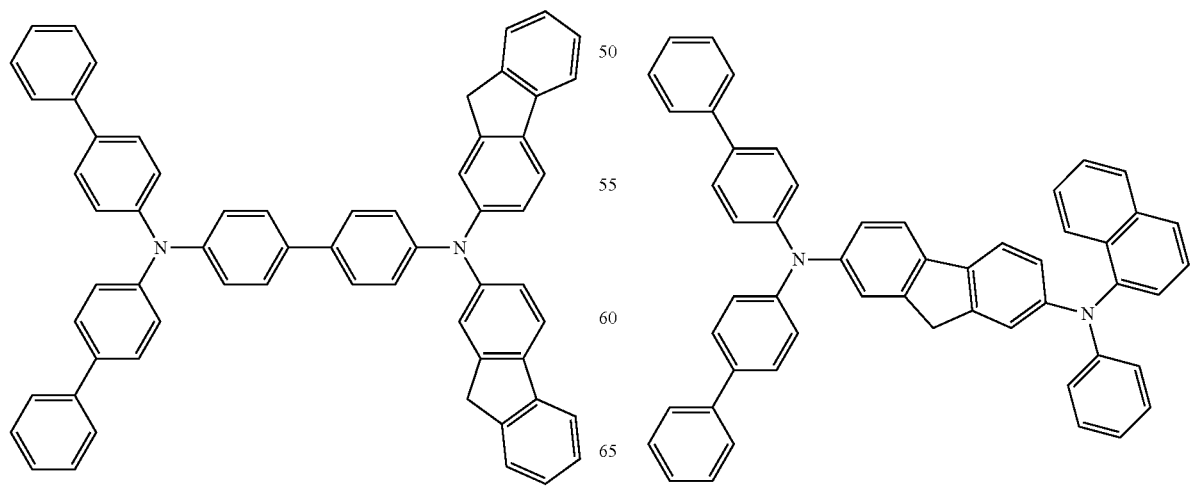

99
-continued
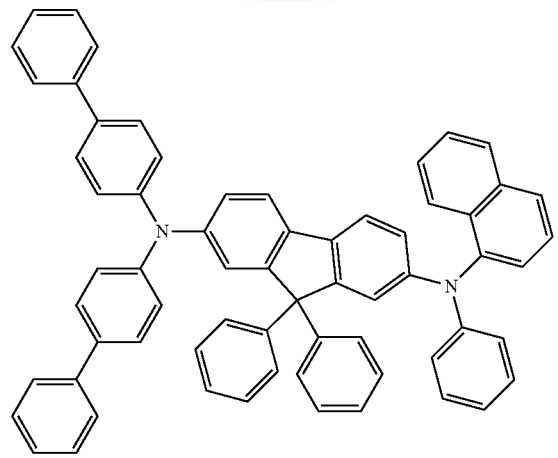
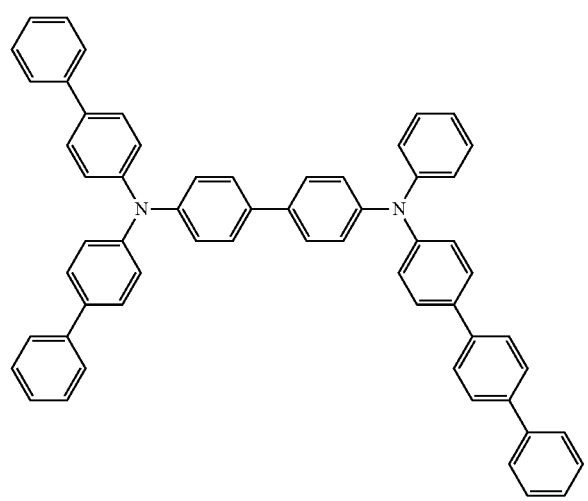
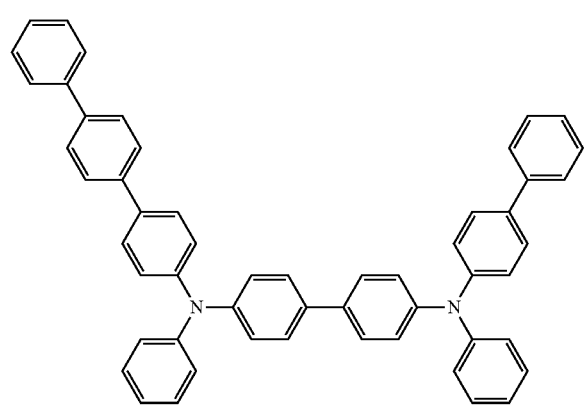
100
-continued
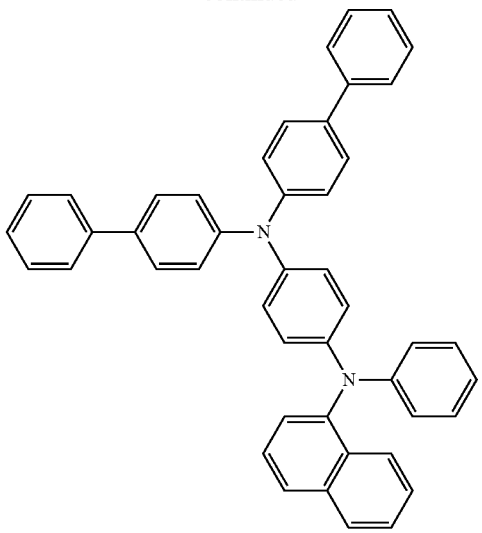
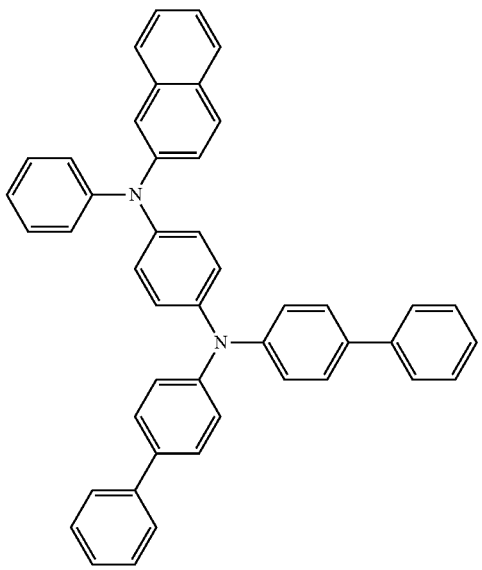
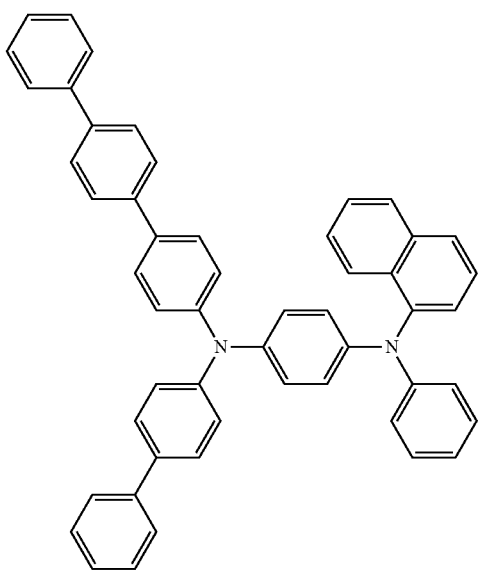

101
-continued
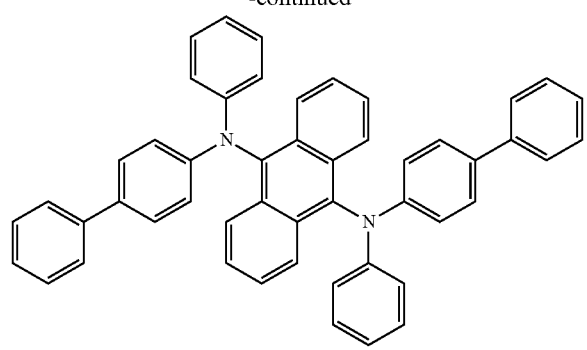
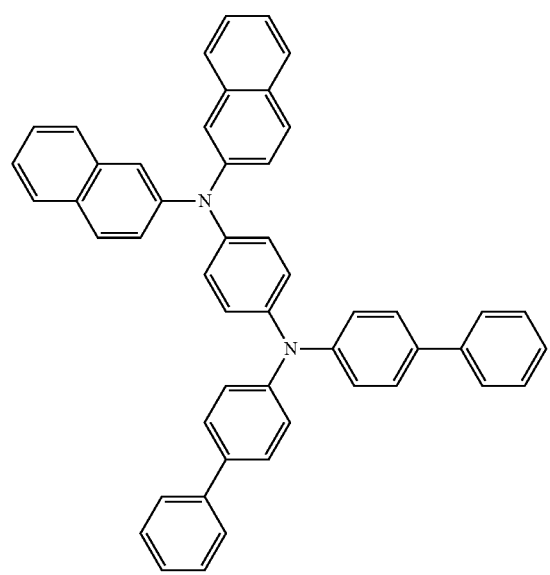
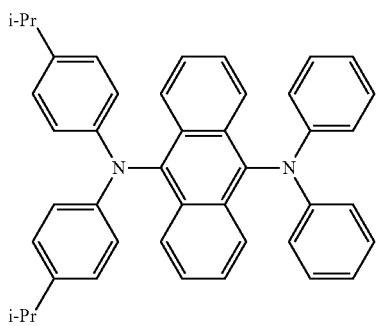
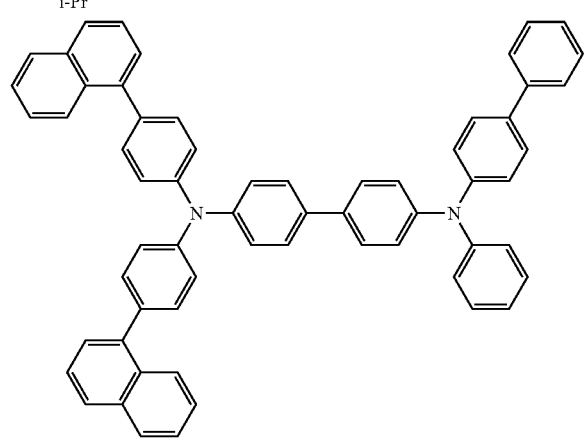
102
-continued
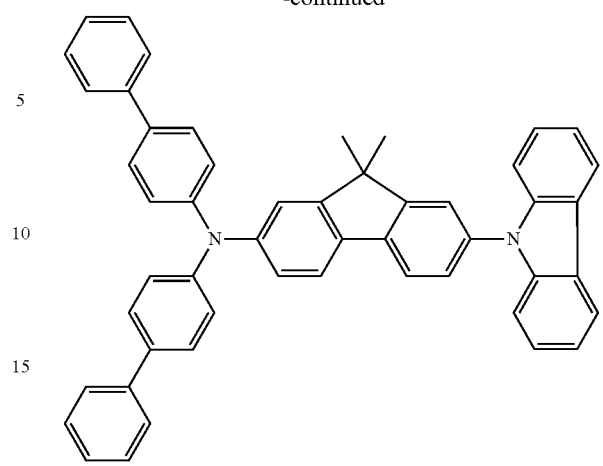
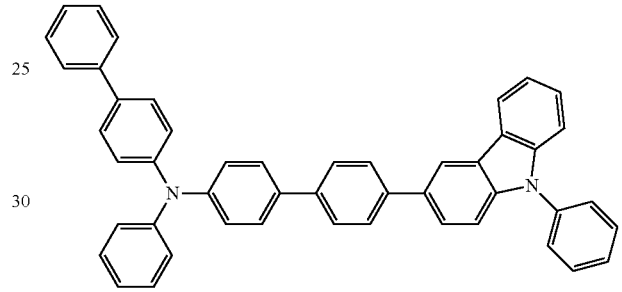
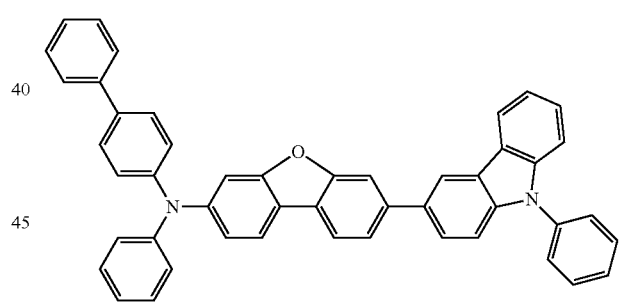
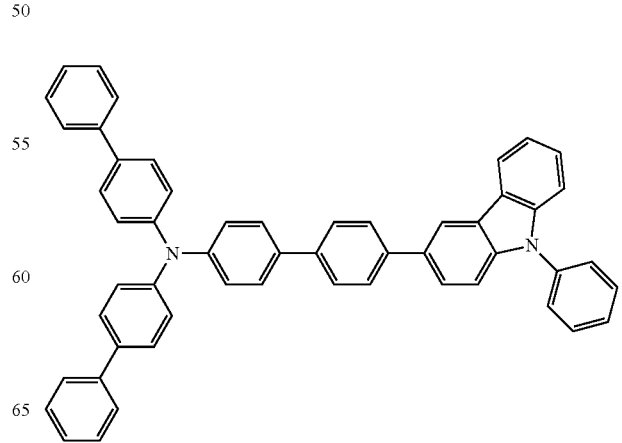

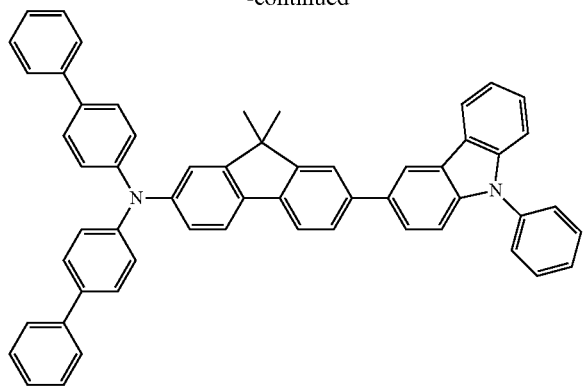
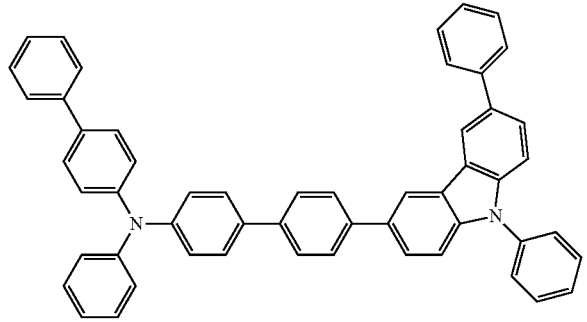
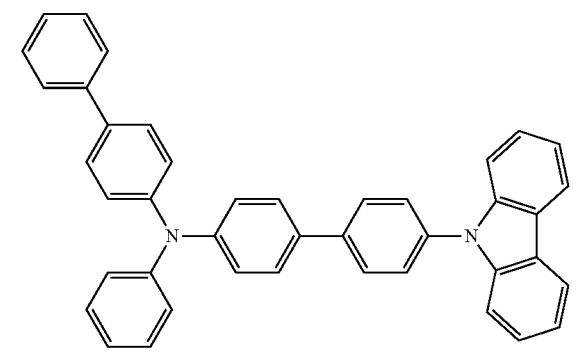
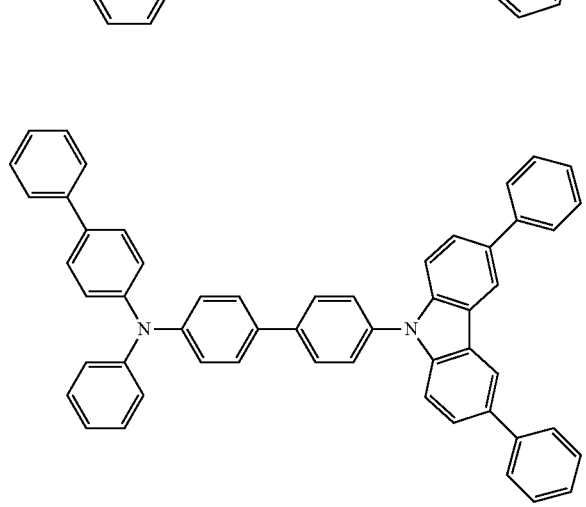
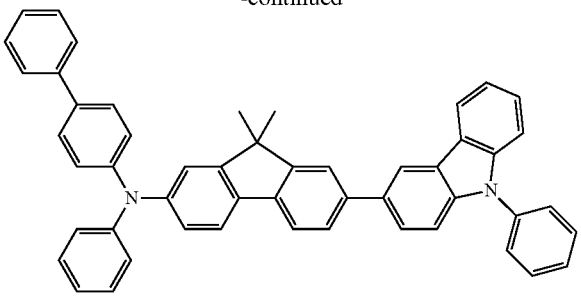
An aromatic amine represented by formula (J) is also preferably used to form the hole transporting layer:
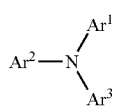
(J)
wherein $Ar^1$ to $Ar^3$ are the same as defined with respect to $Ar^1$ to $Ar^4$ of formula (H). Examples of the compound represented by formula (J) are shown below, although not limited thereto.
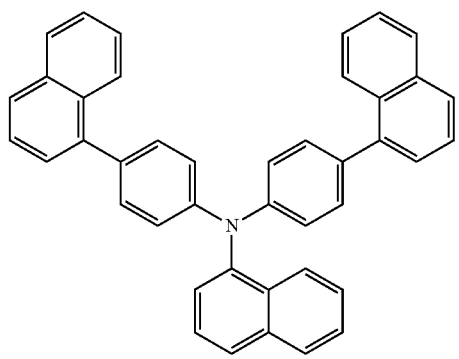
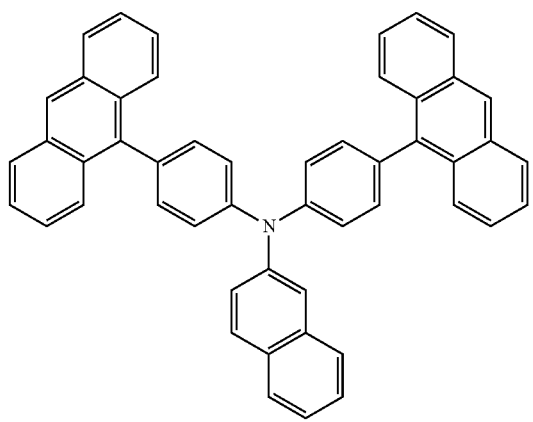

105
-continued
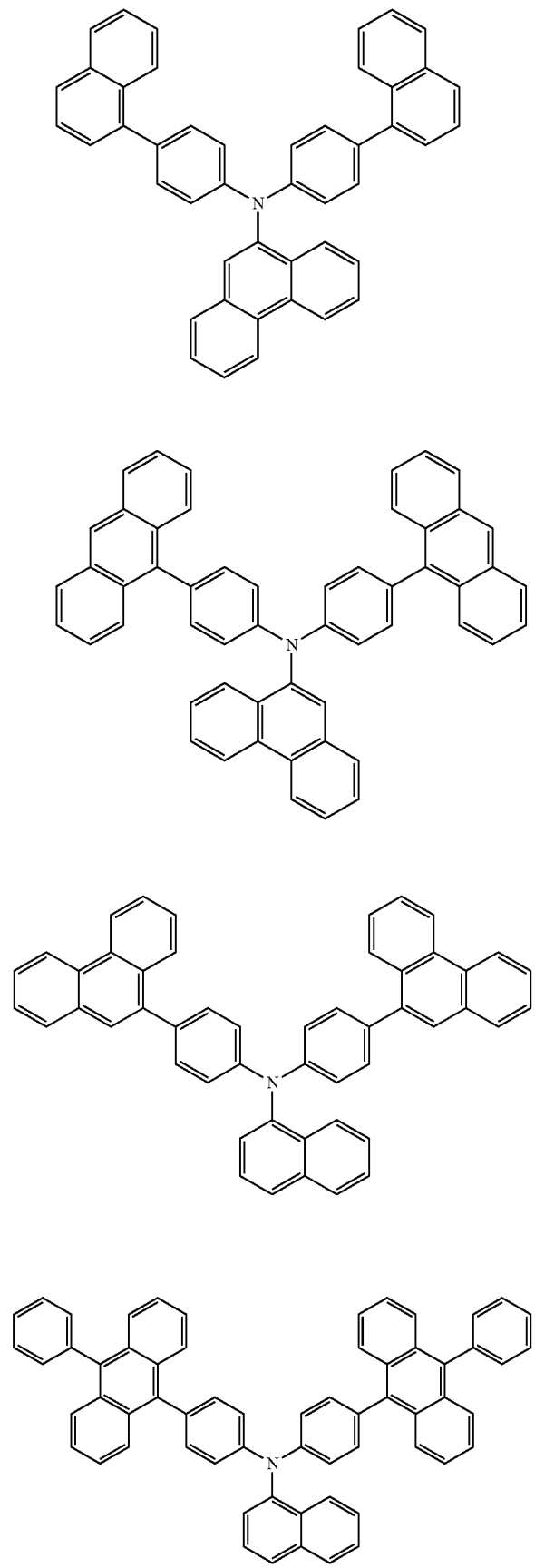
106
-continued
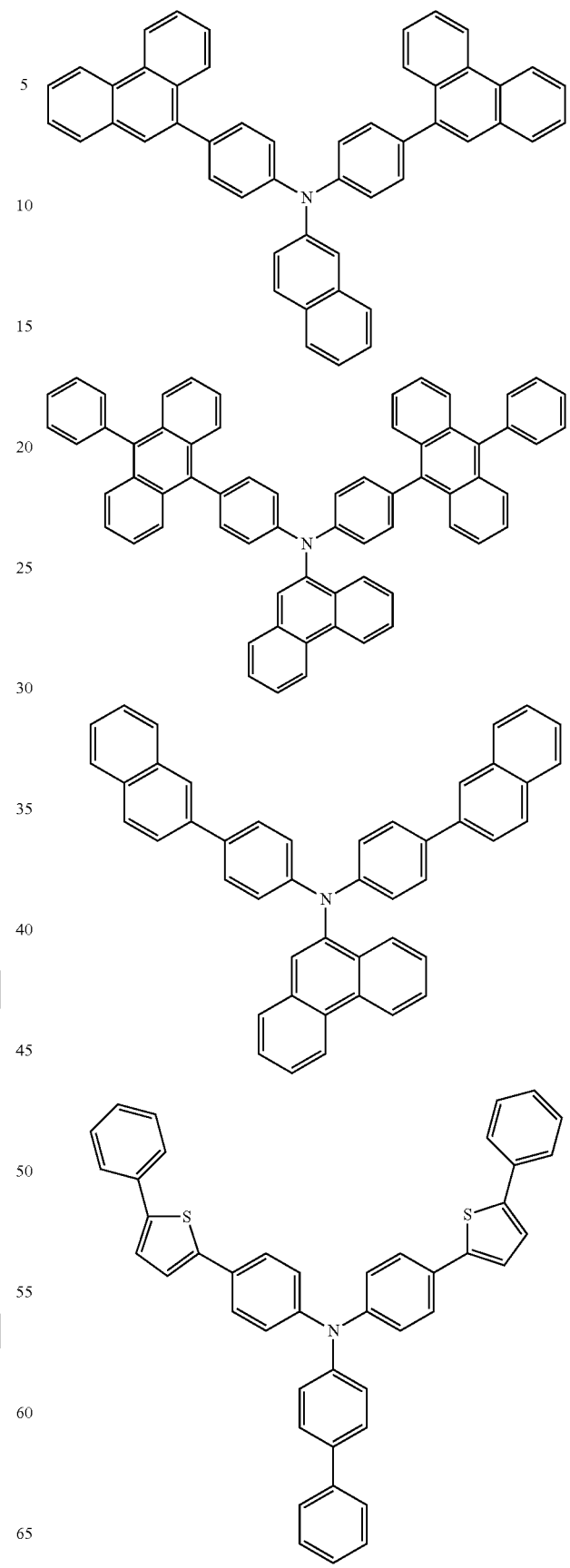

107
-continued

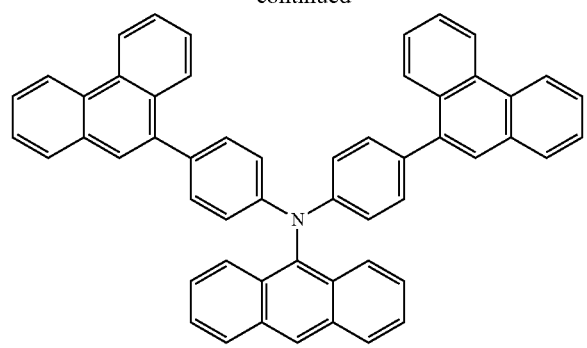
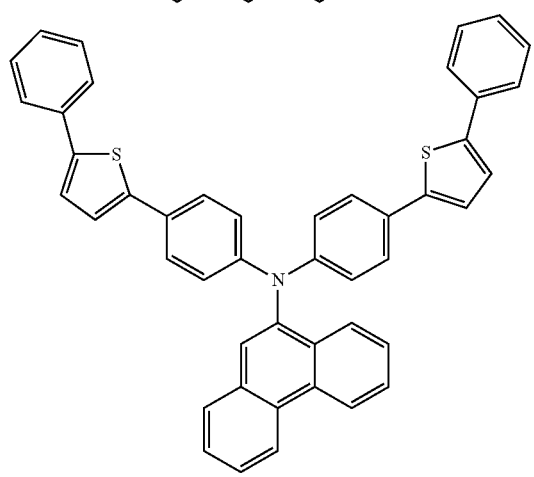
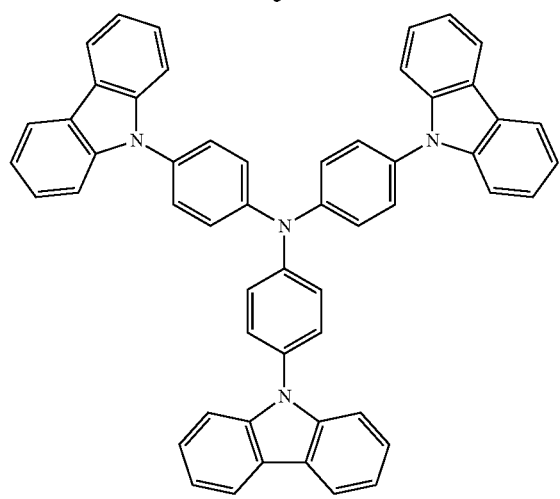
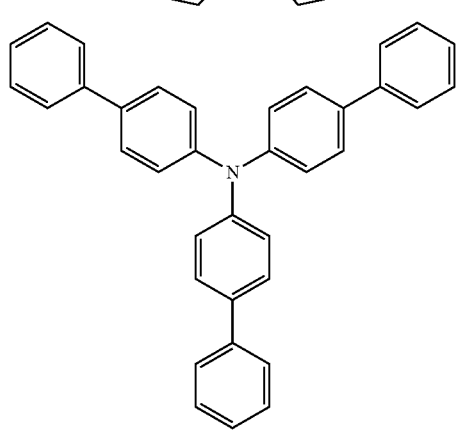

108
-continued

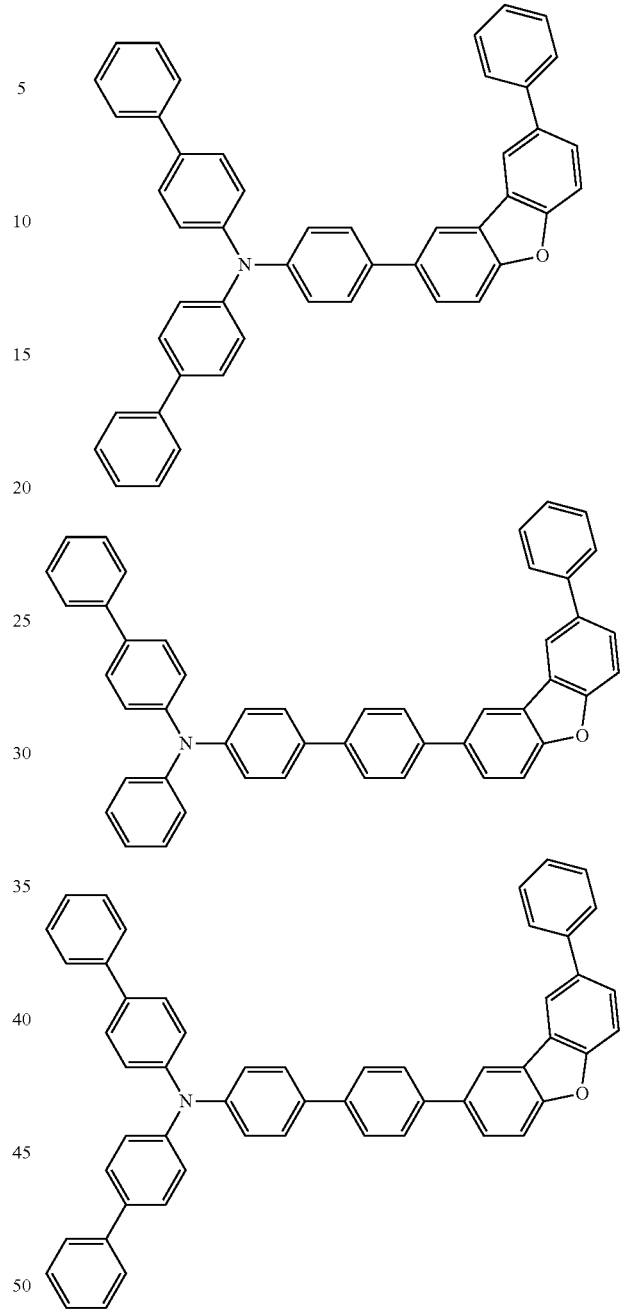

The hole transporting layer may be made into two-layered structure of a first hole transporting layer (anode side) and a second hole transporting layer (cathode side).

The thickness of the hole transporting layer is preferably 10 to 200 nm, although not particularly limited thereto.

The organic EL device of the invention may have a layer comprising an acceptor material which is disposed in contact with the anode side of each of the hole transporting layer and the first hole transporting layer. With such a layer, it is expected that the driving voltage is lowered and the production cost is reduced.

The acceptor material is preferably a compound represented by formula (K):

(K)

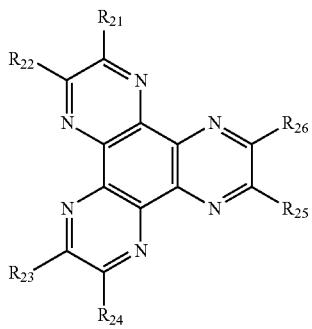

wherein $R_{21}$ to $R_{26}$ may be the same or different and each independently represent a cyano group, —$CONH_2$, a carboxyl group, or —$COOR_{27}$ wherein $R_{27}$ represents an alkyl group having 1 to 20 carbon atoms or a cycloalkyl group having 3 to 20 carbon atoms. One or more of a pair of $R_{21}$ and $R_{22}$, a pair of $R_{23}$ and $R_{24}$, and a pair of $R_{25}$ and $R_{26}$ may bond to each other to form a group represented by —CO—O—CO—.

Examples of $R_{27}$ include a methyl group, an ethyl group, a n-propyl group, an isopropyl group, a n-butyl group, an isobutyl group, a t-butyl group, a cyclopentyl group, and a cyclohexyl group.

The thickness of the layer comprising the acceptor material is preferably 5 to 20 nm, although not particularly limited thereto.

N/P Doping

The carrier injecting properties of the hole transporting layer and the electron transporting layer can be controlled, as described in JP 3695714B, by the doping (n) with a donor material or the doping (p) with an acceptor material.

A typical example of the n-doping is an electron transporting material doped with a metal, such as Li and Cs, and a typical example of the p-doping is a hole transporting material doped with an acceptor material, such as $F_4$TCNQ (2,3,5,6-Tetrafluoro-7,7,8,8-tetracyanoquinodimethane).

Space Layer

For example, in an organic EL device wherein a fluorescent light emitting layer and a phosphorescent light emitting layer are laminated, a space layer is disposed between the fluorescent light emitting layer and the phosphorescent light emitting layer to prevent the diffusion of excitons generated in the phosphorescent light emitting layer to the fluorescent light emitting layer or to control the carrier balance. The space layer may be disposed between two or more phosphorescent light emitting layers.

Since the space layer is disposed between the light emitting layers, a material combining the electron transporting ability and the hole transporting ability is preferably used for forming the space layer. To prevent the diffusion of triplet energy in the adjacent phosphorescent light emitting layer, the triplet energy of the material for the space layer is preferably 2.6 eV or more. The materials described with respect to the hole transporting layer are usable as the material for the space layer. The material for organic EL device of the invention may be used as the material for the space layer.

Blocking Layer

The organic EL device of the invention preferably has a blocking layer, such as an electron blocking layer, a hole blocking layer, and a triplet blocking layer, which is disposed adjacent to the light emitting layer. The electron blocking layer is a layer which prevents the diffusion of electrons from the light emitting layer to the hole transporting layer. The hole blocking layer is a layer which prevents the diffusion of holes from the light emitting layer to the electron transporting layer. The material for organic EL device of the invention may be used as the material for the hole blocking layer.

The triplet blocking layer prevents the diffusion of triplet excitons generated in the light emitting layer to adjacent layers and has a function of confining the triplet excitons in the light emitting layer, thereby preventing the deactivation of energy on molecules other than the emitting dopant of triplet excitons, for example, on molecules in the electron transporting layer.

If a phosphorescent device having a triplet blocking layer satisfies the following energy relationship:

$$E^T_d < E^T_{TB}$$

wherein $E^T_d$ is the triplet energy of the phosphorescent dopant in the light emitting layer and $E^T_{TB}$ is the triplet energy of the compound forming the triplet blocking layer, the triplet excitons of phosphorescent dopant are confined (not diffuse to other molecules). Therefore, the energy deactivation process other than the emission on the phosphorescent dopant may be prevented to cause the emission with high efficiency. However, even in case of satisfying the relationship of $E^T_d < E^T_{TB}$, the triplet excitons may move into other molecules if the energy difference ($\Delta E^T = E^T_{TB} - E^T_d$) is small, because the energy difference $\Delta E^T$ may be overcome by the absorption of ambient heat energy when driving a device at around room temperature as generally employed in practical drive of device. As compared with the fluorescent emission, the phosphorescent emission is relatively likely to be affected by the diffusion of excitons due to the heat absorption because the lifetime of triplet excitons is longer. Therefore, as for the energy difference $\Delta E^T$, the larger as compared with the heat energy of room temperature, the better. The energy difference $\Delta E^T$ is more preferably 0.1 eV or more and particularly preferably 0.2 eV or more. In fluorescent devices, the material for organic EL device of the invention is usable as the material for triplet blocking layer of the TTF device described in WO 2010/134350A1.

The electron mobility of the material for the triplet blocking layer is preferably $10^{-6}$ cm$^2$/Vs or more at an electric field strength in a range of 0.04 to 0.5 MV/cm. There are several methods for measuring the electron mobility of organic material, for example, Time of Flight method. In the present invention, the electron mobility is determined by impedance spectroscopy.

The electron mobility of the electron injecting layer is preferably $10^{-6}$ cm$^2$/Vs or more at an electric field strength in a range of 0.04 to 0.5 MV/cm. Within the above range, the injection of electrons from the cathode to the electron transporting layer is promoted and the injection of electrons to the adjacent blocking layer and light emitting layer is also promoted, thereby enabling to drive a device at lower voltage.

The organic electroluminescence device of the invention usable in electronic equipment, for example, as display parts, such as organic EL panel module, display devices of television sets, mobile phones, personal computer, etc., and light emitting sources of lighting equipment and vehicle lighting equipment.

EXAMPLES

The present invention will be described below in more detail with reference to the examples. However it should be noted that the scope of the invention is not limited thereto.

Example 1 (Synthesis of Compound 1)

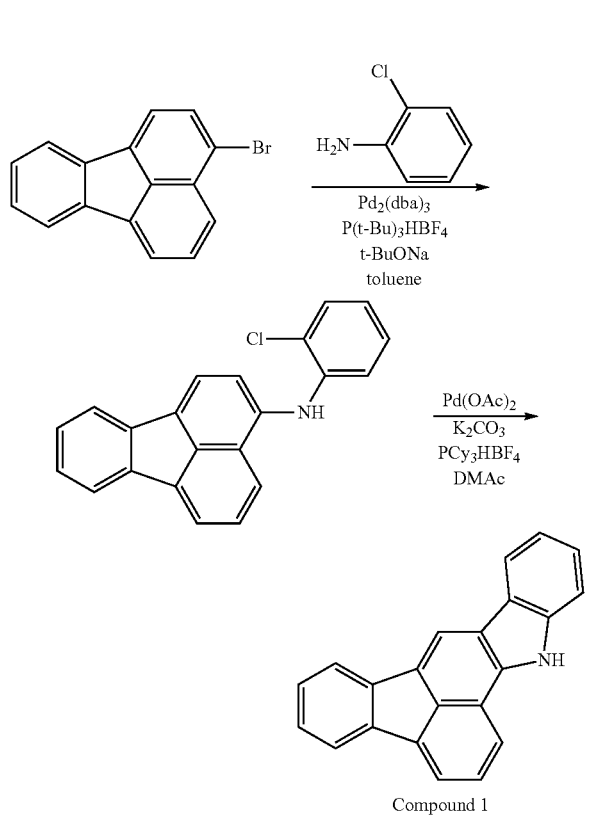

Compound 1

(1) Synthesis of 3-(2-chloroanilino)fluoranthene

Under an argon atmosphere, 7.0 g of 3-bromofluoranthene, 4.76 g of 2-chloroaniline, 0.46 g of tris(dibenzylideneacetone) dipalladium(0), 0.58 g of tri-t-butylphosphine tetrafluorohydroborate, 3.4 g of sodium t-butoxide, and 200 mL of dry toluene were charged in a flask, and the resultant mixture was stirred under heating at 80° C. for 8 h. After cooling to room temperature, the reaction solution was extracted with toluene and the extract was filtered through celite. The filtrate was concentrated and the residue was purified by silica gel column chromatography to obtain 6.14 g of 3-(2-chloroanilino)fluoranthene (yield: 75%).

(2) Synthesis of Compound 1

Under an argon atmosphere, 6.14 g of 3-(2-chloroanilino) fluoranthene, 0.13 g of palladium acetate, 5.18 g of potassium carbonate, 0.41 g of tricyclohexylphosphine tetrafluorohydroborate, and 40 mL of N,N-dimethylacetamide were charged in a flask, and the resultant mixture was stirred under heating at 140° C. for 24 h. After cooling to room temperature, the reaction solution was extracted with toluene and the insolubles were removed by filtration. The filtrate was concentrated and the residue was purified by silica gel column chromatography to obtain 1.87 g of the compound 1 (yield: 34%).

Example 2 (Synthesis of Compound 2)

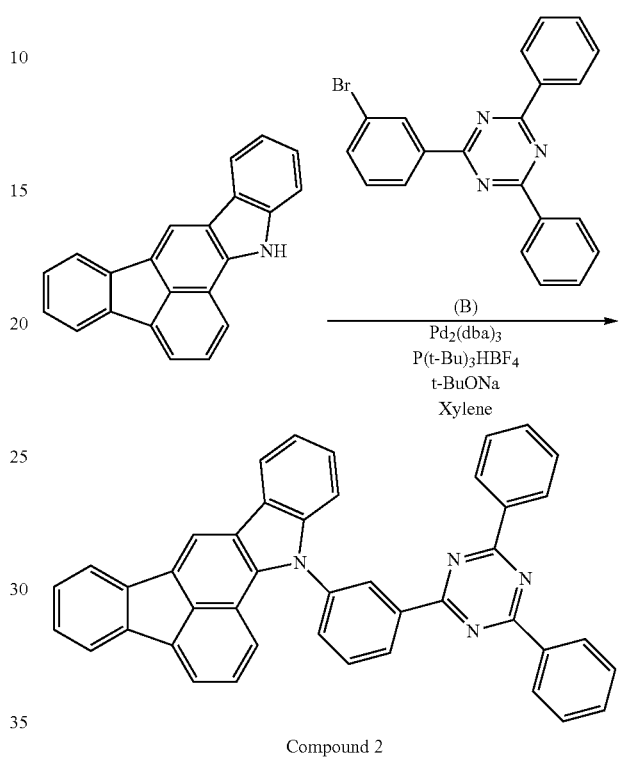

Compound 2

Under an argon atmosphere, 1.87 g of the compound 1, 1.94 g of the intermediate B synthesized by a known method, 0.12 g of tris(dibenzylideneacetone) dipalladium (0), 0.15 g of tri-t-butylphosphine tetrafluorohydroborate, 0.86 g of sodium t-butoxide, and 100 mL of dry xylene were charged in a flask, and the resultant mixture was refluxed for 8 h under heating and stirring. After cooling to room temperature, the reaction solution was extracted with toluene and the extract was filtered through celite. The filtrate was concentrated and the residue was purified by silica gel column chromatography to obtain 2.50 g of a yellow solid. The obtained compound was identified as the target compound by the result of mass spectrometric analysis which showed m/e=598 to the molecular weight of 598.22.

Example 3 (Synthesis of Compound 3)

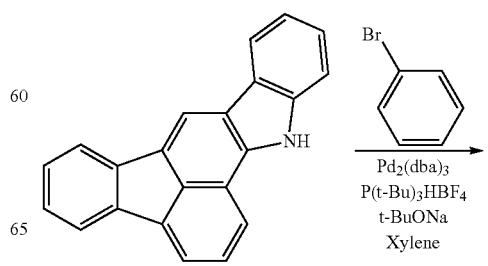

-continued

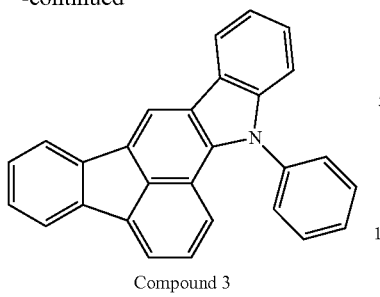

Compound 3

The compound 3 was synthesized in the same manner as in the synthesis of the compound 2 except for using bromobenzene in place of the intermediate B. The obtained compound was identified as the target compound by the result of mass spectrometric analysis which showed m/e=367 to the molecular weight of 367.14.

Example 4 (Synthesis of Compound 4)

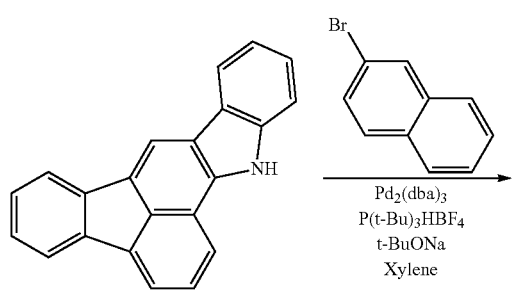

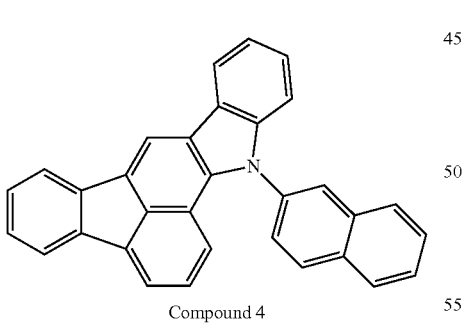

Compound 4

The compound 4 was synthesized in the same manner as in the synthesis of the compound 2 except for using 2-bromonaphthalene in place of the intermediate B. The obtained compound was identified as the target compound by the result of mass spectrometric analysis which showed m/e=417 to the molecular weight of 417.15.

Example 5 (Synthesis of Compound 5)

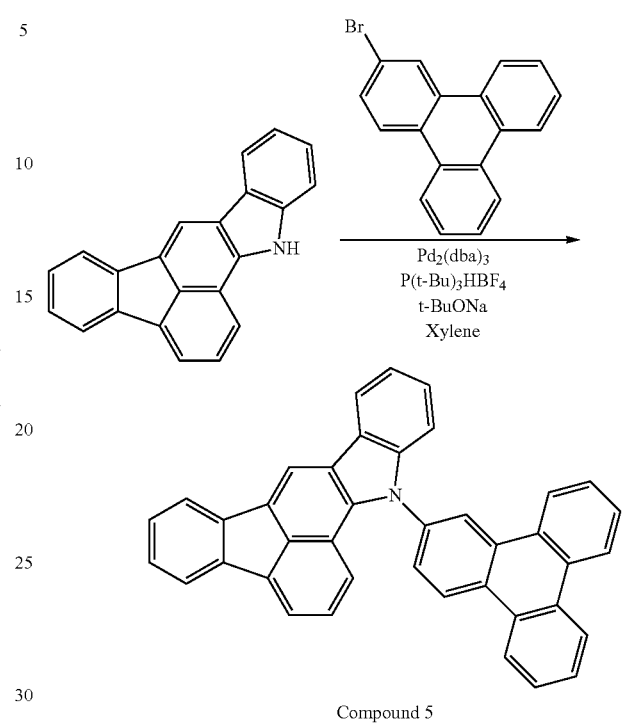

Compound 5

The compound 5 was synthesized in the same manner as in the synthesis of the compound 2 except for using 2-bromotriphenylene in place of the intermediate B. The obtained compound was identified as the target compound by the result of mass spectrometric analysis which showed m/e=517 to the molecular weight of 517.18.

Example 6 (Synthesis of Compound 6)

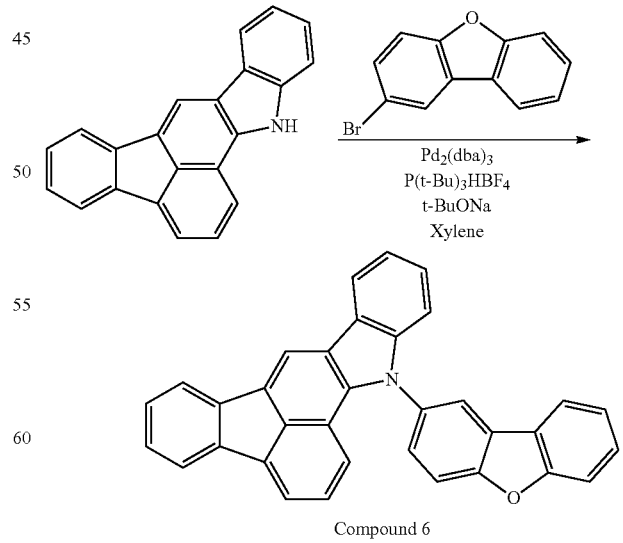

Compound 6

The compound 6 was synthesized in the same manner as in the synthesis of the compound 2 except for using 2-bromodibenzofuran in place of the intermediate B. The obtained compound was identified as the target compound by the result of mass spectrometric analysis which showed m/e=457 to the molecular weight of 457.15.

Example 7 (Synthesis of Compound 7)

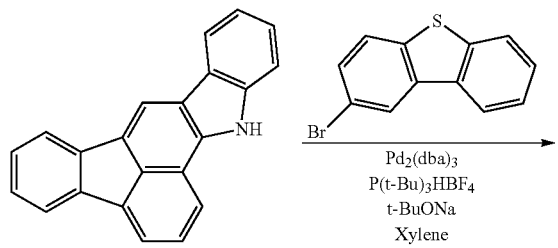

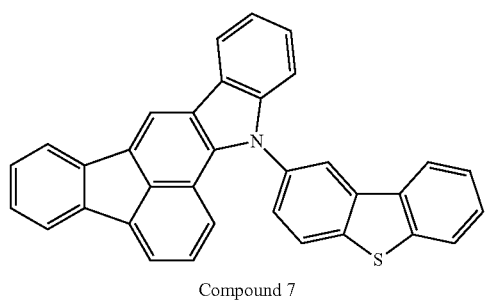

Compound 7

The compound 7 was synthesized in the same manner as in the synthesis of the compound 2 except for using 2-bromodibenzothiophene in place of the intermediate B. The obtained compound was identified as the target compound by the result of mass spectrometric analysis which showed m/e=473 to the molecular weight of 473.12.

Example 8 (Synthesis of Compound 8)

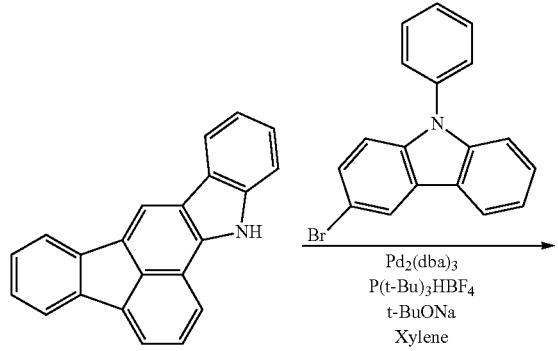

-continued

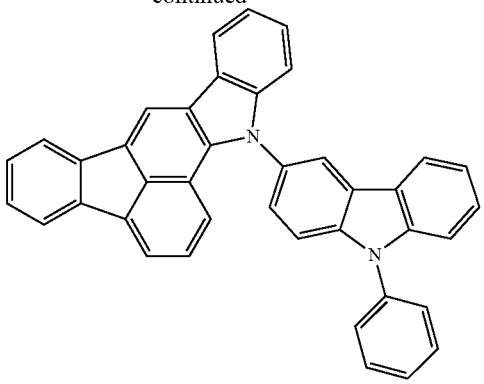

Compound 8

The compound 8 was synthesized in the same manner as in the synthesis of the compound 2 except for using 3-bromo-9-phenylcarbazole in place of the intermediate B. The obtained compound was identified as the target compound by the result of mass spectrometric analysis which showed m/e=532 to the molecular weight of 532.19.

Example 9 (Synthesis of Compound 9)

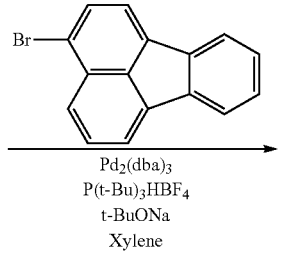

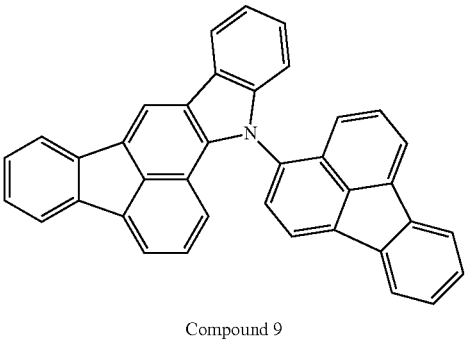

Compound 9

The compound 9 was synthesized in the same manner as in the synthesis of the compound 2 except for using 3-bromofluoranthene in place of the intermediate B. The obtained compound was identified as the target compound by the result of mass spectrometric analysis which showed m/e=491 to the molecular weight of 491.17.

Example 10 (Synthesis of Compound 10)

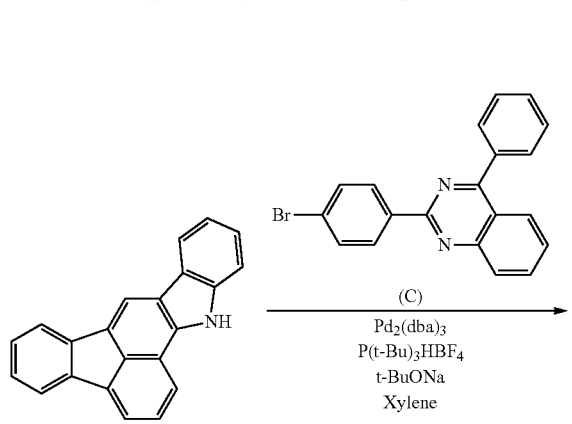

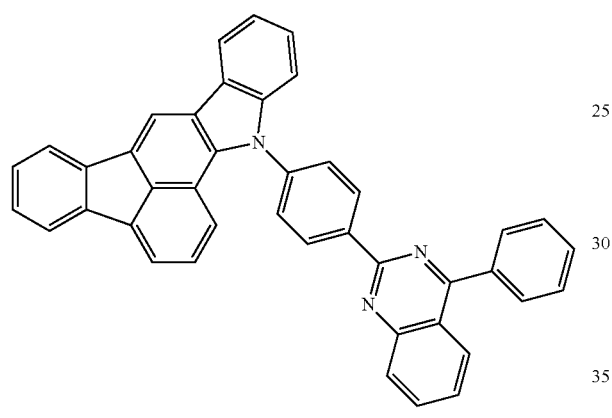

Compound 10

The compound 10 was synthesized in the same manner as in the synthesis of the compound 2 except for using the intermediate C in place of the intermediate B. The obtained compound was identified as the target compound by the result of mass spectrometric analysis which showed m/e=571 to the molecular weight of 571.20.

Example 11 (Synthesis of Compound 11)

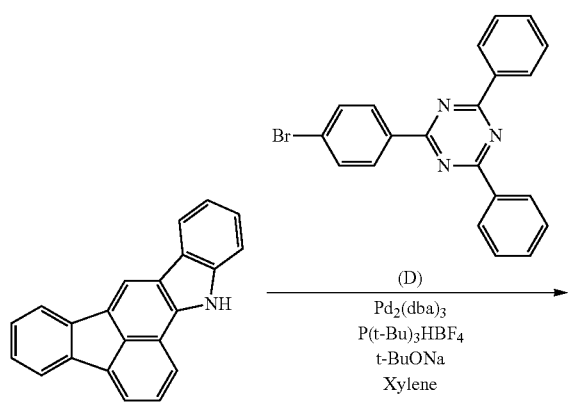

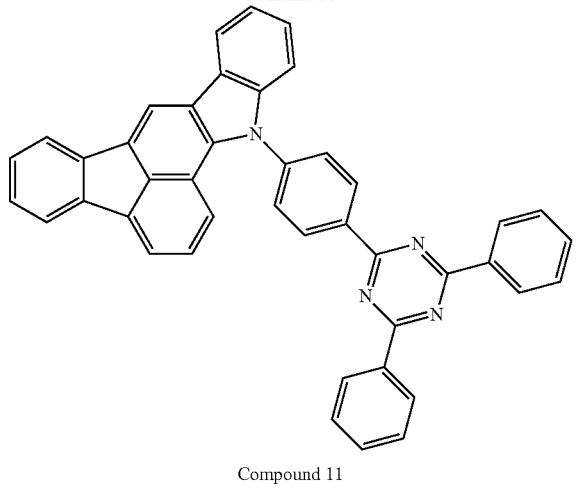

Compound 11

The compound 11 was synthesized in the same manner as in the synthesis of the compound 2 except for using the intermediate D in place of the intermediate B. The obtained compound was identified as the target compound by the result of mass spectrometric analysis which showed m/e=598 to the molecular weight of 598.22.

Example 12 (Synthesis of Compound 12)

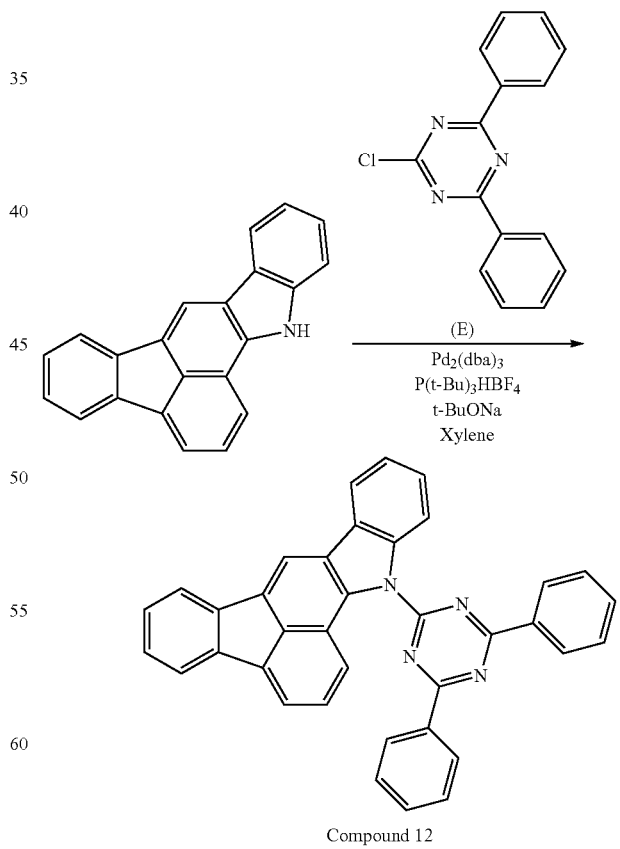

Compound 12

The compound 12 was synthesized in the same manner as in the synthesis of the compound 2 except for using the intermediate E in place of the intermediate B. The obtained compound was identified as the target compound by the result of mass spectrometric analysis which showed m/e=522 to the molecular weight of 522.18.

Example 13 (Synthesis of Compound 13)

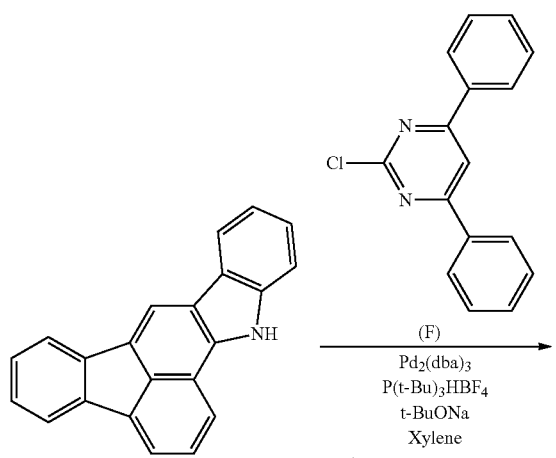

Compound 13

The compound 13 was synthesized in the same manner as in the synthesis of the compound 2 except for using the intermediate F in place of the intermediate B. The obtained compound was identified as the target compound by the result of mass spectrometric analysis which showed m/e=521 to the molecular weight of 521.19.

Example 14 (Synthesis of Compound 14)

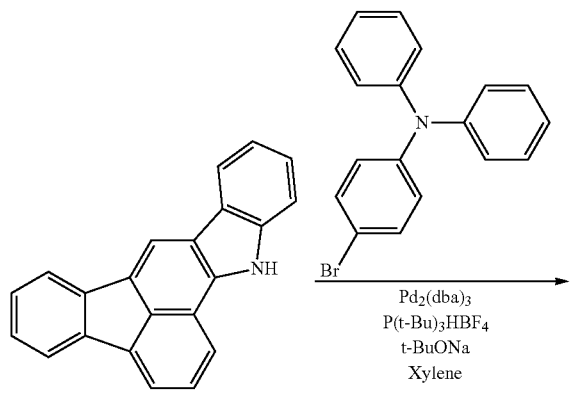

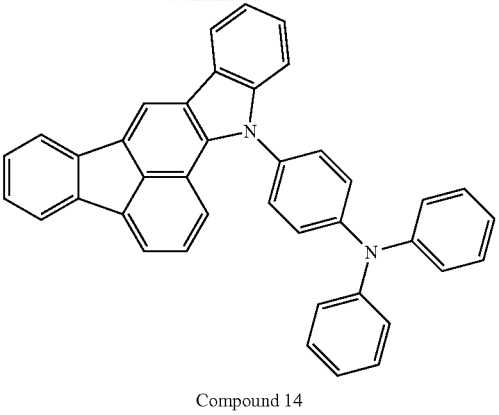

Compound 14

The compound 14 was synthesized in the same manner as in the synthesis of the compound 2 except for using 4-bromotriphenylamine in place of the intermediate B. The obtained compound was identified as the target compound by the result of mass spectrometric analysis which showed m/e=534 to the molecular weight of 534.21.

Example 15 (Synthesis of Compound 15)

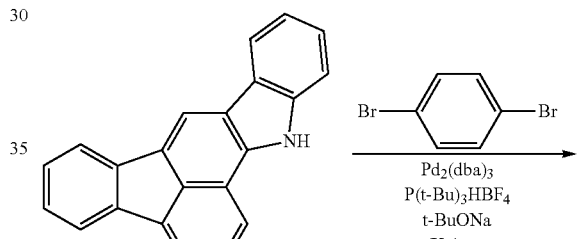

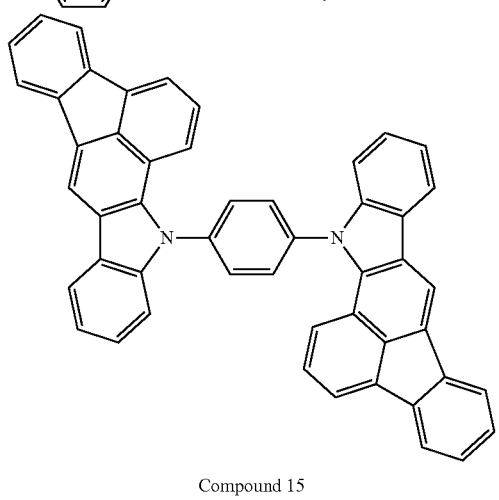

Compound 15

Under an argon atmosphere, 3.74 g of the compound 1, 1.18 g of 1,4-dibromobenzene, 0.24 g of tris(dibenzylideneacetone) dipalladium(0), 0.30 g of tri-t-butylphosphine tetrafluorohydroborate, 1.72 g of sodium t-butoxide, and 100 mL of dry xylene were charged in a flask, and the resultant mixture was refluxed for 8 h under heating and stirring. After cooling to room temperature, the reaction solution was extracted with toluene and the extract was filtered through celite. The filtrate was concentrated and the residue was purified by silica gel column chromatography to obtain 2.70 g of a yellow solid. The obtained compound was identified as the target compound by the result of mass spectrometric analysis which showed m/e=656 to the molecular weight of 656.23.

Example 16 (Synthesis of Compound 16)

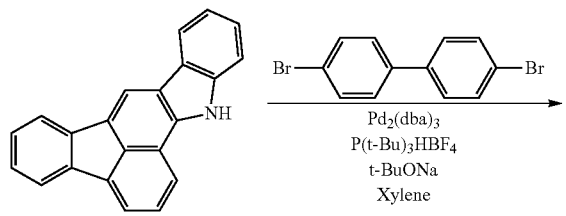

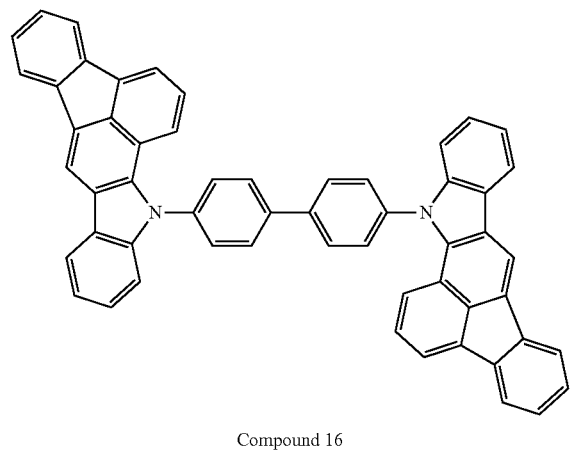

Compound 16

The compound 16 was synthesized in the same manner as in the synthesis of the compound 15 except for using 4,4'-dibromobiphenyl in place of 1,4-dibromobenzene. The obtained compound was identified as the target compound by the result of mass spectrometric analysis which showed m/e=732 to the molecular weight of 732.26.

Example 17 (Synthesis of Compound 17)

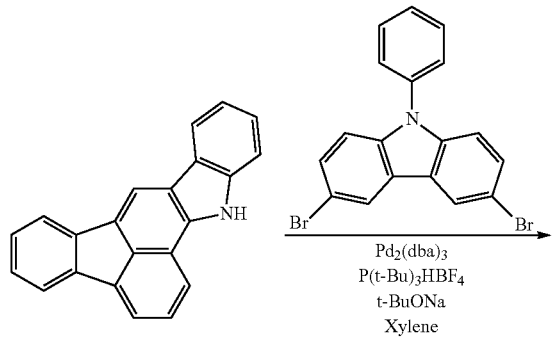

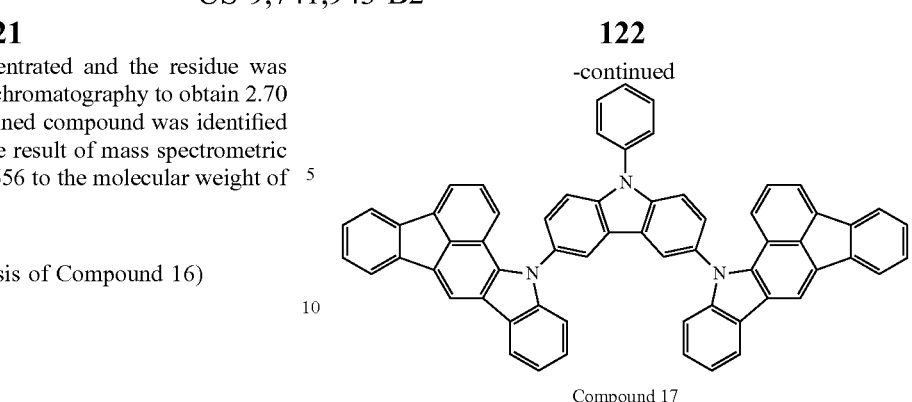

Compound 17

The compound 17 was synthesized in the same manner as in the synthesis of the compound 15 except for using 3,6-dibromo-9-phenylcarbazole in place of 1,4-dibromobenzene. The obtained compound was identified as the target compound by the result of mass spectrometric analysis which showed m/e=821 to the molecular weight of 821.28.

Example 18 (Synthesis of Compound 18)

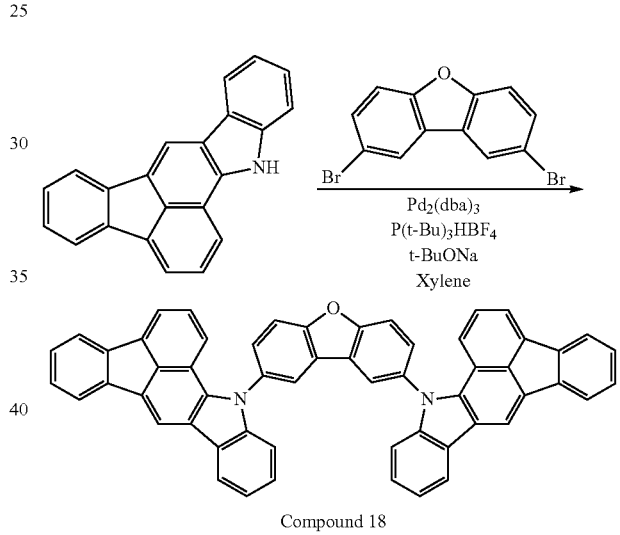

Compound 18

The compound 18 was synthesized in the same manner as in the synthesis of the compound 15 except for using 2,8-dibromodibenzofuran in place of 1,4-dibromobenzene. The obtained compound was identified as the target compound by the result of mass spectrometric analysis which showed m/e=746 to the molecular weight of 746.24.

Example 19 (Synthesis of Compound 19)

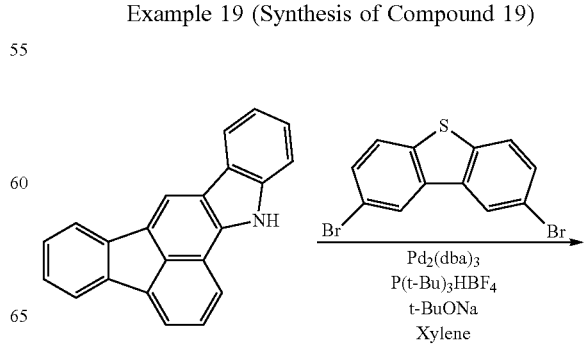

-continued

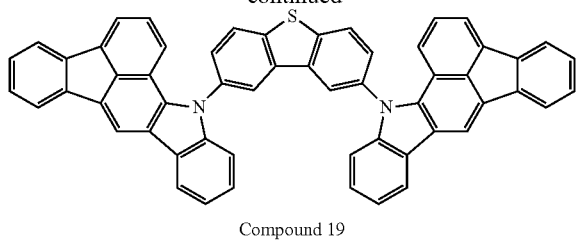

Compound 19

The compound 19 was synthesized in the same manner as in the synthesis of the compound 15 except for using 2,8-dibromodibenzothiophene in place of 1,4-dibromobenzene. The obtained compound was identified as the target compound by the result of mass spectrometric analysis which showed m/e=762 to the molecular weight of 762.21.

Example 20 (Synthesis of Compound 20)

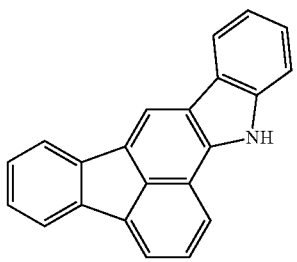 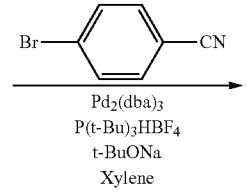

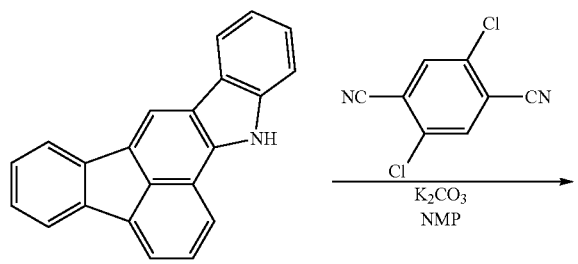

Compound 20

Under an argon atmosphere, 8.73 g of the compound 1, 1.97 g of 2,5-dichloroterephthalonitrile, 5.52 g of potassium carbonate, and 100 mL of N-methylpyrrolidone (NMP) were charged in a flask, and the resultant mixture was stirred at 200° C. for 24 h under heating. After cooling to room temperature, the reaction solution was extracted with toluene and the insolubles were removed by filtration. The filtrate was concentrated and the residue was purified by silica gel column chromatography to obtain the compound 20, which was identified as the target compound by the result of mass spectrometric analysis which showed m/e=706 to the molecular weight of 706.22.

Example 21 (Synthesis of Compound 21)

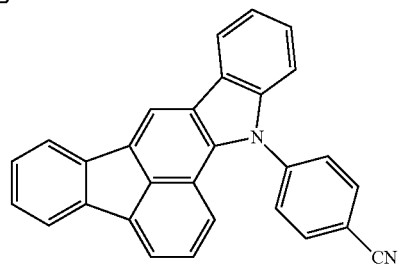

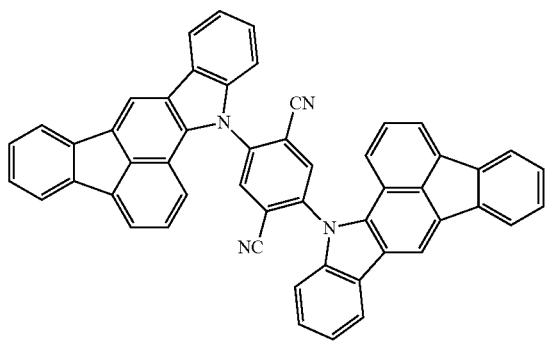

Compound 21

The compound 21 was synthesized in the same manner as in the synthesis of the compound 2 except for using 4-bromobenzonitrile in place of the intermediate B. The obtained compound was identified as the target compound by the result of mass spectrometric analysis which showed m/e=392 to the molecular weight of 392.13.

Example 22 (Synthesis of Compound 22)

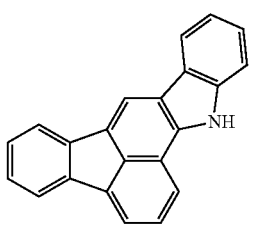 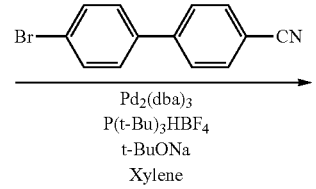

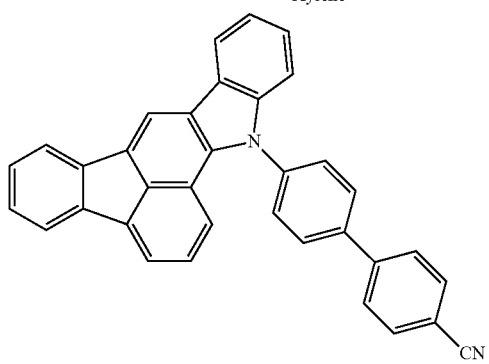

Compound 22

The compound 22 was synthesized in the same manner as in the synthesis of the compound 2 except for using 4-bromo-4'-cyanobiphenyl in place of the intermediate B.

The obtained compound was identified as the target compound by the result of mass spectrometric analysis which showed m/e=468 to the molecular weight of 468.16.

Example 23 (Synthesis of Compound 23)

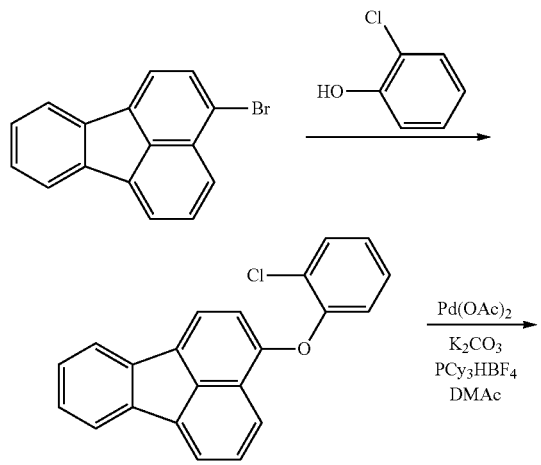

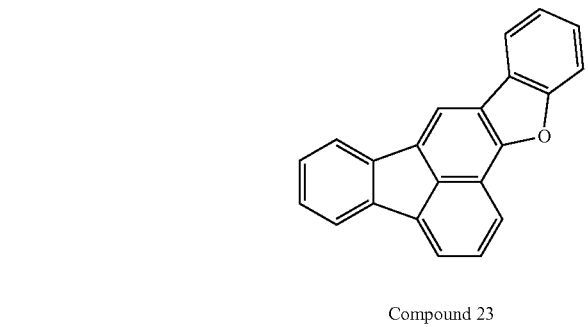

Compound 23

The compound 23 was synthesized in the same manner as in the synthesis of the compound 1 except for using 2-chlorophenol in place of 2-chloroaniline. The obtained compound was identified as the target compound by the result of mass spectrometric analysis which showed m/e=292 to the molecular weight of 292.09.

Example 24 (Synthesis of Compound 24)

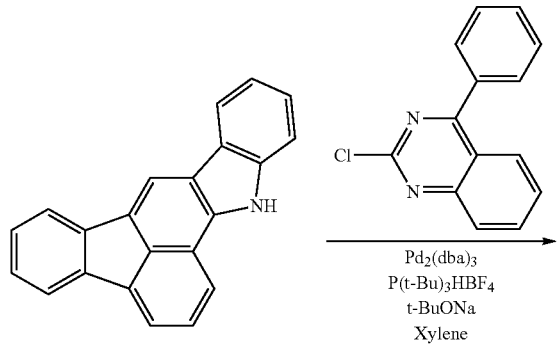

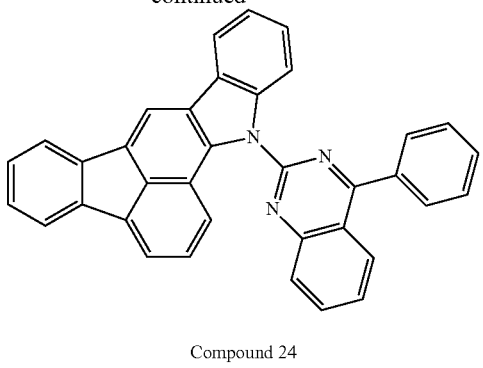

Compound 24

The compound 24 was synthesized in the same manner as in the synthesis of the compound 2 except for using 2-chloro-4-phenylquinazoline in place of the intermediate B. The obtained compound was identified as the target compound by the result of mass spectrometric analysis which showed m/e=495 to the molecular weight of 495.17.

Example 25 (Synthesis of Compound 25)

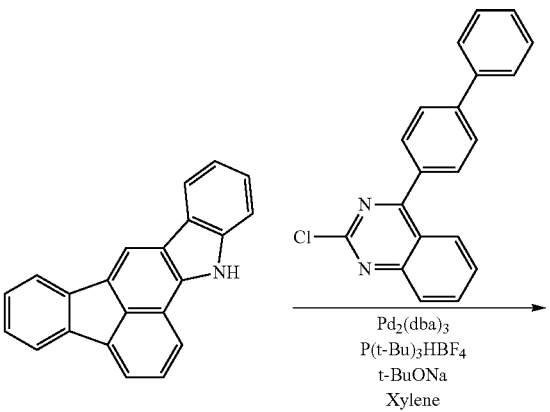

Compound 25

The compound 25 was synthesized in the same manner as in the synthesis of the compound 2 except for using 2-chloro-4-(4-biphenyl)quinazoline in place of the intermediate B. The obtained compound was identified as the target compound by the result of mass spectrometric analysis which showed m/e=571 to the molecular weight of 571.20.

Example 26 (Synthesis of Compound 26)

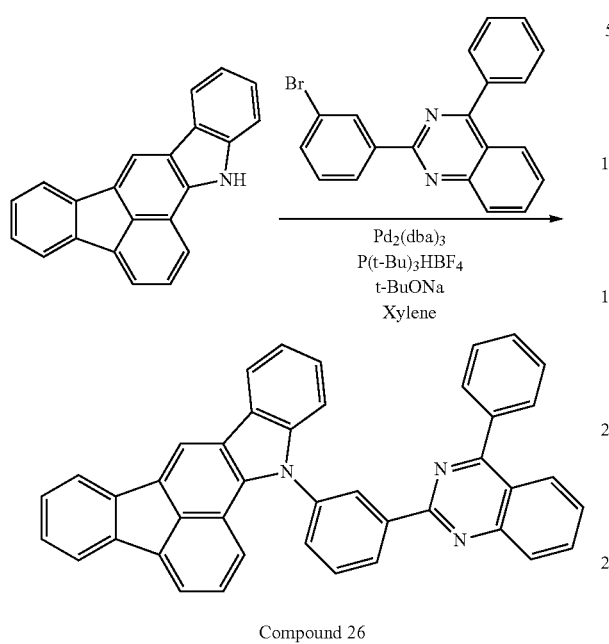

Compound 26

The compound 26 was synthesized in the same manner as in the synthesis of the compound 2 except for using 2-(3-bromophenyl)-4-phenylquinazoline in place of the intermediate B. The obtained compound was identified as the target compound by the result of mass spectrometric analysis which showed m/e=571 to the molecular weight of 571.20.

Example 27 (Synthesis of Compound 27)

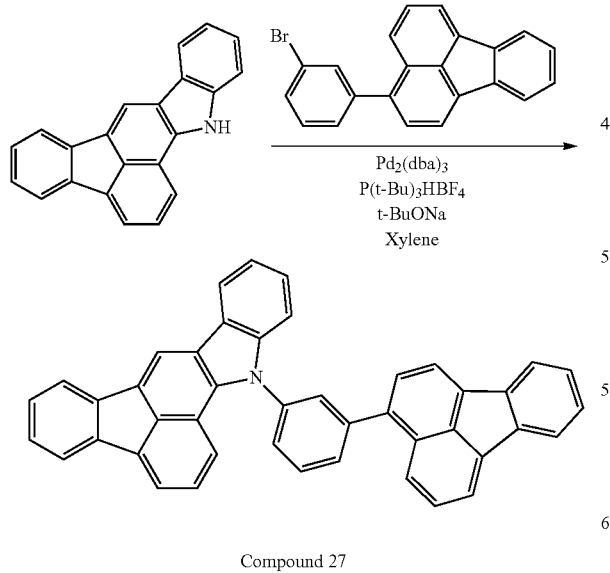

Compound 27

The compound 27 was synthesized in the same manner as in the synthesis of the compound 2 except for using 3-(3-bromophenyl)fluoranthene in place of the intermediate B. The obtained compound was identified as the target compound by the result of mass spectrometric analysis which showed m/e=567 to the molecular weight of 567.20.

Example 28 (Synthesis of Compound 28)

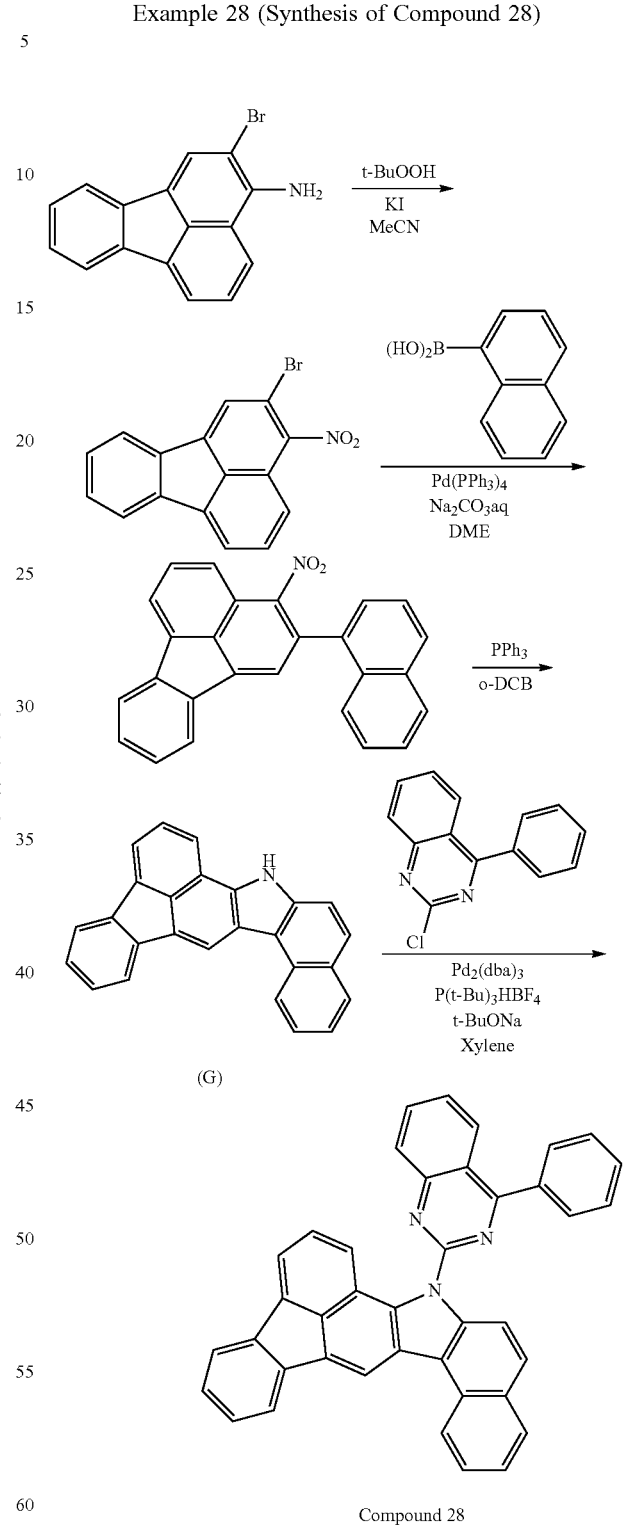

Compound 28

(1) Synthesis of 2-bromo-3-nitrofluoranthene

A mixture of 29.6 g of 2-bromo-3-fluorantheneamine which was synthesized by a method described in WO 2010/123153 and 0.83 g of potassium iodide in 300 mL of acetonitrile was stirred at room temperature while adding 50 g of a 70% by mass aqueous solution of t-butyl hydroperoxide dropwise. The reaction solution was continuously stirred at 80° C. for 15 h under heating. After cooling to room temperature, the reaction was quenched by a saturated aqueous solution of sodium thiosulfate. The reaction solution was extracted with toluene and then the aqueous layer was removed. The organic layer was dried over magnesium sulfate and then the solvent was evaporated off under vacuum. The residue was purified by silica gel column chromatography to obtain 14.7 g of 2-bromo-3-nitrofluoranthene.

(2) Synthesis of 2-(1-naphthyl)-3-nitrofluoranthene

Under an argon atmosphere, 8.53 g of 1-naphthalene boronic acid, 14.7 g of 2-bromo-3-nitrofluoranthene, 1.04 g of tetrakistriphenylphosphine palladium(0), 70 mL of 1,2-dimethoxyethane, 70 mL of toluene, and 70 mL of a 2 M aqueous solution of sodium carbonate were charged in a flask, and the resultant mixture was refluxed for 8 h under heating and stirring. After cooling to room temperature, the reaction solution was extracted with toluene and then the aqueous layer was removed. The organic layer was washed with a saturated saline, dried over magnesium sulfate, and concentrated. The residue was purified by silica gel column chromatography to obtain 10.4 g of 2-(1-naphthyl)-3-nitrofluoranthene.

(3) Synthesis of Intermediate G

Under an argon atmosphere, 10.4 g of 2-(1-naphthyl)-3-nitrofluoranthene, 18.3 g of triphenylphosphine, and 400 mL of o-dichlorobenzene were charged in a flask, and the resultant mixture was refluxed for 48 h under heating and stirring. After cooling to room temperature, 1 L of hexane was added and the precipitated crystal was collected by filtration. The obtained solid was recrystallized from toluene to obtain 3.95 g of the intermediate G.

(4) Synthesis of Compound 28

The compound 28 was synthesized in the same manner as in the synthesis of the compound 2 except for using the intermediate G in place of the compound 1 and using 2-chloro-4-phenylquinazoline in place of the intermediate B. The obtained compound was identified as the target compound by the result of mass spectrometric analysis which showed m/e=545 to the molecular weight of 545.19.

Example 29 (Synthesis of Compound 29)

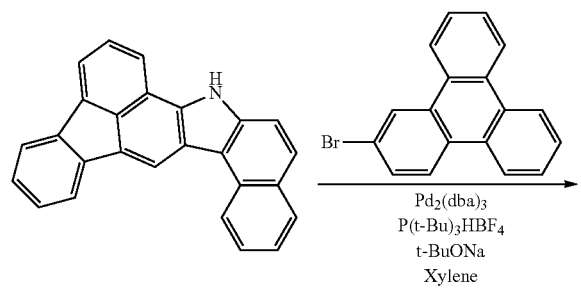

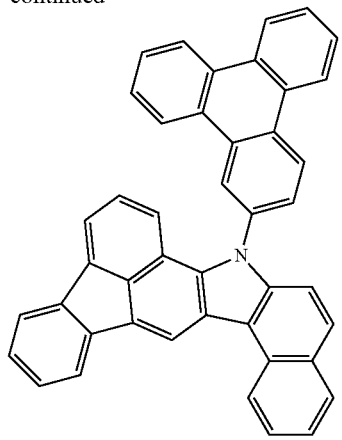

Compound 29

The compound 29 was synthesized in the same manner as in the synthesis of the compound 2 except for using the intermediate G in place of the compound 1 and using 2-bromotriphenylene in place of the intermediate B. The obtained compound was identified as the target compound by the result of mass spectrometric analysis which showed m/e=567 to the molecular weight of 567.20.

Example 30 (Synthesis of Compound 30)

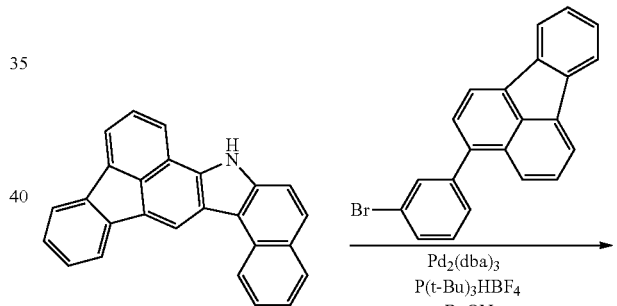

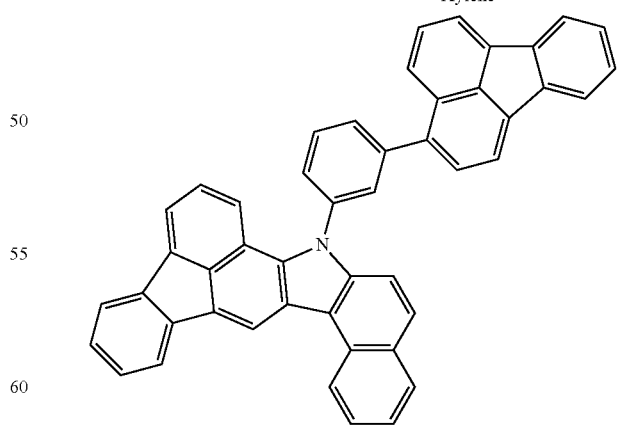

Compound 30

The compound 30 was synthesized in the same manner as in the synthesis of the compound 2 except for using the intermediate G in place of the compound 1 and using 3-(3-bromophenyl)fluoranthene in place of the intermediate B. The obtained compound was identified as the target compound by the result of mass spectrometric analysis which showed m/e=617 to the molecular weight of 617.21.

Example 31 (Synthesis of Compound 31)

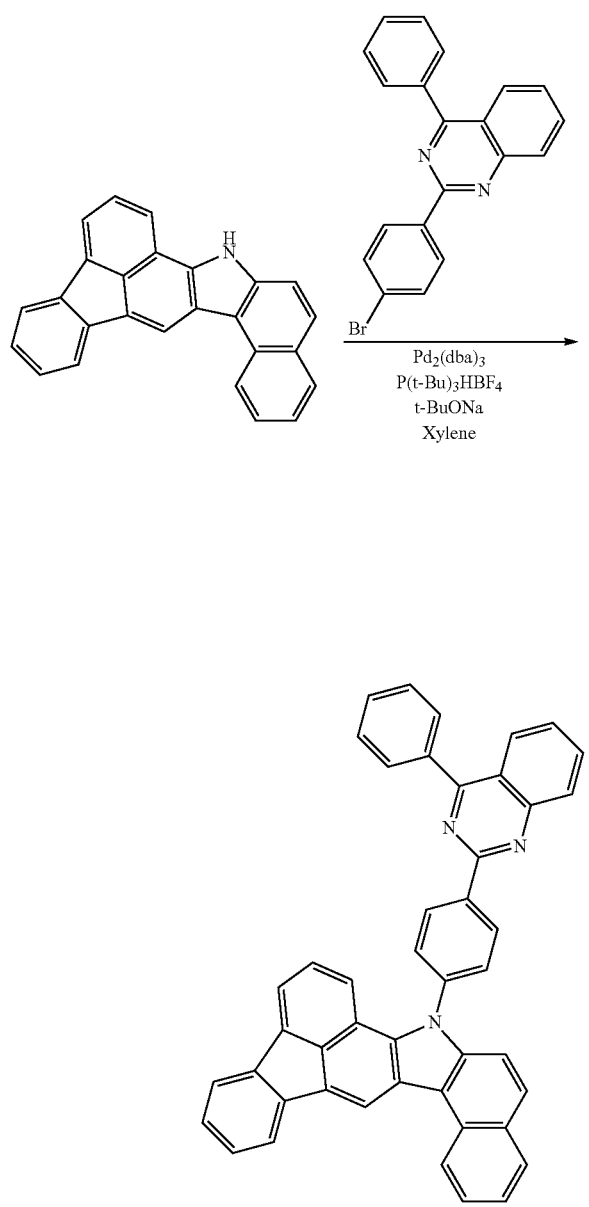

Compound 31

The compound 31 was synthesized in the same manner as in the synthesis of the compound 2 except for using the intermediate G in place of the compound 1 and using the intermediate C in place of the intermediate B. The obtained compound was identified as the target compound by the result of mass spectrometric analysis which showed m/e=621 to the molecular weight of 621.22.

Example 32 (Synthesis of Compound 32)

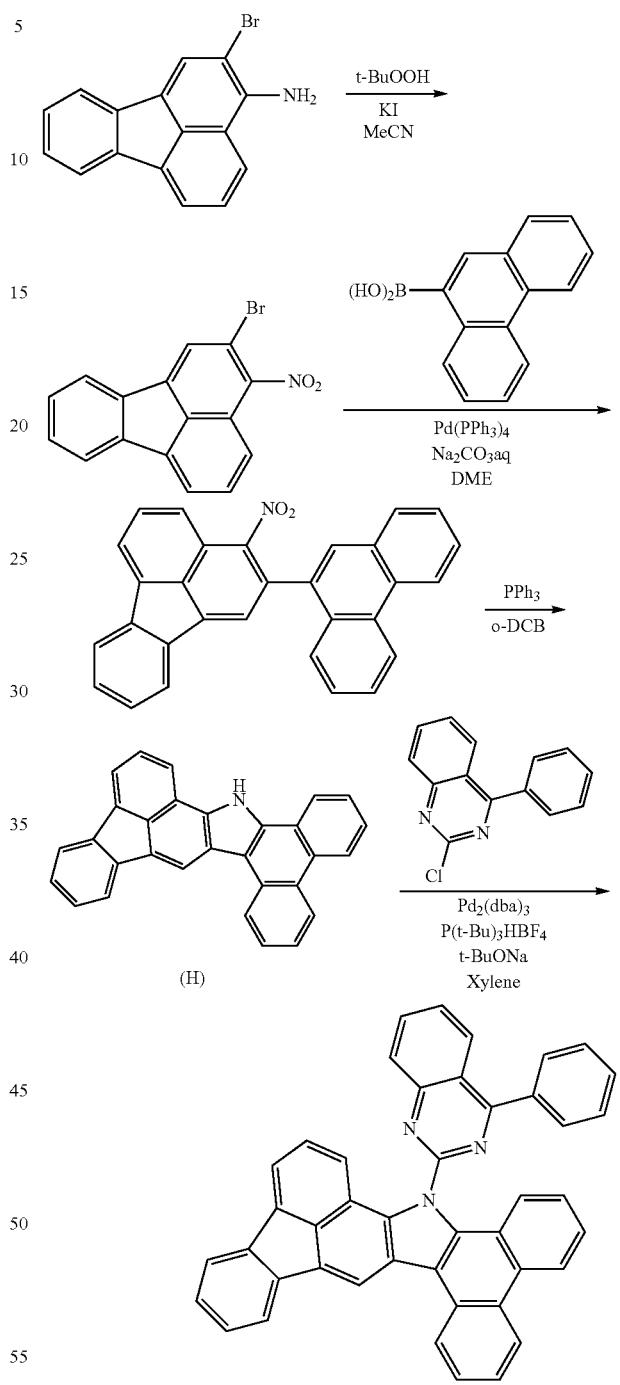

Compound 32

The compound 32 was synthesized according to the above scheme in the same manner as in the synthesis of the compound 28 except for using 9-phenanthrene boronic acid in place of 1-naphthalene boronic acid. The obtained compound was identified as the target compound by the result of mass spectrometric analysis which showed m/e=595 to the molecular weight of 595.20.

Example 33 (Synthesis of Compound 33)

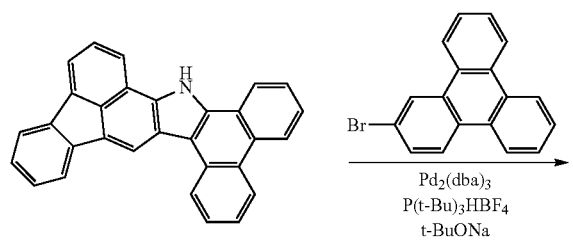

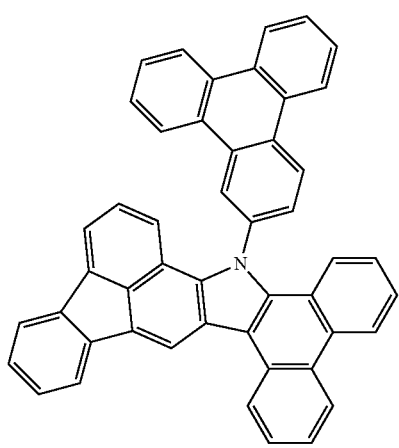

Compound 33

The compound 33 was synthesized in the same manner as in the synthesis of the compound 2 except for using the intermediate H in place of the compound 1 and using 2-bromotriphenylene in place of the intermediate B. The obtained compound was identified as the target compound by the result of mass spectrometric analysis which showed m/e=617 to the molecular weight of 617.21.

Example 34 (Synthesis of Compound 34)

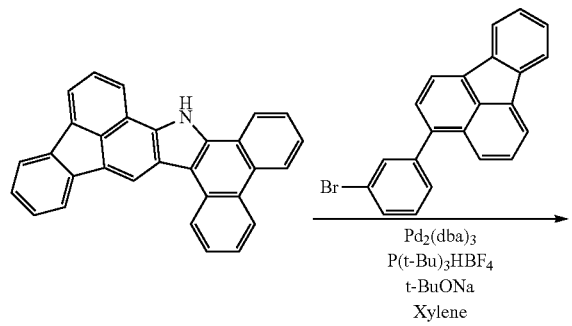

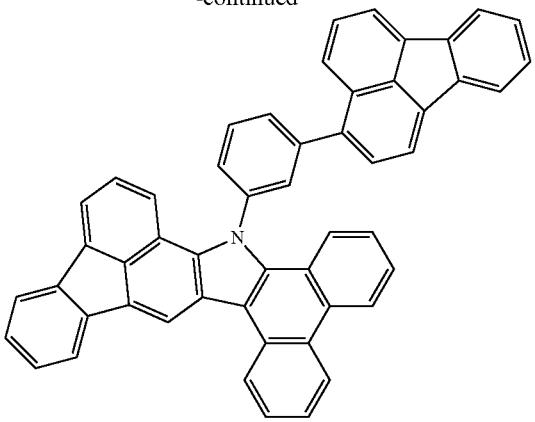

Compound 34

The compound 34 was synthesized in the same manner as in the synthesis of the compound 2 except for using the intermediate H in place of the compound 1 and using 3-(3-bromophenyl)fluoranthene in place of the intermediate B. The obtained compound was identified as the target compound by the result of mass spectrometric analysis which showed m/e=667 to the molecular weight of 667.23.

Example 35 (Synthesis of Compound 35)

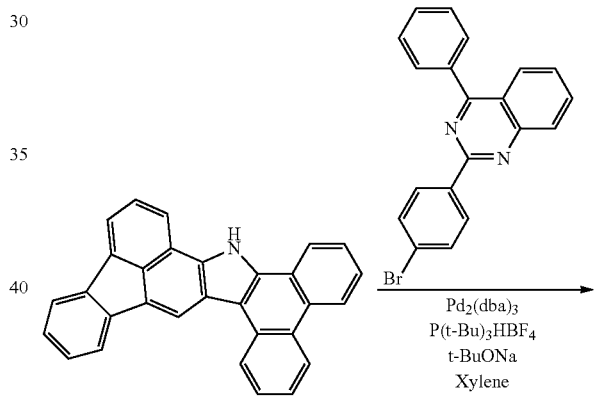

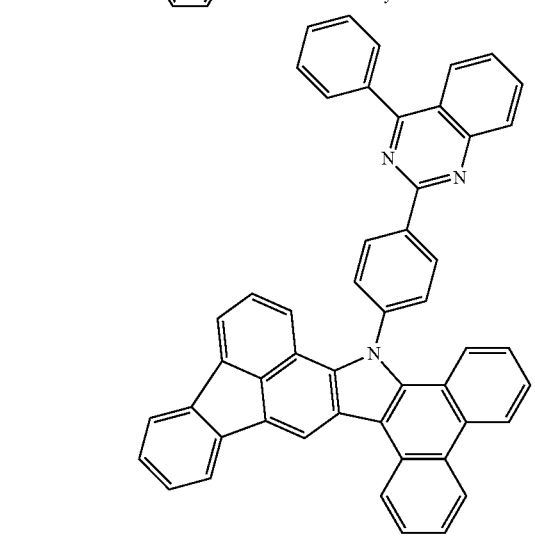

Compound 35

The compound 35 was synthesized in the same manner as in the synthesis of the compound 2 except for using the intermediate H in place of the compound 1 and using the intermediate C in place of the intermediate B. The obtained compound was identified as the target compound by the result of mass spectrometric analysis which showed m/e=671 to the molecular weight of 671.24.

Example 36 (Synthesis of Compound 36)

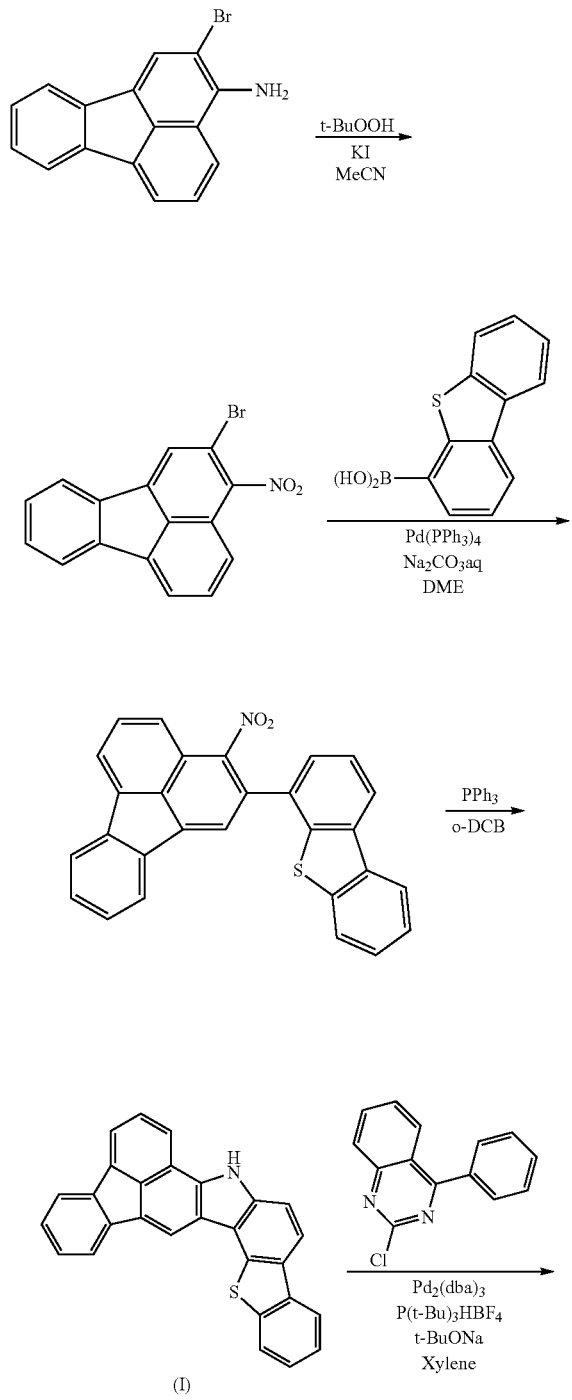

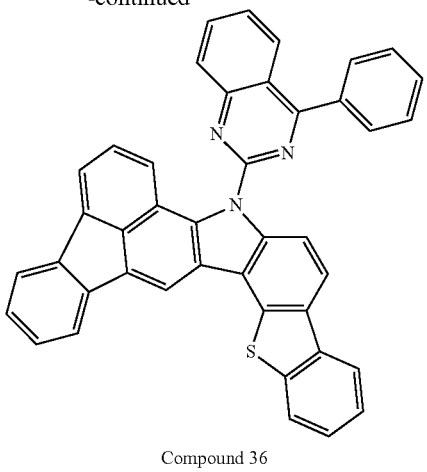

Compound 36

The compound 36 was synthesized according to the above scheme in the same manner as in the synthesis of the compound 28 except for using 4-dibenzothiophene boronic acid in place of 1-naphthalene boronic acid. The obtained compound was identified as the target compound by the result of mass spectrometric analysis which showed m/e=601 to the molecular weight of 601.16.

Example 37 (Synthesis of Compound 37)

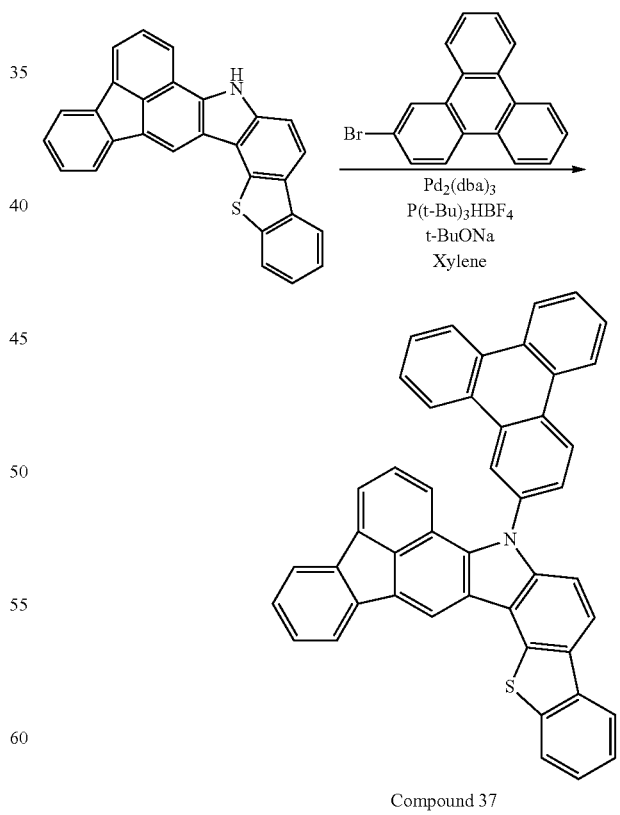

Compound 37

The compound 37 was synthesized in the same manner as in the synthesis of the compound 2 except for using the intermediate I in place of the compound 1 and using 2-bromotriphenylene in place of the intermediate B. The obtained compound was identified as the target compound by the result of mass spectrometric analysis which showed m/e=623 to the molecular weight of 623.17.

Example 38 (Synthesis of Compound 38)

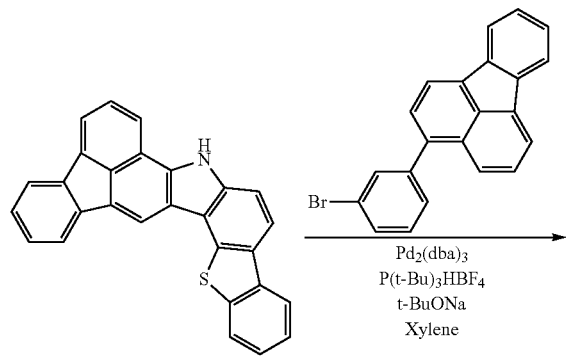

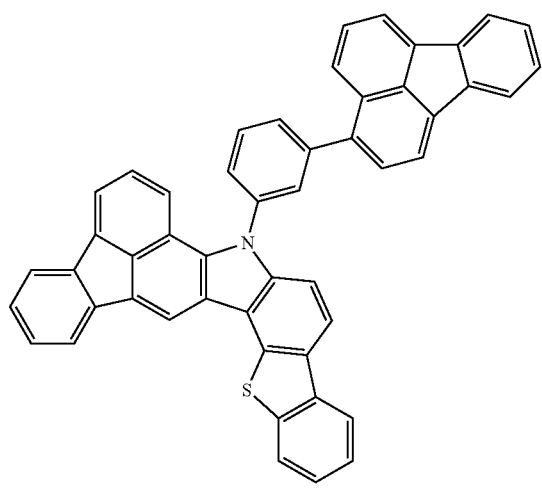

Compound 38

The compound 38 was synthesized in the same manner as in the synthesis of the compound 2 except for using the intermediate I in place of the compound 1 and using 3-(3-bromophenyl)fluoranthene in place of the intermediate B. The obtained compound was identified as the target compound by the result of mass spectrometric analysis which showed m/e=673 to the molecular weight of 673.19.

Example 39 (Synthesis of Compound 39)

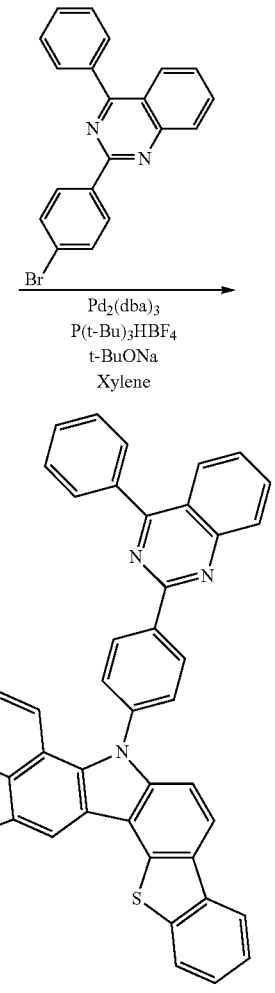

Compound 39

The compound 39 was synthesized in the same manner as in the synthesis of the compound 2 except for using the intermediate I in place of the compound 1 and using the intermediate C in place of the intermediate B. The obtained compound was identified as the target compound by the result of mass spectrometric analysis which showed m/e=677 to the molecular weight of 677.19.

Example 40 (Synthesis of Compound 40)

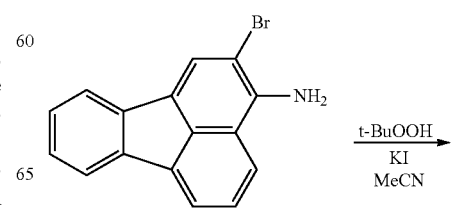

Example 41 (Synthesis of Compound 41)

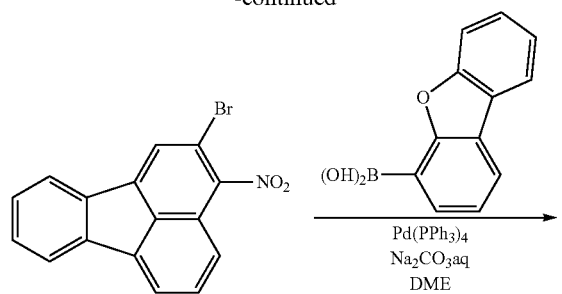

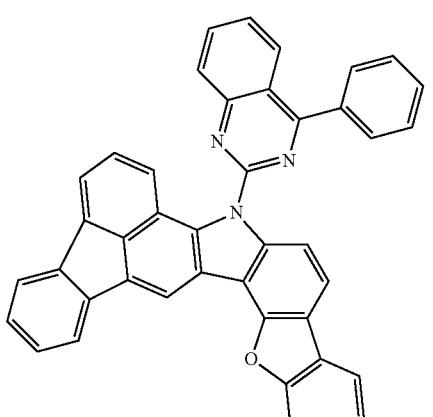

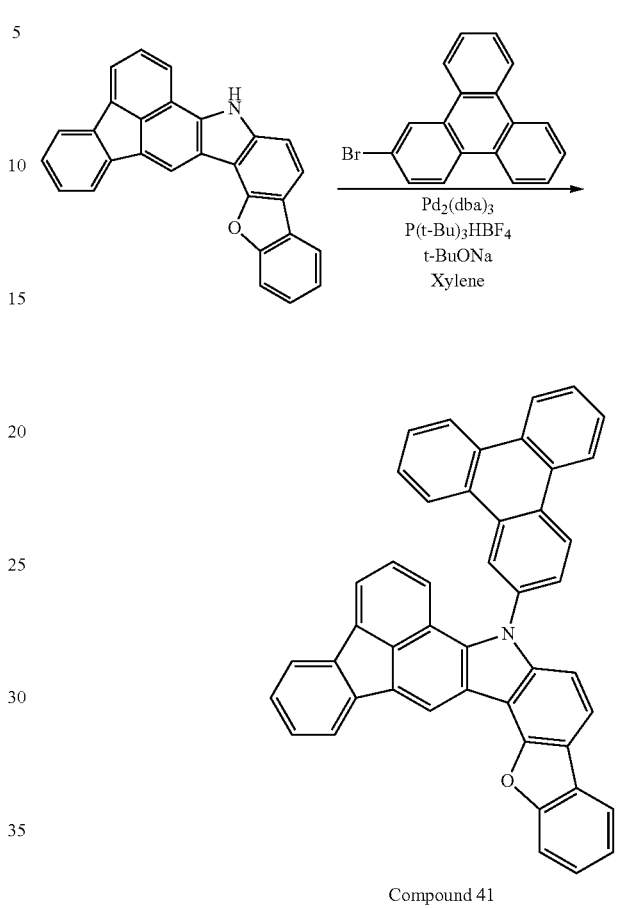

The compound 40 was synthesized according to the above scheme in the same manner as in the synthesis of the compound 28 except for using 4-dibenzofuran boronic acid in place of 1-naphthalene boronic acid. The obtained compound was identified as the target compound by the result of mass spectrometric analysis which showed m/e=585 to the molecular weight of 585.18.

The compound 41 was synthesized in the same manner as in the synthesis of the compound 2 except for using the intermediate J in place of the compound 1 and using 2-bromotriphenylene in place of the intermediate B. The obtained compound was identified as the target compound by the result of mass spectrometric analysis which showed m/e=607 to the molecular weight of 607.19.

Example 42 (Synthesis of Compound 42)

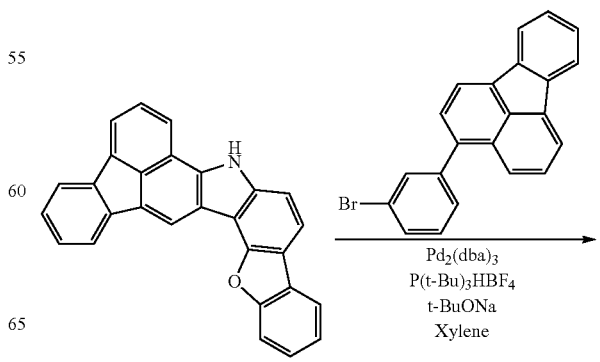

-continued

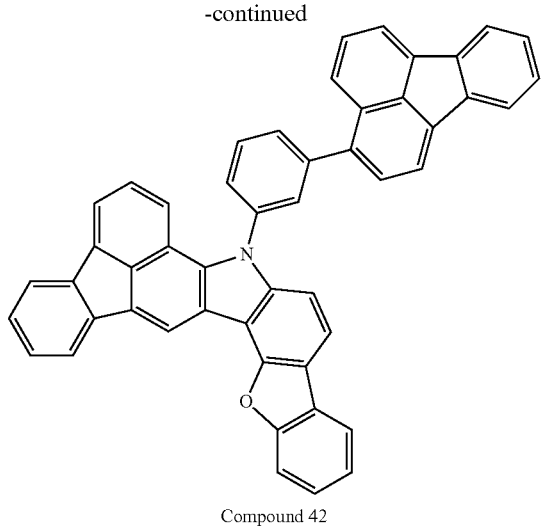

Compound 42

The compound 42 was synthesized in the same manner as in the synthesis of the compound 2 except for using the intermediate J in place of the compound 1 and using 3-(3-bromophenyl)fluoranthene in place of the intermediate B. The obtained compound was identified as the target compound by the result of mass spectrometric analysis which showed m/e=657 to the molecular weight of 657.21.

Example 43 (Synthesis of Compound 43)

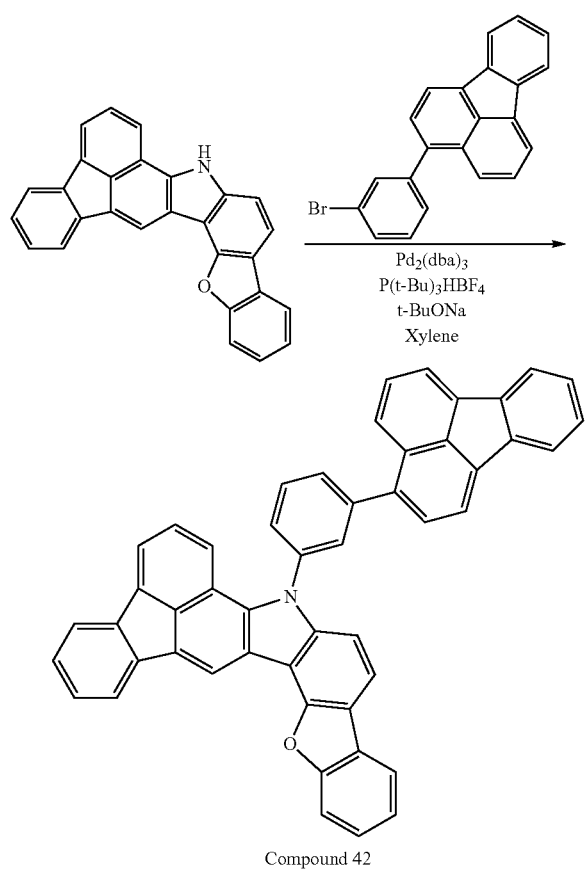

Compound 42

The compound 43 was synthesized in the same manner as in the synthesis of the compound 2 except for using the intermediate J in place of the compound 1 and using the intermediate C in place of the intermediate B. The obtained compound was identified as the target compound by the result of mass spectrometric analysis which showed m/e=661 to the molecular weight of 661.22.

Example 44 (Synthesis of Compound 44)

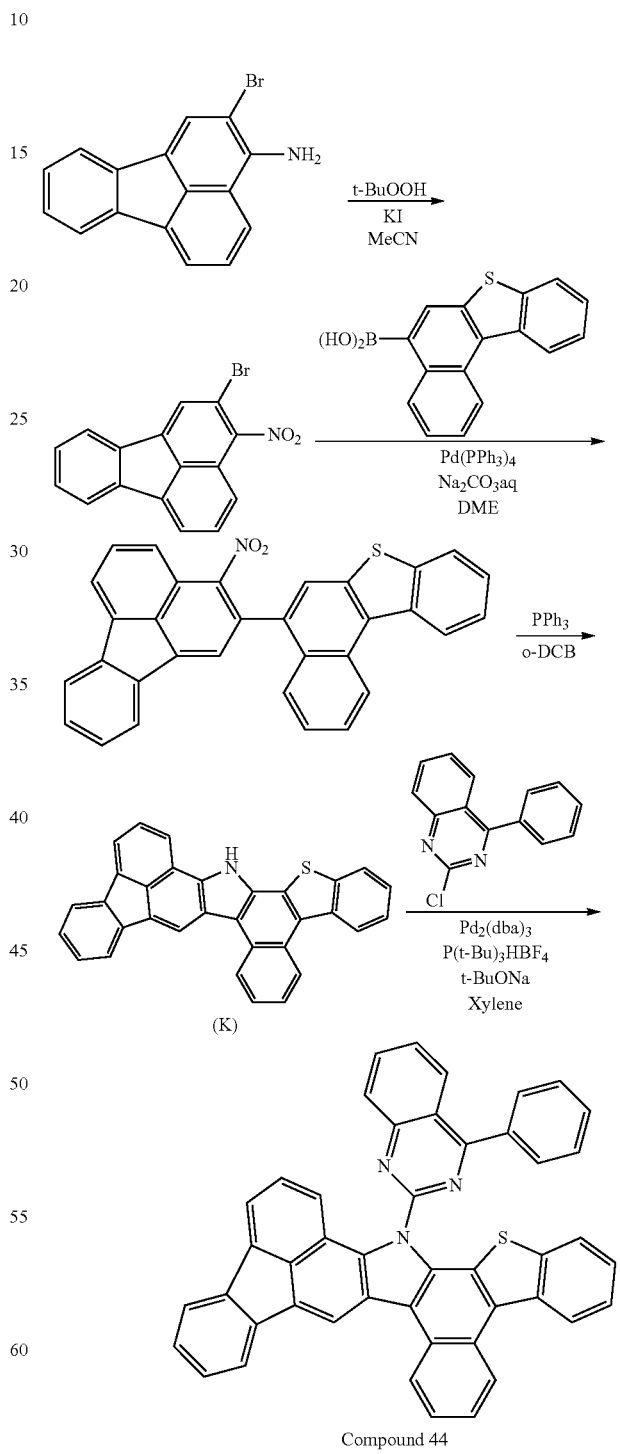

Compound 44

The compound 44 was synthesized according to the above scheme in the same manner as in the synthesis of the compound 28 except for using benzo[b]naphtho[1,2-d]thiophene-5-boronic acid which was synthesized by a known method in place of 1-naphthalene boronic acid. The obtained compound was identified as the target compound by the result of mass spectrometric analysis which showed m/e=651 to the molecular weight of 651.18.

Example 45 (Synthesis of Compound 45)

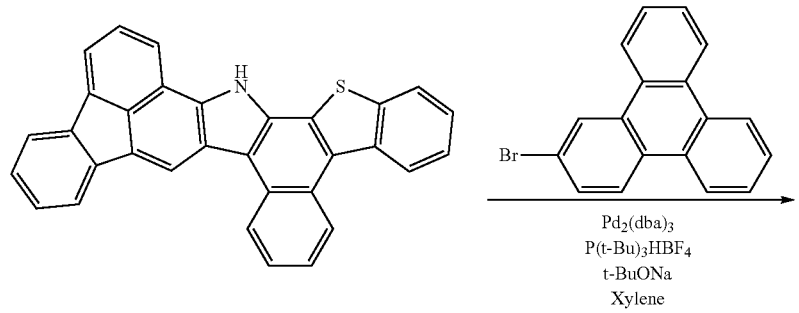

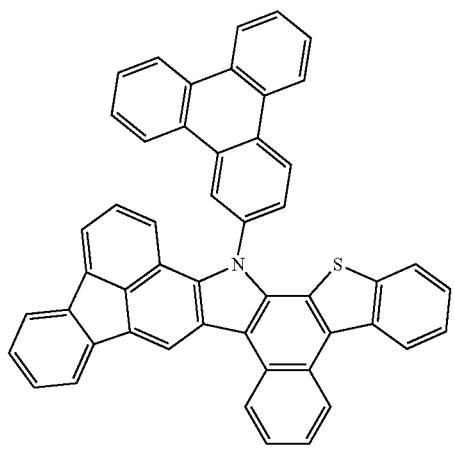

Compound 45

The compound 45 was synthesized in the same manner as in the synthesis of the compound 2 except for using the intermediate K in place of the compound 1 and using 2-bromotriphenylene in place of the intermediate B. The obtained compound was identified as the target compound by the result of mass spectrometric analysis which showed m/e=673 to the molecular weight of 673.19.

Example 46 (Synthesis of Compound 46)

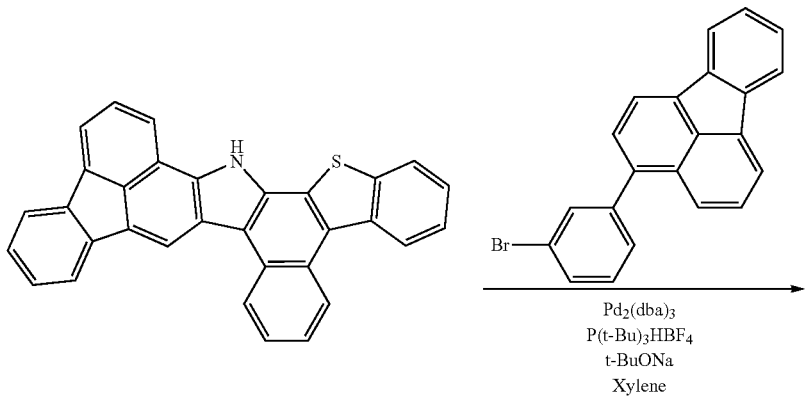

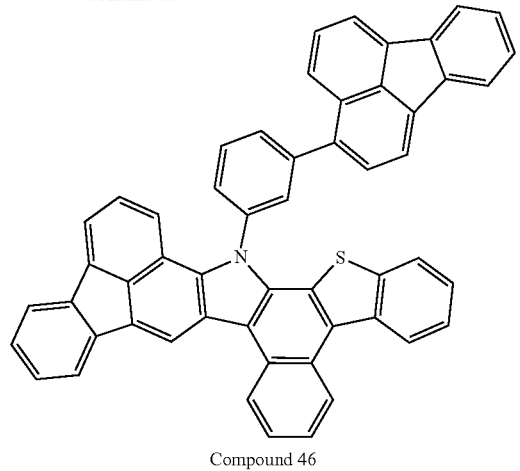

Compound 46

The compound 46 was synthesized in the same manner as in the synthesis of the compound 2 except for using the intermediate K in place of the compound 1 and using 3-(3-bromophenyl)fluoranthene in place of the intermediate B. The obtained compound was identified as the target compound by the result of mass spectrometric analysis which showed m/e=723 to the molecular weight of 723.20.

Example 47 (Synthesis of Compound 47)

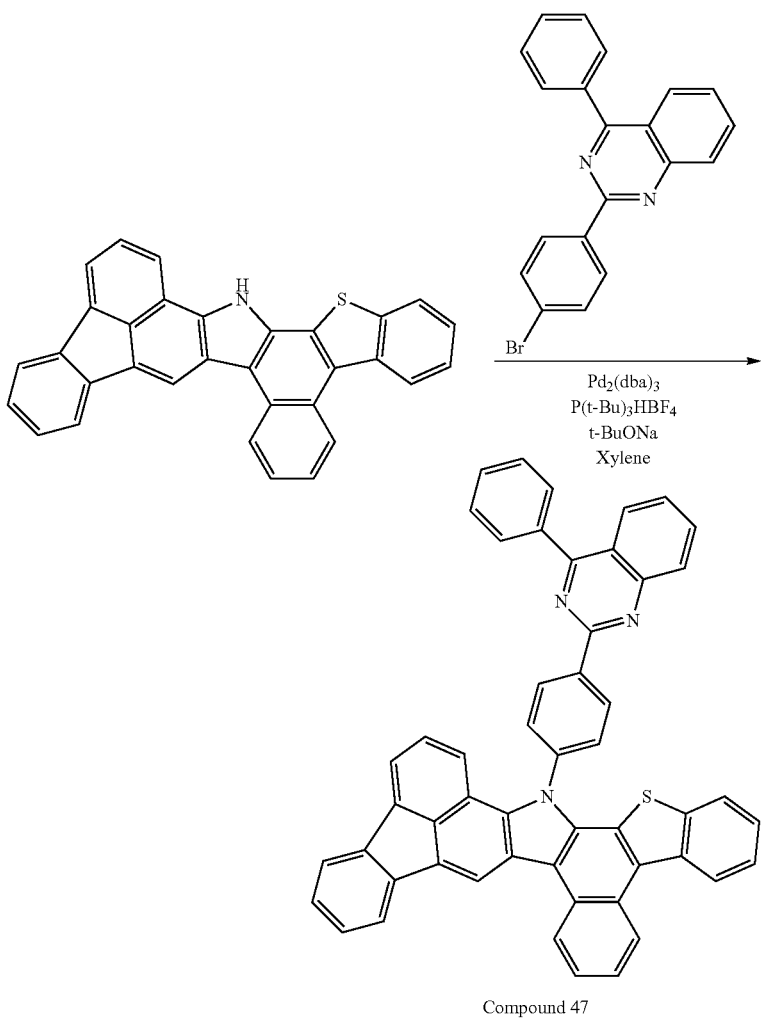

Compound 47

The compound 47 was synthesized in the same manner as in the synthesis of the compound 2 except for using the intermediate K in place of the compound 1 and using the intermediate C in place of the intermediate B. The obtained compound was identified as the target compound by the result of mass spectrometric analysis which showed m/e=727 to the molecular weight of 727.21.

Example 48 (Synthesis of Compound 48)

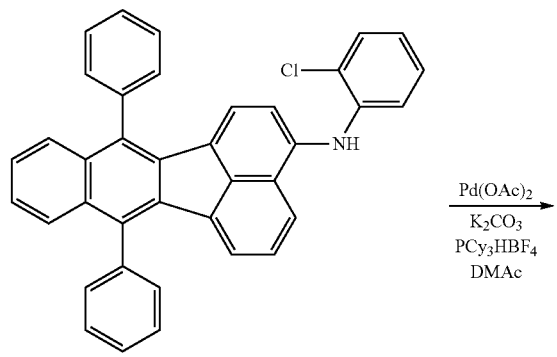

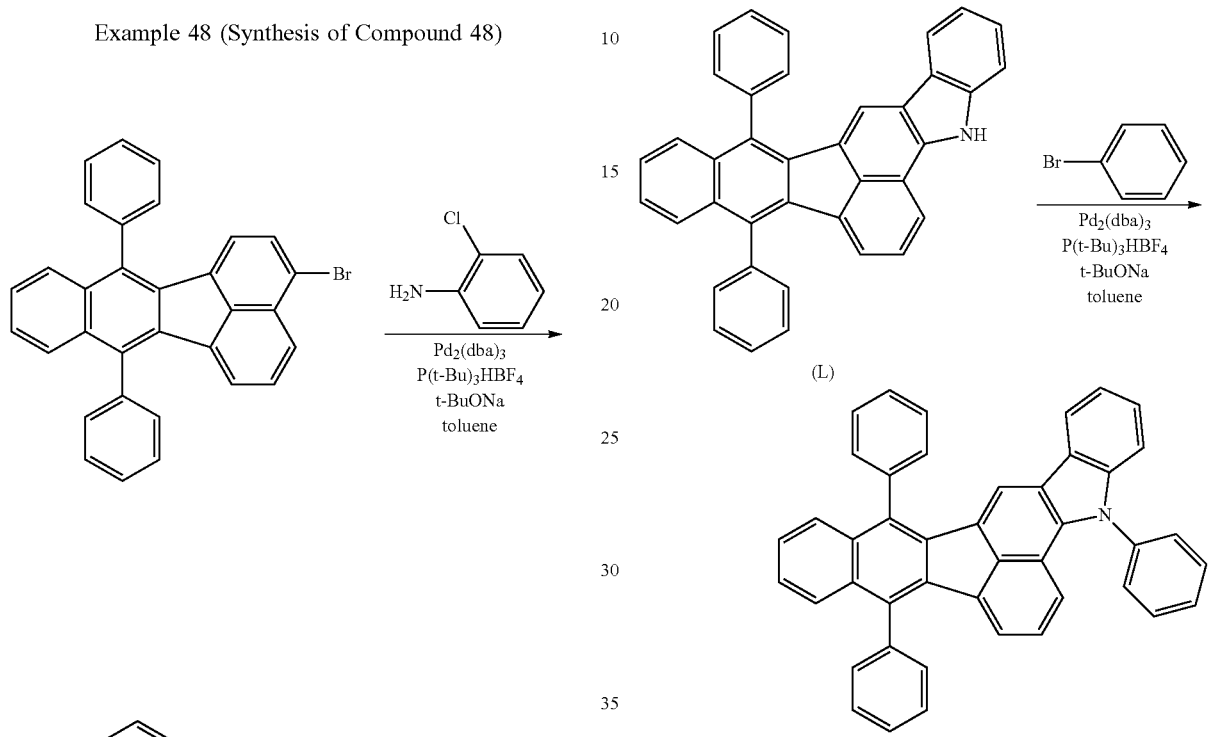

Compound 48

The compound L was synthesized in the same manner as in the synthesis of the compound 1 except for using 3-bromo-7,12-diphenylbenzo[k]fluoranthene in place of 3-bromofluoranthene. The compound 48 was synthesized in the same manner as in the synthesis of the compound 2 except for using the compound L in place of the compound 1 and using bromobenzene in place of the intermediate B. The obtained compound was identified as the target compound by the result of mass spectrometric analysis which showed m/e=569 to the molecular weight of 569.21.

Example 49 (Synthesis of Compound 49)

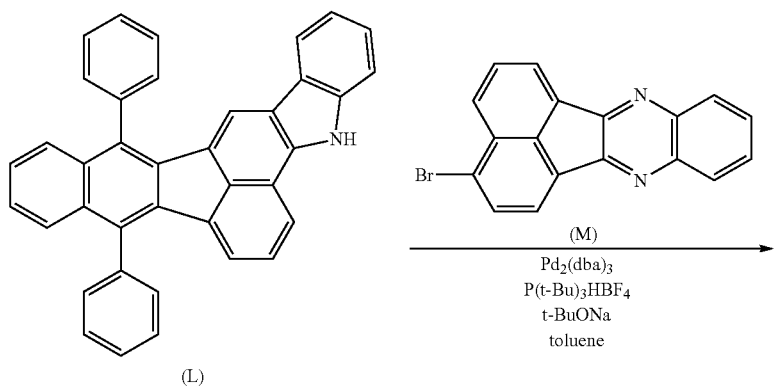

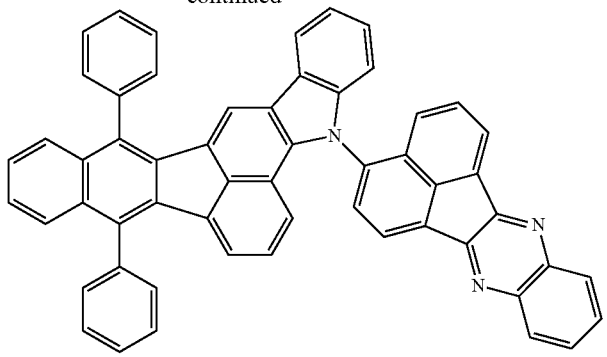

Compound 49

The compound 49 was synthesized in the same manner as in the synthesis of the compound 2 except for using the compound L in place of the compound 1 and using the intermediate M which was synthesized by a known method in place of the intermediate B. The obtained compound was identified as the target compound by the result of mass spectrometric analysis which showed m/e=745 to the molecular weight of 745.25.

Example 50 (Production of Organic EL Device)

A glass substrate of 25 mm×75 mm×1.1 mm thickness having an ITO transparent electrode (product of Geomatec Company) was cleaned by ultrasonic cleaning in isopropyl alcohol for 5 min and then UV ozone cleaning for 30 min.

The cleaned glass substrate having a transparent electrode line with a thickness of 130 nm was mounted to a substrate holder of a vacuum vapor deposition apparatus. The following compound HT-1 as a first hole transporting material was vapor-deposited so as to cover the transparent electrode to form a first hole transporting layer with a thickness of 45 nm. Successively after forming the first hole transporting layer, the following compound HT-2 as a second hole transporting material was vapor-deposited to form a second hole transporting layer with a thickness of 10 nm.

On the second hole transporting layer, the compound 2 (host material) obtained in Example 2 and the following compound RD-1 (phosphorescent material) were vapor co-deposited to form a phosphorescent light emitting layer with a thickness of 40 nm. The concentration of the compound RD-1 in the light emitting layer was 5.0% by mass. The co-deposited film works as a light emitting layer.

Successively after forming the light emitting layer, the following compound ET-1 was vapor-deposited into a film with a thickness of 40 nm. The film of the compound ET-1 works as a first electron transporting layer.

Then, LiF was vapor-deposited into a film with a thickness of 1 nm at a film-forming speed of 0.01 nm/sec to form an electron injecting electrode (cathode). On the LiF film, metallic Al was vapor-deposited to form a metallic cathode with a thickness of 80 nm, thereby obtaining an organic EL device.

The compounds used in the Example 50 and Comparative Example 1 are shown below.

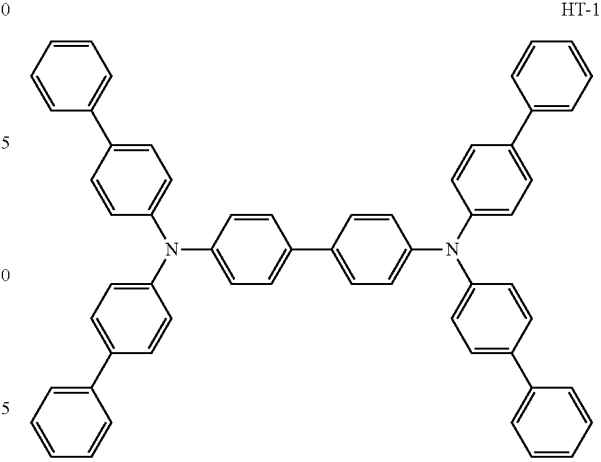

HT-1

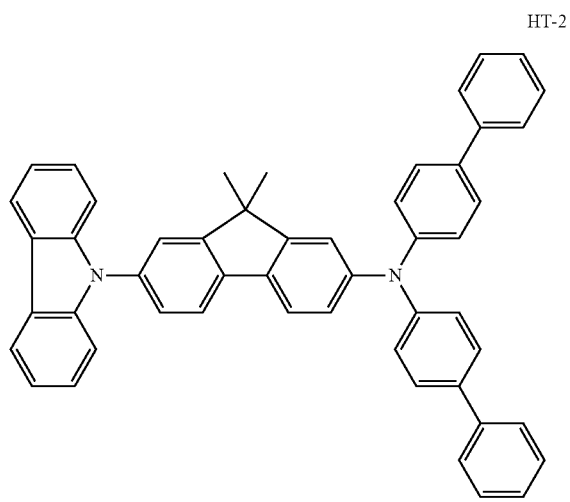

HT-2

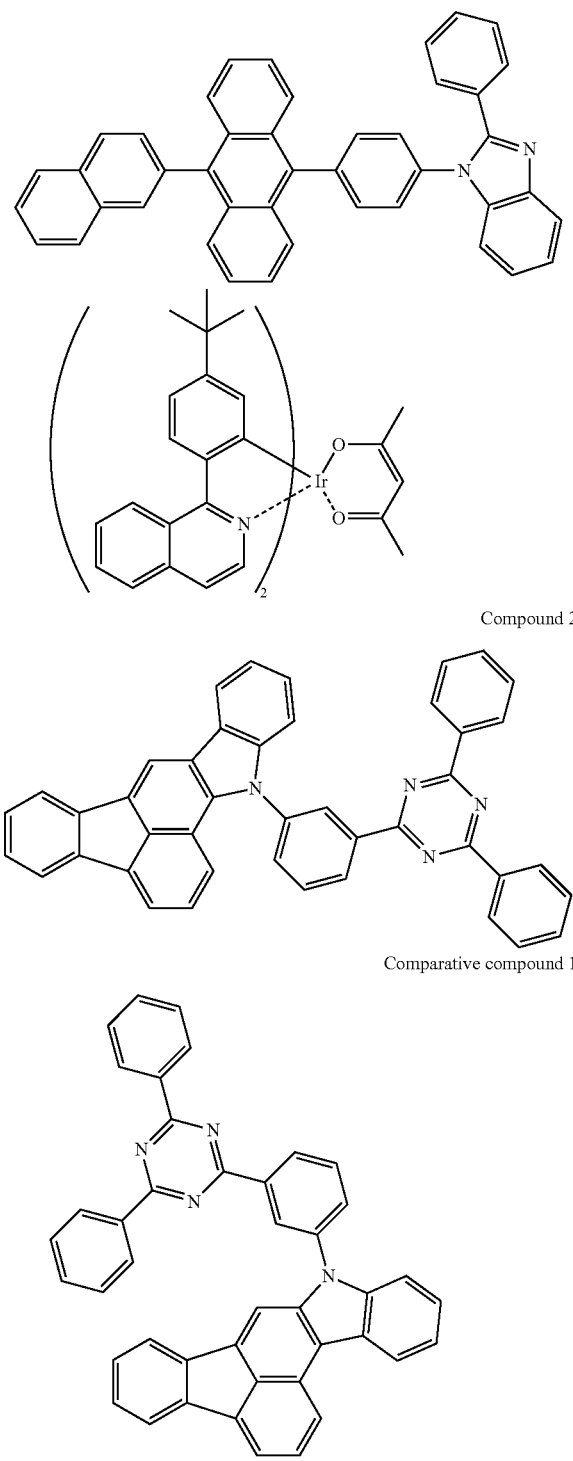

ET-1

Compound 2

Comparative compound 1

The organic EL device thus obtained was evaluated for the emission performance in the following manner, and the compound 2 was measured for the triplet energy as described below.

Evaluation of Emission Performance of Organic EL Device

By driving the obtained organic EL device at room temperature by a constant direct current (current density: 10 mA/cm$^2$), the external quantum efficiency (%) was measured using a spectroradiometer (CS-1000 manufactured by Minolta). The result are shown in Tables 1 and 2.

Measurement of Triplet Energy

The triplet energy (EgT) was determined by the following method.

Each compound was measured by a known phosphorimetric method (for example, the method described in "World of Photochemistry," 1993, p. 50, edited by The Chemical Society of Japan). Specifically, each compound was dissolved in EPA solvent (diethyl ether:isopentane: ethanol=5:5:5 by volume) in a concentration of 10 μmol/L to prepare a specimen for phosphorimetry. Spectroscopic grade solvents were used. The specimen for phosphorimetry was placed in a quartz cell and irradiated with excitation ray at 77 K. Then, the phosphorescence intensity was measured at different wavelengths to obtain a phosphorescent spectrum with a vertical axis indicating the phosphorescent intensity and a horizontal axis indicating the wavelength.

On the phosphorescence spectrum, a line tangent to the rising portion at the short-wavelength side of the phosphorescent spectrum was drawn, and the wavelength λedge (nm) at the intersection of the tangent line and the horizontal axis was read. The obtained wavelength was converted into the energy value by the following expression to determine EgT:

$$EgT \text{ (eV)}=1239.85/\lambda\text{edge}.$$

The line tangent to the rising portion at the short-wavelength side of the phosphorescent spectrum was drawn as follows. Considering the tangent lines drawn at the points which are taken along the curve from the short-wavelength side of the phosphorescent spectrum toward the peak at the shortest wavelength, the slope of the tangent line increases as the spectrum curve rises, i.e., as the value of the vertical axis increases. The tangent line having the maximum slope was employed as the line tangent to the rising portion at the short-wavelength side of the phosphorescent spectrum.

The peak having an intensity which was 10% or lower of the maximum peak intensity of the spectrum was not employed as the peak at the shortest wavelength. The tangent line drawn at the point which was closest to the peak at the shortest wavelength and gave the largest slope of the tangent line was employed as the line tangent to the rising portion at the short-wavelength side of the phosphorescent spectrum.

The phosphorimetric measurement was made by using a spectrofluoro-photometer F-4500 manufactured by Hitachi High-Technologies Corporation together with an optional unit for low-temperature measurement. The measuring instrument is not limited thereto, and the measurement may be made by using a combination of a cooling device, a cell for low-temperature use, a source of excitation ray, and a photoreceptor.

Comparative Example 1

An organic EL device was produced in the same manner as in Example 50 except for forming the light emitting layer by using the comparative compound 1 in place of the compound 2 as a host material. The measured results of the external quantum efficiency of the organic EL device and the triplet energy of the comparative compound 1 are shown in Table 1.

TABLE 1

| | Light emitting layer host material | Voltage (V) | External quantum efficiency (%) | Triplet energy (EgT) (eV) |
|---|---|---|---|---|
| Example 50 | compound 2 | 3.21 | 16.6 | 2.3 |
| Comparative Example 1 | comparative compound 1 | 3.32 | 13.1 | 2.2 |

As seen from Table 1, the fused fluoranthene compound of the invention has a large triplet energy as compared with the comparative compound 1. These compounds are both fused fluoranthene compounds, but different from each other in the fused orientation. With this difference, the compound of the invention maintains a high triplet level, thereby making it possible to maintain and achieve a high efficiency. In fact, the results of Table 1 show that the compound 50 exhibits an external quantum efficiency higher than that of the comparative compound 1.

In addition, as compared with the fused orientation of the comparative compound 1, in the fused fluoranthene compound 2 of the invention, the substituent on N and the fused fluoranthene skeleton are largely rotated with each other and are torsionally oriented at about right angles. With such a torsional orientation, in the device of Example 1 in which the compound 2 was used in the light emitting layer as a host material, the steric exclusion between the host molecules may increase and the concentration quenching due to the association of the dopant molecules which are dispersed in the host molecules in a proportion of about several presents may be prevented. This may be attributable to the high efficiency.

Example 51

The cleaned glass substrate having a transparent electrode line with a thickness of 130 nm used in Example 50 was mounted to a substrate holder of a vacuum vapor deposition apparatus. First, the following compound HA-1 as a hole injecting material was vapor-deposited so as to cover the transparent electrode to form a hole injecting layer with a thickness of 10 nm. Successively after forming the hole injecting layer, the following compound HT-3 as a first hole transporting material was vapor-deposited to form a first hole transporting layer with a thickness of 20 nm. Thereafter, the following compound HT-4 as a second hole transporting material was vapor-deposited to form a second hole transporting layer with a thickness of 10 nm.

On the second hole transporting layer, the compound 10 (host material) obtained in Example 10 and the following compound RD-1 (phosphorescent material) were vapor co-deposited to form a phosphorescent light emitting layer with a thickness of 40 nm. The concentration of the compound RD-1 in the light emitting layer was 5.0% by mass. The co-deposited film works as a light emitting layer.

Successively after forming the light emitting layer, the following compound ET-1 was vapor-deposited into a film with a thickness of 45 nm. The film of the compound ET-1 works as a first electron transporting layer.

Then, LiF was vapor-deposited into a film with a thickness of 1 nm at a film-forming speed of 0.01 nm/sec to form an electron injecting electrode (cathode). On the LiF film, metallic Al was vapor-deposited to form a metallic cathode with a thickness of 80 nm, thereby obtaining an organic EL device.

The compounds used in the Examples 51 to 58 and Comparative Examples 2 and 3 are shown below.

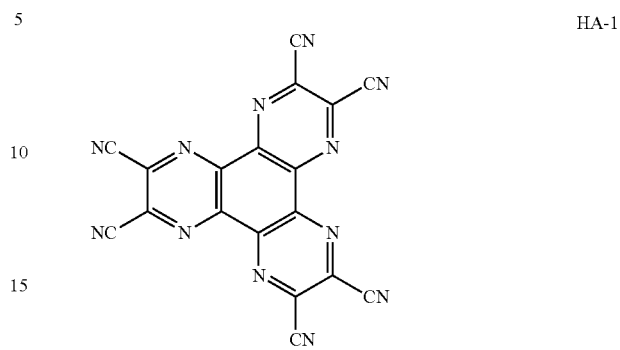

HA-1

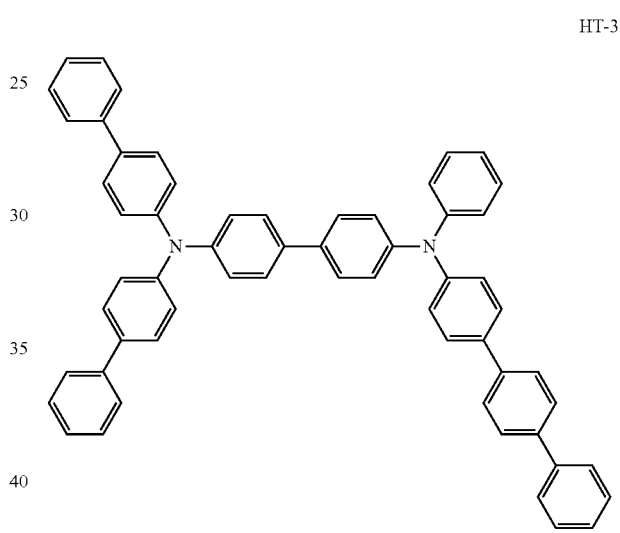

HT-3

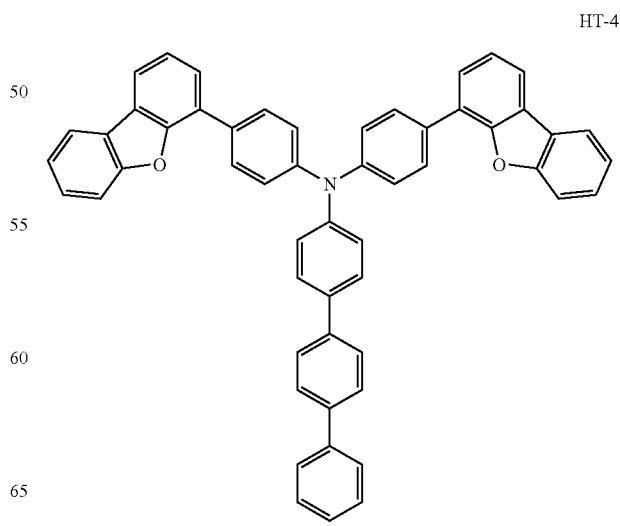

HT-4

Compound 10
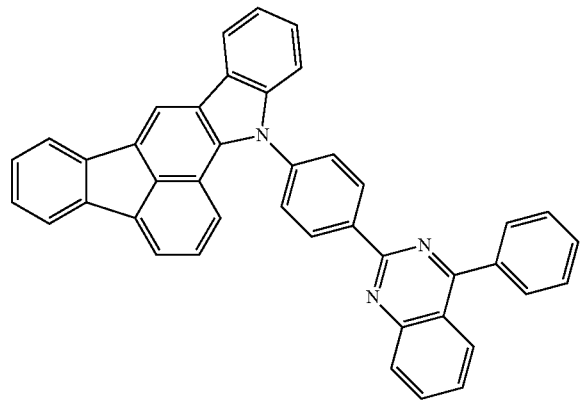
RD-1
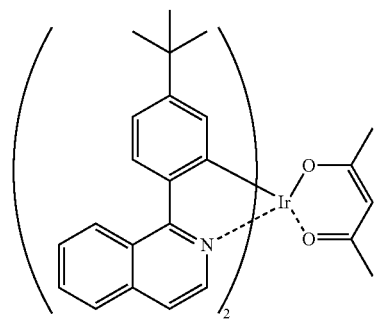
ET-1
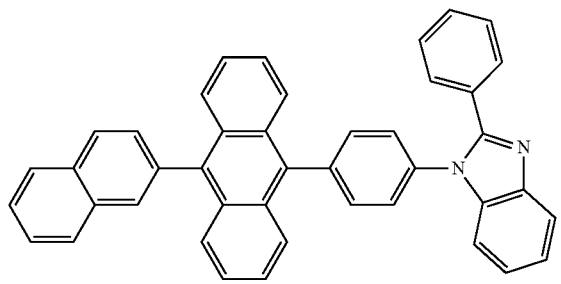
Examples 52 to 58
Each device was produced in the same manner as in Example 51 except for using each compound shown in Table 2 in place of the compound 10. The results of evaluations are shown in Table 2.
Compound 24
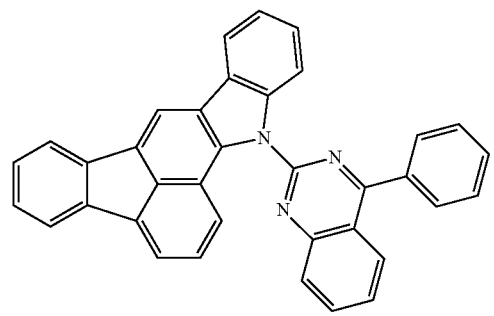
Compound 27
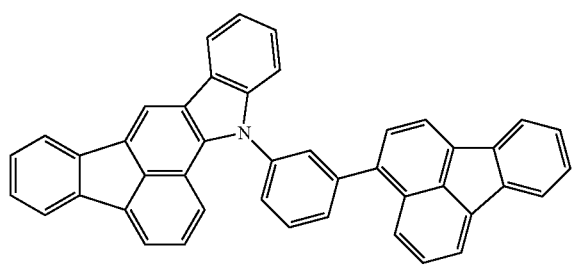
Compound 31
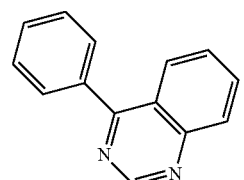
Compound 35
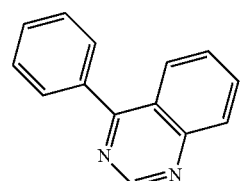
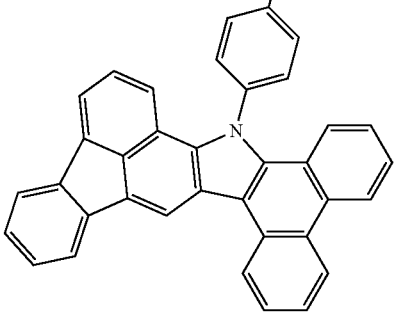

Compound 39
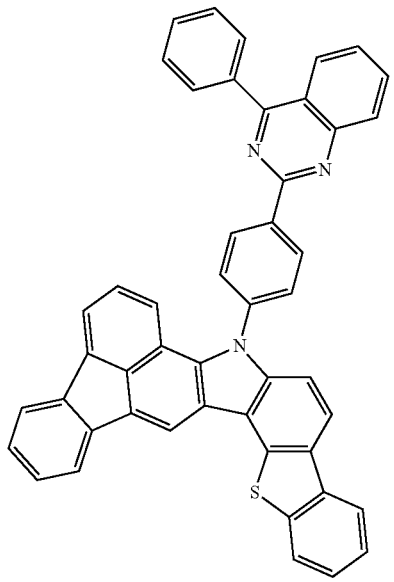
Compound 43
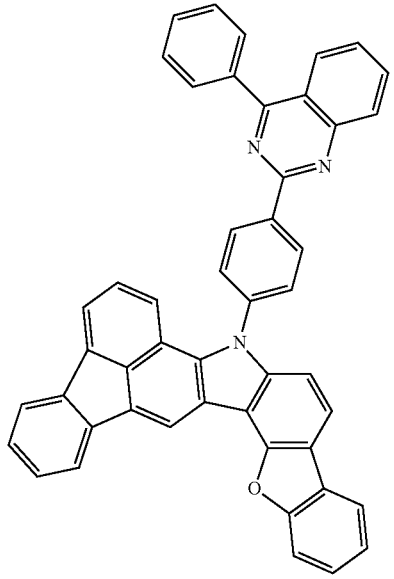
Compound 47
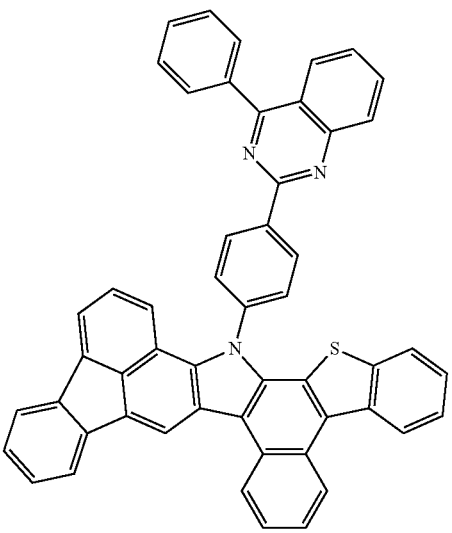
Comparative Examples 2 and 3
Each device was produced in the same manner as in Example 51 except for using each of the comparative compounds 2 and 3 in the light emitting layer in place of the compound 10. The results of evaluations are shown in Table 2.
Comparative compound 2
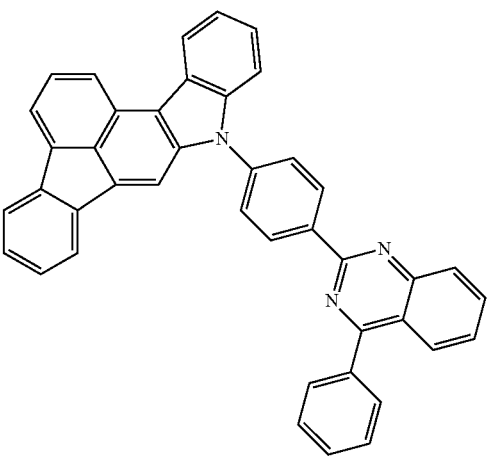

Comparative compound 3

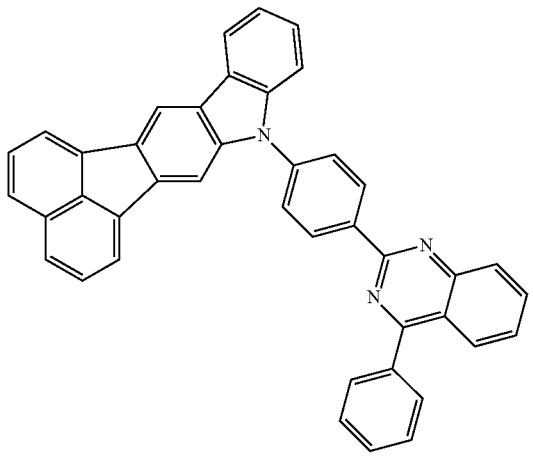

| | Light emitting layer host material | Voltage (V) | External quantum efficiency (%) |
|---|---|---|---|
| Example 51 | compound 10 | 3.4 | 17.5 |
| Example 52 | compound 24 | 3.8 | 17.1 |
| Example 53 | compound 27 | 3.6 | 17.9 |
| Example 54 | compound 31 | 3.3 | 16.9 |
| Example 55 | compound 35 | 3.3 | 16.9 |
| Example 56 | compound 39 | 3.4 | 16.8 |
| Example 57 | compound 43 | 3.4 | 16.9 |
| Example 58 | compound 47 | 3.2 | 16.7 |
| Comparative Example 2 | comparative compound 2 | 3.3 | 12.1 |
| Comparative Example 3 | comparative compound 3 | 3.4 | 13.1 |

Upon comparing Examples 51 to 58 with Comparative Examples 2 and 3 of Table 2, it can be seen that the organic EL devices each employing the fused fluoranthene compound of the invention exhibit the external quantum efficiencies higher than those of the devices employing the comparative fused fluoranthene compounds.

REFERENCE NUMERALS

1 Organic electroluminescence device
2 Substrate
3 Anode
4 Cathode
5 Light emitting layer
6 Anode-side organic thin film layer
7 Cathode-side organic thin film layer
10 Organic thin film layer

What is claimed is:

1. An organic electroluminescence device, comprising:
a cathode;
an anode; and
an organic thin film layer comprising one or more layers disposed between the cathode and the anode, wherein the organic thin film layer comprises a light emitting layer and at least one layer of the organic thin film layer comprises a fused fluoranthene compound represented by formula (a):

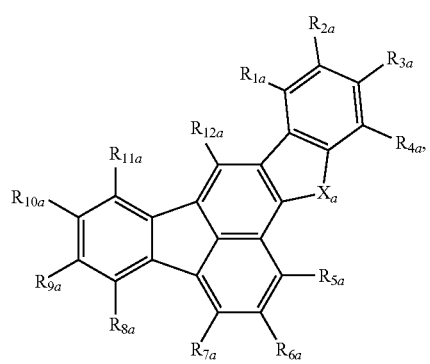

(a)

wherein:
$X_a$ represents $Si(R_{13a})(R_{14a})$, a sulfur atom, or an oxygen atom; and
each of $R_{1a}$ to $R_{14a}$ independently represents a hydrogen atom or a substituent, and adjacent groups of $R_{1a}$ to $R_{14a}$ may be bonded to each other to form a saturated or unsaturated ring structure.

2. The organic electroluminescence device according to claim 1, wherein the fused fluoranthene compound is represented by formula (b):

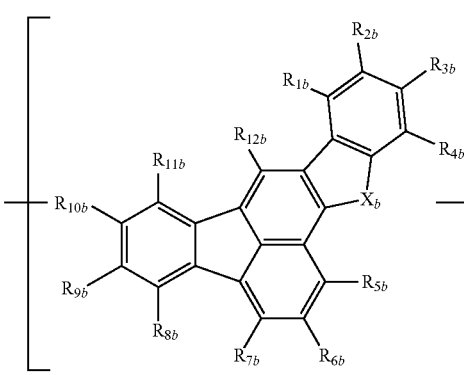

(b)

wherein:
$X_b$ represents $Si(R_{13b})(R_{14b})$, a sulfur atom, or an oxygen atom;
each of $R_{1b}$ to $R_{14b}$ independently represents, a hydrogen atom, a substituent, or a bond to $L_b$, and adjacent groups of $R_{1b}$ to $R_{14b}$ may be bonded to each other to form a saturated or unsaturated ring structure; and
$L_b$ represents a single bond or a divalent linking group.

3. The organic electroluminescence device according to claim 1, wherein the fused fluoranthene compound is represented by formula (c):

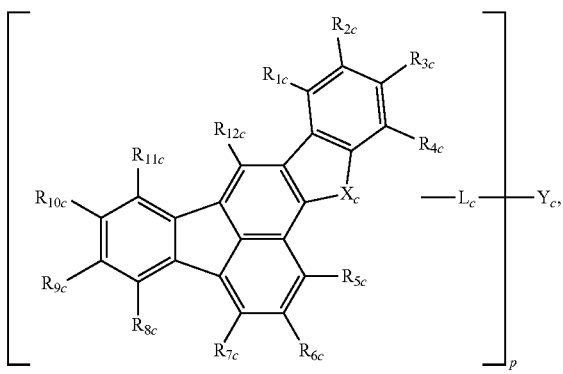

wherein:
$X_c$ represents $Si(R_{13c})(R_{14c})$, a sulfur atom, or an oxygen atom;
each of $R_{1c}$ to $R_{14c}$ independently represents a hydrogen atom, a substituent, or a bond to $L_c$, and adjacent groups of $R_{1c}$ to $R_{14c}$ may be bonded to each other to form a saturated or unsaturated ring structure;
$Y_c$ represents a substituted or unsubstituted p-valent aromatic hydrocarbon group having 6 to 60 ring carbon atoms or a substituted or unsubstituted p-valent heterocyclic group having 3 to 60 ring atoms;
$L_c$ represents a single bond, a substituted or unsubstituted divalent aromatic hydrocarbon group having 6 to 60 ring carbon atoms, a substituted or unsubstituted divalent heterocyclic group having 3 to 60 ring atoms, or a substituted or unsubstituted alkylene group having 1 to 50 carbon atoms; and
p represents an integer of 1 to 6.

4. The organic electroluminescence device according to claim 1, wherein the fused fluoranthene compound is represented by formula (d):

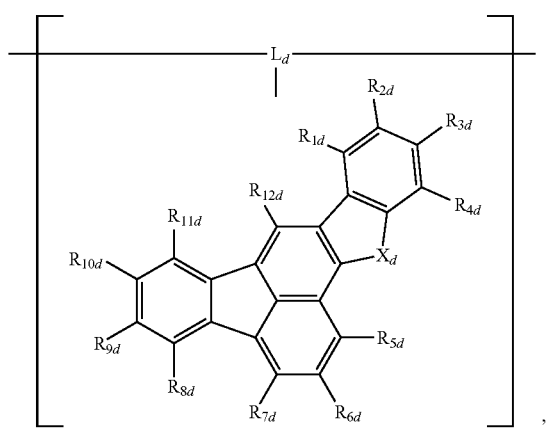

wherein:
$X_d$ represents $Si(R_{13d})(R_{14d})$, a sulfur atom, or an oxygen atom;
each of $R_{1d}$ to $R_{14d}$ independently represents a hydrogen atom, a substituent, or a bond to $L_d$, and adjacent groups of $R_{1d}$ to $R_{14d}$ may be bonded to each other to form a saturated or unsaturated ring structure; and
$L_d$ represents a trivalent organic group.

5. The organic electroluminescence device according to claim 1, wherein at least one of $R_{1a}$ to $R_{14a}$ of formula (a) represents a substituted or unsubstituted alkyl group having 1 to 50 carbon atoms, a substituted or unsubstituted aryl group having 6 to 50 ring carbon atoms, an amino group, a mono- or disubstituted amino group having a substituent selected from a substituted or unsubstituted alkyl group having 1 to 50 carbon atoms and a substituted or unsubstituted aryl group having 6 to 50 ring carbon atoms, or a substituted or unsubstituted heteroaryl group having 5 to 50 ring atoms.

6. The organic electroluminescence device according to claim 5, wherein the aryl group having 6 to 50 ring carbon atoms is a phenyl group, a naphthyl group, a naphthylphenyl group, a biphenylyl group, a terphenylyl group, an acenaphthylenyl group, an anthryl group, a benzanthryl group, an aceanthryl group, a phenanthryl group, a benzophenanthryl group, a phenalenyl group, a fluorenyl group, a 9,9'-spirobifluorenyl group, a benzofluorenyl group, a dibenzofluorenyl group, a picenyl group, a pentaphenyl group, a pentacenyl group, a pyrenyl group, a chrysenyl group, a benzochrysenyl group, a s-indacenyl group, an as-indacenyl group, a fluoranthenyl group, a benzofluoranthenyl group, a tetracenyl group, a triphenylenyl group, a benzotriphenylenyl group, a perylenyl group, a coronyl group, or a dibenzanthryl group.

7. The organic electroluminescence device according to claim 5, wherein the heteroaryl group having 5 to 50 ring atoms is a pyrrolyl group, a furyl group, a thienyl group, a pyridyl group, a pyridazinyl group, a pyrimidinyl group, a pyrazinyl group, a triazinyl group, an imidazolyl group, an oxazolyl group, a thiazolyl group, a pyrazolyl group, an isooxazolyl group, an isothiazolyl group, an oxadiazolyl group, a thiadiazolyl group, a triazolyl group, a tetrazolyl group, an indolyl group, an isoindolyl group, a benzofuranyl group, an isobenzofuranyl group, a benzothiophenyl group, an isobenzothiophenyl group, an indolizinyl group, a quinolizinyl group, a quinolyl group, an isoquinolyl group, a cinnolyl group, a phthalazinyl group, a quinazolinyl group, a quinoxalinyl group, a benzimidazolyl group, a benzoxazolyl group, a benzothiazolyl group, an indazolyl group, a benzisoxazolyl group, a benzisothiazolyl group, a dibenzofuranyl group, a dibenzothiophenyl group, a carbazolyl group, a phenanthridinyl group, an acridinyl group, a phenanthrolinyl group, a phenazinyl group, a phenothiazinyl group, a phenoxazinyl group, an azatriphenylenyl group, a diazatriphenylenyl group, a xanthenyl group, an azacarbazolyl group, an azadibenzofuranyl group, an azadibenzothiophenyl group, a benzofuranobenzothiophenyl group, a benzothienobenzothiophenyl group, a dibenzofuranonaphthyl group, a dibenzothienonaphthyl group, or a dinaphthothienothiophenyl group.

8. The organic electroluminescence device according to claim 5, wherein the substituted or unsubstituted alkyl group having 1 to 50 carbon atoms is a methyl group, an ethyl group, a n-propyl group, an isopropyl group, a n-butyl group, an isobutyl group, a s-butyl group, a t-butyl group, a pentyl group, a hexyl group, a heptyl group, an octyl group, a nonyl group, a decyl group, an undecyl group, a dodecyl group, a tridecyl group, a tetradecyl group, or an octadecyl group.

9. The organic electroluminescence device according to claim 5, wherein the mono- or di-substituted amino group having a substituent selected from a substituted or unsubstituted alkyl group having 1 to 50 carbon atoms and a substituted or unsubstituted aryl group having 6 to 50 ring carbon atoms, wherein the substituted or unsubstituted alkyl group having 1 to 50 carbon atoms is a methyl group, an ethyl group, a n-propyl group, an isopropyl croup, a n-butyl group, an isobutyl group, a s-butyl group, a t-butyl group, a pentyl group, a hexyl group, a heptyl group, an octyl group, a nonyl group, a decyl group, an undecyl group, a dodecyl group, a tridecyl group, a tetradecyl group, or an octadecyl group, and wherein the aryl group having 6 to 50 ring carbon atoms is a phenyl group, a naphthyl group, a naphthylphenyl group, a biphenylyl group, a terphenylyl group, an acenaphthylenyl group, an anthryl group, a benzanthryl group, an aceanthryl group, a phenanthryl group, a benzophenanthryl group, a phenalenyl group, a fluorenyl group, a 9,9'-spirobifluorenyl group, a benzofluorenyl group, a dibenzofluorenyl group, a picenyl group, a pentaphenyl group, a pentacenyl group, a pyrenyl group, a chrysenyl group, a benzochrysenyl group, a s-indacenyl group, an as-indacenyl group, a fluoranthenyl group, a benzofluoranthenyl group, a tetracenyl group, a triphenylenyl group, a benzotriphenylenyl group, a perylenyl group, a coronyl group, or a dibenzanthryl group.

10. The organic electroluminescence device according to claim 1, wherein each of $R_{1a}$ to $R_{14a}$ of formula (a) independently represents a hydrogen atom, a methyl group, an ethyl group, a n-propyl group, an isopropyl group, a n-butyl group, an isobutyl group, a s-butyl group, a t-butyl group, a phenyl group, a naphthyl group, a pyrrolyl group, a furyl group, a thienyl group, a pyridyl group, a pyridazinyl group, a pyrimidinyl group, a pyrazinyl group, a triazinyl group, an imidazolyl group, an oxazolyl group, a thiazolyl group, a pyrazolyl group, a benzofuranyl group, a benzothiophenyl group, a dibenzofuranyl group, a dibenzothiophenyl group, or a carbazolyl group.

11. The organic electroluminescence device according to claim 1, wherein $X_a$ of formula (a) represents an oxygen atom.

12. The organic electroluminescence device according to claim 1, wherein $X_a$ of formula (a) represents a sulfur atom.

13. The organic electroluminescence device according to claim 5, wherein $R_{3a}$ of formula (a) has the substituent, and each of $R_{1a}$, $R_{2a}$, $R_{4a}$, $R_{5a}$, $R_{6a}$, $R_{7a}$, $R_{8a}$, $R_{9a}$, $R_{10a}$, $R_{11a}$ and $R_{12a}$ of formula (a) is a hydrogen atom.

14. The organic electroluminescence device according to claim 5, wherein $R_{1a}$ and $R_{2a}$ of formula (a) are bonded to each other to form a benzene ring.

15. The organic electroluminescence device according to claim 5, wherein $R_{3a}$ and $R_{4a}$ of formula (a) are bonded to each other to form a benzofuran or a benzothiophene.

16. The organic electroluminescence device according to claim 5, wherein $R_{1a}$ and $R_{2a}$ are bonded to each other to form a benzene ring, and $R_{3a}$ and $R_{4a}$ are bonded to each other to form a benzofuran or a benzothiophene.

17. The organic electroluminescence device according to claim 1, wherein the light emitting layer comprises the fused fluoranthene compound.

18. The organic electroluminescence device according to claim 1, wherein the organic electroluminescence device comprises an anode-side organic thin film layer between the anode and the light emitting layer, and the anode-side organic thin film layer comprises the fused fluoranthene compound.

19. The organic electroluminescence device according to claim 1, wherein the organic electroluminescence device comprises a cathode-side organic thin film layer between the cathode and the light emitting layer, and the cathode-side organic thin film layer comprises the fused fluoranthene compound.

20. The organic electroluminescence device according to claim 1, wherein the light emitting layer comprises a phosphorescent material.

21. The organic electroluminescence device according to claim 1, wherein the light emitting layer comprises a fluorescent material.

22. The organic electroluminescence device according to claim 20, wherein the phosphorescent material is an ortho-metallated complex comprising a metal atom selected from iridium (Ir), osmium (Os), and platinum (Pt).

23. An electronic equipment comprising the organic electroluminescence device according to claim 1.

24. An organic electroluminescence device, comprising:
a cathode;
an anode; and
an organic thin film layer comprising one or more layers disposed between the cathode and the anode,
wherein the organic thin film layer comprises a light emitting layer and at least one layer of the organic thin film layer comprises a fused fluoranthene compound which is selected from the following compounds 1 to 26:

Compound 1

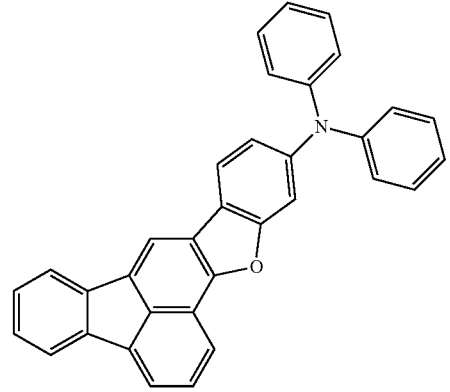

Compound 2

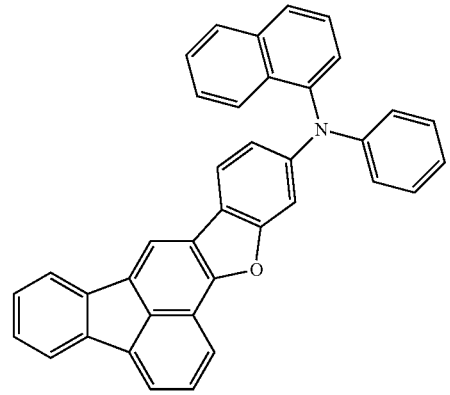

Compound 3
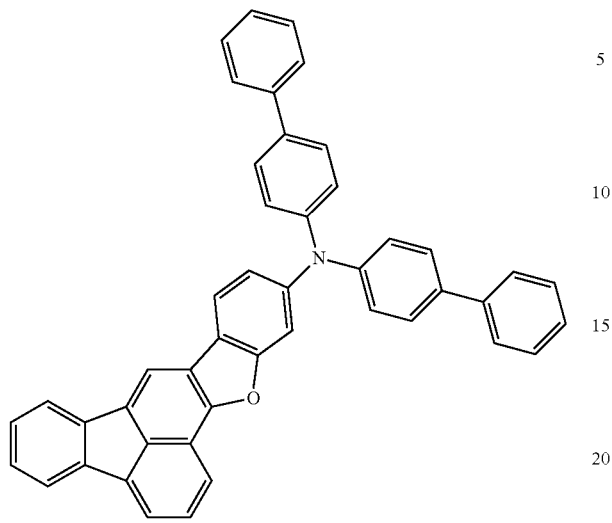
Compound 4
Compound 5
Compound 6
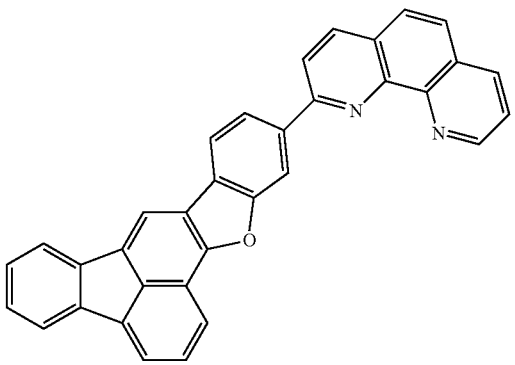
Compound 7
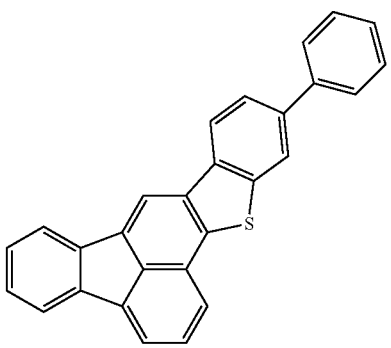
Compound 8
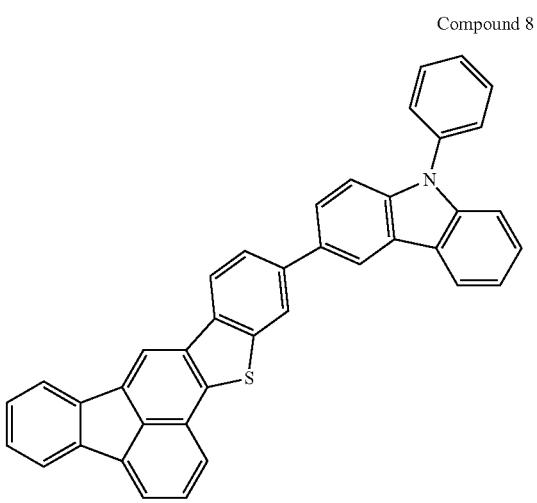
Compound 9
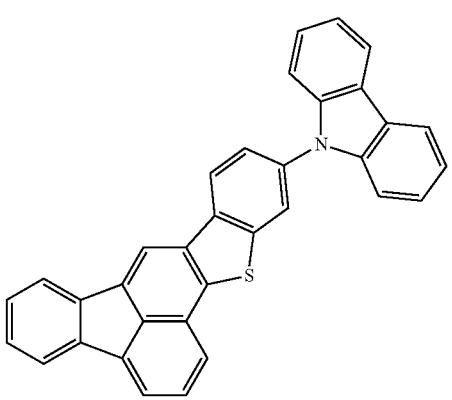

Compound 10
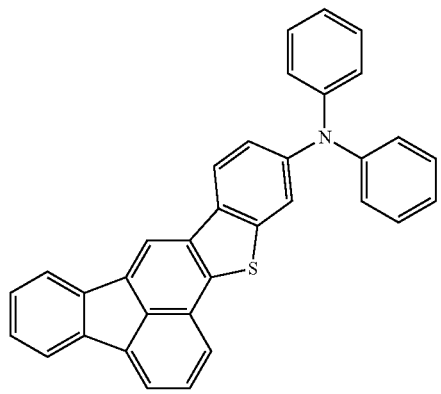
Compound 11
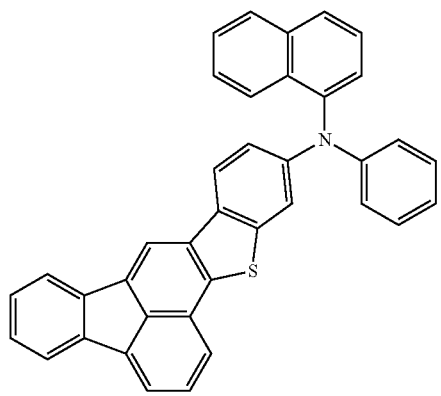
Compound 12
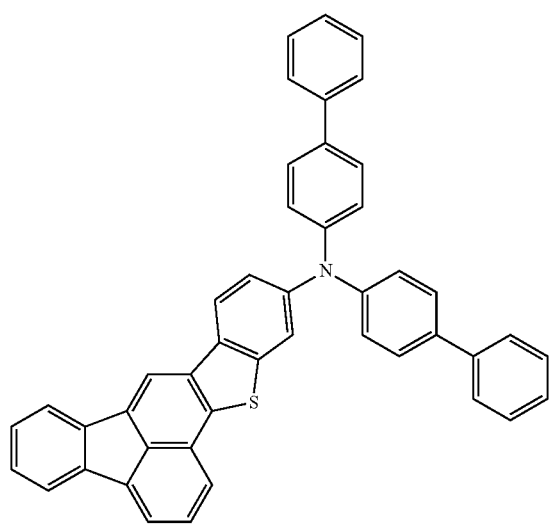
Compound 13
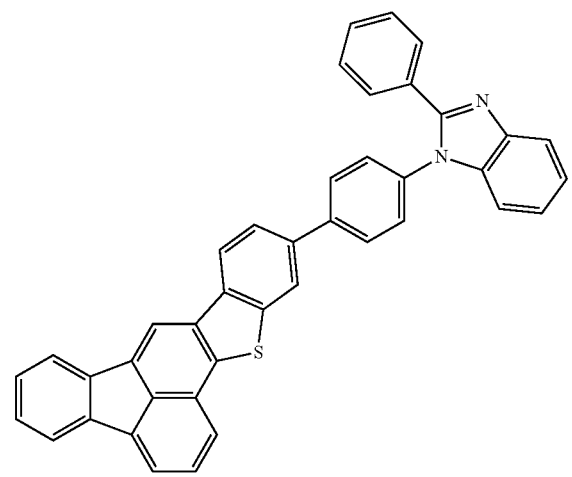
Compound 14
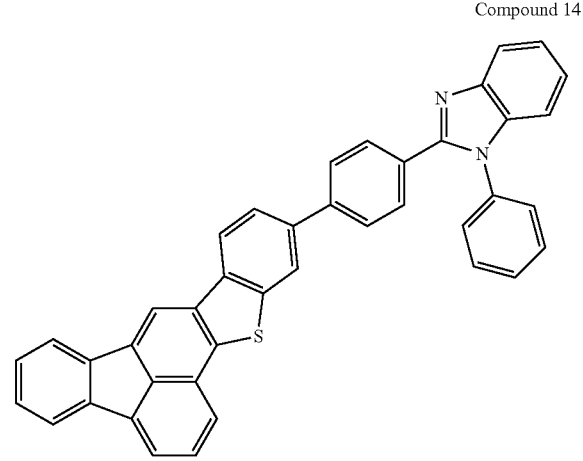
Compound 15
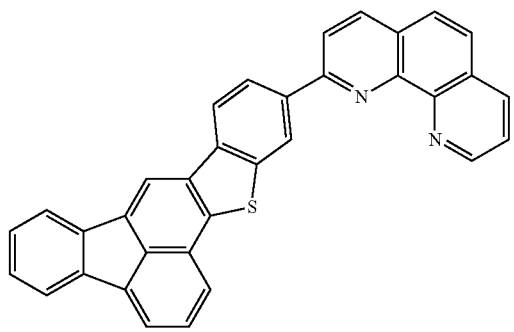

Compound 16
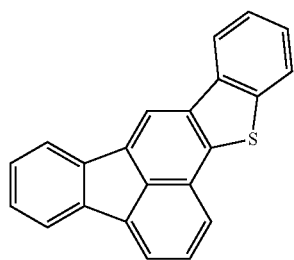
Compound 17
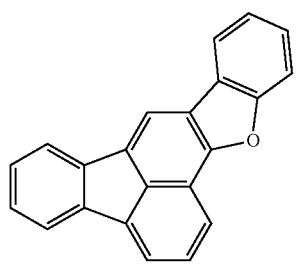
Compound 18
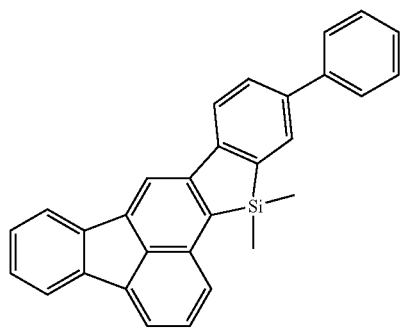
Compound 19
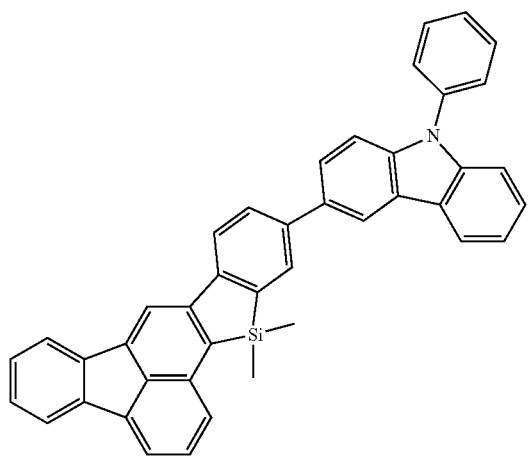
Compound 20
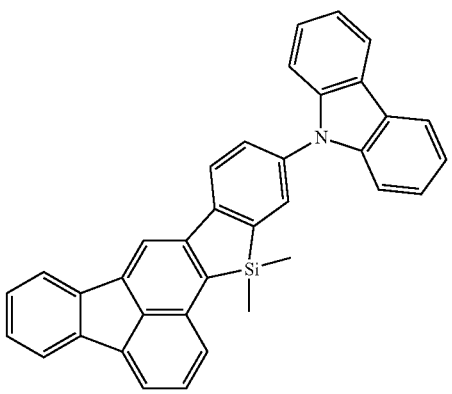
Compound 21
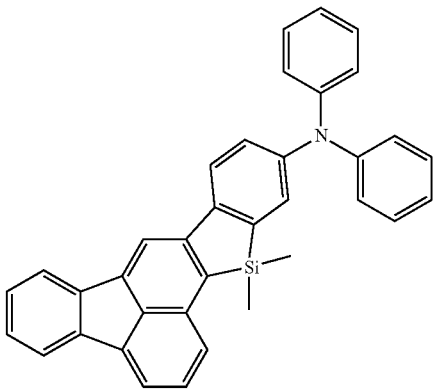
Compound 22
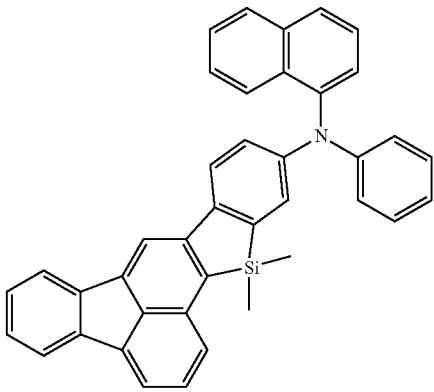

-continued
Compound 23
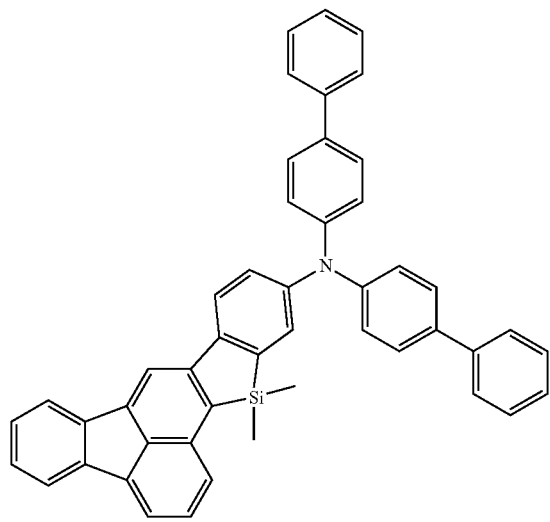
Compound 24
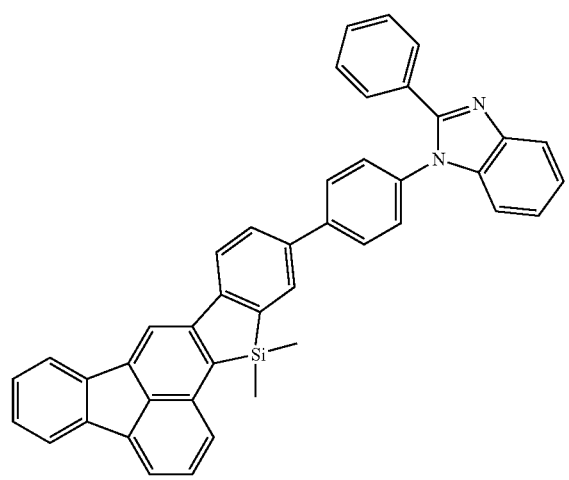
-continued
Compound 25
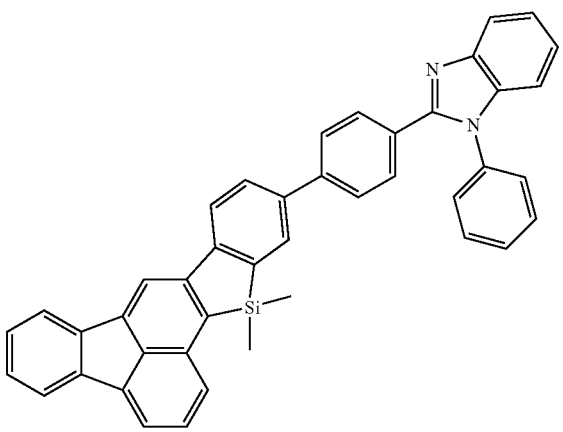
Compound 26
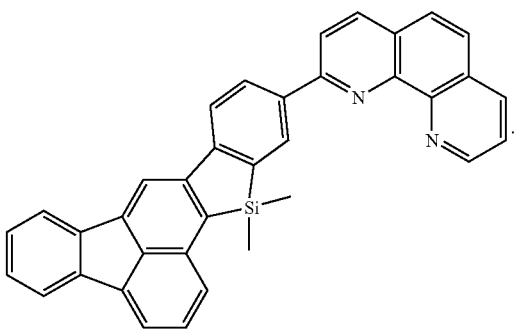
* * * * *